United States Patent [19]

Morisawa et al.

[11] Patent Number: 5,378,690
[45] Date of Patent: Jan. 3, 1995

[54] NEW RENIN-INHIBITORY OLIGOPEPTIDES, THEIR PREPARATION AND THEIR USE

[75] Inventors: Yasuhiro Morisawa; Mitsuru Kataoka; Yuichiro Yabe; Yasuteru Iijima; Hidekuni Takahagi; Hiroyuki Koike, all of Tokyo; Tatsuo Kokubu; Kunio Hiwada, both of Ehime, all of Japan

[73] Assignee: Sankyo Company, Limited, Tokyo, Japan

[21] Appl. No.: 99,776

[22] Filed: Jul. 30, 1993

Related U.S. Application Data

[63] Continuation of Ser. No. 980,322, Nov. 20, 1992, abandoned, which is a continuation of Ser. No. 713,042, Jun. 7, 1991, abandoned, which is a continuation of Ser. No. 133,017, Dec. 15, 1987, abandoned.

[30] Foreign Application Priority Data

Dec. 19, 1986 [JP] Japan ................... 61-302983
Mar. 11, 1987 [JP] Japan ................... 62-56003
May 26, 1987 [JP] Japan ................... 62-127065
May 28, 1987 [JP] Japan ................... 62-129967
Sep. 9, 1987 [JP] Japan ................... 62-225739
Oct. 29, 1987 [JP] Japan ................... 62-273773

[51] Int. Cl.⁶ .................... A61K 37/02; C07K 5/08
[52] U.S. Cl. ........................ 514/18; 514/19; 530/331
[58] Field of Search ............. 514/18, 19; 530/331

[56] References Cited

U.S. PATENT DOCUMENTS 4,548,926 10/1985 Matsueda et al. .
4,698,329 10/1987 Matsueda et al. .

FOREIGN PATENT DOCUMENTS 0152255 8/1985 European Pat. Off. .
0155809 9/1985 European Pat. Off. ............ 530/330
0184855 6/1986 European Pat. Off. .
0186977 7/1986 European Pat. Off. .
0200406 12/1986 European Pat. Off. .
0209897 1/1987 European Pat. Off. .
0228192 7/1987 European Pat. Off. .

OTHER PUBLICATIONS

Burger, *Medicinal Chemistry*, 1960, pp. 565–571, 578–581, 600–601.
Plattner et al. *J. Med. Chem.* 1988, 31(12):2277–2288.
Denkewalter et al. *Progress In Drug Research*, 1966, vol. 10:510–512.
Haber et al. *J. Cardiovasc. Res.* 1987, 10 (Suppl. 7):S54–S58.
Bolis et al. *J. Med. Chem.* 1987, 30(10):1729–1737.

Primary Examiner—Lester L. Lee
Attorney, Agent, or Firm—Frishauf, Holtz, Goodman & Woodward

[57] ABSTRACT

Oligopeptides of formula (I):

where $R^1$–$R^5$ are various organic groups, and A represents a group of formula —NH— or —$(CH_2)_n$—, in which n represents an integer of from 1 to 3, have renin-inhibitory activity and are particularly suitable for oral administration. They may be prepared by condensing their component amino acids or lower oligopeptides using conventional peptide synthesis reactions.

53 Claims, No Drawings

NEW RENIN-INHIBITORY OLIGOPEPTIDES, THEIR PREPARATION AND THEIR USE

This application is a continuation of application Ser. No. 07/980,322, filed Nov. 20, 1992 and now abandoned, which is a continuation of application Ser. No. 07/713,042, filed Jun. 7, 1991 (abandoned), which is a continuation of application Ser. No. 07/133,017 filed Dec. 15, 1987 (abandoned).

BACKGROUND OF THE INVENTION

The present invention relates to a series of new oligopeptides, which have renin-inhibitory and, hence, hypotensive activities, and which are thus of particular value in the treatment of hypertension induced by failures in the renin-angiotensin system of the mammalian, especially human body. The invention also relates to the preparation of such compounds and to their use in such treatment. The oligopeptides of the present invention include in their peptide chain a unit derived from the amino acid commonly known as cyclostatine, whose formal name is (3S, 4S)-4-amino-5-cyclohexyl-3-hydroxypentanoic acid and which is also sometimes referred to as "ACHPA".

There is considerable evidence that reduction of elevated blood pressure reduces the risks of morbidity and mortality. Elevated blood pressure (hypertension) can be caused by a variety of factors and a large number of drugs is available for the treatment of hypertension, the drug of choice being dictated in large measure by the cause of the hypertension.

Some of the factors known to play a role in the onset of hypertension in the mammalian body is an oligopeptide known as angiotensin II. Angiotensin I is a polypeptide formed by the action of renin upon a plasma protein, and this is converted to angiotensin II by the action of ACE (angiotensin converting enzyme). Angiotensin II causes constriction of the arterioles and can produce hypertension. Hypertension of this type can be reduced by reducing the plasma concentration of angiotensin I or II, which, in turn, can be achieved by inhibiting the activity of renin. The number of available drugs having this type of inhibitory activity is very limited, and, to date, no such drug is commercially available.

A variety of peptide derivatives having this type of activity is known. Those prior art compounds believed to be closest to the compounds of the present invention, in that they are based upon the rather uncommon amino acid statine and analogs thereof, are disclosed in European Patent Publications No. 155 809 and No. 184 855 and in copending U.S. patent application Ser. No. 802 038, filed Nov. 26, 1985, now abandoned. Various other prior art discloses other polypeptides having renin-inhibitory activities, but which have some other amino acid unit in place of the cyclostatine unit, which is one of the critical features of the compounds of the present invention, for example U.S. Pat. No. 4 698 329 and U.S. patent application Ser. No. 936 087, filed Nov. 28, 1986, now abandoned.

We have now discovered a series of peptide derivatives having a very marked ability to inhibit the activity of renin, which ability is believed to be significantly better than that of the prior art compounds.

Certain of the compounds of the invention resemble certain of those disclosed in European Patent Publication No. 155 809, although this European Patent Publication also discloses many other compounds which are not relevant to the present invention. However, the compounds of the present invention differ from those of European Patent Publication No. 155 809 primarily in the nature of the groups at the nitrogen terminal end and at the carboxy terminal end of the oligopeptide chain. The compounds of the present invention differ from those of European Patent Publication No. 184 855 primarily in the nature of the groups at the nitrogen terminal end of the oligopeptide chain. The compounds of the present invention differ from those of U.S. patent application Ser. No. 802 038 primarily in the nature of the group at the nitrogen terminal end and also to some extent in the nature of the group at the carboxy terminal end of the oligopeptide chain. The compounds of the present invention differ from those of U.S. patent application Ser. No. 936 087 in the nature of other units in the polypeptide chain.

The compounds of the present invention have, in general, a higher inhibitory activity against renin, much improved absorption when administered by the oral route, lower toxicity, better and stronger enzyme specificity and better water solubility than the compounds of the prior art. These advantages suggest that the compounds of the present invention will be of outstanding value in the treatment of disorders in the mammalian body arising from an imbalances in the level of renin in the blood. In particular, it is well known that the oral route is the preferred route of administration, particularly where (as with the drugs with which the present invention is concerned) drugs are intended for self-administration by the patient, generally over a long period of time. However, a serious disadvantage common to almost all of the known renin-inhibitory oligopeptides, including most of those mentioned in the previous paragraph, is that, in practice, it is necessary to administer them by parenteral routes, e.g. by injection, as suppositories or even by inhalation. This applies even in those cases where the compounds have been suggested for oral use, except for those of U.S. patent application Ser. No. 936 087, since it has subsequently been found that they either are insufficiently stable to enzymes, e.g. esterases, present in the digestive system or are inadequately absorbed from the stomach and/or intestines or both. Of course, the poor stability is expected with oligopeptides, as the mammalian digestive system is specifically designed to break down compounds of that type. Consequently, even if the compounds can be administered orally, such high doses are necessary in order to make up for poor absorption and/or losses caused by digestion as to make oral administration impractical.

BRIEF SUMMARY OF INVENTION

The compounds of the present invention are thus those compounds of formula (I):

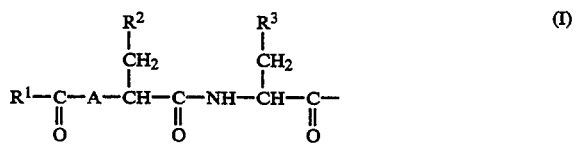

-continued

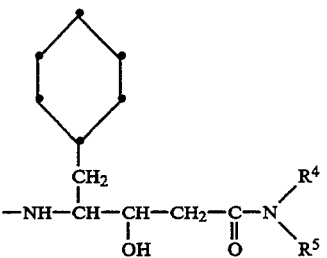

wherein:

$R^1$ represents a $C_1$-$C_6$ alkyl group, a $C_1$-$C_6$ alkyl group having at least one substituent selected from the group consisting of nitrogen-containing heterocyclic groups having from 5 to 8 ring atoms and groups of formula (II):

 (II)

in which $R^6$ and $R^7$ are independently selected from the group consisting of hydrogen atoms, $C_1$-$C_6$ alkyl groups, aryl groups, aralkyl groups and $C_3$-$C_8$ cycloalkyl groups, or a nitrogen-containing heterocyclic group having from 5 to 8 ring atoms or, when A represents a group of formula —(CH$_2$)$_n$—, a group of formula (II), as defined above;

$R^2$ represents a cyclohexyl group, a phenyl group, a phenyl group having at least one substituent selected from the group consisting of substituents (a), defined below, a naphthyl group or a naphthyl group having at least one substituent selected from the group consisting of substituents (a), defined below;

$R^3$ represents an aromatic heterocyclic group having from 5 to 14 ring atoms, a phenyl group, a phenyl group having at least one substituent selected from the group consisting of substituents (a), defined below, or a $C_1$-$C_6$ alkyl group;

R represents a $C_1$-$C_8$ alkyl group or a $C_1$-$C_8$ alkyl group having at least one substituent selected from the group consisting of hydroxy groups, heterocyclic groups having from 5 to 14 ring atoms and groups of formula (III):

 (III)

in which $R^8$ and $R^9$ are independently selected from the group consisting of hydrogen atoms and $C_1$-$C_6$ alkyl groups;

$R^5$ represents a hydrogen atom or a $C_1$-$C_8$ alkyl group;

A represents a group of formula —NH— or —(CH$_2$)$_n$—, in which n represents an integer of from 1 to 3;

said heterocyclic groups and nitrogen-containing heterocyclic groups having from 1 to 5 ring hetero- atoms selected from the group consisting of nitrogen, oxygen and sulfur hereto-atoms and being unsubstituted or having at least one substituent selected from the group consisting of substituents (a) and substituents (b);

Substituents (a)

$C_1$-$C_6$ alkyl groups, $C_1$-$C_4$ alkoxy groups, $C_1$-$C_7$ aliphatic carboxylic acyl groups, $C_1$-$C_7$ aliphatic carboxylic acyloxy groups, aromatic carboxylic acyl groups, aromatic carboxylic acyloxy groups, $C_1$-$C_7$ aliphatic carboxylic acylamino groups, aromatic carboxylic acylamino groups, heterocyclic-carbonyl groups, provided that any such heterocyclic-carbonyl substituent is not itself substituted by a heterocyclic or heterocyclic-carbonyl group, arylalkenoyl groups in which the alkenoyl part is $C_3$-$C_7$, trifluoromethyl groups, halogen atoms, nitro groups, cyano groups, amino groups, $C_1$-$C_4$ alkylamino groups, dialkylamino groups in which each alkyl part is $C_1$-$C_4$, alkylcarbamoyl groups in which the alkyl part is $C_1$-$C_4$, dialkylcarbamoyl groups in which each alkyl part is $C_1$-$C_4$, alkoxycarbonyloxy groups in which the alkoxy part is $C_1$-$C_4$, heterocyclic groups, provided that any such heterocyclic substituent is not itself substituted by a heterocyclic or heterocyclic-carbonyl group, carboxy groups and esters and amides of said carboxy groups, the aromatic parts of said aromatic acyl, acyloxy and acylamino groups being $C_6$-$C10$ carbocyclic aryl groups which are unsubstituted or have at least one substituent selected from the group consisting of $C_1$-$C_4$ alkyl groups, $C_1$-$C_4$ alkoxy groups and halogen atoms;

Substituents (b)

aryl groups and oxygen atoms;

said aryl groups and the aryl parts of said aralkyl groups are $C_6$-$C14$ carbocyclic aryl groups which are unsubstituted or have at least one substituent selected from the group consisting of substituents (a), defined above, provided that, where said substituent (a) is a group containing an aryl group, this is not itself substituted by another group containing an aryl group; and the alkyl parts of said aralkyl groups have from 1 to 4 carbon atoms;

and pharmaceutically acceptable salts thereof.

The invention also provides a method for the treatment or prophylaxis of angiotensin-induced hypertension in a mammal, which may be human or non-human, by the administration thereto of a compound of formula (I) or a pharmaceutically acceptable salt thereof.

The invention also provides a composition for the treatment of angiotensin-induced hypertension in a mammal, which may be human or non-human, which comprises a compound of formula (I) or a pharmaceutically acceptable salt thereof in admixture with a pharmaceutically acceptable carrier or diluent.

The compounds of the invention may be prepared by reacting together two compounds, one having a terminal carboxy group or reactive derivative thereof and the other having a terminal amino group or reactive derivative thereof, under conditions conventional for peptide synthesis, said two compounds corresponding to the fragments derivable by cleavage of any one of the peptide bonds marked α, β and γ in the following formula (I) and, where A is a group —NH—, between that group and the adjacent carboxy group:

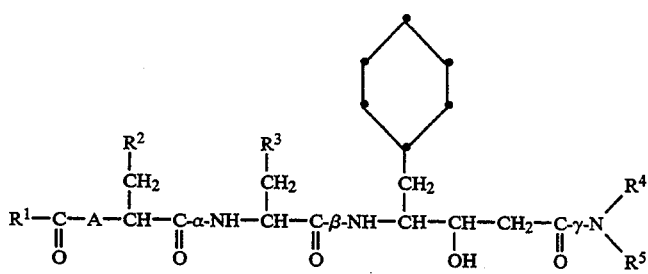

(in which $R^1$–$R^5$ and A are as defined above).

DETAILED DESCRIPTION OF INVENTION

Where $R^1$, $R^3$ or substituent (a) represents an alkyl group containing from 1 to 6 carbon atoms, this may be a straight or branched chain alkyl group and examples include the methyl, ethyl, propyl, isopropyl, butyl, isobutyl, sec-butyl, t-butyl, pentyl, isopentyl, neopentyl, sec-pentyl, t-pentyl, hexyl, isohexyl, 2-methylbutyl and 1,2-dimethylbutyl groups. Of these, we prefer alkyl groups containing from 1 to 4 carbon atoms. In particular, where $R^1$ represents a substituted alkyl group, we prefer the methyl, ethyl, propyl and butyl groups, of which the methyl group is most preferred, the substituents being as defined below. Where $R^1$ represents an unsubstituted alkyl group, we prefer the methyl, ethyl, propyl, isopropyl, butyl, isobutyl, sec-butyl and t-butyl groups, of which the t-butyl group is most preferred. Where $R^3$ represents an alkyl group, we prefer the methyl, ethyl, propyl, isopropyl, butyl and isobutyl groups, of which the isopropyl group is most preferred.

Where $R^4$ or $R^5$ represents an alkyl group containing from 1 to 8 carbon atoms, this may be a straight or branched chain alkyl group and examples include the methyl, ethyl, propyl, isopropyl, butyl, isobutyl, sec-butyl, t-butyl, pentyl, isopentyl, neopentyl, sec-pentyl, t-pentyl, hexyl, isohexyl, 2-methylbutyl, 1,2-dimethylbutyl, heptyl and octyl groups. Where $R^4$ represents a substituted alkyl group, we prefer the methyl, ethyl, propyl, butyl, 2-methylbutyl, 1,2-dimethylbutyl and 2,3-dimethylbutyl groups, of which the ethyl and propyl groups are most preferred, the substituents being as defined below. Where $R^4$ represents an unsubstituted alkyl group, we prefer the propyl, isopropyl, butyl, isobutyl, sec-butyl, t-butyl, pentyl, isopentyl, methylbutyl (e.g. 2-methylbutyl or 1-methylbutyl), hexyl, isohexyl, methylpentyl (e.g. 2-methylpentyl or 3-methylpentyl), heptyl, isoheptyl and octyl groups, of which the 2-methylbutyl and hexyl groups are most preferred.

Where $R^5$ represents an alkyl group, it is preferably the same alkyl group as is represented $R^4$, and is more preferably a $C_4$–$C_6$ alkyl group e.g. a butyl, isobutyl, pentyl, isopentyl or hexyl group. However, $R^5$ most preferably represents a hydrogen atom.

Where $R^6$ or $R^7$ represents an alkyl group, it contains from 1 to 6 carbon atoms and is preferably a $C_1$–$C_4$ alkyl group. Examples of such groups include the $C_1$–$C_6$ alkyl groups represented by $R^1$, $R^3$ or substituent (a), more preferably the methyl, ethyl, propyl, isopropyl, butyl and isobutyl groups.

Where $R^1$ represents an alkyl group having at least one heterocyclic group as a substituent or represents a heterocyclic group, the heterocyclic group has from 5 to 8 ring atoms of which from 1 to 5 are ring heteroatoms selected from the group consisting of nitrogen, oxygen and sulfur hereto-atoms, at least one being a nitrogen atom. The heterocyclic group is attached to the remainder of the molecule (i.e. the alkyl group of $R^1$ on which it is a substituent or the group —CO—A—) through its nitrogen atom or through one of its nitrogen atoms. The heterocyclic group may itself be substituted or unsubstituted, and, if substituted, the substituents are selected from the group consisting of substituents (a) and substituents (b), defined above. Such groups may be aromatic or non-aromatic in character.

Where such a group is an aromatic heterocyclic group, this is a heterocyclic group (as defined above) having aromatic character, i.e. a group having from 5 to 8 ring atoms of which from 1 to 5, preferably from 1 to 4 more preferably from 1 to 3, are nitrogen, oxygen or sulfur hetero-atoms, and at least one is a nitrogen atom, and it may be monocyclic or bicyclic, preferably monocyclic. Preferably, it has from 5 to 7, more preferably 5 or 6, ring atoms, of which from 1 to 3 are such heteroatoms. Examples of such aromatic heterocyclic groups include the pyrrolyl, pyrazolyl, oxazolyl, isoxazolyl, thiazolyl, isothiazolyl, imidazolyl, pyridyl, pyrimidinyl, pyridazinyl and pyrazinyl groups. The more preferred aromatic heterocyclic groups are the imidazolyl and pyridyl groups. Such groups may be unsubstituted or may have at least one of the substituents (a), and (b), defined above. Preferred such substituents are the alkyl, halogen and alkoxy substituents, e.g. as exemplified below.

Where the heterocyclic group, or, indeed, any other substituted group referred to herein, is substituted, there is, in general, no particular limitation on the maximum number of substituents possible except that dictated by the number of substitutable positions (e.g. 5 for pyridyl, 3 for imidazolyl, 4 for pyrimidinyl); however, in particular circumstances (as described more fully below in relation to substituents generally) steric constraints may dictate that less than this maximum number of substituents may be present. In practice, most substituted heterocyclic groups employed in compounds of this type will normally have from 1 to 5, more commonly from 1 to 3, substituents.

Where $R^1$ represents an alkyl group having a non-aromatic heterocyclic group as a substituent or itself represents a non-aromatic heterocyclic group, this has from 5 to 8 ring atoms, of which from 1 to 5, more preferably from 1 to 3 and most preferably 1 or 2, are hetero-atoms selected from the group consisting of nitrogen, oxygen and sulfur atoms, at least one being a nitrogen atom. The most preferred heterocyclic groups contain 5 or 6 ring atoms and most preferably 1 or 2 of these atoms are nitrogen atoms and 0 or 1 of these atoms are selected from the group consisting of oxygen atoms and sulfur atoms. The non-aromatic heterocyclic group may be a fully saturated ring or it may be an unsaturated ring, provided that the unsaturation is not aromatic in character.

Specific examples of preferred non-aromatic heterocyclic groups include the piperidyl (including the 1-piperidyl group known as "piperidino"), pyrrolidinyl (e.g. 1-pyrrolidinyl), morpholinyl (including the morpholino group), thiomorpholinyl (including the thiomorpholino group), oxazolidinyl (including 1-oxazolidinyl), isoxazolidinyl (including 1-isoxazolidinyl), thiazolidinyl (including 1-thiazolidinyl), imidazolidinyl (including 1-imidazolidinyl) and piperazinyl (including 1-piperazinyl). Such a ring may be unsubstituted or may have at least one substituent selected from the group consisting of substituents (a) and (b) defined above. The preferred substituents are: $C_1$–$C_4$ alkyl groups, such as those exemplified above in relation to $R^1$, $R^3$ or substituent (a); $C_1$–$C_4$ alkoxy groups, such as the methoxy, ethoxy, propoxy, isopropoxy, butoxy and isobutoxy groups; phenyl groups, which may be unsubstituted or may themselves have one or more of substituents (a), for example the phenyl, methoxyphenyl, chlorophenyl, fluorophenyl, trifluoromethylphenyl and tolyl groups, especially the phenyl, 2- and 4- methoxyphenyl, 2- and 4-chlorophenyl, 2- and 4-fluorophenyl, 3-trifluoromethylphenyl and 2- and 4-tolyl groups: aromatic heterocyclic groups, such as those exemplified above in relation to the aromatic heterocyclic groups which may be represented by or included in the groups represented by $R^1$ and which, of course, may themselves be unsubstituted or substituted as defined above, provided that, where they are substituted, they are not further substituted by heterocyclic groups, aralkyl groups, in which the alkyl part is $C_1$–$C_4$ and the or each aryl part is as defined above, for example the benzyl and benzhydryl groups; aralkyloxycarbonyl groups, in which the aralkyl part may be any one of those aralkyl groups exemplified below in relation to $R^6$ and $R^7$, especially the benzyloxycarbonyl group: $C_2$–$C_5$ alkoxycarbonyl groups, in which the alkoxy part may be any one of those exemplified below in relation to substituent (a), especially the ethoxycarbonyl and butoxycarbonyl groups; alkylcarbamoyl groups in which the alkyl part has from 1 to 4 carbon atoms, for example a methylcarbamoyl, ethylcarbamoyl, propylcarbamoyl or butylcarbamoyl group; oxygen atoms, representing an oxo substituent; arylalkenoyl groups, in which the aryl part may be any one of those exemplified above and the alkenoyl part is a $C_3$–$C_7$, preferably $C_3$–$C_5$, alkenoyl group, preferably a propenoyl group, for example the cinnamoyl group, which may itself be substituted, and this applies generally to arylalkenoyl groups which may be represented by substituent (a); aliphatic acyl groups, such as those exemplified below in relation to substituent (a) (especially as substituents on nitrogen hereto-atoms); and (also especially as substituents on nitrogen hereto-atoms) heterocyclic-carbonyl groups, including those exemplified below in relation to substituent (a) and others, such as the nicotinoyl and isonicotinoyl groups. The maximum number of substituents is as described generally above in relation to aromatic heterocyclic groups.

Where $R^6$, $R^7$ or substituent (b) represents an aryl group, this is a carbocyclic aryl group having from 6 to 14, preferably from 6 to 10, ring carbon atoms and which may be unsubstituted or have at least one of the substituents (a), defined above. Examples of the unsubstituted aryl groups are the phenyl, indenyl (which may be 1-, 2-, 3-, 4-, 5-, 6- or 7-indenyl) and naphthyl (1- or 2-naphthyl) groups. Where such aryl groups are substituted, they may be any of the groups, e.g. phenyl, indenyl and naphthyl groups, exemplified as unsubstituted aryl groups, and have at least one of the substituents (a), as exemplified herein. Preferred substituents for aryl groups are: $C_1$–$C_4$ alkyl groups, e.g. the methyl, ethyl, propyl, isopropyl, butyl, isobutyl, sec-butyl and t-butyl groups; halogen atoms, e.g. the fluorine, chlorine, bromine and iodine atoms; $C_1$–$C_4$ alkoxy groups, e.g. the methoxy, ethoxy, propoxy, isopropoxy, butoxy, isobutoxy, sec-butoxy and t-butoxy groups; $C_2$–$C_5$ alkoxycarbonyl groups, i.e. groups containing a $C_1$–$C_4$ alkoxy group, such as those alkoxy groups exemplified above; the trifluoromethyl group; the amino group; the cyano group; or the nitro group. Where $R^6$ or $R^7$ represents an aryl group, preferably only one is such an aryl group, and the preferred aryl group is phenyl group.

Where $R^6$ or $R^7$ represents an aralkyl group, the aryl part thereof is a carbocyclic aryl group having from 6 to 14, preferably from 6 to 10 and more preferably 6, ring carbon atoms and which may be unsubstituted or have at least one of the substituents (a), defined above. Examples of the unsubstituted aralkyl groups are the benzyl, phenethyl, benzhydryl and phenylpropyl (e.g. 2-phenylpropyl or 3-phenylpropyl) groups. Where such aralkyl groups are substituted, they may be any of the groups, e.g. benzyl, phenethyl, benzhydryl and phenylpropyl groups, exemplified as unsubstituted aralkyl groups, and have at least one of the substituents (a), as exemplified herein. Preferred substituents for aralkyl groups are as illustrated above in relation to substituted aryl groups.

Where $R^6$ or $R^7$ represents a $C_3$–$C_8$ cycloalkyl group, this may be, for example, the cyclopropyl, cyclobutyl, cyclopentyl, cyclohexyl, cycloheptyl or cyclooctyl group, preferably the cyclohexyl group.

Where $R^3$ represents an aromatic heterocyclic group, this is a heterocyclic group (as defined above) having aromatic character, i.e. a group having from 5 to 14 ring atoms of which from 1 to 5, preferably from 1 to 4 more preferably from 1 to 3, are nitrogen, oxygen or sulfur hetero-atoms, and it may be monocyclic or polycyclic (e.g. bicyclic). Preferably, it has from 5 to 10, more preferably 5 or 6, ring atoms, of which from 1 to 3 are such hereto-atoms. Included amongst the preferred aromatic heterocyclic groups are bicyclic groups comprising a benzene ring fused to a heterocyclic ring (the heterocyclic ring then preferably having 5, 6 or 7 ring atoms of which from 1 to 3 are said hereto-atoms). Examples of such aromatic heterocyclic groups include the furyl, thienyl, oxazolyl, isoxazolyl, thiazolyl, imidazolyl, pyridyl, pyrazinyl, benzofuryl, benzothienyl, indolyl, benzothiazolyl, benzimidazolyl, quinolyl and isoquinolyl groups. Such groups may be unsubstituted or may have at least one of the substituents (a) and (b) defined above. Preferred such substituents are those specified above in relation to the aromatic heterocyclic groups which may be represented by or included in the group represented by $R^1$. The maximum number of such substituents is generally also as described above in relation to such groups.

Where $R^4$ represents an alkyl group substituted by a heterocyclic group, this may be any of the heterocyclic groups exemplified above in relation to $R^1$ and/or $R^3$, preferably a morpholinyl, thiomorpholinyl, pyrrolidinyl, piperazinyl, piperidyl, imidazolyl or pyridyl group, which may be unsubstituted or substituted as defined above and e.g. as exemplified above in relation to substituents on aromatic heterocyclic groups.

Where $R^4$ represents the aforementioned group of formula (III), the groups $R^8$ and $R^9$ may be as exemplified above in relation to the same groups which may be represented by $R^6$ and $R^7$.

Where A represents a group of formula —$(CH_2)_n$—, n may be any one of the integers 1, 2 and 3, but is most preferably 1.

Where substituent (a) represents an alkoxy group, this may be a straight or branched chain alkoxy group having from 1 to 4 carbon atoms, and examples include the methoxy, ethoxy, propoxy, isopropoxy, butoxy, isobutoxy, sec-butoxy and t-butoxy groups.

Where substituent (a) represents an aliphatic acyl group, this is preferably a $C_2$–$C_5$ aliphatic acyl group, and may be a straight or branched chain group, whose carbon chain may be saturated or unsaturated. It is preferably a $C_2$–$C_5$ alkanoyl group or a $C_3$–$C_5$ alkenoyl or alkynoyl group. Examples of such groups include the acetyl, propionyl, butyryl, isobutyryl, valeryl, isovaleryl, pivaloyl, acryloyl, propioloyl, methacryloyl, crotonoyl and isocrotonoyl groups.

Where substituent (a) represents an aromatic acyl group, this is preferably an arylcarbonyl group in which the aryl part is as defined above. Preferred such groups are the benzoyl and naphthoyl groups, which may be unsubstituted or have one or more of substituents (a), defined above. Examples include the benzoyl, p-nitrobenzoyl, 1-naphthoyl and 2-naphthoyl groups.

Where substituent (a) represents a heterocyclic acyl group, this is preferably a heterocyclic-carbonyl group where the heterocyclic part is as defined above. More preferably, the heterocyclic part has 5 or 6 ring atoms, of which one or two are nitrogen and optionally another one is oxygen or sulfur. Preferred such groups include the piperidylcarbonyl (e.g. piperidinocarbonyl), pyrrolidinylcarbonyl (e.g. 1- and 2-pyrrolidinylcarbonyl, especially the prolyl and N-substituted prolyl groups, e.g. N-t-butoxycarbonyl-prolyl and N-benzyloxycarbonyl-prolyl groups), morpholinylcarbonyl (e.g. morpholinocarbonyl), oxazolidinylcarbonyl (e.g. 1-oxazolidinylcarbonyl), thiazolidinylcarbonyl (e.g. 1-thiazolidinylcarbonyl), imidazolidinylcarbonyl (e.g. 1-imidazolidinylcarbonyl), piperazinylcarbonyl (e.g. 1-piperazinylcarbonyl) and perhydro-1,4-thiazinylcarbonyl (more commonly known as thiomorpholinylcarbonyl, e.g. thiomorpholinocarbonyl) groups.

Where substituent (a) represents an aliphatic carboxylic acyloxy group, this has from 1 to 7 carbon atoms, more preferably from 2 to 6 carbon atoms, for example the formyloxy, acetoxy, propionyloxy, butyryloxy, isobutyryloxy, valeryloxy, isovaleryloxy, pivaloyloxy, hexanoyloxy and heptanoyloxy groups.

Where substituent (a) represents an aromatic carboxylic acyloxy group, the aromatic part may be any one of those aryl groups exemplified above but is preferably a phenyl group which may be unsubstituted or have one or more substituents, for example the benzoyloxy or p-nitrobenzoyloxy groups.

Where substituent (a) represents an $C_1$–$C_7$ aliphatic acylamino group, this is more preferably such a group having from 2 to 5 carbon atoms, such as the formamido, acetamido, propionamido, butyramido, isobutyramido, valeramido, isovaleramido, pivaloylamino, hexanoylamino and heptanoylamino groups.

Where substituent (a) represents an aromatic carboxylic acylamino group, the aromatic part may be any one of those aryl groups exemplified above but is preferably a phenyl group which may be unsubstituted or have one or more substituents, for example the benzoylamino or p-nitrobenzoylamino groups.

Where substituent (a) represents a halogen atom, this may be the fluorine, chlorine, bromine or iodine atom.

Where substituent (a) represents a mono- or dialkylamino group in which the or each alkyl part is a $C_1$–$C_4$ alkyl group, it may be, for example the methylamino, ethylamino, propylamino, isopropylamino, butylamino, isobutylamino, sec-butylamino, dimethylamino, methyl(ethyl)amino, diethylamino, dipropylamino, diisopropylamino, dibutylamino, methyl(butyl)amino, ethyl(butyl)amino or diisobutylamino group.

Where substituent (a) represents a mono- or dialkylcarbamoyl group in which the or each alkyl part a $C_1$–$C_4$ alkyl group, it may be, for example the methylcarbamoyl, ethylcarbamoyl, propylcarbamoyl, isopropylcarbamoyl, butylcarbamoyl, isobutylcarbamoyl, sec-butylcarbamoyl, dimethylcarbamoyl, methyl(ethyl)carbamoyl, diethylcarbamoyl, dipropylcarbamoyl, diisopropylcarbamoyl, dibutylcarbamoyl, methyl(butyl)carbamoyl, ethyl(butyl)carbamoyl or diisobutylcarbamoyl group.

Where substituent (a) represents an alkoxycarbonyloxy group in which the alkoxy part is $C_1$–$C_4$, this is a $C_2$–$C_5$ alkoxycarbonyl group, e.g. the methoxycarbonyl, ethoxycarbonyl, propoxycarbonyl, isopropoxycarbonyl, butoxycarbonyl, isobutoxycarbonyl, sec-butoxycarbonyl or t-butoxycarbonyl group.

Where substituent (a) represents a heterocyclic group, this may be any one of the heterocyclic groups exemplified above in relation to $R^1$, $R^3$ or $R^4$, provided that any such heterocyclic substituent is not itself substituted by a heterocyclic group.

Specific examples of groups which may be represented by $R^1$ include the 1-pyrrolidinyl, piperidino, 2-methylpiperidino, 3-methylpiperidino, 4-methylpiperidino, 2-ethylpiperidino, 3-ethoxycarbonylpiperidino, 4-benzylpiperidino, morpholino, 2,6-dimethylmorpholino, thiomorpholino, 1-piperazinyl, 4-methyl-l-piperazinyl, 4-benzyl-1-piperazinyl, 4-ethoxycarbonyl-1-piperazinyl, 4-phenyl-1-piperazinyl, 4-pyridyl-l-piperazinyl (2-, 3- or 4- pyridyl), 4-(4-fluorophenyl)-1-piperazinyl, 4-(4-chlorophenyl)-1-piperazinyl, 4-(2-chlorophenyl)-1-piperazinyl, 4-(3-chlorophenyl)-1-piperazinyl, 4-(2-methoxyphenyl)-1-piperazinyl, 4-(2-methylphenyl)-1-piperazinyl, 4-(2-pyrimidinyl)-1-piperazinyl, 4-(4-trifluoromethylphenyl)-1-piperazinyl, 4-(3-trifluoromethylphenyl)-1-piperazinyl, amino, methylamino, ethylamino, propylamino, isopropylamino, dimethylamino, diethylamino, dipropylamino, diisopropylamino, methylbutylamino, dibutylamino, diisobutylamino, benzylamino, phenethylamino, 2-(4-chlorophenyl)ethylamino, t-butyl, N-methyl-N-cyclohexylamino, N-methyl-N-benzylamino, N-ethyl-N-benzylamino, N-isopropyl-N-benzylamino, N-methyl-N-(4-methylbenzyl)amino, 1-pyrrolidinylmethyl, piperidinomethyl, 1-piperidinoethyl, 2-methylpiperidinomethyl, 3-methylpiperidinomethyl, 4-methylpiperidinomethyl, 2-ethylpiperidinomethyl, 3-ethoxycarbonylpiperidinomethyl, 3-piperidinylmethyl, 1-morpholinoethyl, morpholinomethyl, 2,6-dimethylmorpholinomethyl, thiomorpholinomethyl, 1-thiomorpholinoethyl, 2-morpholinoethyl, 3-morpholinopropyl, 2-thiomorpholinoethyl, 3-thiomorpholinopropyl, 1-piperazinylmethyl, 4-methyl-1-piperazinylmethyl, 4-benzyl-1-piperazinylmethyl, 4-ethoxycarbonyl-1-piperazinylmethyl, 4-phenyl-1-piperazinylmethyl, 4-(2-methoxyphenyl)-1-piperazinylmethyl, 4-(3-methoxyphenyl)-1-piperazinylmethyl, 4-(4-methoxyphenyl)-1-piperazinylmethyl, 4-(4-chlorobenzhydryl)-1-piperazinylmethyl, 4-(2-pyrimidinyl)-1-piperazinylmethyl, 4-pyridyl-1-piperazinylmethyl (2-, 3or 4- pyridyl), 4-(3-trifluoromethylphenyl)-1-piperazinylmethyl, 4-(4-fluorophenyl)-1-piperazinylmethyl, 4-(4-chlorophenyl)-1-piperazinylmethyl, 4-(2-chlorophenyl)-1-piperazinylmethyl, 4-(3-chlorophenyl)-1-piperazinylmethyl, 4-benzylpiperidinomethyl, 1-t-butoxycarbonyl-2-pyrrolidinyl, 2-pyrrolidinyl, 1-benzyloxycarbonyl-2-pyrrolidinyl, aminomethyl, methylaminomethyl, ethylaminomethyl, propylaminomethyl, 2-aminoethyl, phenylaminomethyl, benzylaminomethyl, 2-benzylaminoethyl, isopropylaminomethyl, N,N-dimethylaminomethyl, N,N-diethylaminomethyl, N,N-dipropylaminomethyl, N,N-diisopropylaminomethyl, N-methyl-N-butylaminomethyl, N,N-dibutylaminomethyl, N,N-diisobutylaminomethyl, N-methyl-N-cyclohexylaminomethyl, N,N-dicyclohexylaminomethyl, N-methyl-N-benzylaminomethyl, N-ethyl-N-benzylaminomethyl, N-isopropyl-N-benzylaminomethyl, N-methyl-N-phenethylaminomethyl, phenethylaminomethyl, N-methyl-N-phenylaminomethyl, N-methyl-N-(4-chlorophenyl)aminomethyl, N-ethyl-N-phenylaminomethyl, N-methyl-N-(4-methoxybenzyl)aminomethyl, N-methyl-N-(4-chlorobenzyl)aminomethyl, N-methyl-N-(4-methylbenzyl)aminomethyl, N-ethyl-N-(4-methylbenzyl)aminomethyl, 3-piperidyl, 1-benzyloxycarbonyl-3-piperidyl, 1-morpholinopropyl, 1-morpholinobutyl, 1-pyrrolidinylethyl, 1-(4-methyl-1piperazinyl)ethyl, 1-(4-phenyl-1-piperazinyl)ethyl and 1-benzyloxycarbonyl-3-piperidylmethyl groups.

Specific examples of groups which may be represented by $R^2$ include the cyclohexyl, phenyl, 2-fluorophenyl, 2-trifluoromethylphenyl, 2,3,4,5,6-pentafluorophenyl, 1-naphthyl, 2-naphthyl and 4-methoxyphenyl groups.

Specific examples of groups which may be represented by $R^3$ include the 2-furyl, 2-thienyl, 2-pyridyl, 3-pyridyl, 4-pyridyl, phenyl, 2-fluorophenyl, 2-trifluoromethylphenyl, 5-isoxazolyl, 4-thiazolyl, 4-oxazolyl, 4-methyl-5-thiazolyl, 5-imidazolyl, 3-indolyl, 4-fluoro-3-indolyl, methyl, ethyl, propyl, isopropyl, butyl and isobutyl groups.

Specific examples of groups which may be represented by $R^4$ include the 3-(dimethylamino)propyl, 3-(diethylamino)propyl, 2-(diethylamino)ethyl, 2-(dimethylamino)ethyl, 2-(1-pyrrolidinyl)ethyl, 2-piperidinoethyl, 2-morpholinoethyl, 2-thiomorpholinoethyl, 2-(1-methyl-2-pyrrolidinyl)ethyl, 2-(1-ethyl-2-pyrrolidinyl)ethyl, 1-ethyl-2-pyrrolidinylmethyl, 2-(4-methyl -1-piperazinyl)ethyl, 4-piperidylmethyl, 1-ethyl-3-piperidyl, 1-benzyl-4-piperidyl, 2-(4-ethoxycarbonyl-1-piperazinyl)ethyl, 2-(4-phenyl-1-piperazinyl)ethyl, 2-(1-piperazinyl)ethyl, 2-[4-(2-pyridyl)-1-piperazinyl]ethyl, 2-(4-benzyl-1-piperazinyl)ethyl, 3-morpholinopropyl, 3-morpholinobutyl, 3-(2 -methylpiperidino)propyl, 2-(2-ethoxycarbonyl-1-pyrrolidinyl)ethyl, 2-(2-carbamoyl-1-pyrrolidinyl)ethyl, 2-(2-propylcarbamoyl-1-pyrrolidinyl)ethyl, 2-morpholinopropyl, 3-(2-oxo-1-pyrrolidinyl)propyl, 2-(2-oxopiperidino)ethyl, 2-(2-oxomorpholino)ethyl, 1-hydroxymethyl-2-methylbutyl, 2-pyridylmethyl, 2-(2-pyridyl)ethyl, 2-(5-imidazolyl)ethyl, 2-(1-imidazolyl)ethyl, 2-(2,6-dimethylmorpholino)ethyl, 1-methyl-2-piperidinoethyl, 1-methyl-2-morpholinoethyl, 2-hydroxy-3-morpholinopropyl, 2-hydroxy-3-piperidinopropyl, 2-hydroxy-3-(4-methyl-1-piperazinyl)propyl, 1-(morpholinomethyl)-2-methylbutyl, 1-(piperidinomethyl)-2-methylbutyl, 1-methylbutyl, methyl, ethyl, propyl, isopropyl, butyl, isobutyl, sec-butyl, pentyl, isopentyl, 2-methylpentyl, 3-methylpentyl, hexyl, isohexyl, heptyl, isoheptyl and octyl groups.

Specific examples of groups which may be represented by $R^5$ include the hydrogen atom and the methyl, ethyl, propyl, isopropyl, butyl, isobutyl, sec-butyl, pentyl, isopentyl, 1-methylbutyl, 2-methylbutyl, 2-methylpentyl, 3-methylpentyl, hexyl, isohexyl, heptyl, isoheptyl and octyl groups.

The more preferred groups which may be represented by $R^1$ include the 1-pyrrolidinyl, piperidino, morpholino, 2,6-dimethylmorpholino, thiomorpholino, 4-methyl-1-piperazinyl, 4-phenyl-1-piperazinyl, 4-(2-pyridyl)-1-piperazinyl, 4-(4-fluorophenyl)-1-piperazinyl, 4-(4-chlorophenyl)-1-piperazinyl, 4-(2-chlorophenyl)-1-piperazinyl, 4-(2-methoxyphenyl)-1-piperazinyl, 4-(2-pyrimidinyl)-1-piperazinyl, diethylamino, methylbutylamino, N-methyl-N-cyclohexylamino, N-methyl-N-benzylamino, 1-pyrrolidinylmethyl, piperidinomethyl, morpholinomethyl, 2,6-dimethylmorpholinomethyl, thiomorpholinomethyl, 1-morpholinoethyl, 2-morpholinoethyl, 3-morpholinopropyl, 4-methyl-1-piperazinylmethyl, 4-phenyl-1-piperazinylmethyl, 4-(2-methoxyphenyl)-1-piperazinylmethyl, 4-(4-chlorobenzhydryl)-1-piperazinylmethyl., 4-(2-pyrimidinyl)-1-piperazinylmethyl, 4-(2-pyridyl)-1-piperazinylmethyl, 4-(4-fluorophenyl)-1-piperazinylmethyl, 4-(4-chlorophenyl)-1-piperazinylmethyl, 4-(2-chlorophenyl)-1-piperazinylmethyl, 4-benzylpiperidinomethyl, N,N-dimethylaminomethyl, N,N-diethylaminomethyl, N-methyl-N-butylaminomethyl, N,N-diisobutylaminomethyl, N,N-dicyclohexylaminomethyl, N-methyl-N-cyclohexylaminomethyl, N-methyl-N-benzylaminomethyl, N-ethyl-N-benzylaminomethyl, N-isopropyl-N-benzylaminomethyl and N-methyl-N-phenylaminomethyl groups.

The more preferred groups which may be represented by $R^2$ include the phenyl and 1-naphthyl groups.

The more preferred groups which may be represented by $R^3$ include the 2-thienyl, 5-isoxazolyl, 4-thiazolyl, 5-imidazolyl, 3-indolyl and isopropyl groups.

The more preferred groups which may be represented by $R^4$ include the 2-(1-pyrrolidinyl)ethyl, 2-piperidinoethyl, 2-morpholinoethyl, 3-morpholinopropyl, 2-morpholinopropyl, 3-(2-oxo-1-pyrrolidinyl)propyl, 2-methylbutyl, 1-methyl-2-piperidinoethyl, 1-(morpholinomethyl)-2-methylbutyl, 1-(piperidinomethyl)-2-methylbutyl, propyl, isopropyl, butyl, isobutyl, sec-butyl, pentyl, isopentyl, 2-methylpentyl, hexyl and isohexyl groups.

$R^5$ preferably represents a hydrogen atom or a propyl group, more preferably a hydrogen atom.

One class of compounds of the present invention are those compounds of formula (I) in which:

$R^1$ represents a nitrogen-containing heterocyclic group having 5 or 6 ring atoms or a group of formula (II):

(II)

in which $R^6$ and $R^7$ are independently selected from the group consisting of hydrogen atoms and $C_1$-$C_4$ alkyl groups:

$R^2$ represents a cyclohexyl group, a phenyl group or a naphthyl group;

$R^3$ represents an imidazolyl group, a thiazolyl group or an isoxazolyl group;

$R^4$ represents a $C_1$-$C_4$ alkyl group having at least one substituent selected from the group consisting of heterocyclic groups having 5 or 6 ring atoms and groups of formula (III):

(III)

in which $R^8$ and $R^9$ are independently selected from the group consisting of hydrogen atoms and $C_1$-$C_4$ alkyl groups;

$R^5$ represents a hydrogen atom;

A represents a group of formula —$CH_2$—;

said heterocyclic groups and nitrogen-containing heterocyclic groups having from 1 to 3 ring heteroatoms selected from the group consisting of nitrogen, oxygen and sulfur hetero-atoms;

and pharmaceutically acceptable salts thereof.

Another preferred class of compounds of the present invention are those compounds of formula (I) in which:

$R^1$ represents a $C_1$-$C_6$ alkyl group having at least one substituent selected from the group consisting of pyridyl groups, non-aromatic nitrogen-containing heterocyclic groups having 5 or 6 ring atoms and groups of formula (II):

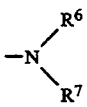
(II)

in which $R^6$ and $R^7$ are independently selected from the group consisting of hydrogen atoms, $C_1$-$C_6$ alkyl groups, phenyl groups, aralkyl groups and $C_3$-$C_8$ cycloalkyl groups:

$R^2$ represents a phenyl group or a naphthyl group;

$R^3$ represents an aromatic heterocyclic group having 5 or 6 ring atoms;

$R^4$ represents a $C_1$-$C_8$ alkyl group having at least one substituent selected from the group consisting of hydroxy groups, pyridyl groups, non-aromatic heterocyclic groups having 5 or 6 ring atoms and groups of formula (III):

(III)

in which $R^8$ and $R^9$ are independently selected from the group consisting of hydrogen atoms and $C_1$-$C_6$ alkyl groups;

R represents a hydrogen atom;

A represents a group of formula —NH—;

said heterocyclic groups and nitrogen-containing heterocyclic groups having from 1 to 3 ring heteroatoms selected from the group consisting of nitrogen, oxygen and sulfur hereto-atoms;

and pharmaceutically acceptable salts thereof.

A still further class of compounds of the present invention are those compounds of formula (I) in which:

$R^1$ represents a $C_1$-$C_6$ alkyl group, a $C_1$-$C_2$ alkyl group having an least one substituent selected from the group consisting of nitrogen-containing heterocyclic groups having 5 or 6 ring atoms and groups of formula (II):

(II)

in which $R^6$ and $R^7$ are independently selected from the group consisting of hydrogen atoms, $C_1$-$C_6$ alkyl groups, aralkyl groups and $C_3$-$C_7$ cycloalkyl groups, a nitrogen-containing heterocyclic group having 5 or 6 ring atoms or a group of formula (II), as defined above;

$R^2$ represents a phenyl group, a phenyl group having at least one substituent selected from the group consisting of substituents (a), defined above, a naphthyl group or a naphthyl group having at least one substituent selected from the group consisting of substituents (a), defined above;

$R^3$ represents an aromatic heterocyclic group having from 5 to 10 ring atoms, a phenyl group, a phenyl group having at least one substituent selected from the group consisting of substituents (a), defined above, or a $C_1$-$C_6$ alkyl group;

$R^4$ represents a $C_1$-$C_6$ alkyl group or a $C_1$-$C_6$ alkyl group having at least one substituent selected from the group consisting of hydroxy groups, pyridyl groups, imidazolyl groups, non-aromatic heterocyclic groups having 5 or 6 ring atoms and groups of formula (III):

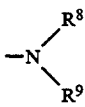
(III)

in which $R^8$ and $R^9$and are independently selected from the group consisting of hydrogen atoms and $C_1$-$C_6$ alkyl groups;

R represents a hydrogen atom;

A represents a group of formula —$(CH_2)_n$—, in which n represents an integer of from 1 to 3;

said heterocyclic groups and nitrogen-containing heterocyclic groups having from 1 to 3 ring heteroatoms selected from the group consisting of nitrogen, oxygen and sulfur hetero-atoms;

and pharmaceutically acceptable salts thereof.

A still further class of compounds of the present invention are those compounds of formula (I) in which:

$R^1$ represents a $C_1$-$C_6$ alkyl group having at least one substituent selected from the group consisting of pyridyl groups, non-aromatic nitrogen-containing heterocyclic groups having 5 or 6 ring atoms and groups of formula (II):

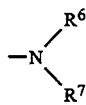
(II)

in which $R^6$ and $R^7$ are independently selected from the group consisting of hydrogen atoms, $C_1$–$C_6$ alkyl groups, phenyl groups, aralkyl groups and $C_3$–$C_7$ cycloalkyl groups, or a nitrogen-containing heterocyclic group having 5 or ring atoms;

$R^2$ represents a phenyl group, a phenyl group having at least one substituent selected from the group consisting of substituents (a), defined above, a naphthyl group or a naphthyl group having at least one substituent selected from the group consisting of substituents (a), defined above;

$R^3$ represents an aromatic heterocyclic group having 5 or 6 ring atoms, a phenyl group, a phenyl group having at least one substituent selected from the group consisting of substituents (a), defined above, or a $C_1$–$C_6$ alkyl group;

$R^4$ represents a $C_1$–$C_6$ alkyl group having at least one substituent selected from the group consisting of hydroxy groups, pyridyl groups, imidazolyl groups, non-aromatic heterocyclic groups having 5 or 6 ring atoms and groups of formula (III):

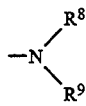
(III)

in which $R^8$ and $R^9$ are independently selected from the group consisting of hydrogen atoms and $C_1$–$C_6$ alkyl groups;

$R^5$ represents a hydrogen atom;

A represents a group of formula —NH—;

said heterocyclic groups and nitrogen-containing heterocyclic groups having from 1 to 3 ring heteroatoms selected from the group consisting of nitrogen, oxygen and sulfur hereto-atoms;

and pharmaceutically acceptable salts thereof.

A still further class of compounds of the present invention are those compounds of formula (I) in which:

$R^1$ represents a $C_1$–$C_6$ alkyl group having at least one substituent selected from the group consisting of pyridyl groups, non-aromatic nitrogen-containing heterocyclic groups having 5 or 6 ring atoms and groups of formula (II):

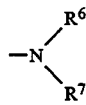
(II)

in which $R^6$ and $R^7$ are independently selected from the group consisting of hydrogen atoms, $C_1$–$C_6$ alkyl groups, phenyl groups, aralkyl groups and $C_3$–$C_7$ cycloalkyl groups, or a nitrogen-containing heterocyclic group having 5 or 6 ring atoms;

$R^2$ represents a cyclohexyl group;

$R^3$ represents an aromatic heterocyclic group having 5 or 6 ring atoms, a phenyl group, a phenyl group having at least one substituent selected from the group consisting of substituents (a), defined below, or a $C_1$–$C_6$ alkyl group;

$R^4$ represents a $C_1$–$C_6$ alkyl group or a $C_1$–$C_6$ alkyl group having at least one substituent selected from the group consisting of hydroxy groups, pyridyl groups, imidazolyl groups, non-aromatic heterocyclic groups having 5 or 6 ring atoms and groups of formula (III):

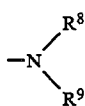
(III)

in which $R^8$ and $R^9$ are independently selected from the group consisting of hydrogen atoms and $C_1$–$C_6$ alkyl groups;

$R^5$ represents a hydrogen atom;

A represents a group of formula —NH—;

said heterocyclic groups and nitrogen-containing heterocyclic groups having from 1 to 3 ring heteroatoms selected from the group consisting of nitrogen, oxygen and sulfur hetero-atoms;

and pharmaceutically acceptable salts thereof.

A still further class of compounds of the present invention are those compounds of formula (I) in which:

$R^1$ represents a $C_1$–$C_6$ alkyl group having at least one substituent selected from the group consisting of non-aromatic nitrogen-containing heterocyclic groups having 5 or 6 ring atoms and groups of formula (II):

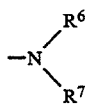
(II)

in which $R^6$ and $R^7$ are independently selected from the group consisting of hydrogen atoms, $C_1$–$C_6$ alkyl groups, phenyl groups, aralkyl groups and $C_3$–$C_7$ cycloalkyl groups, a pyridyl group or a non-aromatic nitrogen-containing heterocyclic group having from 5 to 8 ring atoms or, when A represents a group of formula —(CH$_2$)$_n$—, a group of formula (II), as defined above;

$R^2$ represents a cyclohexyl group, a phenyl group, a phenyl group having at least one substituent selected from the group consisting of substituents (a), defined above, a naphthyl group or a naphthyl group having at least one substituent selected from the group consisting of substituents (a), defined above;

$R^3$ represents an aromatic heterocyclic group having 5 or 6 ring atoms, a phenyl group, a phenyl group having at least one substituent selected from the group consisting of substituents (a), defined above, or a $C_1$–$C_6$ alkyl group;

$R^4$ represents a $C_1$–$C_8$ alkyl group;

$R^5$ represents a hydrogen atom or a $C_1$–$C_8$ alkyl group;

A represents a group of formula —NH—;

said heterocyclic groups and nitrogen-containing heterocyclic groups having from 1 to 3 ring hereto-atoms selected from the group consisting of nitrogen, oxygen and sulfur hereto-atoms;

and pharmaceutically acceptable salts thereof.

Preferred compounds of the present invention are as follows:

1. Those compounds of formula (I), defined above, in which:

$R^1$ represents a $C_3$-$C_6$ alkyl group, a $C_1$-$C_4$ alkyl group having at least one substituent selected from the group consisting of nitrogen-containing heterocyclic groups having from 5 to 8 ring atoms and groups of formula (II):

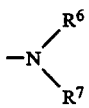

(II)

in which $R^6$ and $R^7$ are independently selected from the group consisting of hydrogen atoms, $C_1$-$C_4$ alkyl groups, phenyl groups, aralkyl groups and $C_5$-$C_7$ cycloalkyl groups, or a nitrogen-containing heterocyclic group having from 5 to 8 ring atoms or, when A represents a group of formula —(CH2)$_n$—, a group of formula (II), as defined above;

$R^2$ represents a cyclohexyl group, a phenyl group, a phenyl group having at least one substituent selected from the group consisting of substituents (a'), defined below, a naphthyl group or a naphthyl group having at least one substituent selected from the group consisting of substituents (a'), defined below;

$R^3$ represents an aromatic heterocyclic group having from 5 to 10 ring atoms, a phenyl group, a phenyl group having at least one substituent selected from the group consisting of substituents (a'), defined below, or a $C_1$-$C_4$ alkyl group;

$R^4$ represents a $C_1$-$C_8$ alkyl group or a $C_1$-$C_6$ alkyl group having at least one substituent selected from the group consisting of hydroxy groups, heterocyclic groups having 5 or 6 ring atoms and groups of formula (III):

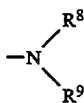

(III)

in which $R^8$ and $R^9$ are independently selected from the group consisting of hydrogen atoms and $C_1$-$C_4$ alkyl groups;

$R^5$ represents a hydrogen atom or a $C_1$-$C_6$ alkyl group;

A represents a group of formula —NH— or —(CH2)$_n$—, in which n represents an integer of from 1 to 3;

said heterocyclic groups and nitrogen-containing heterocyclic groups having from 1 to 3 ring heteroatoms selected from the group consisting of nitrogen, oxygen and sulfur hetero-atoms and being unsubstituted or having at least one substituent selected from the group consisting of substituents (a') and substituents (b);

Substituents (a')

$C_1$-$C_6$ alkyl groups, $C_1$-$C_4$ alkoxy groups, trifluoromethyl groups, halogen atoms, nitro groups, cyano groups, amino groups, $C_1$-$C_4$ alkylamino groups, dialkylamino groups in which each alkyl part is $C_1$-$C_4$, alkylcarbamoyl groups in which the alkyl part is $C_1$-$C_4$, dialkylcarbamoyl groups in which each alkyl part is $C_1$-$C_4$, alkoxycarbonyloxy groups in which the alkoxy part is $C_1$-$C_4$, heterocyclic groups, provided that any such heterocyclic substituent is not itself substituted by a heterocyclic or heterocyclic-carbonyl group, carboxy groups and esters and amides of said carboxy groups;

said aryl groups and the aryl parts of said aralkyl groups are $C_6$-$C_{10}$ carbocyclic aryl groups which are unsubstituted or have at least one substituent selected from the group consisting of substituents (a'), defined above; and the alkyl parts of said aralkyl groups have from 1 to 3 carbon atoms;

and pharmaceutically acceptable salts thereof.

2. Those compounds of formula (I), defined above, which:

$R^1$ represents a $C_3$ or $C_4$ alkyl group, a $C_1$-$C_4$ alkyl group having at least one substituent selected from the group consisting of nitrogen-containing heterocyclic groups having 5 or 6 ring atoms and groups of formula (II):

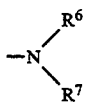

(II)

in which $R^6$ and $R^7$ are independently selected from the group consisting of hydrogen atoms, $C_1$-$C_4$ alkyl groups, phenyl groups, unsubstituted aralkyl groups and $C_5$ or $C_6$ cycloalkyl groups, or a nitrogen-containing heterocyclic group having 5 or 6 ring atoms or, when A represents a group of formula —(CH2)$_n$—, a group of formula (II), as defined above;

$R^2$ represents a cyclohexyl group, a phenyl group, or a naphthyl group;

$R^3$ represents an aromatic heterocyclic group having from 5 to 9 ring atoms, a phenyl group, a phenyl group having at least one substituent selected from the group consisting of substituents (a''), defined below, or a $C_3$ alkyl group;

$R^4$ represents a $C_1$-$C_6$ alkyl group or a $C_1$-$C_6$ alkyl group having at least one substituent selected from the group consisting of hydroxy groups, heterocyclic groups having 5 or 6 ring atoms and groups of formula (III):

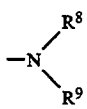

(III)

in which $R^8$ and $R^9$ are independently selected from the group consisting of hydrogen atoms, methyl groups and ethyl groups;

$R^5$ represents a hydrogen atom;

A represents a group of formula —NH— or —(CH2)$_n$—, in which n represents an integer of from 1 to 3;

said heterocyclic groups and nitrogen-containing heterocyclic groups having from 1 to 3 ring heteroatoms selected from the group consisting of nitrogen, oxygen and sulfur hereto-atoms and being unsubstituted or having at least one substituent selected from the group consisting of substituents (a″) and substituents (b);

Substituents (a″):

$C_1$–$C_4$ alkyl groups, $C_1$–$C_2$ alkoxy groups, trifluoromethyl groups, halogen atoms, nitro groups, cyano groups, amino groups, $C_1$–$C_4$ alkylamino groups, dialkylamino groups in which each alkyl part is $C_1$–$C_2$, alkylcarbamoyl groups in which the alkyl part is $C_1$–$C_4$, dialkylcarbamoyl groups in which each alkyl part is $C_1$–$C_2$, alkoxycarbonyloxy groups in which the alkoxy part is $C_1$–$C_4$, heterocyclic groups, provided that any such heterocyclic substituent is not itself substituted by a heterocyclic or heterocyclic-carbonyl group, carboxy groups and esters and amides of said carboxy groups;

the aryl parts of said aralkyl groups are phenyl groups which are unsubstituted or have at least one substituent selected from the group consisting of substituents (a″), defined above; and the alkyl parts of said aralkyl groups have from 1 to 3 carbon atoms;

and pharmaceutically acceptable salts thereof.

3. Those compounds defined in 1. and 2. above, in which n is 1.

4. Those compounds of formula (I), defined above, in which:

$R^1$ represents a branched chain $C_3$ or $C_4$ alkyl group, a $C_1$–$C_4$ alkyl group having at least one substituent selected from the group consisting of nitrogen-containing heterocyclic groups having 5 or 6 ring atoms and groups of formula (II):

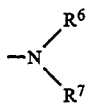

(II)

in which $R^6$ and $R^7$ are independently selected from the group consisting of hydrogen atoms, $C_1$–$C_4$ alkyl groups, phenyl groups, unsubstituted aralkyl groups and $C_5$ or $C_6$ cycloalkyl groups, or a nitrogen-containing heterocyclic group having 5 or 6 ring atoms and combined through its nitrogen atom or a group of formula (II), as defined above;

$R^2$ represents a cyclohexyl group, a phenyl group, or a naphthyl group;

$R^3$ represents an aromatic heterocyclic group having from 5 to 9 ring atoms, a phenyl group or a $C_3$ alkyl group;

$R^4$ represents a $C_1$–$C_6$ alkyl group or a $C_1$–$C_6$ alkyl group having at least one substituent selected from the group consisting of hydroxy groups, heterocyclic groups having 5 or 6 ring atoms and groups of formula (III):

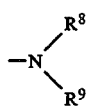

(III)

in which $R^8$ and $R^9$ are independently selected from the group consisting of hydrogen atoms, methyl groups and ethyl groups;

$R^5$ represents a hydrogen atom;

A represents a group of formula —$CH_2$—;

said heterocyclic groups, aromatic heterocyclic groups and nitrogen-containing heterocyclic groups having from 1 to 3 ring hereto-atoms selected from the group consisting of nitrogen, oxygen and sulfur hereto-atoms and being unsubstituted or having at least one substituent selected from the group consisting of substituents (a″) and substituents (b), defined above; the aryl parts of said aralkyl groups are phenyl groups which are unsubstituted or have at least one substituent selected from the group consisting of substituents (a″), defined above; and the alkyl parts of said aralkyl groups have from 1 to 3 carbon atoms; and pharmaceutically acceptable salts thereof.

5. Those compounds of formula (I), defined above, in which:

$R^1$ represents a $C_1$–$C_4$ alkyl group having at least one substituent selected from the group consisting of pyridyl groups, non-aromatic nitrogen-containing heterocyclic groups having 5 or 6 ring atoms and groups of formula (II):

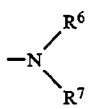

(II)

in which $R^6$ and $R^7$ are independently selected from the group consisting of $C_1$–$C_4$ alkyl groups, phenyl groups, unsubstituted aralkyl groups and $C_5$ or $C_6$ cycloalkyl groups, or a pyridyl group, a non-aromatic nitrogen-containing heterocyclic group having 5 or 6 ring atoms, or, when A represents a group of formula —$CH_2$—, a group of formula (II), as defined above;

$R^2$ represents a cyclohexyl group, a phenyl group or a naphthyl group;

$R^3$ represents an aromatic heterocyclic group having from 5 to 9 ring atoms, a phenyl group, a phenyl group having at least one substituent selected from the group consisting of substituents (a″), defined below, or a $C_3$ alkyl group;

$R^4$ represents a $C_3$ or $C_4$ alkyl group or a $C_1$–$C_6$ alkyl group having at least one substituent selected from the group consisting of heterocyclic groups having 5 or 6 ring atoms and dialkylamino groups, in which each alkyl part is $C_1$–$C_4$;

R represents a hydrogen atom;

A represents a group of formula —NH— or —$CH_2$—;

said heterocyclic groups, aromatic heterocyclic groups and nitrogen-containing heterocyclic groups having from 1 to 3 ring hereto-atoms selected from the group consisting of nitrogen, oxygen and sulfur hereto-atoms and being unsubstituted or having at least one substituent selected from the group consisting of substituents (a″) and substituents (b), defined above;

the aryl parts of said aralkyl groups are phenyl groups; and the alkyl parts of said aralkyl groups have from 1 to 3 carbon atoms;

and pharmaceutically acceptable salts thereof.

6. Those compounds of formula (I), defined above, in which:

$R^1$ represents a $C_1$–$C_4$ alkyl group having at least one substituent selected from the group consisting of non-aromatic nitrogen-containing heterocyclic groups having 5 or 6 ring atoms and groups of formula (II):

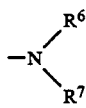

(II)

in which $R^6$ and $R^7$ are independently selected from the group consisting of $C_1$–$C_4$ alkyl groups, phenyl groups, unsubstituted aralkyl groups and cyclohexyl groups, or a non-aromatic nitrogen-containing heterocyclic group having 5 or 6 ring atoms, or, when A represents a group of formula —$CH_2$—, a group of formula (II), as defined above;

$R^2$ represents a phenyl group, or a naphthyl group;

$R^3$ represents an aromatic heterocyclic group having 5 or 6 ring atoms, an indolyl group, a phenyl group or a $C_3$ or $C_4$ alkyl group;

$R^4$ represents a $C_3$ or $C_4$ alkyl group or a $C_1$–$C_6$ alkyl group having at least one substituent selected from the group consisting of heterocyclic groups having 5 or 6 ring atoms and dialkylamino groups, in which each alkyl part is $C_1$–$C4$;

$R^5$ represents a hydrogen atom;

A represents a group of formula —NH— or —$CH_2$—;

said heterocyclic groups, aromatic heterocyclic groups and nitrogen-containing heterocyclic groups having from 1 to 3 ring hetero-atoms selected from the group consisting of nitrogen, oxygen and sulfur hetero-atoms and being unsubstituted or having at least one substituent selected from the group consisting of substituents (a'') and substituents (b), defined above;

the aryl parts of said aralkyl groups are phenyl groups; and the alkyl parts of said aralkyl groups have 1 or 2 carbon atoms;

and pharmaceutically acceptable salts thereof.

Still more preferred compounds of the invention are those compounds of formula (I) in which:

7. $R^1$ represents a t-butyl group, a $C_1$–$C_3$ alkyl group having a single substituent selected from the group consisting of:

groups of formula (II), defined above in which $R^6$ represents a $C_1$–$C_4$ alkyl group and $R^7$ represents a $C_1$–$C_4$ alkyl group, a benzyl group or a cyclohexyl group, and heterocyclic groups having 5 or 6 ring atoms, of which at least one is a nitrogen atom and from 0 to 2 are hetero-atoms selected from the group consisting of nitrogen, oxygen and sulfur hereto-atoms, a group of formula (II), defined above in which $R^6$ represents a $C_1$–$C_4$ alkyl group and $R^7$ represents a $C_1$–$C_4$ alkyl group, a benzyl group or a cyclohexyl group, or a heterocyclic group having 5 or 6 ring atoms, of which at least one is a nitrogen atom and from 0 to 2 are hereto-atoms selected from the group consisting of nitrogen, oxygen and sulfur hereto-atoms.

8. $R^1$ represents a $C_1$–$C_3$ alkyl group having a single substituent selected from the group consisting of:

morpholino, thiomorpholino, piperidyl and pyrrolidinyl groups; piperazinyl groups which themselves have a single substituent selected from the group consisting of $C_1$–$C_3$ alkyl groups, $C_2$–$C_4$ alkoxycarbonyl groups, benzyl groups, phenyl groups, benzhydryl groups, pyridyl groups and phenyl and benzhydryl groups having a substituent selected from the group consisting of halogen atoms, is $C_1$–$C_4$ benzylamino groups; and $C_1$–$C_3$ alkoxy groups and trifluoromethyl groups; dialkylamino groups in which each alkyl part is $C_1$–$C_4$; benzylamino groups; and N-alkyl-N-benzylamino, N-alkyl-N-phenethylamino and N-alkyl-N-cyclohexylamino groups in which the alkyl part is $C_1$–$C_4$;

a morpholino group; a thiomorpholino group; a piperidyl group; a pyrrolidinyl group; a piperazinyl group which has a single substituent selected from the group consisting of $C_1$–$C_3$ alkyl groups, $C_2$–$C_4$ alkoxycarbonyl groups, phenyl groups, pyridyl groups and phenyl groups having a substituent selected from the groups consisting of halogen atoms, $C_1$–$C_3$ alkoxy groups and trifluoromethyl groups; a dialkylamino group in which each alkyl part is $C_1$–$C_4$; or an N-alkyl-N-benzylamino, N-alkyl-N-phenethylamino or N-alkyl-N-cyclohexylamino group in which the alkyl part is $C_1$–$C_4$.

9. $R^1$ represents a $C_1$–$C_3$ alkyl group having a single substituent selected from the group consisting of:

morpholino, thiomorpholino, piperidyl and pyrrolidinyl groups; piperazinyl groups which themselves have a single substituent selected from the group consisting of $C_1$–$C_3$ alkyl groups, $C_2$–$C_4$ alkoxycarbonyl groups, benzyl groups, phenyl groups, benzhydryl groups, phenyl and benzhydryl groups having a substituent selected from the group consisting of halogen atoms, $C_1$–$C_3$ alkoxy groups and trifluoromethyl groups and pyridyl groups; benzylamino groups; dialkylamino groups in which each alkyl part is $C_1$–$C_4$; and N-alkyl-N-benzylamino, N-alkyl-N-phenethylamino and N-alkyl-N-cyclohexylamino groups in which the alkyl part is $C_1$–$C_4$;

a morpholino group; a piperazinyl group which has a single substituent selected from the group consisting of $C_1$–$C_3$ alkyl groups, ethoxycarbonyl groups, phenyl groups and phenyl groups having a substituent selected from the group consisting of halogen atoms, $C_1$–$C_3$ alkoxy groups and trifluoromethyl groups; or an N-alkyl-N-benzylamino or N-alkyl-N-cyclohexylamino group in which the alkyl part is $C_1$–$C_4$.

1-. $R^1$ represents a 4-phenyl-1-piperazinyl, N-methyl-N-benzylamino, morpholino, N-methyl-N-cyclohexylaminothyl, N-methyl-N-benzylaminomethyl, N-isopropyl-N-benzylaminomethyl, benzylaminomethyl, 4-phenyl-1-piperazinylmethyl, diethylaminomethyl, N-methyl-N-butylaminomethyl, N-methyl-N-phenylaminomethyl, morpholinomethyl, 3-morpholinopropyl, 4-(4-fluorophenyl)-1-piperazinylmethyl, 4-(4-chlorophenyl)-1-piperazinylmethyl, 4-( 4-methoxyphenyl)-1-piperazinylmethyl, N-methyl-N-phenethylaminomethyl, diisobutylaminomethyl or 4-(4-chlorobenzhydryl)-1-piperazinylmethyl group.

11. $R^2$ represents a phenyl or naphthyl group, especially a naphthyl group.

12. $R^3$ represents a thienyl, isoxazolyl, thiazolyl, imidazolyl, pyridyl, indolyl, phenyl or isopropyl group.

13. $R^3$ represents a thienyl, isoxazolyl, thiazolyl, imidazolyl or isopropyl group.

14. $R^4$ represents a $C_3$–$C_6$ alkyl group or a $C_1$–$C_4$ alkyl group having a single substituent selected from the group consisting of heterocyclic groups having 5 or 6 ring atoms.

15. $R^4$ represents a propyl, butyl, isobutyl, sec-butyl, pentyl, isopentyl, 2-methylbutyl, hexyl, isohexyl or 2-methylpentyl group, a $C_1$-$C_3$ alkyl group having a morpholino or 2-oxopyrrolidinyl substituent or a 1-morpholinomethyl-2-methylbutyl group.

16. $R^4$ represents a 2-morpholinoethyl, propyl, butyl, isobutyl, pentyl, isopentyl, 2-methylbutyl, hexyl, 3-(2-oxo-1-pyrrolidinyl)propyl or a 1-morpholinomethyl-2-methylbutyl group.

17. A represents a group of formula —NH— or —$(CH_2)_n$—, in which n represents 1 or 2.

In general, where reference is made herein to "substituted" groups, there is no specific maximum limit to the number of possible substituents, although, in specific cases, steric constraints may impose a practical maximum limit. In principle, the maximum number of substituents is determined by the number of substitutable atoms and, where the substituent is relatively small, complete substitution may be possible. For example, where the substituent is relatively small such as a halogen (e.g. fluorine or chlorine) atom, the substituted group may range from the monohalo to perhalo groups, e.g. from monohaloalkyl to perhaloalkyl. Where the substituent is "bulkier", e.g. a t-butyl group, steric effects may prevent substitution of all substitutable positions. However, these effects are well-known to those skilled in the art and require no further discussion here.

The compounds of the invention contain at least three asymmetric carbon atoms, that is to say the carbon atom to which the group represented by $R^2CH_2$ is attached, that to which the group represented by $R^3CH_2$ is attached and that to which the cyclohexylmethyl group is attached, and can, depending upon the values of the various substituent groups defined above, also contain other asymmetric carbon atoms. Accordingly, a variety of optical isomers are possible. The present invention envisages both the individual isolated isomers as well as mixtures (e.g. racemates) thereof. However, we particularly prefer those isomers in which: the carbon atom to which the group represented by $R^2CH_2$ is attached is in the S-configuration; the carbon atom to which the group represented by $R^3CH_2$ is attached is in the S-configuration; the carbon atom to which the cyclohexylmethyl group is attached is in the S-configuration. More preferred are those compounds in which the carbon atom to which the cyclohexylmethyl group is attached is in the S-configuration and the carbon atom to which the group represented by $R^3CH_2$ is attached is in the S-configuration, and still more preferred are those compounds in which all three of the carbon atoms referred to above are in the S-configuration. Where optically active starting materials are employed to produce the compounds of the invention and/or stereo-specific routes are employed, it may be possible to produce individual isomers of the compounds of the invention. In other cases, mixtures of various isomers may be produced and, in such a case, these mixtures may be used as such or the individual isomers may be isolated by well-known techniques.

The compounds of the invention contain basic nitrogen atoms and, depending upon the value of certain of the substituents, may also contain free carboxy groups. Accordingly, the compounds of the invention will normally form acid addition salts and may, where they contain at least one carboxy group, also form salts with cations. The nature of the acid or cation employed to form such a salt is not critical to the invention, except where the compounds of the invention are intended for therapeutic use, in which case the resulting salt must be pharmaceutically acceptable which, as is well-known to those skilled in the art, means that salt must not have an increased toxicity or substantially increased toxicity or a reduced activity or substantially reduced activity, as compared with the free compound of formula (I). However, where the compounds of the invention are intended for non-therapeutic use, e.g. as intermediates, even this limitation need not apply.

Examples of acids which can be employed to form acid addition salts include: mineral acids, such as hydrochloric acid, sulfuric acid and phosphoric acid; organic carboxylic acids, such as oxalic acid, maleic acid, succinic acid and citric acid; and organic sulfonic acids, such as methanesulfonic acid, benzenesulfonic acid and p-toluenesulfonic acid. The compounds may also form salts with: alkali and alkaline earth metals, such as sodium, potassium, calcium and magnesium; and organic bases, such as dicyclohexylamine.

Where the compounds contain a carboxy group and can form esters, the nature of the ester group is not critical, and it can be chosen having regard to the normal criteria applied to the choice of esters for pharmaceutically active compounds. By way of example only, suitable esters include: lower alkyl esters, such as the $C_2$-$C_5$ alkyl esters, e.g. the methyl esters, ethyl esters, propyl esters, isopropyl esters, butyl esters, isobutyl esters, sec-butyl esters or t-butyl esters; aralkyl esters, in which the aryl part is as defined above, but is preferably phenyl (which may be substituted or unsubstituted) and the alkyl part is $C_1$-$C_4$ alkyl (preferably methyl, ethyl or propyl), for example, the benzyl esters, p-methylbenzyl esters, p-chlorobenzyl esters and p-methoxybenzyl esters; and phenacyl esters.

Where the compounds contain a carboxy group, they may also form amides, and preferred amides are those compounds in which the carboxy group has been replaced by one of the carbamoyl groups illustrated above in relation to substituent (a).

Examples of specific compounds of the invention are given in the following formulae (I-1) to (I-8), in which the substituents are as defined in the corresponding one of Tables 1 to 6 [i.e. Table 1 relates to formula (I-1), Table 2 relates to formula (I-2) and so on]. The compounds of the invention are hereinafter, where appropriate, identified by the numbers appended to them in these Tables. In the Tables, the following abbreviations are used:

| | |
|---|---|
| Boc | t-butoxycarbonyl |
| Bu | butyl |
| iBu | isobutyl |
| sBu | sec-butyl |
| tBu | t-butyl |
| Bz | benzyl |
| Bzhy | benzhydryl |
| Car | carbamoyl |
| Et | ethyl |

| | |
|---|---|
| Etc | ethoxycarbonyl |
| Hp | heptyl |
| iHp | isoheptyl |
| Hx | hexyl |
| cHx | cyclohexyl |
| iHx | isohexyl |
| Imid | imidazolyl |
| Ind | indolyl |
| Isox | isoxazolyl |
| Me | methyl |
| Mor | morpholino |
| Np | naphthyl |
| Oc | octyl |
| Ph | phenyl |
| Pip | piperidyl |
| Piz | piperazinyl |
| Pn | pentyl |
| iPn | isopentyl |
| Pr | propyl |
| iPr | isopropyl |
| Pym | pyrimidinyl |
| Pyr | pyridyl |
| Pyrd | pyrrolidinyl |
| TFM | trifluoromethyl |
| Thi | thienyl |
| Thiz | thiazolyl |
| Thz | perhydro-1,4-thiazin-4-yl (= thiomorpholino) |

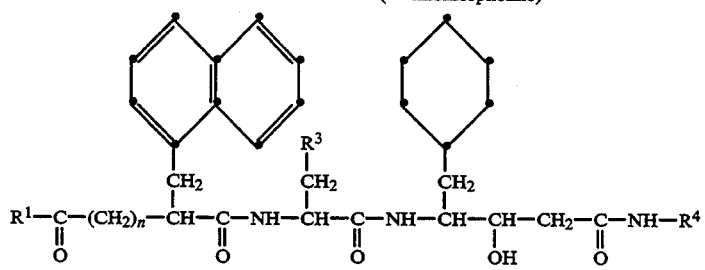
(I-1)

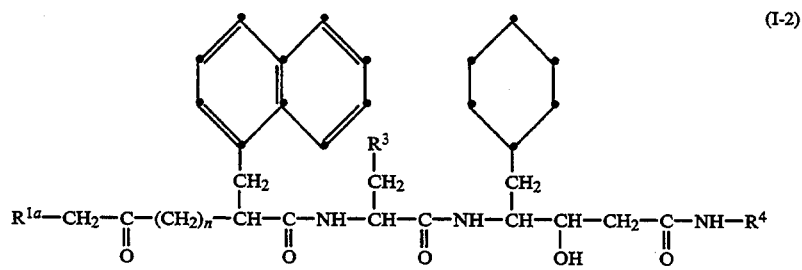
(I-2)

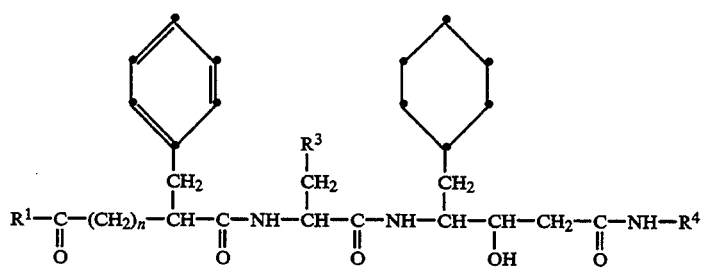
(I-3)

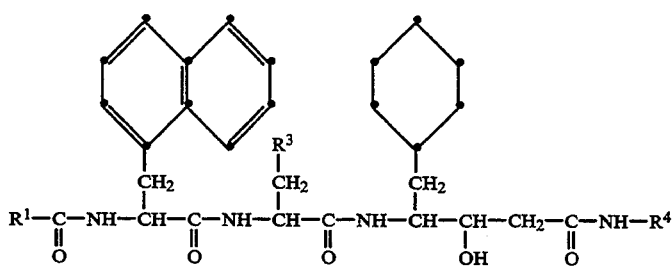
(I-4)

-continued

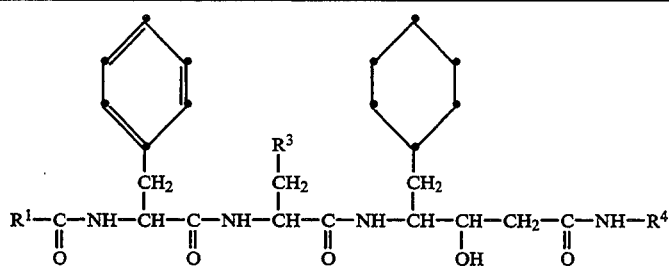

(I-5)

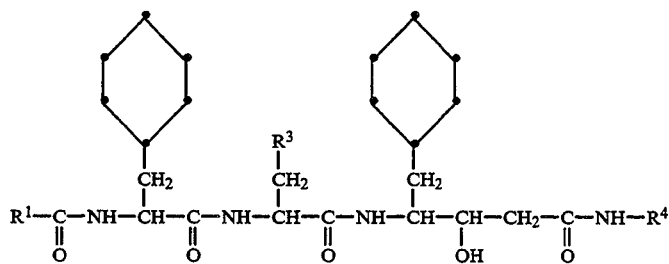

(I-6)

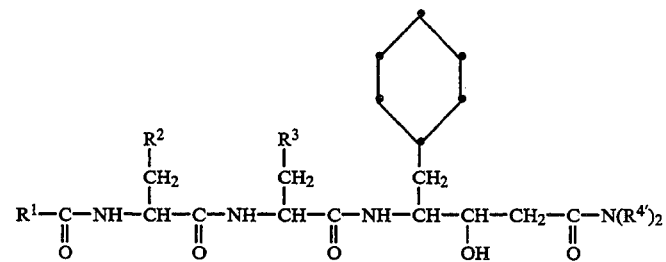

(I-7)

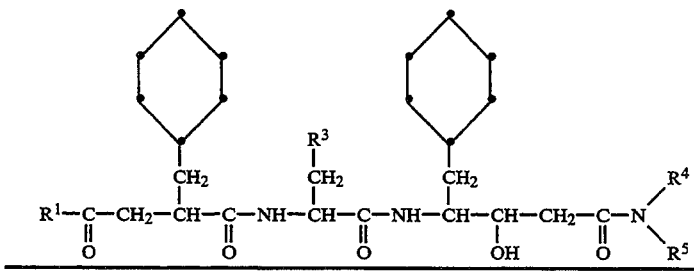

(I-8)

TABLE 1

| Cpd No. | R¹ | R³ | R⁴ | n |
|---|---|---|---|---|
| 1-1 | H₂N— | 5-Imid | 2-MorEt | 1 |
| 1-2 | H₂N— | 4-Thiz | 2-MorEt | 1 |
| 1-3 | MeHN— | 4-Thiz | 2-MorEt | 1 |
| 1-4 | EtHN— | 4-Thiz | 2-MorEt | 1 |
| 1-5 | PrHN— | 4-Thiz | 2-MorEt | 1 |
| 1-6 | PrHN— | 4-Thiz | 2-(1-Me-2-Pyrd)Et | 1 |
| 1-7 | PrHN— | 4-Thiz | 2-(1-Pyrd)Et | 1 |
| 1-8 | PrHN— | 4-Thiz | 2-(4-Me-1-Piz)Et | 1 |
| 1-9 | PrHN— | 5-Imid | 2-(4-Me-1-Piz)Et | 1 |
| 1-10 | PrHN— | 5-Isox | 2-MorEt | 1 |
| 1-11 | PrHN— | 5-Isox | 2-(4-Me-1-Piz)Et | 1 |
| 1-12 | PrHN— | 5-Imid | 2-(4-Me-1-Piz)Et | 1 |
| 1-13 | PrHN— | 5-Imid | 2-MorEt | 1 |
| 1-14 | Me₂HN— | 4-Thiz | 2-MorEt | 1 |
| 1-15 | Et₂HN— | 4-Thiz | 2-MorEt | 1 |
| 1-16 | Et₂HN— | 4-Thiz | 2-(1-Pip)Et | 1 |
| 1-17 | Et₂HN— | 4-Thiz | 2-(4-Me-1-Piz)Et | 1 |
| 1-18 | Pr₂HN— | 4-Thiz | 2-(1-Pyrd)Et | 1 |
| 1-19 | 1-Pyrd | 4-Thiz | 2-(1-Pyrd)Et | 1 |
| 1-20 | 1-Pyrd | 4-Thiz | 3-MorPr | 1 |
| 1-21 | 1-Pyrd | 4-Thiz | 2-(1-Pyrd)Et | 1 |
| 1-22 | 1-Pyrd | 4-Thiz | 2-(1-Pip)Et | 1 |
| 1-23 | 1-Pyrd | 4-Thiz | 2-(4-Me-1-Piz)Et | 1 |

TABLE 1-continued

| Cpd No. | R¹ | R³ | R⁴ | n |
|---|---|---|---|---|
| 1-24 | 1-Pyrd | 4-Isox | 2-MorEt | 1 |
| 1-25 | 1-Pyrd | 5-Imid | 2-MorEt | 1 |
| 1-26 | 1-Pyrd | 5-Imid | 2-(4-Me-1-Piz)Et | 1 |
| 1-27 | 1-Pip | 5-Imid | 2-MorEt | 1 |
| 1-28 | 1-Pip | 5-Imid | 3-MorPr | 1 |
| 1-29 | 1-Pip | 5-Imid | 2-(1-Pip)Et | 1 |
| 1-30 | 1-Pip | 5-Imid | 2-(4-Me-1-Piz)Et | 1 |
| 1-31 | 1-Pip | 5-Isox | 2-(4-Me-1-Piz)Et | 1 |
| 1-32 | 1-Pip | 5-Isox | 2-(1-Et-2-Pyrd)Et | 1 |
| 1-33 | 1-Pip | 4-Thiz | 2-(1-Et-2-Pyrd)Et | 1 |
| 1-34 | 1-Pip | 4-Thiz | 2-MorEt | 1 |
| 1-35 | 1-Pip | 4-Thiz | 2-(4-Me-1-Piz)Et | 1 |
| 1-36 | Mor | 4-Thiz | 2-(Et₂N)Et | 1 |
| 1-37 | Mor | 4-Thiz | 3-(Et₂N)Pr | 1 |
| 1-38 | Mor | 4-Thiz | 2-(1-Pyrd)Et | 1 |
| 1-39 | Mor | 4-Thiz | 2-(1-Pip)Et | 1 |
| 1-40 | Mor | 4-Thiz | 2-MorEt | 1 |
| 1-41 | Mor | 4-Thiz | 2-ThzEt | 1 |
| 1-42 | Mor | 4-Thiz | 2-(1-Me-2-Pyrd)Et | 1 |
| 1-43 | Mor | 4-Thiz | 2-(1-Et-2-Pyrd)Et | 1 |
| 1-44 | Mor | 4-Thiz | 2-(4-Me-1-Piz)Et | 1 |
| 1-45 | Mor | 4-Thiz | 2-(4-Etc-1-Piz)Et | 1 |
| 1-46 | Mor | 4-Thiz | 2-[4-(2-Pyr)- | 1 |

TABLE 1-continued

| Cpd No. | R¹ | R³ | R⁴ | n |
|---|---|---|---|---|
| 1-47 | Mor | 4-Thiz | 2-(4-Ph-1-Piz]Et | 1 |
| 1-48 | Mor | 4-Thiz | 2-(1-Piz)Et | 1 |
| 1-49 | Mor | 4-Thiz | 4-PipMe | 1 |
| 1-50 | Mor | 4-Thiz | 3-MorPr | 1 |
| 1-51 | Mor | 4-Thiz | 3-(2-Me-1-Pip)Pr | 1 |
| 1-52 | Mor | 4-Thiz | 2-(4-Bz-1-Piz)Et | 1 |
| 1-53 | Mor | 4-Isox | 3-(Me₂N)Pr | 1 |
| 1-54 | Mor | 4-Isox | 2-(1-Me-2-Pyrd)Et | 1 |
| 1-55 | Mor | 4-Isox | 2-(4-Me-1-Piz)Et | 1 |
| 1-56 | Mor | 4-Isox | 3-MorPr | 1 |
| 1-57 | Mor | 4-Isox | 2-(4-Etc-1-Piz)Et | 1 |
| 1-58 | Mor | 4-Isox | 2-(1-Et-2-Pyrd)Et | 1 |
| 1-59 | Mor | 4-Isox | 2-(1-Pip)Et | 1 |
| 1-60 | Mor | 4-Isox | 2-MorEt | 1 |
| 1-61 | Mor | 4-Isox | 3-(Et₂N)Pr | 1 |
| 1-62 | Mor | 5-Imid | 3-(Me₂N)Pr | 1 |
| 1-63 | Mor | 5-Imid | 3-(Et₂N)Et | 1 |
| 1-64 | Mor | 5-Imid | 2-(1-Pyrd)Et | 1 |
| 1-65 | Mor | 5-Imid | 2-(1-Me-2-Pyrd)Et | 1 |
| 1-66 | Mor | 5-Imid | 2-MorEt | 1 |
| 1-67 | Mor | 5-Imid | 3-MorPr | 1 |
| 1-68 | Mor | 5-Imid | 2-(4-Me-1-Piz)Et | 1 |
| 1-69 | 4-Me-1-Piz | 5-Imid | 2-(4-Me-1-Piz)Et | 1 |
| 1-70 | 4-Me-1-Piz | 5-Imid | 2-MorEt | 1 |
| 1-71 | 4-Me-1-Piz | 5-Imid | 2-(1-Pyrd)Et | 1 |
| 1-72 | 4-Me-1-Piz | 5-Imid | 2-(1-Pip)Et | 1 |
| 1-73 | 4-Me-1-Piz | 5-Imid | 2-(1-Me-2-Pyrd)Et | 1 |
| 1-74 | 4-Me-1-Piz | 5-Imid | 3-(Et₂N)Pr | 1 |
| 1-75 | 4-Me-1-Piz | 5-Isox | 3-(Et₂N)Pr | 1 |
| 1-76 | 4-Me-1-Piz | 5-Isox | 2-(4-Me-1-Piz)Et | 1 |
| 1-77 | 4-Me-1-Piz | 5-Isox | 2-MorEt | 1 |
| 1-78 | 4-Me-1-Piz | 4-Thiz | 2-MorEt | 1 |
| 1-79 | 4-Me-1-Piz | 4-Thiz | 2-(4-Me-1-Piz)Et | 1 |
| 1-80 | 4-Me-1-Piz | 4-Thiz | 2-(1-Pyrd)Et | 1 |
| 1-81 | 4-Me-1-Piz | 4-Thiz | 2-(1-Pip)Et | 1 |
| 1-82 | 4-Etc-1-Piz | 4-Thiz | 2-MorEt | 1 |
| 1-83 | 4-Etc-1-Piz | 5-Isox | 2-MorEt | 1 |
| 1-84 | 4-Etc-1-Piz | 5-Imid | 2-MorEt | 1 |
| 1-85 | 4-Ph-1-Piz | 5-Imid | 2-MorEt | 1 |
| 1-86 | 4-Ph-1-Piz | 4-Thiz | 2-MorEt | 1 |
| 1-87 | 4-Ph-1-Piz | 4-Thiz | 2-(4-Me-1-Piz)Et | 1 |
| 1-88 | 4-Ph-1-Piz | 5-Isox | 2-MorEt | 1 |
| 1-89 | 4-Ph-1-Piz | 5-Isox | (1-Et-2-Pyrd)Me | 1 |
| 1-90 | 4-Bz-1-Piz | 5-Isox | (1-Et-2-Pyrd)Me | 1 |
| 1-91 | 4-Bz-1-Piz | 5-Isox | 2-MorEt | 1 |
| 1-92 | 1-Pyrd | 4-Thiz | 2-MorEt | 1 |
| 1-93 | Thz | 4-Thiz | 2-MorEt | 1 |
| 1-94 | 2,6-diMeMor | 4-Thiz | 2-MorEt | 1 |
| 1-95 | 4-(2-MeOPh)-1-Piz | 4-Thiz | 2-MorEt | 1 |
| 1-96 | 4-(2-ClPh)-1-Piz | 4-Thiz | 2-MorEt | 1 |
| 1-97 | 4-(4-FPh)-1-Piz | 4-Thiz | 2-MorEt | 1 |
| 1-98 | Mor | 4-Thiz | 2-PyrMe | 1 |
| 1-99 | Mor | 4-Thiz | (1-Et-2-Pyrd)Me | 1 |
| 1-100 | cHx(Me)N— | 4-Thiz | 2-MorEt | 1 |
| 1-101 | Bz(Me)N— | 4-Thiz | 2-MorEt | 1 |
| 1-102 | Mor | 4-Thiz | 3-(2-oxo-1-Pyrd)Pr | 1 |
| 1-103 | cHx(Me)N— | 4-Thiz | 3-(2-oxo-1-Pyrd)Pr | 1 |
| 1-104 | BzNH— | 4-Thiz | 2-MorEt | 1 |
| 1-105 | (2-PhEt)NH— | 4-Thiz | 2-MorEt | 1 |
| 1-106 | tBu | 4-Thiz | 2-MorEt | 1 |
| 1-107 | cHx(Me)N— | 5-Isox | 2-MorEt | 1 |
| 1-108 | Bz(Me)N— | 5-Isox | 2-MorEt | 1 |
| 1-109 | Bz(Me)N— | 5-Isox | 3-(2-oxo-1-Pyrd)Pr | 1 |
| 1-110 | Mor | 2-Thi | 3-(2-oxo-1-Pyrd)Pr | 1 |
| 1-111 | Mor | 2-Thi | 2-MorEt | 1 |
| 1-112 | Mor | Ph | 2-MorEt | 1 |
| 1-113 | Bz(Me)N— | Ph | 2-MorEt | 1 |
| 1-114 | cHx(Me)N— | Ph | 2-MorEt | 1 |
| 1-115 | Mor | iPr | 2-MorEt | 1 |
| 1-116 | cHx(Me)N— | iPr | 2-MorEt | 1 |
| 1-117 | Bz(Me)N— | iPr | 2-MorEt | 1 |
| 1-118 | Mor | 3-Ind | 2-MorEt | 1 |
| 1-119 | Mor | 4-Thiz | 2-(1-Imid)Et | 1 |
| 1-120 | Mor | 4-Thiz | 2-MorPr | 1 |
| 1-121 | 2,6-diMeMor | 4-Thiz | 2-MorEt | 1 |
| 1-122 | 4-(2-Pyr)-1-Piz | 4-Thiz | 2-MorEt | 1 |
| 1-123 | 4-(2-Pym)-1-Piz | 4-Thiz | 2-MorEt | 1 |
| 1-124 | Et₂N— | iPr | 2-MorEt | 1 |
| 1-125 | Me(Bu)N— | iPr | 2-MorEt | 1 |
| 1-126 | Mor | iPr | 2-MeBu | 1 |
| 1-127 | Mor | 4-Thiz | 2-(1-Imid)Et | 1 |
| 1-128 | tBu | 4-Thiz | 2-MorEt | 1 |
| 1-129 | tBu | 5-Isox | 2-MorEt | 1 |
| 1-130 | tBu | 4-Thiz | 2-MeBu | 1 |
| 1-131 | Mor | 4-Thiz | 2-MeBu | 1 |
| 1-132 | Mor | 4-Thiz | iPn | 1 |
| 1-133 | Mor | 4-Thiz | 1-HOMe-2-MeBu | 1 |
| 1-134 | cHx(Me)N— | 4-Thiz | 2-MeBu | 1 |
| 1-135 | Bz(Me)N— | 4-Thiz | 2-MeBu | 1 |
| 1-136 | 4-Ph-1-Piz | 4-Thiz | 2-MeBu | 1 |
| 1-137 | tBu | 5-Isox | 2-MeBu | 1 |
| 1-138 | Mor | 5-Isox | 2-MeBu | 1 |
| 1-139 | cHx(Me)N— | 5-Isox | 2-MeBu | 1 |
| 1-140 | Bz(Me)N— | 5-Isox | 2-MeBu | 1 |
| 1-141 | Mor | Ph | 2-MorEt | 2 |
| 1-142 | Mor | 4-Thiz | 2-MorEt | 2 |
| 1-143 | Mor | 4-Thiz | 3-(2-oxo-1-Pyrd)Pr | 2 |
| 1-144 | cHx(Me)N— | 4-Thiz | 3-(2-oxo-1-Pyrd)Pr | 2 |
| 1-145 | cHx(Me)N— | 4-Thiz | 2-MorEt | 2 |
| 1-146 | Bz(Me)N— | 4-Thiz | 2-MorEt | 2 |
| 1-147 | Mor | 4-Thiz | 2-MorEt | 3 |
| 1-148 | cHx(Me)N— | 4-Thiz | 2-MeBu | 3 |

TABLE 2

| Cpd No. | R¹ᵃ | R³ | R⁴ | n |
|---|---|---|---|---|
| 2-1 | Mor | 4-Thiz | 2-MorEt | 1 |
| 2-2 | cHx(Me)N— | 4-Thiz | 2-MorEt | 1 |
| 2-3 | Bz(Me)N— | 4-Thiz | 2-MorEt | 1 |
| 2-4 | 4-Ph-1-Piz | 4-Thiz | 2-MorEt | 1 |
| 2-5 | Mor | 4-Thiz | 3-(2-oxo-1-Pyrd)Pr | 1 |
| 2-6 | Mor | 5-Isox | 3-(2-oxo-1-Pyrd)Pr | 1 |
| 2-7 | Mor | 5-Isox | 2-MorEt | 1 |
| 2-8 | Bz(Me)N— | iPr | 2-MorEt | 1 |
| 2-9 | Mor | 4-Thiz | 2-MeBu | 1 |
| 2-10 | cHx(Me)N— | 4-Thiz | 2-MeBu | 1 |
| 2-11 | Bz(Me)N— | 4-Thiz | 2-MeBu | 1 |

TABLE 3

| Cpd No. | R¹ | R³ | R⁴ | n |
|---|---|---|---|---|
| 3-1 | Mor | 4-Thiz | 2-(4-Me-1-Piz)Et | 1 |
| 3-2 | Mor | 4-Thiz | 2-MorEt | 1 |
| 3-3 | Mor | 5-Imid | 2-MorEt | 1 |
| 3-4 | 1-Pip | 5-Imid | 2-MorEt | 1 |
| 3-5 | 1-Pip | 4-Thiz | 2-MorEt | 1 |
| 3-6 | 2,6-diMeMor | 4-Thiz | 2-MorEt | 1 |
| 3-7 | 2,6-diMeMor | 4-Thiz | 2-(1-Et-2-Pyrd)Et | 1 |
| 3-8 | 4-Me-1-Piz | 5-Imid | 2-MorEt | 1 |
| 3-9 | 4-Me-1-Piz | 4-Thiz | 2-MorEt | 1 |
| 3-10 | 4-Me-1-Piz | 5-Isox | 2-MorEt | 1 |
| 3-11 | 4-Etc-1-Piz | 5-Isox | 2-MorEt | 1 |
| 3-12 | 4-Etc-1-Piz | 4-Thiz | 2-MorEt | 1 |
| 3-13 | 4-Ph-1-Piz | 4-Thiz | 2-MorEt | 1 |
| 3-14 | 4-(2-ClPh)-1-Piz | 4-Thiz | 2-MorEt | 1 |
| 3-15 | 4-(2-MePh)-1-Piz | 4-Thiz | 2-MorEt | 1 |
| 3-16 | Bz(Me)N— | 4-Thiz | 2-MorEt | 1 |
| 3-17 | Mor | 5-Isox | 2-MorEt | 1 |
| 3-18 | Mor | 5-Isox | 3-(2-oxo-1-Pyrd)Pr | 1 |
| 3-19 | Bz(Me)N— | 5-Isox | 2-MorEt | 1 |
| 3-20 | 4-Ph-1-Piz | 5-Isox | 2-MorEt | 1 |
| 3-21 | cHx(Me)N— | 5-Isox | 2-MorEt | 1 |
| 3-22 | Mor | iPr | 3-(2-oxo-1-Pyrd)Pr | 1 |
| 3-23 | Mor | iPr | 2-MeBu | 1 |

TABLE 3-continued

| Cpd No. | R¹ | R³ | R⁴ | n |
|---|---|---|---|---|
| 3-24 | cHx(Me)N— | iPr | 2-MeBu | 1 |
| 3-25 | Bz(Me)N— | iPr | 2-MeBu | 1 |
| 3-26 | tBu | iPr | 2-MeBu | 1 |
| 3-27 | tBu | 5-Isox | 2-MeBu | 1 |
| 3-28 | Mor | 5-Isox | 2-MeBu | 1 |
| 3-29 | cHx(Me)N— | 5-Isox | 2-MeBu | 1 |
| 3-30 | Bz(Me)N— | 5-Isox | 2-MeBu | 1 |
| 3-31 | cHx₂N— | 4-Thiz | 2-MorEt | 1 |
| 3-32 | 1-Pyrd | 4-Thiz | 2-MorEt | 1 |
| 3-33 | 1-Pyrd | 4-Thiz | 2-(1-Et-2-Pyrd)Et | 1 |

TABLE 4

| Cpd. No. | R¹ | R³ | R⁴ |
|---|---|---|---|
| 4-1 | H₂NMe | 4-Thiz | 2-MorEt |
| 4-2 | 2-H₂NEt | 4-Thiz | 2-MorEt |
| 4-3 | (MeHN)Me | 4-Thiz | 2-MorEt |
| 4-4 | (EtHN)Me | 4-Thiz | 2-MorEt |
| 4-5 | (PrHN)Me | 4-Thiz | 2-MorEt |
| 4-6 | (PrHN)Me | 4-Thiz | 2-(1-Me-2-Pyrd)Et |
| 4-7 | (PrHN)Me | 4-Thiz | 2-(1-Pyrd)Et |
| 4-8 | (PrHN)Me | 4-Thiz | 2-(4-Me-1-Piz)Et |
| 4-9 | (PrHN)Me | 5-Isox | 2-(4-Me-1-Piz)Et |
| 4-10 | (PrHN)Me | 5-Isox | 2-MorEt |
| 4-11 | (PrHN)Me | 5-Isox | 2-(4-Me-1-Piz)Et |
| 4-12 | (PrHN)Me | 5-Imid | 2-(4-Me-1-Piz)Et |
| 4-13 | (PrHN)Me | 5-Imid | 2-MorEt |
| 4-14 | (Me₂N)Me | 4-Thiz | 2-MorEt |
| 4-15 | (Et₂N)Me | 4-Thiz | 2-MorEt |
| 4-16 | [Bu(Me)N]Me | 4-Thiz | 2-MorEt |
| 4-17 | [Bu(Me)N]Me | 4-Thiz | 2-ThzEt |
| 4-18 | [Bu(Me)N]Me | 4-Thiz | 2-(1-Pip)Et |
| 4-19 | [Bu(Me)N]Me | 4-Thiz | 2-(4-Me-1-Piz)Et |
| 4-20 | [Bu(Me)N]Me | 5-Isox | 2-MorEt |
| 4-21 | [Bu(Me)N]Me | 5-Isox | 2-ThzEt |
| 4-22 | (Pr₂N)Me | 5-Isox | 2-MorEt |
| 4-23 | (Pr₂N)Me | 4-Thiz | 2-MorEt |
| 4-24 | (iPr₂N)Me | 4-Thiz | 2-MorEt |
| 4-25 | (Bu₂N)Me | 4-Thiz | 2-MorEt |
| 4-26 | (Bu₂N)Me | 5-Isox | 2-MorEt |
| 4-27 | [Me(cHx)N]Me | 4-Thiz | 2-MorEt |
| 4-28 | [Me(Ph)N]Me | 4-Thiz | 2-MorEt |
| 4-29 | [Et(4-MePh)N]Me | 4-Thiz | 2-MorEt |
| 4-30 | [Me(Bz)N]Me | 4-Thiz | 2-MorEt |
| 4-31 | [Et(Bz)N]Me | 4-Thiz | 2-MorEt |
| 4-32 | [Me(2-PhEt)N]Me | 4-Thiz | 2-MorEt |
| 4-33 | (1-Pyrd)Me | 4-Thiz | 2-(1-Pip)Et |
| 4-34 | (1-Pyrd)Me | 4-Thiz | 2-(4-Me-1-Piz)Et |
| 4-35 | (1-Pyrd)Me | 4-Thiz | 2-MorEt |
| 4-36 | (1-Pyrd)Me | 5-Isox | 2-MorEt |
| 4-37 | (1-Pyrd)Me | 5-Isox | 2-(1-Pyrd)Et |
| 4-38 | (1-Pyrd)Me | 5-Imid | 2-MorEt |
| 4-39 | (1-Pip)Me | 4-Thiz | 2-MorEt |
| 4-40 | (1-Pip)Me | 4-Thiz | 3-MorPr |
| 4-41 | (1-Pip)Me | 4-Thiz | 2-(1-Pip)Et |
| 4-42 | (1-Pip)Me | 4-Thiz | 2-(4-Me-1-Piz)Et |
| 4-43 | (1-Pip)Me | 5-Isox | 2-MorEt |
| 4-44 | (1-Pip)Me | 5-Imid | 2-MorEt |
| 4-45 | MorMe | 5-Imid | 2-MorEt |
| 4-46 | MorMe | 5-Imid | 3-MorPr |
| 4-47 | MorMe | 5-Imid | 2-(4-Me-1-Piz)Et |
| 4-48 | MorMe | 4-Thiz | 2-(NEt₂)Et |
| 4-49 | MorMe | 4-Thiz | 3-(NMe₂)Pr |
| 4-50 | MorMe | 4-Thiz | 2-(1-Pyrd)Et |
| 4-51 | MorMe | 4-Thiz | 2-(1-Pip)Et |
| 4-52 | MorMe | 4-Thiz | 2-(1-Et-2-Pyrd)Et |
| 4-53 | MorMe | 4-Thiz | (1-Et-2-Pyrd)Me |
| 4-54 | MorMe | 4-Thiz | (4-Pip)Me |
| 4-55 | MorMe | 4-Thiz | 2-MorEt |
| 4-56 | MorMe | 4-Thiz | 3-MorPr |
| 4-57 | MorMe | 4-Thiz | 2-OH-3-MorPr |
| 4-58 | MorMe | 4-Thiz | 2-ThzEt |
| 4-59 | MorMe | 4-Thiz | 2-OH-3-(1-Pip)Pr |
| 4-60 | MorMe | 4-Thiz | 2-OH-3-(4-Me-1-Piz)Pr |
| 4-61 | MorMe | 4-Thiz | 2-(4-Etc-1-Piz)Et |
| 4-62 | MorMe | 4-Thiz | 2-[4-(2-Pyr)Piz]Et |
| 4-63 | MorMe | 4-Thiz | (2-Pyr)Me |
| 4-64 | MorMe | 4-Thiz | 2-(2-Pyr)Et |
| 4-65 | MorMe | 4-Thiz | 2-(1-Piz)Et |
| 4-66 | MorMe | 4-Thiz | 3-(2-Me-1-Pip)Pr |
| 4-67 | (2,6-diMeMor)Me | 4-Thiz | 2-MorEt |
| 4-68 | MorMe | 5-Isox | 2-(NEt₂)Et |
| 4-69 | MorMe | 5-Isox | 2-(1-Pyrd)Et |
| 4-70 | MorMe | 5-Isox | 2-(1-Me-2-Pyrd)Et |
| 4-71 | MorMe | 5-Isox | 2-(2-Etc-1-Pyrd)Et |
| 4-72 | MorMe | 5-Isox | 2-(2-PrCar-1-Pyrd)Et |
| 4-73 | MorMe | 5-Isox | 2-OH-3-(1-Pip)Pr |
| 4-74 | MorMe | 5-Isox | 2-MorEt |
| 4-75 | MorMe | 5-Isox | 3-MorPr |
| 4-76 | MorMe | 5-Isox | 2-OH-3-MorPr |
| 4-77 | MorMe | 5-Isox | (4-Pip)Me |
| 4-78 | MorMe | 5-Isox | 2-(4-Me-1-Piz)Et |
| 4-79 | MorMe | 2-Thi | 2-MorEt |
| 4-80 | MorMe | 2-Pyr | 2-MorEt |
| 4-81 | MorMe | 3-Ind | 2-MorEt |
| 4-82 | (4-Me-1-Piz)Me | 4-Thiz | 2-MorEt |
| 4-83 | (4-Me-1-Piz)Me | 4-Thiz | 2-(4-Me-1-Piz)Et |
| 4-84 | (4-Me-1-Piz)Me | 4-Thiz | 2-(1-Pyrd)Et |
| 4-85 | (4-Me-1-Piz)Me | 4-Thiz | 2-(1-Pip)Et |
| 4-86 | (4-Me-1-Piz)Me | 4-Thiz | 3-MorPr |
| 4-87 | (4-Me-1-Piz)Me | 4-Thiz | (1-Et-2-Pyrd)Me |
| 4-88 | (4-Me-1-Piz)Me | 5-Isox | (1-Et-2-Pyrd)Me |
| 4-89 | (4-Me-1-Piz)Me | 5-Isox | 2-(1-Pyrd)Et |
| 4-90 | (4-Me-1-Piz)Me | 5-Isox | 2-(1-Pip)Et |
| 4-91 | (4-Me-1-Piz)Me | 5-Isox | 2-MorEt |
| 4-92 | (4-Me-1-Piz)Me | 5-Imid | 2-MorEt |
| 4-93 | ThzMe | 4-Thiz | 2-MorEt |
| 4-94 | ThzMe | 4-Thiz | 3-MorPr |
| 4-95 | ThzMe | 4-Thiz | 2-(1-Pip)Et |
| 4-96 | ThzMe | 5-Isox | 2-(1-Pip)Et |
| 4-97 | ThzMe | 5-Isox | 2-MorEt |
| 4-98 | 2-MorEt | 5-Isox | 2-MorEt |
| 4-99 | 2-MorEt | 4-Thiz | 2-MorEt |
| 4-100 | 2-MorEt | 4-Thiz | 2-(1-Pyrd)Et |
| 4-101 | 3-MorPr | 4-Thiz | 2-MorEt |
| 4-102 | 3-MorPr | 4-Thiz | 3-MorPr |
| 4-103 | 3-MorPr | 5-Isox | 3-MorPr |
| 4-104 | 3-MorPr | 5-Isox | 2-MorEt |
| 4-105 | (4-Etc-1-Piz)Me | 5-Isox | 2-MorEt |
| 4-106 | (4-Etc-1-Piz)Me | 5-Isox | 2-(4-Me-1-Piz)Et |
| 4-107 | (4-Etc-1-Piz)Me | 4-Thiz | 2-MorEt |
| 4-108 | (4-Etc-1-Piz)Me | 4-Thiz | 2-(4-Me-1-Piz)Et |
| 4-109 | (4-Etc-1-Piz)Me | 5-Imid | 2-MorEt |
| 4-110 | (4-Ph-1-Piz)Me | 4-Thiz | 2-MorEt |
| 4-111 | (4-Ph-1-Piz)Me | 4-Thiz | 2-(NEt₂)Et |
| 4-112 | (4-Ph-1-Piz)Me | 5-Isox | 2-MorEt |
| 4-113 | (4-Ph-1-Piz)Me | 5-Isox | 2-(NEt₂)Et |
| 4-114 | [4-(4-FPh)-1-Piz]Me | 5-Isox | 2-MorEt |
| 4-115 | [4-(4-FPh)-1-Piz]Me | 4-Thiz | 2-MorEt |
| 4-116 | [4-(4-MeOPh)-1-Piz]Me | 4-Thiz | 2-MorEt |
| 4-117 | [4-(2-ClPh)-1-Piz]Me | 4-Thiz | 2-MorEt |
| 4-118 | [4-(2-Pyr)-1-Piz]Me | 4-Thiz | 2-MorEt |
| 4-119 | (4-Bz-1-Piz)Me | 4-Thiz | 2-MorEt |
| 4-120 | (4-Bz-1-Pip)Me | 4-Thiz | 2-MorEt |
| 4-121 | (4-Bz-1-Pip)Me | 5-Isox | 2-MorEt |
| 4-122 | 3-Pip | 5-Isox | 2-MorEt |
| 4-123 | 3-Pip | 4-Thiz | 2-MorEt |
| 4-124 | 1-Boc-3-Pip | 4-Thiz | 2-MorEt |
| 4-125 | 1-Boc-3-Pyrd | 4-Thiz | 2-MorEt |
| 4-126 | 1-Boc-3-Pyrd | 5-Isox | 2-MorEt |
| 4-127 | 2-Pyrd | 5-Isox | 2-MorEt |
| 4-128 | 2-Pyrd | 4-Thiz | 2-MorEt |
| 4-129 | (PhNH)Me | 4-Thiz | 2-MorEt |
| 4-130 | (BzNH)Me | 4-Thiz | 2-MorEt |
| 4-131 | Me(cHx)NMe | 5-Isox | 2-MorEt |
| 4-132 | [(2-PhEt)NH]Me | 5-Isox | 2-MorEt |
| 4-133 | [(2-PhEt)NH]Me | 4-Thiz | 2-MorEt |
| 4-134 | 1-MorEt | 4-Thiz | 2-MorEt |
| 4-135 | 1-MorEt | 4-Thiz | 3-MorPr |
| 4-136 | 1-MorEt | 4-Thiz | 2-(4-Me-1-Piz)Et |
| 4-137 | 1-MorEt | 5-Isox | 2-(4-Me-1-Piz)Et |
| 4-138 | 1-MorEt | 5-Isox | 2-MorEt |

TABLE 4-continued

| Cpd. No. | R¹ | R³ | R⁴ |
|---|---|---|---|
| 4-139 | 1-MorPr | 4-Thiz | 2-MorEt |
| 4-140 | 1-MorBu | 4-Thiz | 2-MorEt |
| 4-141 | 1-(1-Pyrd)Et | 4-Thiz | 2-MorEt |
| 4-142 | 1-(1-Pip)Et | 4-Thiz | 2-MorEt |
| 4-143 | 1-(4-Me-1-Piz)Et | 4-Thiz | 2-MorEt |
| 4-144 | 1-ThzEt | 4-Thiz | 2-MorEt |
| 4-145 | 1-ThzEt | 5-Isox | 2-MorEt |
| 4-146 | 1-ThzEt | 5-Isox | 3-MorPr |
| 4-147 | 1-(4-Ph-1-Piz)Et | 4-Thiz | 2-MorEt |
| 4-148 | 1-(4-Ph-1-Piz)Et | 5-Isox | 2-MorEt |
| 4-149 | MorMe | 5-Isox | 1-Me-2-MorEt |
| 4-150 | MorMe | 5-Isox | 2-MorPr |
| 4-151 | MorMe | 5-Isox | 2-Me-3-MorPr |
| 4-152 | 1-MorEt | 5-Isox | 2-Me-3-MorPr |
| 4-153 | 1-MorEt | 5-Isox | 1-Me-3-MorPr |
| 4-154 | 1-MorEt | 5-Imid | 2-Me-3-MorPr |
| 4-155 | MorMe | 4-Thiz | 1-Me-2-MorEt |
| 4-156 | MorMe | 4-Thiz | 2-MorPr |
| 4-157 | MorMe | 4-Thiz | 1-Me-3-MorPr |
| 4-158 | MorMe | 4-Thiz | 2-Me-3-MorPr |
| 4-159 | MorMe | 4-Thiz | 3-MorBu |
| 4-160 | 1-MorEt | 4-Thiz | 2-Me-3-MorPr |
| 4-161 | 1-MorEt | 4-Thiz | 1-Me-2-MorEt |
| 4-162 | 1-MorEt | 4-Thiz | 2-MorPr |
| 4-163 | 1-MorPr | 4-Thiz | 2-MorPr |
| 4-164 | 1-MorPr | 4-Thiz | 2-Me-3-MorPr |
| 4-165 | (1-Boc-3-Pip)Me | 4-Thiz | 2-MorEt |
| 4-166 | Me(cHx)NMe | 2-Thi | 2-MorEt |
| 4-167 | Me(Bz)NMe | 2-Thi | 2-MorEt |
| 4-168 | 1-PipMe | 2-Thi | 2-MorEt |
| 4-169 | [4-(2-ClPh)-1-Piz]Me | 2-Thi | 2-MorEt |
| 4-170 | (4-Me-1-Piz)Me | 2-Thi | 2-MorEt |
| 4-171 | (4-Ph-1-Piz)Me | 2-Thi | 2-MorEt |
| 4-172 | [4-(4-FPh)-1-Piz]Me | 2-Thi | 2-MorEt |
| 4-173 | (4-Ph-1-Piz)Me | 3-Ind | 2-MorEt |
| 4-174 | 1-PipMe | 3-Ind | 2-MorEt |
| 4-175 | Me(cHx)NMe | 3-Ind | 2-MorEt |
| 4-176 | Me₂NMe | 3-Ind | 2-MorEt |
| 4-177 | Me(Bz)NMe | 3-Ind | 2-MorEt |
| 4-178 | Me(Bu)NMe | 3-Ind | 2-MorEt |
| 4-179 | MorMe | 4-Thiz | 3-(2-oxo-1-Pyrd)Pr |
| 4-180 | Me(Bz)NMe | 3-Ind | 3-(2-oxo-1-Pyrd)Pr |
| 4-181 | Me(cHx)NMe | 3-Ind | 3-(2-oxo-1-Pyrd)Pr |
| 4-182 | Me(Bz)NMe | 3-Ind | 2-MorEt |
| 4-183 | MorMe | Ph | 2-MorEt |
| 4-184 | MorMe | Ph | 3-(2-oxo-1-Pyrd)Pr |
| 4-185 | Me(cHx)NMe | Ph | 2-MorEt |
| 4-186 | Me(cHx)NMe | Ph | 3-(2-oxo-1-Pyrd)Pr |
| 4-187 | Me(Bu)NMe | Ph | 3-(2-oxo-1-Pyrd)Pr |
| 4-188 | Me(Bu)NMe | Ph | 2-MorEt |
| 4-189 | Me(Bz)NMe | Ph | 2-MorEt |
| 4-190 | Me(Bz)NMe | Ph | 3-(2-oxo-1-Pyrd)Pr |
| 4-191 | MorMe | iPr | 3-(2-oxo-1-Pyrd)Pr |
| 4-192 | MorMe | iPr | 2-MorEt |
| 4-193 | Me(cHx)NMe | iPr | 2-MorEt |
| 4-194 | Me(cHx)NMe | iPr | 3-(2-oxo-1-Pyrd)Pr |
| 4-195 | Me(Ph)NMe | iPr | 3-(2-oxo-1-Pyrd)Pr |
| 4-196 | Me(Ph)NMe | iPr | 2-MorEt |
| 4-197 | Me(Bz)NMe | iPr | 2-MorEt |
| 4-198 | Me(Bz)NMe | iPr | 3-(2-oxo-1-Pyrd)Pr |
| 4-199 | Me(Bu)NMe | iPr | 3-(2-oxo-1-Pyrd)Pr |
| 4-200 | Me(Bu)NMe | iPr | 2-MorEt |
| 4-201 | [Me(2-PhEt)N]Me | iPr | 2-MorEt |
| 4-202 | [4-(2-Pyr)-1-Piz]Me | iPr | 2-MorEt |
| 4-203 | [4-(2-Pym)-1-Piz]Me | iPr | 2-MorEt |
| 4-204 | [4-(4-FPh)-1-Piz]Me | iPr | 2-MorEt |
| 4-205 | [4-(2-ClPh)-1-Piz]Me | iPr | 2-MorEt |
| 4-206 | [4-(2-MeOPh)-1-Piz]Me | iPr | 2-MorEt |
| 4-207 | Me(Bz)NMe | 5-Imid | 2-MorEt |
| 4-208 | Me(Bz)NMe | 5-Imid | 3-(2-oxo-1-Pyrd)Pr |
| 4-209 | Me(cHx)NMe | 5-Imid | 3-(2-oxo-1-Pyrd)Pr |
| 4-210 | Me(cHx)NMe | 5-Imid | 2-MorEt |
| 4-211 | (4-Ph-1-Piz)Me | 5-Imid | 2-MorEt |
| 4-212 | (4-Ph-1-Piz)Me | 5-Imid | 3-(2-oxo-1-Pyrd)Pr |
| 4-213 | MorMe | 4-Thiz | 2-(5-Imid)Et |
| 4-214 | iBu₂NMe | 4-Thiz | 2-MorEt |
| 4-215 | cHx₂NMe | 4-Thiz | 2-MorEt |
| 4-216 | iPr(Bz)NMe | 5-Isox | 2-MorEt |
| 4-217 | Me(Bz)NMe | 5-Isox | 2-MorEt |
| 4-218 | [4-(4-ClBzhy)-1-Piz]Me | 4-Thiz | 2-MorEt |
| 4-219 | iPr(Bz)NMe | 4-Thiz | 2-MorEt |
| 4-220 | [4-(4-ClPh)-1-Piz]Me | 4-Thiz | 2-MorEt |
| 4-221 | [4-(3-TFMPh)-1-Piz]Me | 4-Thiz | 2-MorEt |
| 4-222 | [4-(2-Pym)-1-Piz]Me | 4-Thiz | 2-MorEt |
| 4-223 | Me(Bz)NMe | 4-Thiz | 2-(2-oxo-1-Pyrd)Pr |
| 4-224 | Et(Br)NMe | 4-Thiz | 2-(2-oxo-1-Pyrd)Et |
| 4-225 | Me(cHx)NMe | 4-Thiz | 2-(2-oxo-1-Pyrd)Et |
| 4-226 | Me(Ph)NMe | 4-Thiz | 2-(2-oxo-1-Pyrd)Et |
| 4-227 | (4-Ph-1-Piz)Me | 4-Thiz | 2-(2-oxo-1-Pyrd)Et |
| 4-228 | [4-(3-TFMPh)-1-Piz]Me | 4-Thiz | 2-(2-oxo-1-Pyrd)Et |
| 4-229 | [4-(2-MeOPh)-1-Piz]Me | 4-Thiz | 2-(2-oxo-1-Pyrd)Et |
| 4-230 | [4-(2-ClPh)-1-Piz]Me | 4-Thiz | 2-(2-oxo-1-Pyrd)Et |
| 4-231 | Bu₂NMe | 4-Thiz | 2-(2-oxo-1-Pyrd)Et |
| 4-232 | cHx₂NMe | 4-Thiz | 2-(2-oxo-1-Pyrd)Et |
| 4-233 | (4-Bz-1-Piz)Me | 4-Thiz | 2-MorEt |
| 4-234 | Et(Bz)NMe | iPr | 2-MorEt |
| 4-235 | cHx₂NMe | Ph | 3-(2-oxo-1-Pyrd)Pr |
| 4-236 | iBu₂NMe | Ph | 3-(2-oxo-1-Pyrd)Pr |
| 4-237 | Me(cHx)NMe | 5-Isox | 3-(2-oxo-1-Pyrd)Pr |
| 4-238 | Me(Bz)NMe | 5-Isox | 3-(2-oxo-1-Pyrd)Pr |
| 4-239 | Et(Bz)NMe | 5-Isox | 3-(2-oxo-1-Pyrd)Pr |
| 4-240 | (4-Ph-1-Piz)Me | 5-Isox | 3-(2-oxo-1-Pyrd)Pr |
| 4-241 | MorMe | 5-Isox | 2-MeBu |
| 4-242 | (4-Ph-1-Piz)Me | 5-Isox | 2-MeBu |
| 4-243 | Me(cHx)NMe | 5-Isox | 2-MeBu |
| 4-244 | Me(Bz)NMe | 5-Isox | 2-MeBu |
| 4-245 | Me(Bz)NMe | 4-Thiz | 2-MeBu |
| 4-246 | Me(cHx)NMe | 4-Thiz | 2-MeBu |
| 4-247 | (4-Ph-1-Piz)Me | 4-Thiz | 2-MeBu |
| 4-248 | MorMe | 4-Thiz | 2-MeBu |
| 4-249 | MorMe | 4-Thiz | 1-(HOMe)-2-MeBu |
| 4-250 | MorMe | 4-Thiz | iBu |
| 4-251 | MorMe | Ph | 2-MeBu |
| 4-252 | MorMe | 3-Ind | 2-MeBu |
| 4-253 | MorMe | iPr | 2-MeBu |
| 4-254 | MorMe | 5-Imid | 2-MeBu |
| 4-255 | Me(cHx)NMe | 5-Imid | 2-MeBu |
| 4-256 | MorMe | 4-Thiz | Me |
| 4-257 | MorMe | 4-Thiz | Et |
| 4-258 | MorMe | 4-Thiz | Pr |
| 4-259 | MorMe | 4-Thiz | iPr |
| 4-260 | MorMe | 4-Thiz | Bu |
| 4-261 | MorMe | 4-Thiz | sBu |
| 4-262 | MorMe | 4-Thiz | Pn |
| 4-263 | MorMe | 4-Thiz | iPn |
| 4-264 | MorMe | 4-Thiz | 1-MeBu |
| 4-265 | MorMe | 4-Thiz | Hx |
| 4-266 | MorMe | 4-Thiz | iHx |
| 4-267 | MorMe | 4-Thiz | 3-MePn |
| 4-268 | MorMe | 4-Thiz | 2-MePn |
| 4-269 | MorMe | 4-Thiz | Hp |
| 4-270 | MorMe | 4-Thiz | iHp |
| 4-271 | MorMe | 4-Thiz | Oc |
| 4-272 | MorMe | 5-Isox | Pr |
| 4-273 | MorMe | 5-Isox | iBu |
| 4-274 | MorMe | 5-Isox | Pn |
| 4-275 | MorMe | 5-Isox | iHx |
| 4-276 | MorMe | 5-Imid | Pr |
| 4-277 | MorMe | 5-Imid | iBu |
| 4-278 | MorMe | 5-Imid | Pn |
| 4-279 | MorMe | 5-Imid | iPn |
| 4-280 | MorMe | 5-Imid | Hx |
| 4-281 | MorMe | 5-Imid | Hp |
| 4-282 | MorMe | 2-Thi | Hx |
| 4-283 | 2-MorEt | 4-Thiz | Pr |
| 4-284 | 2-MorEt | 4-Thiz | iBu |

TABLE 4-continued

| Cpd. No. | R¹ | R³ | R⁴ |
| --- | --- | --- | --- |
| 4-285 | 2-MorEt | 4-Thiz | Pn |
| 4-286 | 2-MorEt | 5-Isox | iHx |
| 4-287 | 1-MorEt | 3-Thi | Hx |
| 4-288 | 1-MorEt | 5-Isox | iPn |
| 4-289 | 1-MorEt | 5-Imid | Pn |
| 4-290 | Me(Bz)NMe | 4-Thiz | Pr |
| 4-291 | Me(Bz)NMe | 4-Thiz | iBu |
| 4-292 | Me(Bz)NMe | 4-Thiz | iPn |
| 4-293 | Me(Bz)NMe | 4-Thiz | iHx |
| 4-294 | Me(Ph)NMe | 4-Thiz | iPn |
| 4-295 | Me(Ph)NMe | 2-Thi | Pn |
| 4-296 | Me(cHx)NMe | 4-Thiz | iPr |
| 4-297 | Me(cHx)NMe | 4-Thiz | Bu |
| 4-298 | Me(cHx)NMe | 4-Thiz | Hx |
| 4-299 | Me(cHx)NMe | 5-Imid | Pn |
| 4-300 | Me(Bz)NMe | 5-Imid | 2-MeBu |
| 4-301 | Me(Bz)NMe | 5-Imid | Hx |
| 4-302 | 1-PipMe | 4-Thiz | Hx |
| 4-303 | Me(Bz)NMe | iPr | Hx |
| 4-304 | Me(Bz)NMe | iPr | 2-MeBu |

TABLE 5

| Cpd. No. | R¹ | R³ | R⁴ |
| --- | --- | --- | --- |
| 5-1 | MorMe | 4-Thiz | 2-MorEt |
| 5-2 | Me(Bz)NMe | 4-Thiz | 2-MorEt |
| 5-3 | Me(cHx)NMe | 4-Thiz | 2-MorEt |
| 5-4 | Me(cHx)NMe | 4-Thiz | 3-(2-oxo-1-Pyrd)Pr |
| 5-5 | (4-Ph-1-Piz)Me | 4-Thiz | 3-(2-oxo-1-Pyrd)Pr |
| 5-6 | (4-Ph-1-Piz)Me | iPr | 3-(2-oxo-1-Pyrd)Pr |
| 5-7 | MorMe | iPr | 2-MorEt |
| 5-8 | Me(cHx)NMe | iPr | 2-MorEt |
| 5-9 | Me(Bz)NMe | iPr | 2-MorEt |
| 5-10 | (4-Ph-1-Piz)Me | iPr | 2-MorEt |
| 5-11 | cHx₂NMe | iPr | 2-MorEt |
| 5-12 | iBu₂NMe | iPr | 2-MorEt |
| 5-13 | MorMe | Ph | 2-MorEt |
| 5-14 | MorMe | iPr | 2-MeBu |
| 5-15 | (4-Ph-1-Piz)Me | iPr | 2-MeBu |
| 5-16 | Me(cHx)NMe | iPr | 2-MeBu |
| 5-17 | Me(Bz)NMe | iPr | 2-MeBu |
| 5-18 | MorMe | 4-Thiz | 2-MeBu |
| 5-19 | Me(cHx)NMe | 4-Thiz | 2-MeBu |
| 5-20 | Me(Bz)NMe | 4-Thiz | 2-MeBu |
| 5-21 | (4-Ph-1-Piz)Me | 4-Thiz | 2-MeBu |
| 5-22 | MorMe | 5-Isox | 2-MeBu |
| 5-23 | Me(cHx)NMe | 5-Isox | 2-MeBu |
| 5-24 | Me(Bz)NMe | 5-Isox | 2-MeBu |
| 5-25 | MorMe | 5-Imid | 2-MeBu |
| 5-26 | Me(cHx)NMe | 5-Imid | 2-MeBu |
| 5-27 | Me(Bz)NMe | 5-Imid | 2-MeBu |
| 5-28 | MorMe | 4-Thiz | Pr |
| 5-29 | MorMe | 4-Thiz | Bu |
| 5-30 | MorMe | 4-Thiz | iBu |
| 5-31 | MorMe | 4-Thiz | Pn |
| 5-32 | MorMe | 4-Thiz | iPn |
| 5-33 | MorMe | 4-Thiz | Hx |
| 5-34 | MorMe | 5-Isox | iPn |
| 5-35 | MorMe | 5-Imid | Hx |
| 5-36 | MorMe | iPr | Pn |
| 5-37 | Me(Bz)NMe | 4-Thiz | Hx |
| 5-38 | Me(Bz)NMe | 5-Isox | iPn |
| 5-39 | Me(cHx)NMe | 5-Isox | Hx |
| 5-40 | 1-PipMe | 4-Thiz | 2-MeBu |
| 5-41 | 2-MorEt | 4-Thiz | 2-MeBu |
| 5-42 | 3-MorPr | 4-Thiz | 2-MeBu |

TABLE 6

| Cpd. No. | R¹ | R³ | R⁴ |
| --- | --- | --- | --- |
| 6-1 | H₂NMe | 4-Thiz | 2-MorEt |
| 6-2 | 2-H₂NEt | 4-Thiz | 2-MorEt |
| 6-3 | (MeHN)Me | 4-Thiz | 2-MorEt |
| 6-4 | (EtHN)Me) | 4-Thiz | 2-MorEt |
| 6-5 | (PrHN)Me | 4-Thiz | 2-MorEt |
| 6-6 | (PrHN)Me | 4-Thiz | 2-(1-Me-2-Pyrd)Et |
| 6-7 | (PrHN)Me | 4-Thiz | 2-(1-Pyrd)Et |
| 6-8 | (PrHN)Me | 4-Thiz | 2-(4-Me-1-Piz)Et |
| 6-9 | (PrHN)Me | 5-Isox | 2-(4-Me-1-Piz)Et |
| 6-10 | (PrHN)Me | 5-Isox | 2-MorEt |
| 6-11 | (PrHN)Me | 5-Isox | 2-(4-Me-1-Piz)Et |
| 6-12 | (PrHN)Me | 5-Imid | 2-(4-Me-1-Piz)Et |
| 6-13 | (PrHN)Me | 5-Imid | 2-MorEt |
| 6-14 | (Me₂N)Me | 4-Thiz | 2-MorEt |
| 6-15 | (Et₂N)Me | 4-Thiz | 2-MorEt |
| 6-16 | [Bu(Me)N]Me | 4-Thiz | 2-MorEt |
| 6-17 | [Bu(Me)N]Me | 4-Thiz | 2-ThzEt |
| 6-18 | [Bu(Me)N]Me | 4-Thiz | 2-(1-Pip)Et |
| 6-19 | [Bu(Me)N]Me | 4-Thiz | 2-(4-Me-1-Piz)Et |
| 6-20 | [Bu(Me)N]Me | 5-Isox | 2-MorEt |
| 6-21 | [Bu(Me)N]Me | 5-Isox | 2-ThzEt |
| 6-22 | (Pr₂N)Me | 5-Isox | 2-MorEt |
| 6-23 | (Pr₂N)Me | 4-Thiz | 2-MorEt |
| 6-24 | (iPr₂N)Me | 4-Thiz | 2-MorEt |
| 6-25 | (Bu₂N)Me | 4-Thiz | 2-MorEt |
| 6-26 | (Bu₂N)Me | 5-Isox | 2-MorEt |
| 6-27 | [Me(cHx)N]Me | 4-Thiz | 2-MorEt |
| 6-28 | [Me(Ph)N]Me | 4-Thiz | 2-MorEt |
| 6-29 | [Et(4-MePh)N]Me | 4-Thiz | 2-MorEt |
| 6-30 | [Me(Bz)N]Me | 4-Thiz | 2-MorEt |
| 6-31 | [Et(Bz)N]Me | 4-Thiz | 2-MorEt |
| 6-32 | [Me(2-PhEt)N]Me | 4-Thiz | 2-MorEt |
| 6-33 | (1-Pyrd)Me | 4-Thiz | 2-(1-Pip)Et |
| 6-34 | (1-Pyrd)Me | 4-Thiz | 2-(4-Me-1-Piz)Et |
| 6-35 | (1-Pyrd)Me | 4-Thiz | 2-MorEt |
| 6-36 | (1-Pyrd)Me | 5-Isox | 2-MorEt |
| 6-37 | (1-Pyrd)Me | 5-Isox | 2-(1-Pyrd)Et |
| 6-38 | (1-Pyrd)Me | 5-Imid | 2-MorEt |
| 6-39 | (1-Pip)Me | 4-Thiz | 2-MorEt |
| 6-40 | (1-Pip)Me | 4-Thiz | 3-MorPr |
| 6-41 | (1-Pip)Me | 4-Thiz | 2-(1-Pip)Et |
| 6-42 | (1-Pip)Me | 4-Thiz | 2-(4-Me-1-Piz)Et |
| 6-43 | (1-Pip)Me | 5-Isox | 2-MorEt |
| 6-44 | (1-Pip)Me | 5-Imid | 2-MorEt |
| 6-45 | MorMe | 5-Imid | 2-MorEt |
| 6-46 | MorMe | 5-Imid | 3-MorPr |
| 6-47 | MorMe | 5-Imid | 2-(4-Me-1-Piz)Et |
| 6-48 | MorMe | 4-Thiz | 2-(NEt₂)Et |
| 6-49 | MorMe | 4-Thiz | 3-(NMe₂)Pr |
| 6-50 | MorMe | 4-Thiz | 2-(1-Pyrd)Et |
| 6-51 | MorMe | 4-Thiz | 2-(1-Pip)Et |
| 6-52 | MorMe | 4-Thiz | 2-(1-Et-2-Pyrd)Et |
| 6-53 | MorMe | 4-Thiz | (1-Et-2-Pyrd)Me |
| 6-54 | MorMe | 4-Thiz | (4-Pip)Me |
| 6-55 | MorMe | 4-Thiz | 2-MorEt |
| 6-56 | MorMe | 4-Thiz | 3-MorPr |
| 6-57 | MorMe | 4-Thiz | 2-OH-3-MorPr |
| 6-58 | MorMe | 4-Thiz | 2-ThzEt |
| 6-59 | MorMe | 4-Thiz | 2-OH-3-(1-Pip)Pr |
| 6-60 | MorMe | 4-Thiz | 2-OH-3-(4-Me-1-Piz)Pr |
| 6-61 | MorMe | 4-Thiz | 2-(4-Etc-1-Piz)Et |
| 6-62 | MorMe | 4-Thiz | 2-[4-(2-Pyr)Piz]Et |
| 6-63 | MorMe | 4-Thiz | (2-Pyr)Me |
| 6-64 | MorMe | 4-Thiz | 2-(2-Pyr)Et |
| 6-65 | MorMe | 4-Thiz | 2-(1-Piz)Et |
| 6-66 | MorMe | 4-Thiz | 3-(2-Me-1-Pip)Pr |
| 6-67 | (2,6-diMeMor)Me | 4-Thiz | 2-MorEt |
| 6-68 | MorMe | 5-Isox | 2-(NEt₂)Et |
| 6-69 | MorMe | 5-Isox | 2-(1-Pyrd)Et |
| 6-70 | MorMe | 5-Isox | 2-(1-Me-2-Pyrd)Et |
| 6-71 | MorMe | 5-Isox | 2-(2-Etc-1-Pyrd)Et |
| 6-72 | MorMe | 5-Isox | 2-(2-PrCar-1-Pyrd)Et |
| 6-73 | MorMe | 5-Isox | 2-OH-3-(1-Pip)Pr |
| 6-74 | MorMe | 5-Isox | 2-MorEt |
| 6-75 | MorMe | 5-Isox | 3-MorPr |
| 6-76 | MorMe | 5-Isox | 2-OH-3-MorPr |
| 6-77 | MorMe | 5-Isox | (4-Pip)Me |
| 6-78 | MorMe | 5-Isox | 2-(4-Me-1-Piz)Et |
| 6-79 | MorMe | 2-Thi | 2-MorEt |
| 6-80 | MorMe | 2-Pyr | 2-MorEt |
| 6-81 | MorMe | 3-Ind | 2-MorEt |
| 6-82 | (4-Me-1-Piz)Me | 4-Thiz | 2-MorEt |
| 6-83 | (4-Me-1-Piz)Me | 4-Thiz | 2-(4-Me-1-Piz)Et |
| 6-84 | (4-Me-1-Piz)Me | 4-Thiz | 2-(1-Pyrd)Et |
| 6-85 | (4-Me-1-Piz)Me | 4-Thiz | 2-(1-Pip)Et |

TABLE 6-continued

| Cpd. No. | R¹ | R³ | R⁴ |
|---|---|---|---|
| 6-86 | (4-Me-1-Piz)Me | 4-Thiz | 3-MorPr |
| 6-87 | (4-Me-1-Piz)Me | 4-Thiz | (1-Et-2-Pyrd)Me |
| 6-88 | (4-Me-1-Piz)Me | 5-Isox | (1-Et-2-Pyrd)Me |
| 6-89 | (4-Me-1-Piz)Me | 5-Isox | 2-(1-Pyrd)Et |
| 6-90 | (4-Me-1-Piz)Me | 5-Isox | 2-(1-Pip)Et |
| 6-91 | (4-Me-1-Piz)Me | 5-Isox | 2-MorEt |
| 6-92 | (4-Me-1-Piz)Me | 5-Imid | 2-MorEt |
| 6-93 | ThzMe | 4-Thiz | 2-MorEt |
| 6-94 | ThzMe | 4-Thiz | 3-MorPr |
| 6-95 | ThzMe | 4-Thiz | 2-(1-Pip)Et |
| 6-96 | ThzMe | 5-Isox | 2-(1-Pip)Et |
| 6-97 | ThzMe | 5-Isox | 2-MorEt |
| 5-98 | 2-MorEt | 5-Isox | 2-MorEt |
| 6-99 | 2-MorEt | 4-Thiz | 2-MorEt |
| 6-100 | 2-MorEt | 4-Thiz | 2-(1-Pyrd)Et |
| 6-101 | 3-MorPr | 4-Thiz | 2-MorEt |
| 6-102 | 3-MorPr | 4-Thiz | 3-MorPr |
| 6-103 | 3-MorPr | 5-Isox | 3-MorPr |
| 6-104 | 3-MorPr | 5-Isox | 2-MorEt |
| 6-105 | (4-Etc-1-Piz)Me | 5-Isox | 2-MorEt |
| 6-106 | (4-Etc-1-Piz)Me | 5-Isox | 2-(4-Me-1-Piz)Et |
| 6-107 | (4-Etc-1-Piz)Me | 4-Thiz | 2-MorEt |
| 6-108 | (4-Etc-1-Piz)Me | 4-Thiz | 2-(4-Me-1-Piz)Et |
| 6-109 | (4-Etc-1-Piz)Me | 5-Imid | 2-MorEt |
| 6-110 | (4-Ph-1-Piz)Me | 4-Thiz | 2-MorEt |
| 6-111 | (4-Ph-1-Piz)Me | 4-Thiz | 2-(NEt₂)Et |
| 6-112 | (4-Ph-1-Piz)Me | 5-Isox | 2-MorEt |
| 6-113 | (4-Ph-1-Piz)Me | 5-Isox | 2-(NEt₂)Et |
| 6-114 | [4-(4-FPh)-1-Piz]Me | 5-Isox | 2-MorEt |
| 6-115 | [4-(4-FPh)-1-Piz]Me | 4-Thiz | 2-MorEt |
| 6-116 | [4-(4-MeOPh)-1-Piz]Me | 4-Thiz | 2-MorEt |
| 6-117 | [4-(2-ClPh)-1-Piz]Me | 4-Thiz | 2-MorEt |
| 6-118 | [4-(2-Pyr)-1-Piz]Me | 4-Thiz | 2-MorEt |
| 6-119 | (4-Bz-1-Piz)Me | 4-Thiz | 2-MorEt |
| 6-120 | (4-Bz-1-Pip)Me | 4-Thiz | 2-MorEt |
| 6-121 | (4-Bz-1-Pip)Me | 5-Isox | 2-MorEt |
| 6-122 | 3-Pip | 5-Isox | 2-MorEt |
| 6-123 | 3-Pip | 4-Thiz | 2-MorEt |
| 6-124 | 1-Boc-3-Pip | 4-Thiz | 2-MorEt |
| 6-125 | 1-Boc-2-Pyrd | 4-Thiz | 2-MorEt |
| 6-126 | 1-Boc-2-Pyrd | 5-Isox | 2-MorEt |
| 6-127 | 2-Pyrd | 5-Isox | 2-MorEt |
| 6-128 | 2-Pyrd | 4-Thiz | 2-MorEt |
| 6-129 | (PhNH)Me | 4-Thiz | 2-MorEt |
| 6-130 | (BzNH)Me | 4-Thiz | 2-MorEt |
| 6-131 | (BzNH)Me | 5-Isox | 2-MorEt |
| 6-132 | [(2-PhEt)NH]Me | 5-Isox | 2-MorEt |
| 6-133 | [(2-PhEt)NH]Me | 4-Thiz | 2-MorEt |
| 6-134 | 1-MorEt | 4-Thiz | 2-MorEt |
| 6-135 | 1-MorEt | 4-Thiz | 3-MorPr |
| 6-136 | 1-MorEt | 4-Thiz | 2-(4-Me-1-Piz)Et |
| 6-137 | 1-MorEt | 5-Isox | 2-(4-Me-1-Piz)Et |
| 6-138 | 1-MorEt | 5-Isox | 2-MorEt |
| 6-139 | 1-MorPr | 4-Thiz | 2-MorEt |
| 6-140 | 1-MorBu | 4-Thiz | 2-MorEt |
| 6-141 | 1-(1-Pyrd)Et | 4-Thiz | 2-MorEt |
| 6-142 | 1-(1-Pip)Et | 4-Thiz | 2-MorEt |
| 6-143 | 1-(4-Me-1-Piz)Et | 4-Thiz | 2-MorEt |
| 6-144 | 1-ThzEt | 4-Thiz | 2-MorEt |
| 6-145 | 1-ThzEt | 5-Isox | 2-MorEt |
| 6-146 | 1-ThzEt | 5-Isox | 3-MorPr |
| 6-147 | 1-(4-Ph-1-Piz)Et | 4-Thiz | 2-MorEt |
| 6-148 | 1-(4-Ph-1-Piz)Et | 5-Isox | 2-MorEt |
| 6-149 | MorMe | 5-Isox | 1-Me-2-MorEt |
| 6-150 | MorMe | 5-Isox | 2-MorPr |
| 6-151 | MorMe | 5-Isox | 2-Me-3-MorPr |
| 6-152 | 1-MorEt | 5-Isox | 2-Me-3-MorPr |
| 6-152 | 1-MorEt | 5-Isox | 2-Me-3-MorPr |
| 6-153 | 1-MorEt | 5-Isox | 1-Me-3-MorPr |
| 6-154 | 1-MorEt | 5-Imid | 2-Me-3-MorPr |
| 6-155 | MorMe | 4-Thiz | 1-Me-2-MorEt |
| 6-156 | MorMe | 4-Thiz | 2-MorPr |
| 6-157 | MorMe | 4-Thiz | 1-Me-3-MorPr |
| 6-158 | MorMe | 4-Thiz | 2-Me-3-MorPr |
| 6-159 | MorMe | 4-Thiz | 3-MorBu |
| 6-160 | 1-MorEt | 4-Thiz | 2-Me-3-MorPr |
| 6-161 | 1-MorEt | 4-Thiz | 1-Me-2-MorEt |
| 6-162 | 1-MorEt | 4-Thiz | 2-MorPr |
| 6-163 | 1-MorPr | 4-Thiz | 2-MorPr |
| 6-164 | 1-MorPr | 4-Thiz | 2-Me-3-MorPr |
| 6-165 | (1-Boc-3-Pip)Me | 4-Thiz | 2-MorEt |
| 6-166 | Me(cHx)NMe | 2-Thi | 2-MorEt |
| 6-167 | Me(Bz)NMe | 2-Thi | 2-MorEt |
| 6-168 | 1-PipMe | 2-Thi | 2-MorEt |
| 6-169 | [4-(2-ClPh)-1-Piz]Me | 2-Thi | 2-MorEt |
| 6-170 | (4-Me-1-Piz)Me | 2-Thi | 2-MorEt |
| 6-171 | (4-Ph-1-Piz)Me | 2-Thi | 2-MorEt |
| 6-172 | [4-(4-FPh)-1-Piz]Me | 2-Thi | 2-MorEt |
| 6-173 | (4-Ph-1-Piz)Me | 3-Ind | 2-MorEt |
| 6-174 | 1-PipMe | 3-Ind | 2-MorEt |
| 6-175 | Me(cHx)NMe | 3-Ind | 2-MorEt |
| 6-176 | Me₂NMe | 3-Ind | 2-MorEt |
| 6-177 | Me(Bz)NMe | 3-Ind | 2-MorEt |
| 6-178 | Me(Bu)NMe | 3-Ind | 2-MorEt |
| 6-179 | MorMe | 4-Thiz | 3-(2-oxo-1-Pyrd)Pr |
| 6-180 | Me(Bz)NMe | 3-Ind | 3-(2-oxo-1-Pyrd)Pr |
| 6-181 | Me(cHx)NMe | 3-Ind | 3-(2-oxo-1-Pyrd)Pr |
| 6-182 | Me(Bz)NMe | 3-Ind | 2-MorEt |
| 6-183 | MorMe | Ph | 2-MorEt |
| 6-184 | MorMe | Ph | 3-(2-oxo-1-Pyrd)Pr |
| 6-185 | Me(cHx)NMe | Ph | 2-MorEt |
| 6-186 | Me(cHx)NMe | Ph | 3-(2-oxo-1-Pyrd)Pr |
| 6-187 | Me(Bu)NMe | Ph | 3-(2-oxo-1-Pyrd)Pr |
| 6-188 | Me(Bu)NMe | Ph | 2-MorEt |
| 6-189 | Me(Bz)NMe | Ph | 2-MorEt |
| 6-190 | Me(Bz)NMe | Ph | 3-(2-oxo-1-Pyrd)Pr |
| 6-191 | MorMe | iPr | 3-(2-oxo-1-Pyrd)Pr |
| 6-192 | MorMe | iPr | 2-MorEt |
| 6-193 | Me(cHx)NMe | iPr | 2-MorEt |
| 6-194 | Me(cHx)NMe | iPr | 3-(2-oxo-1-Pyrd)Pr |
| 6-195 | Me(Ph)NMe | iPr | 3-(2-oxo-1-Pyrd)Pr |
| 6-196 | Me(Ph)NMe | iPr | 2-MorEt |
| 6-197 | Me(Bz)NMe | iPr | 2-MorEt |
| 6-198 | Me(Bz)NMe | iPr | 3-(2-oxo-1-Pyrd)Pr |
| 6-199 | Me(Bu)NMe | iPr | 3-(2-oxo-1-Pyrd)Pr |
| 6-200 | Me(Bu)NMe | iPr | 2-MorEt |
| 6-201 | [Me(2-PhEt)N]Me | iPr | 2-MorEt |
| 6-202 | [4-(2-Pyr)-1-Piz]Me | iPr | 2-MorEt |
| 6-203 | [4-(2-Pym)-1-Piz]Me | iPr | 2-MorEt |
| 6-204 | [4-(4-FPh)-1-Piz]Me | iPr | 2-MorEt |
| 6-205 | [4-(2-ClPh)-1-Piz]Me | iPr | 2-MorEt |
| 6-206 | [4-(2-MeOPh)-1-Piz]Me | iPr | 2-MorEt |
| 6-207 | Me(Bz)NMe | 5-Imid | 2-MorEt |
| 6-208 | Me(Bz)NMe | 5-Imid | 3-(2-oxo-1-Pyrd)Pr |
| 6-209 | Me(cHx)NMe | 5-Imid | 3-(2-oxo-1-Pyrd)Pr |
| 6-210 | Me(cHx)NMe | 5-Imid | 2-MorEt |
| 6-211 | (4-Ph-1-Piz)Me | 5-Imid | 2-MorEt |
| 6-212 | (4-Ph-1-Piz)Me | 5-Imid | 3-(2-oxo-1-Pyrd)Pr |
| 6-213 | MorMe | 4-Thiz | 3-(5-Imid)Pr |
| 6-214 | iBu₂NMe | 4-Thiz | 2-MorEt |
| 6-215 | cHx₂NMe | 4-Thiz | 2-MorEt |
| 6-216 | iPr(Bz)NMe | 5-Isox | 2-MorEt |
| 6-217 | Me(Bz)NMe | 5-Isox | 2-MorEt |
| 6-218 | [4-(4-ClBzhy)-1-Piz]Me | 4-Thiz | 2-MorEt |
| 6-219 | iPr(Bz)NMe | 4-Thiz | 2-MorEt |
| 6-220 | [4-(4-ClPh)-1-Piz]Me | 4-Thiz | 2-MorEt |
| 6-221 | [4-(3-TFMPh)-1-Piz]Me | 4-Thiz | 2-MorEt |
| 6-222 | [4-(2-Pym)-1-Piz]Me | 4-Thiz | 2-MorEt |
| 6-223 | Me(Bz)NMe | 4-Thiz | 2-(2-oxo-1-Pyrd)Et |
| 6-224 | Et(Bz)NMe | 4-Thiz | 2-(2-oxo-1-Pyrd)Et |
| 6-225 | Me(cHx)NMe | 4-Thiz | 2-(2-oxo-1-Pyrd)Et |
| 6-226 | Me(Ph)NMe | 4-Thiz | 2-(2-oxo-1-Pyrd)Et |
| 6-227 | (4-Ph-1-Piz)Me | 4-Thiz | 2-(2-oxo-1-Pyrd)Et |
| 6-228 | [4-(3-TFMPh)- | 4-Thiz | 2-(2-oxo-1-Pyrd)Et |

TABLE 6-continued

| Cpd. No. | R¹ | R³ | R⁴ |
|---|---|---|---|
| | 1-Piz]Me | | |
| 6-229 | [4-(2-MeOPh)-1-Piz]Me | 4-Thiz | 2-(2-oxo-1-Pyrd)Et |
| 6-230 | [4-(2-ClPh)-1-Piz]Me | 4-Thiz | 2-(2-oxo-1-Pyrd)Et |
| 6-231 | Bu₂NMe | 4-Thiz | 2-(2-oxo-1-Pyrd)Et |
| 6-232 | cHx₂NMe | 4-Thiz | 2-(2-oxo-1-Pyrd)Et |
| 6-233 | (4-Bz-1-Piz)Me | 4-Thiz | 2-MorEt |
| 6-234 | Et(Bz)NMe | iPr | 2-MorEt |
| 6-235 | cHx₂NMe | Ph | 3-(2-oxo-1-Pyrd)Pr |
| 6-236 | iBu₂NMe | Ph | 3-(2-oxo-1-Pyrd)Pr |
| 6-237 | Me(cHx)NMe | 5-Isox | 3-(2-oxo-1-Pyrd)Pr |
| 6-238 | Me(Bz)NMe | 5-Isox | 3-(2-oxo-1-Pyrd)Pr |
| 6-239 | Et(Bz)NMe | 5-Isox | 3-(2-oxo-1-Pyrd)Pr |
| 6-240 | (4-Ph-1-Piz)Me | 5-Isox | 3-(2-oxo-1-Pyrd)Pr |
| 6-241 | MorMe | 5-Isox | 2-MeBu |
| 6-242 | (4-Ph-1-Piz)Me | 5-Isox | 2-MeBu |
| 6-243 | Me(cHx)NMe | 5-Isox | 2-MeBu |
| 6-244 | Me(Bz)NMe | 5-Isox | 2-MeBu |
| 6-245 | Me(Bz)NMe | 4-Thiz | 2-MeBu |
| 6-246 | Me(cHx)NMe | 4-Thiz | 2-MeBu |
| 6-247 | (4-Ph-1-Piz)Me | 4-Thiz | 2-MeBu |
| 6-248 | MorMe | 4-Thiz | 2-MeBu |
| 6-249 | MorMe | 4-Thiz | 1-(HOMe)-2-MeBu |
| 6-250 | MorMe | 4-Thiz | iBu |
| 6-251 | MorMe | Ph | 2-MeBu |
| 6-252 | MorMe | 3-Ind | 2-MeBu |
| 6-253 | MorMe | iPr | 2-MeBu |
| 6-254 | MorMe | 5-Imid | 2-MeBu |
| 6-255 | Me(cHx)NMe | 5-Imid | 2-MeBu |
| 6-256 | Me(Bz)NMe | 4-Thiz | 1-(1-PipMe)-2-MeBu |
| 6-257 | Me(Bz)NMe | 4-Thiz | 1-(MorMe)-2-MeBu |
| 6-258 | Me(Bz)NMe | 4-Thiz | 2-(1-Pip)Et |
| 6-259 | MorMe | 4-Thiz | Bu |
| 6-260 | MorMe | 4-Thiz | Pn |
| 6-261 | MorMe | 4-Thiz | iPn |
| 6-262 | MorMe | 4-Thiz | Hx |
| 6-263 | Me(Bz)NMe | 4-Thiz | Bu |
| 6-264 | Me(Bz)NMe | 4-Thiz | Hx |
| 6-265 | Me(cHx)NMe | 4-Thiz | iPn |
| 6-266 | Me(cHx)NMe | 4-Thiz | Hx |
| 6-267 | 2-MorEt | 4-Thiz | Hx |

TABLE 7

| Cpd. No. | R¹ | R² | R³ | R⁴ |
|---|---|---|---|---|
| 7-1 | MorMe | 1-Np | 4-Thiz | iBu |
| 7-2 | MorMe | 1-Np | 4-Thiz | Pn |
| 7-3 | MorMe | 1-Np | 4-Thiz | iHx |
| 7-4 | MorMe | 1-Np | 5-Isox | Bu |
| 7-5 | MorMe | Ph | 4-Thiz | Bu |
| 7-6 | MorMe | cHx | 4-Thiz | Hx |

TABLE 8

| Cpd. No. | R¹ | R³ | R⁴ | R⁵ |
|---|---|---|---|---|
| 8-1 | Mor | 4-Thiz | 2-MorEt | H |
| 8-2 | Mor | 4-Thiz | Pr | H |
| 8-3 | Mor | 4-Thiz | Pn | H |
| 8-4 | Mor | 4-Thiz | Bu | Bu |
| 8-5 | Mor | 5-Imid | Hx | H |
| 8-6 | Mor | 5-Isox | Hx | H |
| 8-7 | Mor | iPr | 3-(2-oxo-1-Pyrd)Pr | H |
| 8-8 | Me(cHx)N | 4-Thiz | 2-MorEt | H |
| 8-9 | Me(cHx)N | 4-Thiz | Hx | H |
| 8-10 | Me(Bz)N | 4-Thiz | 2-MorEt | H |

Also preferred are the pharmaceutically acceptable salts of the above compounds, especially the hydrochlorides.

Of the compounds listed above, the following compounds are preferred, that is to say Compounds No. 1-40, 1-86, 1-101, 1-108, 1-131, 1-146, 4-15, 4-16, 4-27, 4-28, 4-30, 4-31, 4-45, 4-55, 4-79, 4-81, 4-101, 4-115, 4-116, 4-117, 4-119, 4-131, 4-179, 4-180, 4-183, 4-184, 4-185, 4-186, 4-191, 4-192, 4-193, 4-194, 4-195, 4-196, 4-197, 4-198, 4-199, 4-201, 4-208, 4-214, 4-217, 4-218, 4-219, 4-223, 4-234, 4-237, 4-238, 4-241, 4-244, 4-248, 4-250, 4-258, 4-260, 4-262, 4-263, 4-265, 4-298, 4-300, 4-304, 5-14, 5-19, 5-24, 5 -29, 5-33, 6-30 and 6-257, of which the following are most preferred:

1-40. N-{N-[3-Morpholinocarbonyl-2-(1-naphthylmethyl)propyl]-3-(4-thiazolyl)-alanyl}-cyclostatin(2-morpholinoethyl)amide, especially N-{N-[(2R)-3-morpholinocarbonyl-2-(1-naphthylmethyl)propionyl]-3-(4-thiazolyl)-DL-alanyl}-cyclostatin-(2-morpholinoethyl)amide and N-{N-[(2R)-3-morpholinocarbonyl-2-(1-naphthylmethyl)propionyl]-3-(4-thiazolyl)-L-alanyl}-cyclostatin-(2-morpholinoethyl)amide;

1-101. N-{N-[3(N-Benzyl-N-methylcarbamoyl)-2-(1-naphthylmethyl)propionyl]-3-(4-thiazolyl)-alanyl}-cyclostatin-(2-morpholinoethyl)amide, especially N-{N-[(2R)-3-(N-benzyl-N-methylcarbamoyl)-2-(1-naphthylmethyl)propionyl]-3-(4-thiazolyl)-L-alanyl}-cyclostatin-(2-morpholinoethyl)amide;

1-108. N-{N-[3-(N-Benzyl-N-methylcarbamoyl)-2-(1-naphthylmethyl)propionyl]-3-(5-isoxazolyl)-alanyl}-cyclostatin-(2-morpholinoethyl)amide, especially N-{N-[(2R)-3-(N-Benzyl-N-methylcarbamoyl)-2-(1-naphthylmethyl)propionyl]-3-(5-isoxazolyl)-L-alanyl}-cyclostatin-( 2-morpholinoethyl)amide;

1-131. N-{N-[3-Morpholinocarbonyl-2-(1-napnthylmethyl)propionyl]-3-(4-thiazolyl)-alanyl}-cyclostatin-(2-methylbutyl)amide, especially N-{N-[(2R)-3-morpholinocarbonyl-2-(1-naphthylmethyl)propionyl]-3-(4-thiazolyl)-L-alanyl}-cyclostatin-[(S)-2-methylbutyl]amide;

4-27. N-{N-[N-(N-Cyclohexyl-N-methylaminoacetyl)-3-(1-naphthyl)-alanyl]-3-(4-thiazolyl)-alanyl}-cyclostatin-(2-morpholinoethyl)amide, especially N-{N-[N-(N-cyclohexyl-N-methylaminoacetyl)-3-(1-naphthyl)-L-alanyl]-3-(4-thiazolyl)-L-alanyl}-cyclostatin-(2-morpholinoethyl)amide;

4-28. N-[N-[N-(N-Methylanilinoacetyl)-3-(1-naphthyl)-alanyl]-3-(4-thiazolyl)-alanyl}-cyclostatin-(2-morpholinoethyl)amide, especially N-{N-[N-(N-methylanilinoacetyl)-3-(1-naphthyl)-L-alanyl]-3-(4-thiazolyl)-L-alanyl}-cyclostatin-(2-morpholinoethyl)amide;

4-194. N-{N-[N-(N-Cyclohexyl-N-methylaminoacetyl)-3-(1-naphthyl)-alanyl]-leucyl}-cyclostatin-[3-(2-oxo-1-pyrrolidinyl)propyl]amide, especially N-{N-[N-(N-cyclohexyl-N-methylaminoacetyl)-3-(1-naphthyl)-L-alanyl]-L-leucyl}-cyclostatin-[3-(2-oxo-1-pyrrolidinyl)propyl]amide;

4-208. N-{N-[N-(N-Benzyl-N-methylaminoacetyl)-3-(1-naphthyl)-alanyl]-3-(5-imidazolyl)-alanyl}-cyclostatin-[3-(2-oxo-1-pyrrolidinyl)propyl]amide;

4-217. N-{N-[N-(N-Benzyl-N-methylaminoacetyl)-3-(1-naphthyl)-alanyl]-3-(5-isoxazolyl)-alanyl}-cyclostatin-(2-morpholinoethyl)amide;

4-218. N-[N-{-[4-(4-Chlorobenzhydryl)-1-piperazinylacetyl]-3-(1-naphthyl)-alanyl}-3-(4-thiazolyl)-alanyl]-cyclostatin-(2-morpholinoethyl)amide, especially N-[N-[N-[4-(4-chlorobenzhydryl)-1-piperazinylacetyl]-3-(1-naphthyl)-L-alanyl}-3-(4-thiazolyl)-L-alanyl]-cyclostatin-(2-morpholinoethyl)amide;

4-219 N-{N-[N-(N-Benzyl-N-isopropylaminoacetyl)-3-(1-naphthyl)-alanyl]-3-(4-thiazolyl)-alanyl}-cyclostatin-(2-morpholinoethyl)amide, especially N-{N-[N-(N-benzyl-N-isopropylaminoacetyl)-3-(1-naphthyl)-L-alanyl]-3-(4-thiazolyl)-L-alanyl}-cyclostatin-(2-morpholinoethyl)amide;

4-237. N-{N-[N-(N-Cyclohexyl-N-methylaminoacetyl)-3-(1-naphthyl)-alanyl]-3-(5-isoxazolyl)-alanyl}-cyclostatin-[3-(2-oxo-1-pyrrolidinyl)propyl]amide;

4-238. N-{N-[N-(N-Benzyl-N-methylaminoacetyl)-3-(1-naphthyl)-alanyl]-3-(5-isoxazolyl)-alanyl}-cyclostatin-[3-(2-oxo-1-pyrrolidinyl)propyl]amide;

4-241. N-{N-[N-Morpholinoacetyl-3-(1-naphthyl)-alanyl]3-(5-isoxazolyl)-alanyl}-cyclostatin-(2-methylbutyl)amide;

4-248. N-{N-[N-Morpholinoacetyl-3-(1-naphthyl)-alanyl]-3-(4-thiazolyl)-alanyl}-cyclostatin-(2-methylbutyl)amide, especially N-{N-[N-morpholinoacetyl-3-(1-naphthyl)-L-alanyl]-3-(4-thiazolyl)-L-alanyl}-cyclostatin-](S)-2-methylbutyl]amide;

4-250. N-{N-[N-Morpholinoacetyl-3-(1-naphthyl)alanyl]-3-(4-thiazolyl)-alanyl}-cyclostatinisobutylamide;

4-258. N-{N-[N-Morpholinoacetyl-3-(1-naphthyl)-alanyl]- 3-(4-thiazolyl)-alanyl}-cyclostatinpropylamide;

4-260. N-{N-[N-Morpholinoacetyl-3-(1-naphthyl)alanyl]-3-(4-thiazolyl)-alanyl}-cyclostatinbutylamide;

4-262. N-{N-[N-Morpholinoacetyl-3-(1-naphthyl)alanyl]-3-(4-thiazolyl)-alanyl}-cyclostatinpentylamide;

4-263. N-{N-[N-Morpholinoacetyl-3-(1-naphthyl)alanyl]-3-(4-thiazolyl)-alanyl)-cyclostatinisopentylamide;

4-265. N-{N-[N-Morpholinoacetyl-3-(1-naphthyl)alanyl]-3-(4-thiazolyl)-alanyl}-cyclostatin-hexylamide, especially N-{N-[N-morpholinoacetyl-3-(1-naphthyl)-L-alanyl]-3-(4-thiazolyl)-L-alanyl}-cyclostatin-hexylamide;

5-14. N-[N-(N-Morpholinoacetyl-phenylalanyl)-leucyl]-cyclostatin-(2-methylbutyl)amide, especially N-[N-(N-morpholinoacetyl-L-phenylalanyl)-L-leucyl]-cyclostatin-[(S)-2-methylbutyl]amide;

5-24. N-[N-(N-Morpholinoacetyl-phenylalanyl)-3-(5-isoxazolyl)-alanyl}-cyclostatin-(2-methylbutyl)amide;

5-29. N-[N-(N-Morpholinoacetyl-phenylalanyl)-3-(4-thiazolyl)-alanyl]-cyclostatin-butylamide, especially N-[N-(N-morpholinoacetyl-L-phenylalanyl)-3-(4-thiazolyl)-L-alanyl]-cyclostatin-butylamide;

5-33. N-[N-(N-Morpholinoacetyl-phenylalanyl)-3-(4-thiazolyl)-alanyl]-cyclostatin-hexylamide, especially N-[N-(N-morpholinoacetyl-L-phenylalanyl)-3-(4-thiazolyl)-L-alanyl]cyclostatin-hexylamide;

and the pharmaceutically acceptable salts of the above compounds, especially the hydrochlorides.

The compounds of the present invention are oligopeptides and may, therefore, be prepared, as is well known in the art by reacting together the component amino acids in any appropriate order, by reacting together two or more lower oligopeptides (again, if necessary, in an appropriate order) or by reacting one or more component amino acids with one or more lower oligopeptides (again, if necessary, in an appropriate order). However, provided that the correct sequence of amino acid residues in the oligopeptide of formula (I) is achieved, there is no particular restriction upon the order in which these reactions are carried out. In general terms, the compounds of the invention may be prepared by reacting together compounds of formulae:

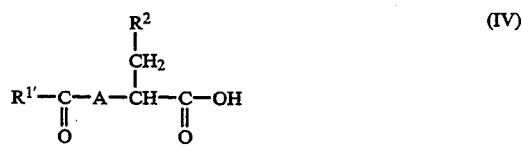

or a reactive derivative thereof,

or a reactive derivative thereof.

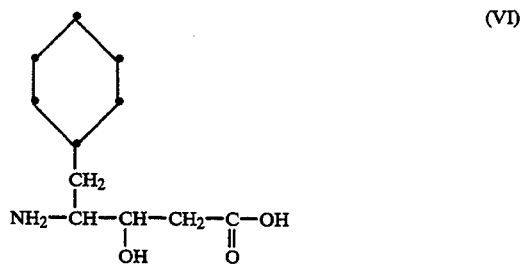

or a reactive derivative thereof, and

or a reactive derivative thereof (in the above formulae $R^2$–$R^5$ and A are as defined above and $R^{1'}$ represents any of the groups represented by $R^1$ or an active group), and, where $R^{1'}$ represents said active group, converting it to any one of the groups represented by $R^1$;

or by reacting a peptide compound derivable by reaction of some of said compounds of formulae (IV), (V), (VI) or (VII) or said reactive derivatives with the remainder of said compounds or said reactive derivative(s) or with a peptide compound or compounds derivable by reaction of said remainder or reactive derivative(s) thereof, the reaction(s) being in an order corresponding to the order of the residues derived from said compounds of formulae (IV), (V), (VI) and (VII) in said compound of formula (I). Also, where A represents a group of formula —NH—, the compound of formula (IV) may, if desired, be replaced by the two compounds of formulae (IVa) and (IVb):

and

-continued

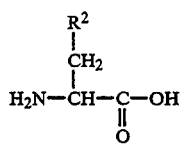
(IVb)

(in which $R^1$ and $R^2$ are as defined above).

If required, the resulting compound of formula (I) may be subjected to any one or more of various optional reactions, for example salification.

In specific embodiments of the process of the present invention, the compounds of the invention may be prepared by any of the following Reaction Schemes A, B, C, D and E.

Reaction Scheme B

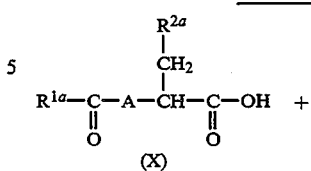
(X)

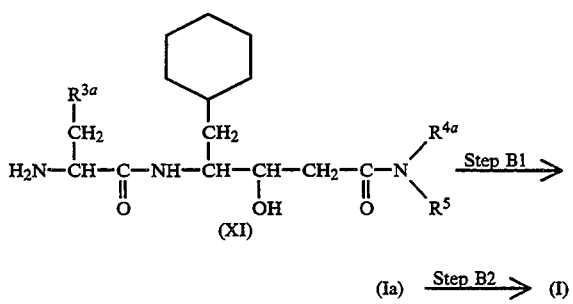
(XI)

(Ia) $\xrightarrow{\text{Step B2}}$ (I)

Reaction Scheme A

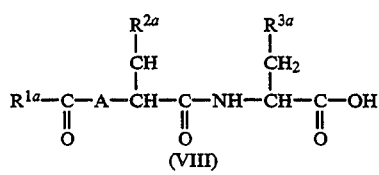
(VIII)

+

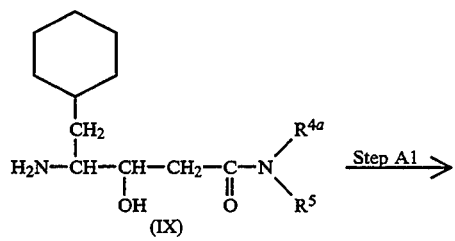
(IX)

$\xrightarrow{\text{Step A1}}$

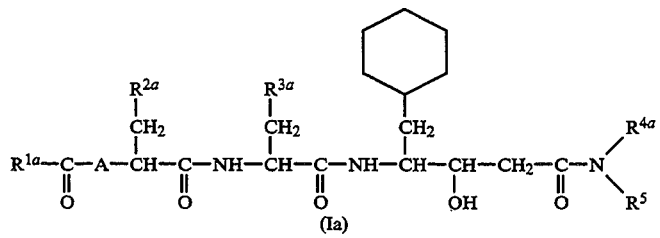
(Ia)

$\Big\downarrow$ Step A2

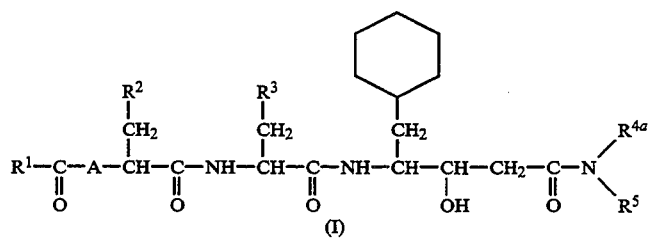
(I)

Reaction Scheme C
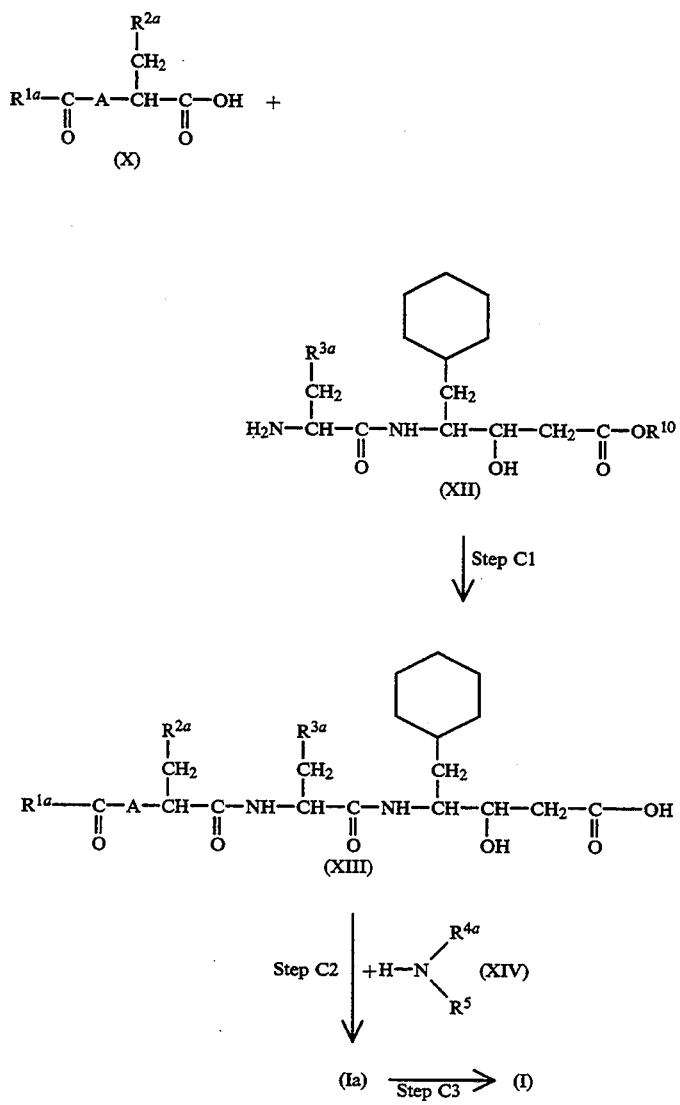
Reaction Scheme D
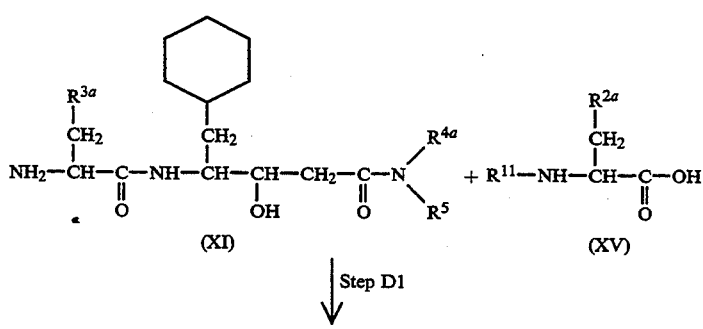

Reaction Scheme D

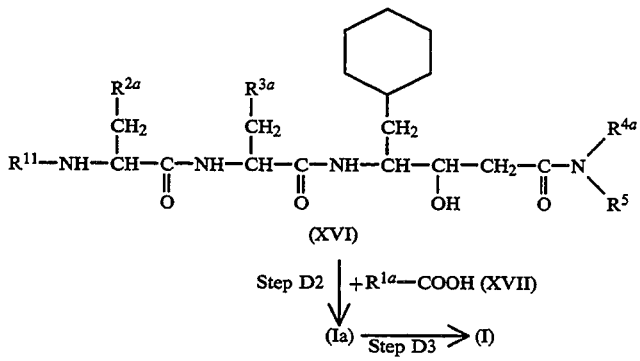

Reaction Scheme E

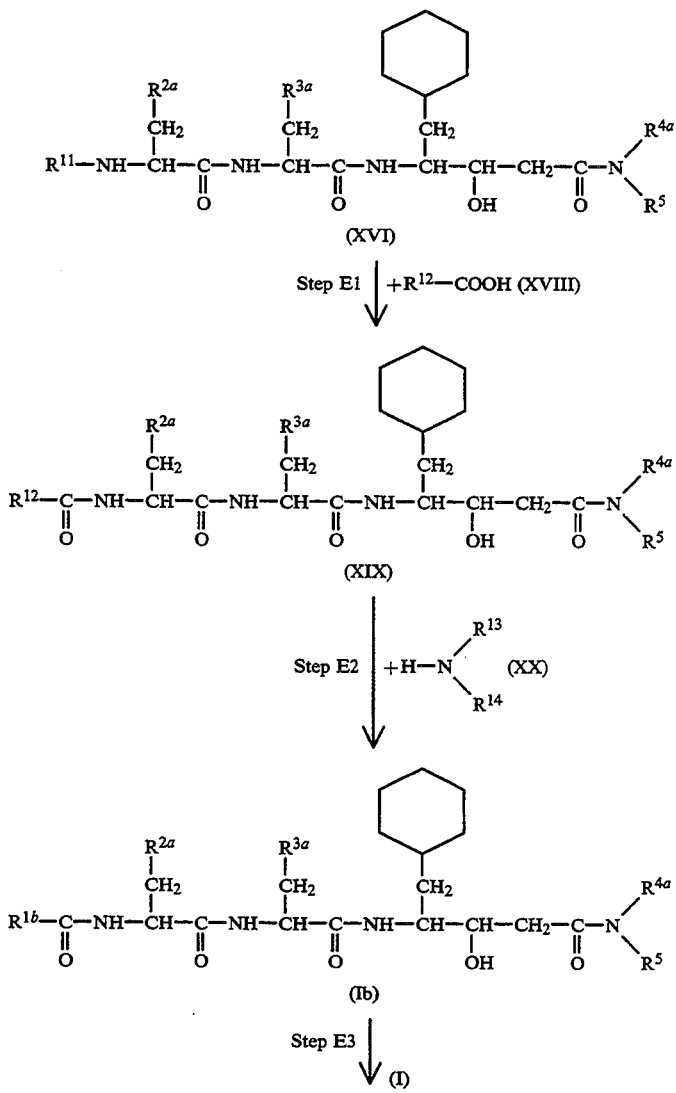

In the above formulae, $R^1$, $R^2$, $R^3$, $R^4$, $R^5$ and A are as defined above; $R^{1a}$, $R^{2a}$, $R^{3a}$ and $R^{4a}$ may represent any of the groups defined for $R^1$, $R^2$, $R^3$ and $R^4$, respectively, but in which any groups which may undesirably participate in the respective reactions have been protected; $R^{1b}$ represents an alkyl group substituted by a group of formula:

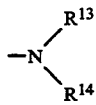

(in which $R^{13}$ and $R^{14}$ are as defined below); $R^{10}$ represents a $C_1$-$C_6$, preferably $C_1$-$C_4$, alkyl group or an aralkyl group; $R^{11}$ represents an amino-protecting group; $R^{12}$ represents a haloalkyl group; and $R^{13}$ and $R^{14}$ are the same or different and each represents a hydrogen atom, a $C_1$-$C_6$ alkyl group, an aryl group, an aralkyl group or a $C_3$-$C_8$ cycloalkyl group, as defined for $R^1$, or together with the nitrogen atom to which they are attached, represent a non-aromatic heterocyclic group, as defined for $R^1$.

In these reactions, the free acids and amides shown may, if desired or if required by the particular reaction chosen, be replaced by an appropriate active derivative, as described in more detail hereafter.

There is no particular restriction on the nature of the protecting group which may be represented by $R^{1a}$, $R^{4a}$ and $R^{11}$ and any such group commonly used in the field of amino acid chemistry may equally be employed here. For example, suitable amino-protecting groups include: carbonate residues, especially aralkyloxycarbonyl groups, such as the benzyloxycarbonyl and p-methoxybenzyloxycarbonyl groups, alkoxycarbonyl groups, such as the t-butoxycarbonyl group, and other carbonate residues, such as the 9-fluorenylmethyloxycarbonyl groups. Examples of imino-protecting groups include the 2,4-dinitrophenyl group.

The principal reactions in Reaction Schemes A, B, C, D and E are standard condensation reactions of the type conventionally used in peptide synthesis and they may be carried out according to any of the well known techniques employed in peptide synthesis, for example by the azide method, the active ester method, the mixed acid anhydride method, the carbodiimide method or the condensation method. The reactive derivatives employed in these reactions are those reactive derivatives conventionally employed in such methods. Certain of these methods are described in more detail below.

Azide Method

First, the carboxylic acid of formula (VIII) (Reaction Scheme A), (X) (Reaction Scheme B or C), (XIII) (Reaction Scheme C), (XV) (Reaction Scheme D), (XVII) (Reaction Scheme D) or (XVIII) (Reaction Scheme E), as such, or, more usually, in the form of its corresponding alkyl ester, is treated with hydrazine in an inert solvent, to give the corresponding acid hydrazide. The nature of the solvent employed is not critical and any solvent commonly employed in this type of reaction may equally be employed here; however, we generally find it convenient to use a polar solvent, especially a fatty acid amide, such as dimethylformamide. Also, the reaction temperature is not critical and the reaction will take place over a wide range of temperatures; we generally find it convenient to carry out the reaction at about ambient temperature. The resulting hydrazide is then reacted with a nitrite, to convert it into an azide, after which the azide is reacted with the amine of formula (IX) (Reaction Scheme A), (XI) (Reaction Scheme B or D), (XII) (Reaction Scheme C), (XIV) (Reaction Scheme C) or (XVI) (Reaction Scheme D or E).

Examples of nitrites which may be employed include: alkali metal nitrites, such as sodium nitrite; and alkyl nitrites, such as isoamyl nitrite.

The reaction of the acid hydrazide with the nitrite and the subsequent reaction of the resulting azide with the amine of formula (IX) (Reaction Scheme A), (XI) (Reaction Scheme B or D), (XII) (Reaction Scheme C), (XIV) (Reaction Scheme C) or (XVI) (Reaction Scheme D or E) are commonly carried out in the same reaction solution, without intermediate isolation of the azide. Both reactions are preferably carried out in the presence of an inert solvent. The nature of the solvent is not critical, provided that it does not interfere with the reaction. Suitable solvents include, for example: amides, such as dimethylformamide or dimethylacetamide; sulfoxides, such as dimethyl sulfoxide; and pyrrolidones, such as M-methylpyrrolidone. Although there is no criticality as to the reaction temperature, the reaction with the nitrite is preferably effected at a relatively low temperature. e.g. from $-50°$ C. to $0°$ C., whilst the reaction of the azide with the amine is preferably effected at a temperature of from $-10°$ C. to $+10°$ C. The time required for each of these reactions will vary, depending upon the nature of the reagents and the reaction temperature, but a period of from 5 minutes to 1 hour and a period of from 10 hours to 5 days will normally suffice for the reaction with the nitrite and the reaction of the azide with the amine, respectively.

Active Ester Method

In this method, the carboxylic acid of formula (VIII) (Reaction Scheme A), (X) (Reaction Scheme B or C), (XIII) (Reaction Scheme C), (XV) (Reaction Scheme D), (XVII) (Reaction Scheme D) or (XVIII) (Reaction Scheme E) is first converted to an active ester by reacting it with a suitable reagent for producing active esters, after which this active ester is reacted with the amine of formula (IX) (Reaction Scheme A), (XI) (Reaction Scheme B or D), (XII) (Reaction Scheme C), (XIV) (Reaction Scheme C) or (XVI) (Reaction Scheme D or E).

Formation of the active ester is preferably effected by reacting the carboxylic acid of formula (VIII), (X), (XIII), (XV), (XVII) or (XVIII) with, for example, an N-hydroxyimide compound, such as N-hydroxysuccinimide, 1-hydroxybenzotriazole or N-hydroxy-5-norbornene-2,3-dicarboximide. The reaction to form the active ester is preferably effected in the presence of a condensing agent, such as dicyclohexylcarbodiimide or carbonyldiimidazole.

The reaction to form the active ester is preferably effected in the presence of an inert solvent, the nature of which is not critical, provided that it has no adverse effect upon the reaction. Suitable solvents include, for example: halogenated hydrocarbons, preferably halogenated aliphatic hydrocarbons, such as methylene chloride or chloroform; ethers, such as diethyl ether or tetrahydrofuran; and amides, such as dimethylformamide or dimethylacetamide.

The reaction temperature may vary over a wide range, for example from $-10°$ C. to room temperature. The time required for the reaction will vary widely, depending upon the nature of the reagents and upon the reaction temperature, but a period of from 30 minutes to 10 hours will normally suffice.

Reaction of this active ester with the amine of formula (IX) (Reaction Scheme A), (XI) (Reaction Scheme B or D), (XII) (Reaction Scheme C), (XIV) (Reaction Scheme C) or (XVI) (Reaction Scheme D or E) may be carried out with or without intermediate isolation of the active ester. Reaction of the active ester with the amine is preferably effected in the presence of an inert solvent, examples of which are as given for the preparation of the active ester itself. The temperature required for the reaction is not particularly critical and, for this reason, we normally prefer to carry out the reaction at about ambient temperature. The time required for the reaction will vary widely, but a period of from 30 minutes to 10 hours will normally suffice.

Mixed Acid Anhydride Method

In this method, the carboxylic acid of formula (VIII) (Reaction Scheme A), (X) (Reaction Scheme B or C), (XIII) (Reaction Scheme C), (XV) (Reaction Scheme D), (XVII) (Reaction Scheme D) or (XVIII) (Reaction Scheme E) is first converted to a mixed acid anhydride, and this is then reacted with the amine of formula (IX) (Reaction Scheme A), (XI) (Reaction Scheme B or D), (XII) (Reaction Scheme C), (XIV) (Reaction Scheme C) or (XVI) (Reaction Scheme D or E).

Preparation of the mixed acid anhydride is effected by reacting the acid of formula (VIII), (X), (XIII), (XV), (XVII) or (XVIII) with a suitable reagent, preferably in the presence of an inert solvent. Suitable reagents include: lower alkyl haloformates, such as ethyl chloroformate or isobutyl chloroformate; and di(lower alkyl) cyanophosphonates, such as diethyl cyanophosphonate. Examples of suitable inert solvents include the amides and ethers referred to in relation to the active ester method.

This reaction is preferably effected in the presence of an organic amine, such as triethylamine or N-methylmorpholine. The reaction temperature may vary over a wide range, for example from $-10°$ C. to room temperature. The period required for the reaction will also vary widely, depending upon such factors as the nature of the reagents and the reaction temperature, but a period of from 30 minutes to 5 hours will normally suffice.

Reaction of the resulting mixed acid anhydride with the amine of formula (IX), (XI), (XII), (XIV) or (XVI) is preferably effected in the presence of an inert solvent, the nature of which is not critical, provided that it does not interfere with the reaction. Suitable solvents include the amides and ethers hereinbefore exemplified in relation to the active ester method. The reaction will take place over a wide range of temperatures, but we generally find it convenient to carry out the reaction at a temperature of from 0° C. to about ambient temperature. The time required for the reaction will vary, depending upon many factors, such as the nature of the reagents and the reaction temperature, but a period of from 1 hour to 24 hours will normally suffice.

Condensation Method

In this method, the carboxylic acid of formula (VIII) (Reaction Scheme A), (X) (Reaction Scheme B or C), (XIII) (Reaction Scheme C), (XV) (Reaction Scheme D), (XVII) (Reaction Scheme D) or (XVIII) (Reaction Scheme E) is directly reacted with the amine of formula (IX) (Reaction Scheme A), (XI) (Reaction Scheme B or D), (XII) (Reaction Scheme C), (XIV) (Reaction Scheme C) or (XVI) (Reaction Scheme D or E). Such a reaction is preferably effected in the presence of a condensing agent, such as dicyclohexylcarbodiimide or carbonyldiimidazole. Otherwise, the reaction conditions and solvents are similar to those already described in relation to the active ester method.

The above reactions are the reactions involved in Steps A1, B1, C1, C2, D1, D2 and E1 of Reaction Schemes A, B, C, D and E. The other reactions involved are as follows.

Step C1

In Reaction Scheme C, Step C1, the reaction involves the reaction of an acid of formula (X) with an amine of formula (XII), as described generally above, followed by hydrolysis to remove the group represented by $R^{10}$. The hydrolysis reaction may be carried out as described in relation to the removal of carboxy protecting groups hereafter.

Step D2

In Reaction Scheme D, Step D2, the amino-protecting group R is first removed, before subjecting the resulting compound to reaction with an acid of formula (XVII), as described generally above. Removal of the amino-protecting group may take place as described hereafter in relation to the removal of protecting groups generally. Step E2

In this step, the compound of formula (XIX), prepared as in Step E1, is reacted with a compound of formula (XX):

(in which $R^{13}$ and $R^{14}$ are as defined above), to give a compound of formula (Ib). The reaction is preferably carried out by treating the compound (XIX) with the amine of formula (XX) in an inert solvent, the nature of which is not critical, provided that it has no adverse effect on the reaction. Suitable solvents are as described above in relation to the peptide-forming reaction of acids and amines in the activated ester reaction.

The reaction is preferably carried out in the presence of a base, the nature of which is not critical to the reaction. Suitable bases include, for example: alkali metal carbonates and bicarbonates, such as sodium carbonate, potassium carbonate or sodium bicarbonate; and organic amines, such as triethylamine or N-methylmorpholine.

The reaction will take place over a wide range of temperatures, and the precise temperature chosen is not critical to the invention. However, we generally find it convenient to carry out the reaction at a temperature in the range from $-30°$ C. to $+100°$ C. (more preferably from 0° C. to 50° C.). The time required for this reaction will vary, depending upon the nature of the reagents and the reaction temperature, but a period of from 30 minutes to 2 days will normally suffice.

Protecting Reactive Groups

Where the reagents employed in any of the above reactions, that is to say the carboxylic acids of formulae (VIII), (X), (XV), (XVII) and (XVIII) or the amines of formulae (IX), (XI), (XII), (XIV), (XVI) and (XX) or their reactive derivatives, contain active groups (e.g. amino, carboxy or imino groups including e.g. the imino group in the imidazolyl moiety of histidine) which are not intended to take part in peptide bond formation but which might interfere with the above reactions or undesirably participate in them, it is desirable that these groups should be protected before the reaction to form the peptide linkage and then, after that reaction, that the protected groups should be deprotected.

There is no particular limitation on the nature of the protecting group employed and such groups are well-known in peptide chemistry. For example, suitable amino-protecting groups include: carbonate residues, such as the benzyloxycarbonyl, R-methoxybenzyloxycarbonyl, t-butoxycarbonyl and 9-fluorenylmethyloxycarbonyl groups. Suitable carboxy-protecting groups include the lower alkyl groups, e.g. the methyl, ethyl, propyl or t-butyl groups, and aralkyl groups, such as the benzyl group. Examples of imino-protecting groups include the 2,4-dinitrophenyl group.

The protecting groups may be inserted and then removed by conventional methods. For example, where the amino-protecting group is a t-butoxycarbonyl group or the carboxy-protecting group is a t-butyl group, this group may be removed by treatment with an acid (e.g. hydrochloric acid, hydrofluoric acid, trifluoroacetic acid or boron trifluoride, preferably in the form of a complex, e.g. the diethyl etherate), optionally in the presence of a cation scavenger (e.g. anisole or thioanisole). Such a reaction is preferably effected in an inert solvent. The nature of the solvent is not critical, provided that it has no adverse effect on the reaction, and examples of suitable solvents include: ethers, such as dioxane; lower alcohols, such as methanol; and amides, such as dimethylformamide. The reaction will take place over a wide range of temperatures, and the precise temperature chosen is not critical; we generally find it convenient to carry out the reaction at, for example, a temperature of from 0° C. to 30° C. The time required for the reaction may vary widely, depending upon many factors, notably the nature of the reagents and the reaction temperature; however, a period of from 20 minutes to 1 hour will normally suffice.

When the amino or imino group is protected by an aralkyloxycarbonyl group or other carbonate residue and wren the carboxy group is protected by an aralkyl group, the protecting group can be removed by catalytic reduction of the protected compound in the presence of hydrogen (for example under a hydrogen pressure of from atmospheric to 10 atmospheres) and in the presence of a suitable hydrogenation catalyst, for example palladium-on-carbon or palladium black. The reaction is preferably effected in the presence of an inert solvent, the nature of which is not critical, provided that it has no adverse effect on the reaction, and examples of suitable solvents include: lower alcohols, such as methanol or ethanol; and ethers, such as tetrahydrofuran. We generally find it convenient to carry out the reaction at about ambient temperature, although this is not critical. The time required for the reaction may vary widely, but a period of from 30 minutes to 8 hours will normally suffice.

When the carboxy group is protected by a lower alkyl group, the protecting group may be removed by reacting the protected compound with an alkali (e.g. an alkali metal compound, preferably hydroxide, such as sodium hydroxide or potassium hydroxide). The reaction is preferably effected in a solvent, the nature of which is not critical, provided that it has no adverse effect on the reaction. An aqueous solvent, such as aqueous methanol or aqueous ethanol is normally preferred. The reaction will take place over a wide range of temperatures, e.g. from 0° to 30° C. The time required for the reaction may vary widely, but a period of from 30 minutes to 5 hours will normally suffice.

Where the imino nitrogen atom in the imidazole moiety of a histidine residue is protected by a 2,4-dinitrophenyl, this may be removed by treating the protected compound with 2-mercaptoethanol. The reaction temperature is not critical, and we generally find it convenient to carry out the reaction at about ambient temperature.

Conversion Reactions

If desired, certain groups in the compound of formula (I) prepared as described above may be converted to certain other groups by appropriate reactions well-known in the field of peptide synthesis. For example, if desired, any acyl group within the resulting compound of formula (I) may be converted to any other acyl group; the reactions and reaction conditions involved in such conversions are well known in the art.

After completion of any of the above reactions or of the final such reaction, the desired compound may be isolated from the reaction mixture by conventional means. For example, one suitable recovery procedure comprises: if necessary, neutralizing the reaction mixture; removing the insoluble residue, if any, by filtration; and then distilling off the solvent to give the desired compound. If necessary, this compound may be further purified by such conventional means as recrystallization, reprecipitation or the various chromatography techniques, such as column chromatography or preparative thin layer chromatography.

Preparation of Starting Materials

The starting material of formula (IX) (Reaction Scheme A) may be prepared, for example, by protecting the amino group of cyclostatine or an analog thereof, which is a compound of formula:

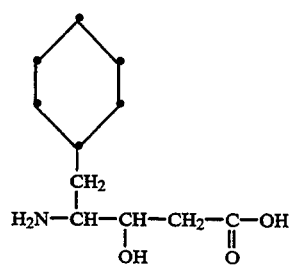

by conventional means, reacting the resulting protected compound with an amine of formula:

by a procedure similar to that described above in relation to Step C2 or E2, and then removing the protecting group. The cyclostatine or analog thereof may be prepared by the method of J. Boger et al. [J. Med. Chem., 28, 1779 (1985)].

Also, in Reaction Scheme C, certain of the starting materials of formula (XII) are known compounds, or they may be prepared, for example, as described by R. P. Ahlqist [Prog. Drug Res., 20, E. Junker, Ed., Birkhauser Verlag (1976)].

Certain of the other starting materials employed in Reaction Schemes A–E, described above, may be prepared as illustrated in the following Reaction Schemes F–J.

Thus, alanine derivatives having an aromatic heterocyclic group as a substituent at the 3-position can easily be prepared by the reactions shown in Reaction Scheme F:

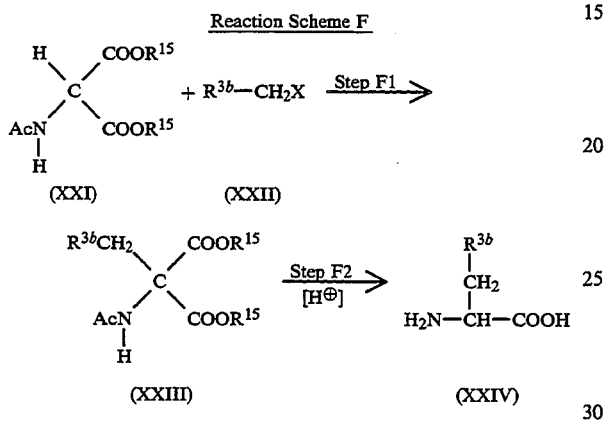

In the above formulae, Ac represents an acetyl group (although this can, if desired, be replaced by another amino-protecting group, e.g. as illustrated above); $R^{3b}$ represents an aromatic heterocyclic group (as included in the groups defined above for $R^3$); X represents a halogen atom (and preferably a bromine atom), and $R^{15}$ represents a lower alkyl group or other carboxy-protecting group removable by treatment with an acid (preferably an ethyl group).

In Step F1 of this reaction scheme, the compound of formula (XXI) is first treated with a base (preferably an alkali metal hydride, such as sodium hydride) and is then reacted with a substituted methyl halide, preferably bromide, of formula (XXII), to give the compound of formula (XXIII). This is then reacted, in Step F2, with an acid (which may be a mineral acid or an organic acid, preferably hydrochloric acid), to give the alanine derivative of formula (XXIV).

Certain of the starting materials of formula (X) (Reaction Schemes B and C) can be prepared as illustrated in Reaction Schemes G, H and I:

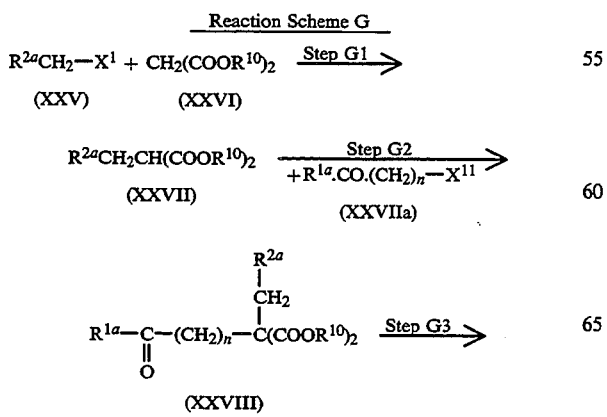

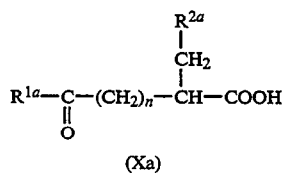

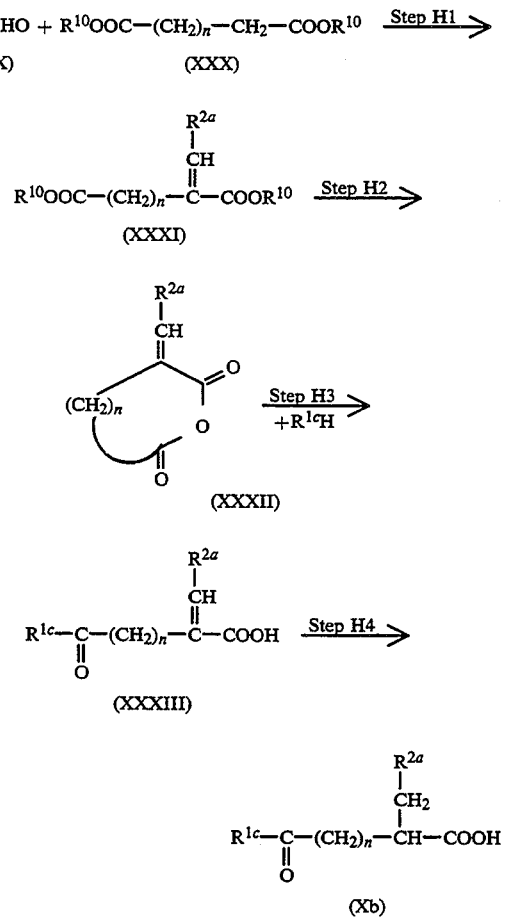

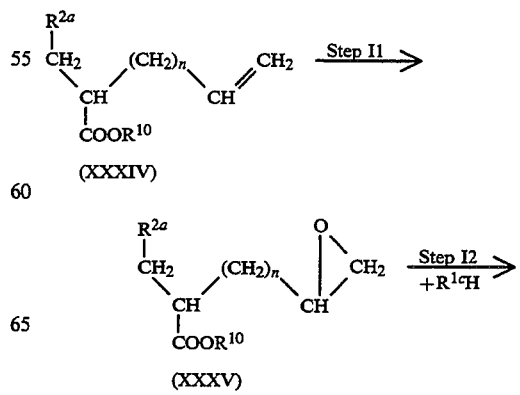

-continued
Reaction Scheme I

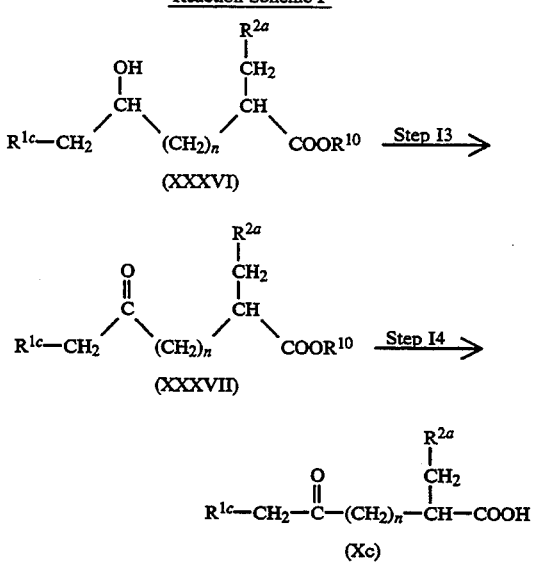

(XXXVI)

(XXXVII)

$$R^{1c}-CH_2-\overset{O}{\underset{\|}{C}}-(CH_2)_n-\overset{\overset{R^{2a}}{|}}{\underset{|}{CH}}-COOH$$

(Xc)

In the above formulae, $R^{1a}$, $R^{2a}$, $R^{10}$ and n are as defined above; $R^{1c}$ represents a heterocyclic group or a group of formula (II), as defined in relation to the groups which may be represented by $R^1$ or which may be substituents on the alkyl groups represented by $R^1$; $X'$ and $X''$ each represents a halogen atom, for example the fluorine, chlorine, bromine or iodine atoms.

The reactions may be carried out as follows:

Reaction Scheme G, Step G1

In this reaction, a substituted methyl halide of formula (XXV) is reacted with a malonic acid ester of formula (XXVI). This reaction may be carried out, for example, by the method described in Organic Synthesis Coll., 3, 705.

Step G2

In this step, the mono-substituted malonic acid ester of formula (XXVII) obtained as described in Step G1 is reacted with a halide of formula (XXVIIa), to give the corresponding di-substituted malonic acid ester of formula (XXVIII), for example by the same method as in Step G1.

Step G3

In this step, the di-substituted malonic acid ester of formula (XXVIII) is subjected to hydrolysis and decarboxylation, to give the desired compound of formula (Xa). This reaction may be carried out by conventional means well known in this art.

Reaction Scheme H, Step H1

This reaction scheme prepares a compound of formula (X) in which $R^1$ represents a heterocyclic group or a group of formula (II), i.e. the group defined as $R^{1c}$. In the first step of this reaction, an aldehyde of formula (XXIX) is reacted with a glutaric acid diester or adipic acid diester of formula (XXX), to give the compound of formula (XXXI).

Step H2

In this step, the compound of formula (XXXI) is subjected to hydrolysis by conventional means to remove the protecting group $R^{10}$ and is then heated in the presence of acetic anhydride, to afford the acid anhydride of formula (XXXII).

Step H3

The anhydride of formula (XXXII) is reacted with an amine of formula $R^{1c}H$, to cause ring opening and give the compound of formula (XXXIII).

Step H4

Finally, the compound of formula (XXXIII) is subjected to catalytic hydrogenation, which may take place under atmospheric pressure in the presence of a suitable catalyst, e.g. palladium-on-carbon or platinum black, to give the desired compound of formula (Xb).

Reaction Scheme I Step I1

In this reaction scheme, there is prepared a compound of formula (X) in which $R^1$ represents a methyl group substituted by a heterocyclic group or substituted by a group of formula (II), as defined above, i.e. a group of formula $R^{1c}$—$CH_2$— (in which $R^{1c}$ is as defined above).

In the first step of this reaction scheme, the compound of formula (XXXIV) is reacted with an oxidizing agent to give the epoxide of formula (XXXV). The oxidation is preferably effected with an organic peracid, such as 3-chloroperbenzoic acid.

The starting material of formula (XXXIV) may be prepared by reacting a propionic acid ester of formula $R^{2a}CH_2CH_2COOR^{10}$ (in which $R^{2a}$ and $R^{10}$ are as defined above) with an alkenyl halide of formula $CH_2=CH-(CH_2)_n-Y$ (in which n is as defined above and Y represents a halogen atom, e.g. as defined for $X'$). Suitable alkenyl halides include, for example, allyl chloride or allyl bromide. The reaction is preferably effected in the presence of a metallic base, such as lithium diisopropylamide, butyllithium, metallic sodium or sodium hydride.

Step I2

In this step, the epoxide of formula (XXXV) is reacted with an amine of formula $R^{1c}H$, to give the compound of formula (XXXVI). The reaction may take place under conditions similar to those employed in Step E2, except that, in this case, the presence of a base is not necessary.

Step I3

In this step, the compound of formula (XXXVI) is oxidized, using an oxidizing agent such as a sulfur trioxide/pyridine complex, pyridinium chlorochromate or pyridinium dichromate, to give the compound of formula (XXXVII).

Step I4

Finally, if necessary, the carboxy-protecting group $R^{10}$ is removed from the compound of formula (XXXVII), to give the compound of formula (Xc).

The compounds prepared in Reaction Schemes G, H and I are mixtures of isomers and, if desired, these may be used as such in the subsequent reactions (e.g. those of Reaction Schemes A–F), or the individual isomers can be separated and recovered using conventional techniques, for example, the various chromatography techniques, such as column chromatography, prior to use in the subsequent reactions.

However, if desired, the compounds of formula (X) can be synthesized stereospecifically, using the methods shown in Reaction Scheme J:

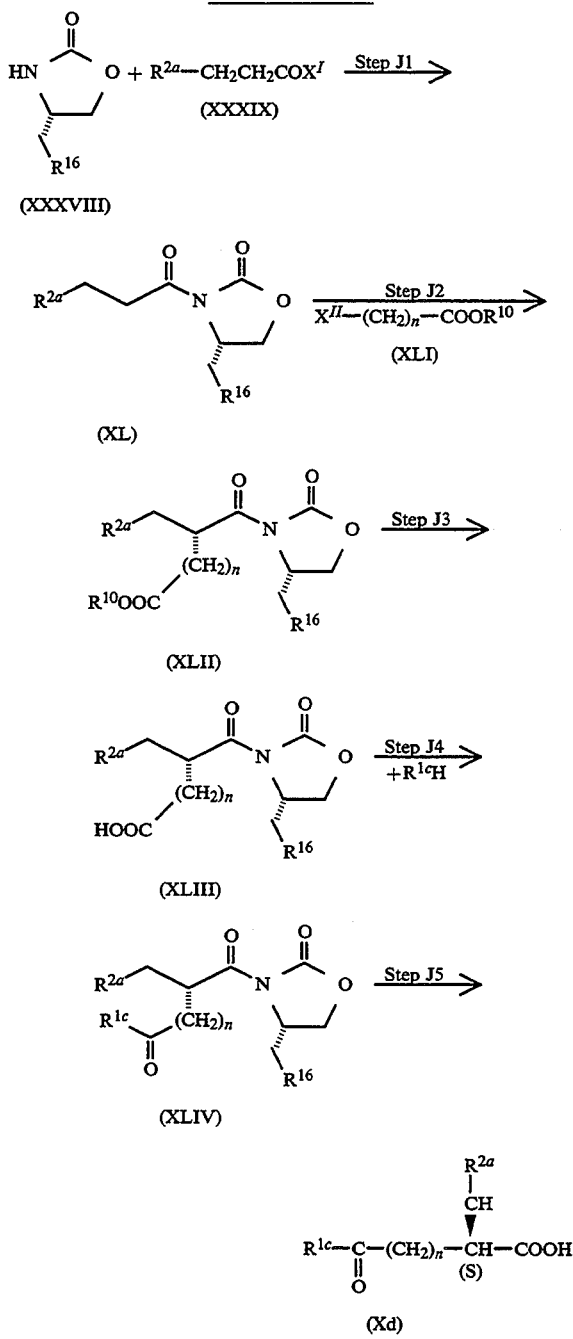

base (e.g. lithium diisopropylamide), and is then reacted stereospecifically with the compound of formula (XLI), to give the compound of formula (XLII).

Step J3

In this step, the compound of formula (XLII) is subjected to catalytic hydrogenation (e.g., hydrogenation in the presence of a palladium-on-carbon catalyst) or to hydrolysis to remove the protecting group $R^{10}$ and give the compound of formula (XLIII).

Step J4

The compound of formula (XLIII) is reacted with an amine of formula $R^{1c}H$, in the presence of a condensing agent (e.g., diethyl cyanophosphonate and triethylamine), to give the compound of formula (XLIV).

Step J5

Finally, this compound of formula (XLIV) is subjected to hydrolysis under conventional conditions to give the compound of formula (Xd).

INHIBITION OF RENIN ACTIVITY

The ability of various compounds of the invention to inhibit the activity of renin was determined according to the following method, which follows essentially the procedure of Kokubu et al. [Hypertension, 5, 191–197 (1983)].

Specifically, each test compound was dissolved in 60% v/v aqueous ethanol. Human renin activity in the presence and absence of each compound was measured using sheep angiotensinogen. The total volume of 1 ml of assay mixture contained 0.1 mole/litre phosphate buffer (pH 7.3), human renin (equivalent to 0.5 ng angiotensin I per ml per minute), sheep angiotensinogen (equivalent to 200 ng angiotensin I) $1 \times 10^{-6}M$ of the test compound, 6% v/v ethanol and angiotensinase inhibitors (10 mmole/litre sodium ethylenediaminetetraacetate and 3.4 mmole/litre 8-hydroxyquinoline). The mixture was allowed to react for 10 minutes at 37° C., and then the reaction was stopped by placing the reaction tube in a boiling water bath for 5 minutes. The mixture was then centrifuged and the supernatant (0.05–0.1 ml) was used to assay remaining angiotensin I.

An identical experiment was carried out, as a control, except that the test compound was omitted. From the values obtained were calculated the % inhibition of renin activity achieved by each test compound. The results are shown in the following Table 9, in which the compounds of the invention are identified by the numbers of the Examples given hereafter in which are described their preparation. The values given are the mean of 3 or 4 experiments.

In the above formula, $R^{1c}$, $R^{2a}$, $R^{10}$, X', X" and n are as defined above and $R^{16}$ represents a phenyl group or a substituted phenyl group, e.g. as illustrated in relation to $R^2$, or a $C_1$-$C_6$ alkyl group, e.g. as illustrated in relation to $R^3$.

Step J1

In this step, the compound of formula (XXXVIII) is treated with a base (especially a base containing an alkali metal, such as butyllithium), to afford an alkali metal salt, which is then reacted with the halogen compound of formula (XXXIX) to give the compound of formula (XL).

Step J2

The compound of formula (XL) is converted to an alkali metal salt by reaction with a metal-containing

TABLE 9

| Compound of Example No. | Inhibitory Activity (%) |
|---|---|
| 2 | 91.2 |
| 3 | 92.2 |
| 8 | 96.5 |
| 9 | 94.0 |
| 11 | 96.9 |
| 13 | 96.6 |
| 15 | 96.3 |
| 31 | 98.2 |
| 42 | 96.7 |
| 43 | 91.2 |
| 64 | 97.5 |
| 65 | 97.4 |
| 66 | 95.7 |
| 69 | 96.1 |
| 73 | 97.7 |
| 76 | 97.1 |
| 98 | 98.1 |

TABLE 9-continued

| Compound of Example No. | Inhibitory Activity (%) |
|---|---|
| 100 | 96.1 |
| 101 | 94.9 |
| 103 | 98.6 |
| 104 | 98.6 |
| 105 | 98.0 |
| 106 | 98.2 |
| 107 | 98.4 |
| 108 | 98.6 |
| 109 | 98.3 |
| 110 | 98.3 |
| 111 | 96.0 |
| 112 | 98.0 |

As can be seen from the results in the Table above, the compounds of the present invention have a substantial inhibitory effect on the activity of human renin and are thus useful for the diagnosis and therapy of renin-/angiotensin-induced hypertension in humans and other animals. Furthermore, we have found from biliary excretion and blood plasma experiments that the compounds are well absorbed from the digestive tract upon oral administration and this has been supported by tests in marmosets. Moreover, the compounds of the invention are readily soluble in water. Furthermore, in animal tests using mice and rats, the compounds of the present invention have demonstrated a lower toxicity than do the prior art compounds. All of these results indicate that the compounds of the invention will be of considerable therapeutic value and that, unlike related compounds proposed previously, they may be administered, in practice, by the oral route, as well as by the more conventional parenteral route.

The compounds of the invention may be formulated in conventional dosage forms, normally in admixture with a pharmaceutical carrier or diluent. For oral administration, the compounds can be formulated, for example, as tablets, capsules, granules, powders or syrups. For parenteral administration, they may be formulated as injections in a suitable liquid or as suppositories. The dosage will vary, depending upon the age, symptoms and body weight of the patient, as well as upon the desired end result; however, we would normally anticipate administering a dose of from 0.01 mg to 100 mg/kg body weight per day, which may be administered as a single dose or in divided doses.

The invention is further illustrated by the following non-limiting Examples. Preparation of certain of the starting materials employed in these Examples is illustrated by the subsequent Preparations. The biological activities of certain of the compounds of the invention are then illustrated in the subsequent Experiments. In the Examples and Preparations, values of optical rotation were measured using the sodium D-line, i.e. all are $[\alpha]_D$. Also, where an Rf value is given in these Examples and Preparations in relation to a product, it was determined by thin layer chromatography on silica gel, using a 10:1 by volume mixture of methylene chloride and methanol as the developing solvent, unless otherwise specified.

EXAMPLE 1

N-{N-[(2R),3-Morpholinocarbonyl-2-(1-naphthylmethyl)propionyl]-3-(4-thiazolyl)-L-alanyl}-cyclostatin-(2-morpholinoethyl)amide 1(a)

N-[N-(t-Butoxycarbonyl)-3-(4-thiazolyl)-L-alanyl]-cyclostatin-(2-morpholinoethyl)amide 0.16 ml (1.05 mmole) of diethyl cyanophosphonate (95%, i.e. of a purity about 95%) and 0.44 ml (3.15 mmole) of triethylamine were added to a solution of 261 mg (0.96 mmole) of N-(t-butoxycarbonyl)-3-(4-thiazolyl)-L-alanine and 384 mg (0.96 mmole) of cyclostatin-(2-morpholinoethyl)amide dihydrochloride [prepared as described in Preparation 17(b)] dissolved in 10 ml of anhydrous tetrahydrofuran under an atmosphere of nitrogen, whilst ice-cooling. The reaction mixture was then stirred at the same temperature for 2 hours. At the end of this time, solvent was removed by distillation under reduced pressure, and the residue was purified by thin layer chromatography on a silica gel plate (developing solvent: a 10 : 1 by volume mixture of chloroform and methanol), to afford 450 mg (81%) of the title compound as white crystals, melting at 73°–75° C.

Mass Spectrum m/e. 582 (M$^+$+1).

1(b)

N-{N-[(2R)-3-Morpholinocarbonyl-2-(1-naphthlmethyl)propionyl]-3-(4-thiazolyl)-L-alanyl}-cyclostatin-(2-morpholinoethyl)amide A solution of 310 mg (0.53 mmole) of N-[N-(t-butoxycarbonyl)-3-(4-thiazolyl)-L-alanyl]-cyclostatin-(2-morpholinoethyl)amide [prepared as described in Example 1(a) above] in 5 ml of a 4N solution of hydrogen chloride in dioxane was stirred at room temperature for 30 minutes, after which the solvent was removed by distillation under reduced pressure. The residue was dried thoroughly, after which it was suspended in 10 ml of anhydrous tetrahydrofuran. 192 mg (0.59 mmole) of (2R)-3-morpholinocarbonyl-2-(1-naphthylmethyl)propionic acid (prepared as described in Preparation 4) were then added to the resulting solution. 0.09 ml (0.59 mmole) of diethyl cyanophosphonate (95%) and 0.36 ml (2.58 mmole) of triethylamine were then added to this mixture, whilst ice-cooling and under an atmosphere of nitrogen, and the reaction mixture was stirred whilst continuing the ice-cooling for 2 hours. At the end of this time, the solvent was removed by distillation under reduced pressure, and the residue was purified by thin layer chromatography on a silica gel plane (developing solvent: a 10 : 1 by volume mixture of chloroform and methanol), to afford 220 mg (52%) of the title compound, melting at 93°–96° C.

Elemental analysis: Calculated for $C_{42}H_{58}O_7N_6S$ $H_2O$ C, 62.35%; H, 7.47%; N, 10.39%; S, 3.96%. Found: C, 62.33%; H, 7.34%; N, 10.09%; S, 3.76%.

EXAMPLE 2

N-{N-[(2R)-3-Morpholinocarbonyl-2-(1-naphthylmethyl)propionyl]-3-(4-thiazolyl)-DL-alanyl}-cyclostatin-(2-morpholinoethyl)amide 2(a)

N-[N-(t-Butoxycarbonyl)-3-(4-thiazolyl)-DL-alanyl]-cyclostatin-(2-morpholinoethyl)amide A solution of 314 mg (0.74 mmole) of N-(t-butoxycarbonyl)-cyclostation-(2-morpholinoethyl)amide [prepared by a procedure similar to that described in Preparation 17(a)] in 5 ml of a 4N solution of hydrogen chloride in dioxane was agitated at room temperature for 30 minutes. At the end of this time, the solvent was removed by distillation under reduced pressure. Diethyl ether was added to the residue, and then the solvent was again removed by distillation under reduced pressure. The residue was dried thoroughly and suspended, together with 200 mg (0.73 mmole) of N-(t-butoxycarbonyl)-(4-thiazolyl)-DL-alanine, in 10 ml of anhydrous tetrahydrofuran. 0.13 ml (0.86 mmole) of diethyl cyanophosphonate (95%) and 0.34 ml (2.44 mmole) of triethylamine were then added to this suspension, whilst ice-cooling and under an atmosphere of nitrogen. The mixture was then stirred whilst continuing the ice-cooling for 2 hours. At the end of this time, the solvent was removed by distillation under reduced pressure, and the residue was purified by thin layer chromatography on a silica gel plate (developing solvent: a 10: 1 by volume mixture of chloroform and methanol), to afford 404 mg (95%) of the title compound as white crystals, melting at 73°–75° C.

Mass Spectrum m/e: 582 (M++1).

Elemental analysis: Calculated for $C_{28}H_{47}N_5O_6S$ $H_2O$: C, 56.07%; H, 8.23%; N, 11.68%; S, 5.34%. Found: C, 56.31%; H, 7.96%; N, 11.41%; S, 5.70%.

2(b)
N-{N-[(2R)-3-Morpholinocarbonyl-2-(1,naphthylmethyl) propionyl]-3-(4-thiazolyl)-DL-alanyl}-cyclostatin-(2-morpholinoethyl)amide A solution of 280 mg (0.48 mmole) of N-[N-(t-butoxycarbonyl)-3-(4-thiazolyl)-DL-alanyl]-cyclostatin-(2-morpholinoethyl)amide [prepared as described in Example 2(a) above] dissolved in 5 ml of a 4N solution of hydrogen chloride in dioxane was stirred at room temperature for 30 minutes. At the end of this time, the solvent was removed by distillation under reduced pressure. The residue was dried thoroughly, after which it was suspended in 10 ml of anhydrous tetrahydrofuran. 173 mg (0.53 mmole) of (2R)-3-morpholinocarbonyl-2-(1-naphthylmethyl)propionic acid (prepared as described in Preparation 4) were then added to the resulting solution, after which 0.09 ml (0.59 mmole) of diethyl cyanophosphonate (95%) and 0.34 ml (2.44 mmole) of triethylamine were added to the mixture, whilst ice-cooling and under an atmosphere of nitrogen. The reaction mixture was then stirred whilst continuing the ice-cooling for 2 hours. At the end of this time, the solvent was removed by distillation under reduced pressure, and the residue was purified by thin layer chromatography on a silica gel plate (developing solvent: a 10: 1 by volume mixture of chloroform and methanol), to afford 175 mg (46%) of the title compound, melting at 92°–95° C.

Elemental analysis: Calculated for $C_{42}H_{58}N_6O_7S$ $H_2O$: C, 62.35%; H, 7.47%; N, 10.39%; B, 3.96%. Found: C, 61.98%; H, 7.25%; N, 10.08%; S, 3.77%.

EXAMPLE 3
N-{N-[(2R)-3-Morpholinocarbonyl-2-(1-naphthylmethyl)propionyl]-3-(5-isoxazolyl)-L-alanyl}-cyclostatin-(2-morpholinoethyl)amide 3(a)
N-[N-(t-Butoxycarbonyl)-3-(5-isoxazolyl)-L-alanyl]-cyclostatin-(2-morpholinoethyl)amide 5 ml of a 4N solution of hydrogen chloride in dioxane were added to a solution of 0.125 g (0.29 mmole) of N-(t-butoxycarbonyl)-cyclostatin-(2-morpholinoethyl)amide [prepared as described in Preparation 17(a)] in 5 ml of dioxane, whilst ice-cooling, and the mixture was then stirred at room temperature for 2 hours. An the end of this time, the reaction mixture was evaporated to dryness under reduced pressure. A solution of 89 mg (0.348 mmole) of N-(t-butoxycarbonyl)-3-(5-isoxazolyl)-L-alanine (prepared as described in Preparation 8) dissolved in 15 ml of dimethylformamide was then added to the resulting residue. 0.13 g (12.76 mmole) of triethylamine and 57 mg (0.348 mmole) of diethyl cyanophosphonate (95%) were added to the mixture, whilst stirring, and the mixture was allowed to react at room temperature for 21 hours. At the end of this time, the solvent was removed by distillation under reduced pressure. Water was added to the residue, and the mixture was extracted with methylene chloride. The extract was dried, and the solvent was removed by distillation under reduced pressure. The residue was purified by column chromatography through silica gel, using a 1: 49 by volume mixture of methanol and methylene chloride as eluent, to afford 85 mg (51.8%) of the title compound as an oily substance.

3(b)
N-{N-[(2R)-3-Morpholinocarbonyl-2-(1-naphthylmethyl)propionyl]-3-(5-isoxazolyl)-L-alanyl}-cyclostatin-(2-morpholinoethyl)amide A solution of 85 mg (0.15 mmole) of N-[N-(t-butoxycarbonyl)-3-(5-isoxazolyl)-DL-alanyl]-cyclostatin-(2-morpholinoethyl)amide [prepared as described in Example 3(a) above] dissolved in 2 ml of a 4N solution of hydrogen chloride in dioxane was stirred at room temperature for 1.5 hours, after which the reaction mixture was evaporated to dryness under reduced pressure. The residue was suspended in tetrahydrofuran, and 49 mg (0.15 mmole) of (2R)-3-morpholinocarbonyl-2-(1-naphthylmethyl)propionic acid (prepared as described in Preparation 4), 67 mg (0.66 mmole) of triethylamine and 29 mg (0.18 mmole) of diethyl cyanophosphonate (95%) were added, whilst stirring, to the resulting suspension. The mixture was then stirred at room temperature for 3 hours, after which it was allowed to stand for 4 days. The solvent was then removed by distillation under reduced pressure, and the residue was purified by preparative thin layer chromatography on a silica gel plate (developing solvent: 10% by volume methanol in methylene chloride), to afford 74 mg (61.7%) of the title compound, melting at 84°–86° C.

Elemental analysis: Calculated for $C_{42}H_{57}N_6O_8$ $H_2O$: C, 63.70%; H, 7.51%; N, 10.61%. Found: C, 63.75%; H, 7.19%; N, 10.41%.

EXAMPLE 4

N-{N-[(2R)-3-Morpholinocarbonyl-2-(1-naphthylmethyl)propionyl]-L-phenylalanyl}-cyclostatin-(2-morpholinoethyl)amide Following a procedure similar to that described in Example 1(b), 100 mg (0.17 mmole) of N-(t-butoxycarbonyl)-L-phenylalanyl-cyclostatin-(2-morpholinoethyl)amide [prepared by a procedure similar to that described in Preparation 1(a), followed by a procedure similar to that described in Example 1(b)] were reacted with 56 mg (0.17 mmole) of (2R)-3-(1-morpholinocarbonyl)-2-(1-naphthylmethyl)propionic acid (prepared as described in Preparation 4), to afford 23 mg of the title compound as a colorless amorphous substance.

Silica gel thin layer chromatography, Rf value 0.56.

Elemental analysis: Calculated for $C_{45}H_{61}N_5O_7$ 2.5 $H_2O$: C, 65.19%; H, 8.02%; N, 8.45%. Found: C, 65.06%; H, 7.87%; N, 8.25%.

EXAMPLE 5

N-{N-[(2R)-3-Morpholinocarbonyl-2-(1-naphthylmethyl)propionyl]-3-(2-thienyl)-DL-alanyl}-cyclostatin-(2-morpholinoethyl)amide

5(a)

N-[N-(t-Butoxycarbonyl)-3-(2-thienyl)-DL-alanyl]-cyclostatin-(2-morpholinoethyl)amide Following a procedure similar to that described in Example 2(a), 200 mg (0.74 mmole) of N-(t-butoxycarbonyl)-3-(2-thienyl)-DL-alanine (prepared by a procedure similar to that described in Preparation 8) were reacted with 300 mg (0.74 mmole) of cyclostatin-(2-morpholinoethyl)amide dihydrochloride [prepared as described in Preparation 17(b)], to afford 310 mg of the title compound as a colorless amorphous substance.

Elemental analysis: Calculated for $C_{29}H_{48}N_4O_6S$: C, 59.97%; H, 8.33%; N, 9.65%; S, 5.52%. Found: C, 59.50%; H, 8.18%; N, 9.62%; S, 5.68%.

5(b)

N-{N-[(2R)-3-Morpholinocarbonyl-2-(1-naphthylmethyl) propionyl]-3-(2-thienyl)-DL-alanyl}-cyclostatin-(2-morpholinoethyl)amide Following a procedure similar to that described in Example 2(b), except that 70 mg (0.12 mmole) of N-[N-(t-butoxycarbonyl)-3-(2-thienyl)-DL-alanyl]-cyclostatin-(2-morpholinoethyl)amide {instead of the N-[N-(t-butoxycarbonyl)-3-(4-thiazolyl)-DL-alanyl]-cyclostatin-(2-morpholinoethyl)amide, and prepared in a manner similar to that described in Preparation 8} were reacted with 40 mg (0.12 mmole) of (2R)-3-morpholinocarbonyl-2-(1-naphthylmethyl)propionic acid, to afford 27 mg of the title compound as a colorless amorphous substance.

Silica gel thin layer chromatography, Rf value 0.59.

Elemental analysis: Calculated for $C_{43}H_{59}N_5O_7S$ 2.5 $H_2O$: C, 61.85%; H, 7.73%; N, 8.39%: S, 3.84%. Found: C, 61.74%; H, 7.50%; N, 8.18%; S, 3.62%.

EXAMPLE 6

N-}N-[(2R)-3-Morpholinocarbonyl-2-(1-naphthylmethyl)propionyl]-L-histidyl}-cyclostatin-(2-morpholinoethyl)amide Following a procedure similar to that described in Example 3(a), 344 mg (0.84 mmole) of N-(t-butoxycarbonyl)-$N^{im}$-tosyl-L-histidine were reacted with 300 mg (0.70 mmole) of N-(t-butoxycarbonyl)-cyclostatin-(2-morpholinoethyl)amide [prepared as described in Preparation 17(a)], to afford 240 mg of N-[N-(t-butoxycarbonyl)-$N^{im}$-tosyl-L-histidyl]-cyclostatin-(2-morpholinoethyl)amide as white crystals.

Then, following a procedure similar to that described in Example 1(b), 220 mg (0.31 mmole) of the N-[N-(t-butoxycarbonyl)-$N^{im}$-tosyl-L-histidyl]-cyclostatin-(2-morpholinoethyl)amide (prepared as described above) were allowed to react with 100 mg (0.31 mmole) of (2R)-3-morpholinocarbonyl-2-(1-napnthylmethyl)propionic acid (prepared as described in Preparation 4) for 15 hours. At the end of this time, a solution of 83 mg (0.61 mmole) of 1-hydroxybenzotriazole in methanol was added, and the mixture was stirred at room temperature for 1 hour. The solvent was then removed by distillation under reduced pressure. The residue was purified by preparative thin layer chromatography on a silica gel plate (developing solvent: an 8: 1 by volume mixture of methylene chloride and methanol), to afford 50 mg of the 2.5-hydrate of the title compound as white crystals, melting at 105°–109° C.

Elemental analysis: Calculated for $C_{42}H_{59}N_7O_7$ 2.5 $H_2O$: C, 61.59%; H, 7.88%; N, 11.97%. Found: C, 61.65%; H, 7.65%; N, 11.73%.

EXAMPLE 7

N-{N-[(2R)-3-Morpholinocarbonyl-2-(1-naphthylmethyl)-propionyl]-L-leucyl}-cyclostatin-(2-morpholinoethyl)amide Following a procedure similar to that described in Example 1(b), 122 mg (0.373 mmole) of (2R)-3-morpholinocarbonyl-2-(1-naphthylmethyl)propionic acid (prepared as described in Preparation 4) were reacted with 200 mg (0.370 mmole) of N-[N-(t-butoxycarbonyl)-L-leucyl]-cyclostatin-(2-morpholinoethyl)amide [prepared by a procedure similar to that described in Example 1(a)], to afford 154 mg of the title compound as a pale yellow amorphous substance.

Silica gel thin layer chromatography, Rf value 0.44.

Elemental analysis: Calculated for $C_{42}H_{63}N_5O_7$ 2.5 $H_2O$: C, 64.18%; H, 8.59%; N, 8.91%. Found: C, 63.82%; H, 8.31%; N. 8.81%.

EXAMPLE 8

N-{N-[(2R)-2-(1-Naphthylmethyl)-3-(2,6-dimethylmorpholinocarbocyl)propionyl]-3-(4-thiazolyl)-DL-alanyl}-cyclostatin-(2-morpholinoethyl)amide Following a procedure similar to that described in Example 2(b), 90 mg (0.25 mmole) of (2R)-3-(2,6-dimethylmorpholinocarbonyl)-2-(1-naphthylmethyl)propionic acid (prepared as described in Preparation 18) were reacted with 150 mg (0.25 mmole) of N-[N-(t-butoxycarbonyl)-3-(4-thiazolyl)-DL-alanyl]-cyclostatin-(2-morpholinoethyl)amide [prepared as described in Example 2(a)], to afford 90 mg of the 4.5-hydrate of the title compound as a white powder.

Silica gel thin layer chromatography, Rf value 0.46.

Elemental analysis: Calculated for $C_{44}H_{62}N_6O_7S$ 4.5 $H_2O$: C, 58.71%; H, 7.95%; N, 9.34%; S, 3.56%. Found: C, 58.73%; H, 7.72%; N, 9.51%; S, 3.60%.

EXAMPLE 9

N-{N-[(2R)-2-(1-Naphthylmethyl)-3-thiomorpholinocarbonylpropionyl]-3-(4-thiazolyl)-DL-alanyl}-cyclostatin-(2-morpholinoethyl)amide Following a procedure similar to that described in Example 2(b), 76 mg (0.22 mmole) of (2R)-2-(1-naphthylmethyl)-3-thiomorpholinocarbonylpropionic acid (prepared as described in Preparation 19) were reacted with 130 mg (0.22 mmole) of N-[N-(t-butoxycarbonyl)-3-(4-thiazolyl)-DL-alanyl]-cyclostatin-(2-morpholinoethyl)amide [prepared as described in Example 2(a)], to afford 80 mg of the 2.5-hydrate of the title compound as a white powder.

Silica gel thin layer chromatography, Rf value 0.56.

Elemental analysis: Calculated for $C_{42}H_{58}N_6O_6S_2$ 2.5 $H_2O$: C, 59.20%; H, 7.45%; N, 9.86%; S, 7.52%. Found: C, 59.23%; H, 7.22%; N, 9.66%; S, 7.82%.

EXAMPLE 10

N-{N-[(2R)-2-(1-Naphthylmethyl)-3-(1-pyrrolidinylcarbonyl)propionyl]-3-(4-thiazolyl)-DL-alanyl}-cyclostatin-(2-morpholinoethyl)amide Following a procedure similar to that described in Example 2(b), 80 mg (0.26 mmole) of (2R)-2-(1-naphthylmethyl)-3-(1-pyrrolidinylcarbonyl)propionic acid [prepared by a procedure similar to that described in Preparation 20(b)] were reacted with 180 mg (0.308 mmole) of N-[N-(t-butoxycarbonyl)-3-(4-thiazolyl)-DL-alanyl]-cyclostatin-(2-morpholinoethyl)amide [prepared as described in Example 2(a)], to afford 140 mg of the title compound as a colorless amorphous substance.

Silica gel thin layer chromatography, Rf value 0.56.

Elemental analysis: Calculated for $C_{42}H_{58}N_6O_6S$ 2.5 $H_2O$: C, 61.51%; H, 7.74%; N, 10.25%; 3.91%. Found: C, 61.42%; H, 7.39%; N, 10.29%; 3.75%.

EXAMPLE 11

N-{N-[(2R)-2-(1-Naphthylmethyl)-3-(piperidinocarbonyl)propionyl]-3-(4-thiazolyl)-DL-alanyl}-cyclostatin-(2-morpholinoethyl)amide Following a procedure similar to that described in Example 2(b), 104 mg (0.32 mmole) of (2R)-2-(1-naphthylmethyl)-3-(piperidinocarbonyl)propionic acid [prepared by a procedure similar to that described in Preparation 21(b)] were reacted with 186 mg (0.32 mmole) of N-[N-(t-butoxycarbonyl)-3-(4-thiazolyl)-DL-alanyl]-cyclostatin-(2-morpholinoethyl)amide [prepared as described in Example 2(a)], to afford 95 mg of the monohydrate of the title compound as a white powder.

Silica gel thin layer chromatography, Rf value 0.39.

Elemental analysis: Calculated for $C_{43}H_{60}N_6O_6S$ $H_2O$: C, 63.99%; H, 7.74%; N, 10.41%. Found: C, 63.85%; H, 7.78%; N, 10.68%.

EXAMPLE 12

N-{N-[(2R)-2-(1-Naphthylmethyl)-3-propylcarbamoylpropionyl]-3-(4-thiazolyl)-DL-alanyl}-cyclostatin-(2-morpholinoethyl)amide Following a procedure similar to that described in Example 2(b), 81 mg (0.27 mmole) of (2R)2-(1-naphthylmethyl)-3-propylcarbamoylpropionic acid [prepared by a procedure similar to that described in Preparation 22(b)] were reacted with 160 mg (0.27 mmole) of N-[N-(t-butoxycarbonyl)-3-(4-thiazolyl)-DL-alanyl]-cyclostatin-(2-morpholinoethyl)amide [prepared as described in Example 2(a)], to afford 100 mg of the hemihydrate of the title compound as a white powder.

Silica gel thin layer chromatography, Rf value 0.52.

Elemental analysis: Calculated for $C_{41}H_{58}N_6O_6S$ ½ $H_2O$: C, 63.79%; H, 7.70%; N, 10.89%; S, 4.15%. Found: C, 63.70%; H, 7.62%; N, 10.66%; S, 4.05%.

EXAMPLE 13

N-{N-[(2R)-2-(1-Naphthylmethyl)-3-(phenethylcarbamoyl)propionyl]-3-(4-thiazolyl)-L-alanyl}-cyclostatin-(2-morpholinoethyl)amide Following a procedure similar to that described in Example 1(b), 100 mg (0.28 mmole) of (2R)-2-(1-naphthylmethyl)-3-(phenethylcarbamoyl)propionic acid [prepared by a procedure similar to that described in Preparation 23(b)] were reacted with 133 mg (0.23 mmole) of N-[N-(t-butoxycarbonyl)-3-(4-thiazolyl)-L-alanyl]-cyclostatin-(2-morpholinoethyl)amide [prepared as described in Example 2(a)], to afford 133 mg (71%) of the title compound, as its sesquihydrate, melting at 110°–115° C.

Elemental analysis: Calculated for $C_{46}H_{60}N_6O_6S$ 3/2 $H_2O$: C, 64.84%; H, 7.45%; N, 9.86%; S, 3.76%. Found: C, 64.85%; H, 7.26%; N, 9.64%; S, 3.64%.

EXAMPLE 14

N-{N-[(2R)-3-(4-Methyl-1-piperazinylcarbonyl)-2-(1-naphthylmethyl)propionyl]-3-(4-thiazolyl)-L-alanyl}-cyclostatin-(2-morpholinoethyl)amide Following a procedure similar to that described in Example 2(b), 100 mg (0.294 mmole) of (2R)-3-(4-methyl-1-piperazinylcarbonyl)-2-(1-naphthylmethyl)propionic acid (prepared as described in Preparation 24) were reacted with 190 mg (0.32 mmole) of N-[N-(t-butoxycarbonyl)-3-(4-thiazolyl)-DL-alanyl]-cyclostatin(2-morpholinoethyl)amide [prepared as described in Example 2(a)]. After completion of the reaction, the product was purified by silica gel thin layer chromatography, using a 10:1 by volume mixture of methylene chloride and methanol as the developing solvent, to afford 34 mg of the dihydrate of the title compound as a colorless amorphous substance.

Silica gel thin layer chromatography, Rf value 0.12.

Elemental analysis: Calculated for $C_{43}H_{61}N_7O_6S$ 2 $H_2O$: C, 61.48%; H, 7.80%; N, 11.67%; S. 3.82%. Found: C, 61.56%; H, 7.82%; N, 11.52%; S, 3.87%.

EXAMPLE 15

N-{N-[(2R)-2-(1-Naphthylmethyl)-3-(4-phenyl-1-piperazinylcarbonyl)propionyl]-3-(4-thiazolyl)-DL-alanyl}-cyclostatin-(2-morpholinoethyl)amide Following a procedure similar to that described in Example 2(b), 90 mg (0.22 mmole) of (2R)2-(1-naphthylmethyl)-3-(4-phenyl-1-piperazinylcarbonyl)propionic acid (prepared by a procedure similar to that described in Preparation 24) were reacted with 130 mg (0.22 mmole) of N-[N-(t-butoxycarbonyl)-3-(4-thiazolyl)-DL-alanyl]-cyclostatin-(2-morpholinoethyl)amide [prepared as described in Example 2(a)], to afford 103 mg of the monohydrate of the title compound as a white powder.

Silica gel thin layer chromatography, Rf value 0.52.

Elemental analysis:

Calculated for $C_{48}H_{63}N_7O_6S \cdot H_2O$: C, 65.21%; H, 7.41%; N, 11.09%; S, 3.63%. Found: C, 65.36%; H, 7.51%; N, 11.22%; S, 3.39%.

EXAMPLE 16

N-{N-[(2R)-3-(N,N-Diethylcarbamoyl)-2-(1-naphthylmethyl)propionyl]-3-(4-thiazolyl)-DL-alanyl}-cyclostatin-(2-morpholinoethyl)amide Following a procedure similar to that described in Example 2(b), 95 mg (0.3 mmole) of (2R)-3-(N,N-diethylcarbamoyl)-2-(1-naphthylmethyl)propionic acid (prepared as described in Preparation 26) were reacted with 210 mg (0.36 mmole) of N-[N-(t-butoxycarbonyl)-3-(4-thiazolyl)-DL-alanyl]-cyclostatin-(2-morpholinoethyl)amide [prepared as described in Example 2(a)], to afford 160 mg of the 2.5-hydrate of the title compound as colorless amorphous substance.

Silica gel thin layer chromatography, Rf value 0.52.

Elemental analysis: Calculated for $C_{42}H_{60}N_6O_6S \cdot 2.5 H_2O$: C, 61.36%; H, 7.97%; N, 10.22%; S, 3.90%. Found: C, 61.45%; H, 7.79%; N, 10.10%; S, 3.88%.

EXAMPLE 17

N-{N-[(2R)-3-(N-Benzyl-N-methylcarbamoyl)-2-(1-naphthylmethyl)propionyl]-3-(4-thiazolyl)-L-alanyl}-cyclostatin-(2-morpholinoethyl)amide Following a procedure similar to that described in Example 1(b), 125 mg (0.35 mmole) of (2R)-3-(N-benzyl-N-methylcarbamoyl)-2-(1-naphthylmethyl)propionic acid (prepared as described in Preparation 32) were reacted with 200 mg (0.34 mmole) of N-[N-(t-butoxycarbonyl)-3-(4-thiazolyl)-L-alanyl]-cyclostatin-(2-morpholinoethyl)amide [prepared as described in Example 2(a)], to afford 214 mg (75%) of the monohydrate of the title compound, melting at 82°–86° C.

Elemental analysis: Calculated for $C_{46}H_{62}N_6O_6S \cdot H_2O$: C, 65.38%; H, 7.63%; N, 9.94%; S, 3.79%. Found: C, 65.30%; H, 7.53%; N, 9.94%; S, 3.90%.

EXAMPLE 18

N-{N-[(2R)-3-(N-Benzyl-N-methylcarbamoyl)-2-(1-naphthylmethyl)propionyl]-L-phenylalanyl}-cyclostation-(2-morpholinoethyl)amide Following a procedure similar to that described in Example 1(b), 207 mg (0.36 mmole) of N-(t-butoxycarbonyl)-L-phenylalanyl-cyclostatin-(2-morpholinoethyl)amide were reacted with 130 mg (0.36 mmole) of (2R)-3-(N-benzyl-N-methylcarbamoyl-2-(1-naphthylmethyl)propionic acid [prepared by a procedure similar to that described in Preparation 32(c)], to afford 57 mg of the monohydrate of the title compound as white crystals, melting at 89°–94° C.

Elemental analysis: Calculated for $C_{49}H_{63}N_5O_6 \cdot H_2O$: C, 70.39%; H, 7.84%; N. 8.38%. Found: C, 70.58%; H, 7.87%; N. 8.10%.

EXAMPLE 19

N-{N-[(2R)-3-(N-Cyclohexyl-N-methylcarbamoyl)-2-(1-naphthylmethyl)propionyl]-3-(4-thiazolyl)-L-alanyl}-cyclostatin-(2-morpholinoethyl)amide Following a procedure similar to that described in Example 1(b), 122 mg (0.35 mmole) of (2R)-3-(N-cyclohexyl-N-methylcarbamoyl)-2-(1-naphthylmethyl)propionic acid (prepared as described in Preparation 31) were reacted with 200 mg (0.34 mmole) of N-[N-(t-butoxycarbonyl)-3-(4-thiazolyl)-L-alanyl]-cyclostatin-(2-morpholinoethyl)amide [prepared as described in Example 2(a)], to afford 215 mg (77%) of the monohydrate of the title compound, melting at 93°–96° C.

Elemental analysis: Calculated for $C_{45}H_{64}N_6O_6S \cdot H_2O$% C, 64.72%; H, 7.97%; N, 10.06%; S, 3.84%. Found: C, 64.52%; H, 7.81%; N, 9.81%; S, 3.91%.

EXAMPLE 20

N-{N-[(2R)-3-(N-Cyclohexyl-N-methylcarbamoyl)-2-(1-naphthylmethyl)propionyl]-L-leucyl}-cyclostatin-(2-morpholinoethyl)amide Following a procedure similar to that described in Example 1(b), 50 mg (0.141 mmole) of (2R)-3-(N-cyclohexyl-N-methylcarbamoyl)-2-(1-naphthylmethyl)propionic acid (prepared as described in Preparation 31) were reacted with 73 mg (0.135 mmole) of N-{N-(t-butoxycarbonyl)-L-leucyl]-cyclostatin-(2-morpholinoethyl)amide [prepared by a procedure similar to that described in Example 1(a)], to afford 81 mg of the trihydrate of the title compound as a colorless amorphous substance.

Silica gel thin layer chromatography, Rf value 0.50.

Elemental analysis: Calculated for $C_{45}H_{69}N_5O_6 \cdot 3 H_2O$: C, 65.11%; H, 9.11%; N, 8.44%. Found: C, 64.92%; H, 8.91%; N, 8.48%.

EXAMPLE 21

N-{N-[(2R)-3-(N-Cyclohexyl-N-methylcarbamoyl)-2-(1-naphthylmethyl)propionyl]-3-(5-isoxazolyl)-L-alanyl}-cyclostatin-(2-morpholinoethyl)amide Following a procedure similar to that described in Example 3(b), 100 mg (0.28 mmole) of (2R)-3-(N-cyclohexyl-N-methylcarbamoly)-2-(1-naphthylmethyl)propionic acid (prepared as described in Preparation 31) were reacted with 160 mg (0.28 mmole) of N-[N-(t-butoxycarbonyl)-3-(5-isoxazolyl)-L-alanyl]-cyclostatin-(2-morpholinoethyl)amide [prepared as described in Example 3(a)], to afford 100 mg of the dihydrate of the title compound as a colorless amorphous substance.

Silica gel thin layer chromatography, Rf value 0.52.

Elemental analysis: Calculated for $C_{45}H_{64}N_6O_7 \cdot 2 H_2O$: C, 64.57%; H, 8.19%; N, 10.14%. Found: C, 64.36%; H, 7.66%; N, 10.06%.

EXAMPLE 22

N-{N-[(2R)-3-Morpholinocarbonyl-2-(1-naphthylmethyl)-propionyl]-3-(4-thiazolyl)-DL-alanyl}-cyclostatin-(2-piperidinoethyl)amide

22(a)

N-[N-(t-Butoxycarbonyl)-3-(4-thiazolyl)-DL-alanyl}-cyclostatin-(2-piperidinoethyl)amide 450 mg (1.06 mmole) of N-(t-butoxycarbonyl)-cyclostatin-(2-piperidinoethyl)amide [prepared by a procedure similar to that described in Preparation 17(a)] were added to 10 ml of a 4N solution of hydrogen chloride in dioxane, and the mixture was stirred as room temperature for 30 minutes. At the end of this time, the solvent was removed by distillation under reduced pressure. The residue was dried thoroughly and then suspended in 20 ml of anhydrous methylene chloride. 260 mg (1.60 mmole) of diethyl cyanophosphonate (95%) and 482 mg (4.77 mmole) of triethylamine were added to the suspension, whilst ice-cooling. The mixture was then stirred at room temperature for 3 hours, after which it was freed from the solvent by evaporation under reduced pressure. The residue was purified by silica gel thin layer chromatography (developing solvent: a 5: 1 by volume mixture of chloroform and methanol), to afford 590 mg (96%) of the title compound as white crystals.

22(b)
N-{N-[(2R)-3-Morpholinocarbonyl-2-(1-naphthylmethyl) propionyl]-3-(4-thiazolyl)-DL-alanyl}-cyclostatin-(2-piperidinoethyl)amide 179 mg (0.31 mmole) of N-[N-(t-butoxycarbonyl)-3-(4-thiazolyl)-DL-alanyl}-cyclostatin-(2-piperidinoethyl)amide [prepared as described in Example 22(a) above] were added to 10 ml of a 4N solution of hydrogen chloride in dioxane, and the mixture was stirred at room temperature for 30 minutes. At the end of this time, the solvent was removed by distillation under reduced pressure, and the residue was dried thoroughly and then suspended in 10 ml of methylene chloride. 100 mg (0.31 mmole) of (2R)-3-morpholinocarbonyl-2-(1-naphthylmethyl) propionic acid (prepared as described in Preparation 4), 75 mg (0.46 mmole) of diethyl cyanophosphonate (95%) and 186 mg (1.84 mmole) of triethylamine were added to the resulting suspension, and the mixture was stirred at room temperature for 3 hours. At the end of this time, the solvent was removed by distillation under reduced pressure, and the residue was purified by silica gel thin layer chromatography (developing solvent: a 5: 1 by volume mixture of chloroform and methanol), to afford 80 mg (31%) of the dihydrate of the title compound, melting at 78°-87° C.

Elemental analysis: Calculated for $C_{43}H_{60}N_6O_6S$ 2 $H_2O$: C, 62.60%; H, 7,81%; N, 10.19%; S, 3.89%. Found: C, 62,44%; H, 7,62%; N, 10.13%; S, 4.06%.

EXAMPLE 23
N-{N-[(2R)-3-Morpholino-2-(1-naphthylmethyl)propionyl]3-(4-thiazolyl)-DL-alanyl}-cyclostatin-[2-(1-pyrrolidinyl)ethyl]amide

23(a)
N-[N-(t-Butoxycarbonyl)-3-(4-thiazolyl)-DL-alanyl]-cyclostatin-[2-(1-pyrrolidinyl)ethyl]amide 350 mg (0.85 mmole) of N-(t-butoxycarbonyl)-cyclostatin-[2-(1-pyrrolidinyl)ethyl]amide [prepared a procedure similar to that described in Preparation 17(a)] were added to 10 ml of a 4N solution of hydrogen chloride in dioxane. The mixture was then stirred at room temperature for 30 minutes, after which it was freed from the solvent by evaporation under reduced pressure, The residue was dried thoroughly and suspended in 20 ml of anhydrous methylene chloride. 208 mg (1.28 mmole) of diethyl cyanophosphonate (95%) and 386 mg (3.82 mmole) of triethylamine were then added to the resulting suspension, and the mixture was stirred at room temperature for 3 hours. At the end of this time, it was concentrated by evaporation under reduced pressure. The residue was purified by silica gel thin layer chromatography (developing solvent: a 5 : 1 by volume mixture of chloroform and methanol), to afford 430 mg (90%) of the title compound as white crystals.

23(b)
N-{N-[(2R)-3-Morpholinocarbonyl-2-(1-naphthylmethyl)propionyl]-3-(4-thiazolyl)-DL-alanyl}-cyclostatin-[2-(1-pyrrolidinyl)ethyl]amide 175 mg (0.31 mmole) of N-[N-(t-butoxycarbonyl)-3-(4-thiazolyl)-DL-alanyl]-cyclostatin-[2-(1-pyrrolidinyl)ethyl]amide [prepared as described in Example 23(a) above] were added to 10 ml of a 4N solution of hydrogen chloride in dioxane, and the mixture was stirred at room temperature for 30 minutes. At the end of this time, the solvent was distilled off under reduced pressure, and the resulting residue was dried thoroughly and suspended in 10 ml of methylene chloride. 100 mg (0.31 mmole) of (2R)-3-morpholinocarbonyl-2-(1-naphthylmethyl) propionic acid (prepared as described in Preparation 4) were added to the suspension, after which 75 mg (0.46 mmole) of diethyl cyanophosphonate (95%) and 186 mg (1.84 mmole) of triethylamine were added, whilst ice-cooling. The mixture was then stirred at room temperature for 3 hours, after which it was freed from the solvent by evaporation under reduced pressure. The residue was purified by silica gel thin layer chromatography (developing solvent: a 5: 1 by volume mixture of chloroform and methanol), to afford 60 mg (23%) of the tetrahydrate of the title compound, melting an 86°-93° C.

Elemental analysis: Calculated for $C_{42}H_{58}N_6O_6S$ 4 $H_2O$: C, 59.50%; H, 7.85%; N, 9.92%; S, 3.79%. Found: C, 59.21%; H, 7.55%; N, 9.68%; S, 4.00%.

EXAMPLE 24
N-{N-[(2R)-3-Morpholinocarbonyl-2-(1-naphthylmethyl)propionyl]-3-(4-thiazolyl)-DL-alanyl}-cyclostatin-(3-morpholinopropyl)amide

24(a)
N-[N-(t-Butoxycarbonyl)-3-(4-thiazolyl)-DL-alanyl]-cyclostatin-(3-morpholinopropyl)amide 1.97 ml (10.85 mmole) of diethyl cyanophosphonate (95%) and 2.76 ml (19.89 mmole) of triethylamine were added to a solution of 2.71 g (9.94 mmole) of N-(t-butoxycarbonyl)-3-(4-thiazolyl)-DL-alanine and 2.64 g (9.94 mmole) of methyl cyclostatinate hydrochloride dissolved in 50 ml of anhydrous tetrahydrofuran, whilst ice-cooling. The mixture was then stirred at room temperature for 3 hours, after which it was freed from the solvent by evaporation under reduced pressure. The residue was purified by silica gel thin layer chromatography (developing solvent: a 30: 1 by volume mixture of methylene chloride and methanol), to afford 3.76 g of methyl N-[N-(t-butoxycarbonyl)-3-(4-thiazolyl)-DL-alanyl]-cyclostatinate as a white powder.

3.5 g (7.24 mmole) of this methyl N-[N-(t-butoxycarbonyl)-3-(4-thiazolyl)-DL-alanyl]-cyclostatinate were dissolved in 10 ml of methanol, and 7.96 ml (7.96 mmole) of a 1N aqueous solution of sodium hydroxide were added to the resulting solution, whilst ice-cooling. The mixture was then stirred at room temperature for 30 minutes, after which it was neutralized by the addition of 7.96 ml (7.96 mmole) of 1N aqueous hydrochloric acid, and then the solvent was removed by distillation. The residue was dissolved in a 1N aqueous solution of sodium hydroxide, and the resulting solution was washed with diethyl ether. The aqueous layer was separated, acidified by adding 6N aqueous hydrochloric acid and then extracted with ethyl acetate. The organic layer was washed with a saturated aqueous solution of sodium chloride, dried over anhydrous sodium sulfate and concentrated by evaporation under reduced pressure. Hexane was added to the residue, to afford 3.18 g of N-[N-(t-butoxycarbonyl)-3-(4-thiazolyl)-DL-alanyl]-cyclostatin as white crystals.

300 mg (0.64 mmole) of this N-[N-(t-butoxycarbonyl)-3-(4-thiazolyl)-DL-alanyl]-cyclostatin and 138 mg (0.96 mmole) of N-(3-aminopropyl)morpholine were dissolved in 5 ml of methylene chloride. 0.17 g (0.96 mmole) of diethyl cyanophosphonate (95%) and 0.13 ml (0.96 mmole) of triethylamine were added to the solution, whilst ice-cooling. The mixture was then stirred at room temperature for 18 hours, after which it was freed from the solvent by evaporation under reduced pressure. The residue was purified by silica gel thin layer chromatography (developing solvent: a 10: 1 by volume mixture of methylene chloride and methanol), to afford 320 mg of the title compound as a white powder.

24(b)
N-{N-[(2R)-3-Morpholinocarbonyl-2-(1-naphthylmethyl)propionyl]-3-(4-thiazolyl)-DL-alanyl}-cyclostatin-(3-morpholinopropyl)amide Following a procedure similar to that described in Example 2(b), 145 mg (0.24 mmole) of N-[N-(t-butoxycarbonyl)-3-(4-thiazolyl)-DL-alanyl]-cyclostatin-(3-morpholinopropyl)amide [prepared as described in Example 24(a)] were reacted with 80 mg (0.24 mmole) of (2R)-3-morpholinocarbonyl-2-(1-naphthylmethyl)propionic acid (prepared as described in Preparation 4), no afford 140 mg of the monohydrate of the title compound as white crystals, melting at 94°–98° C.

Elemental analysis: Calculated for $C_{43}H_{60}N_6O_7S$ $H_2O$: C, 62.75%; H, 7.59%; N, 10.21%; S, 3.90%. Found: C, 62.73%; H, 7.56%; N, 10.04%; S, 3.61%.

EXAMPLE 25
N-{N-[(2R)-3-Morpholinocarbonyl-2-(1-naphthylmethyl)-propionyl]-3-(4-thiazolyl)-L-alanyl}-cyclostatin-[3-(2-oxo-1-pyrrolidinyl)proppyl]amide

25(a)
N-[N-(t-Butoxycarbonyl)-3-(4-thiazolyl)-L-alanyl]-cyclostatin-[3-(2-oxo-1-pyrrolidinyl)propyl]amide Following a procedure similar to that described in Example 3(a), 1.0 g (2.3 mmole) of N-(t-butoxycarbonyl)-cyclostatin-[3-(2-oxo-1-pyrrolidinyl)propyl]amide [prepared by a procedure similar to that described in Preparation 17(a )] was reacted with 0.63 g (2.3 mmole) of N-(t-butoxycarbonyl)-L-3-(4-thiazolyl)alanine, to afford 1.08 g of the title compound as an oil.

25(b)
N-{N-[(2R)-3-Morpholinocarbonyl-2-(1-naphthylmethyl)
propionyl]-3-(4-thiazolyl)-L-alanyl}-cyclostatin-[3-(2-oxo-1-pyrrolidinyl)propyl]amide Following a procedure similar to that described in Example 1(b), 207 mg (0.35 mmole) of N-[N-(t-butoxycarbonyl)-3-(4-thiazolyl)-L-alanyl]-cyclostatin-[3-(2-oxo-1-pyrrolidinyl)propyl]amide [prepared as described in Example 25(a) above] were reacted with 115 mg (0.35 mmole) of (2R)-3-morpholinocarbonyl-2-(1-naphthylmethyl)propionic acid (prepared as described in Preparation 4), to afford 207 mg of the dihydrate of the title compound as a white powder.

Silica gel thin layer chromatography, Rf value 0.53.

Elemental analysis: Calculated for $C_{43}H_{58}N_6O_7S$ 2 $H_2O$: C, 61.55%; H, 7.45%; N, 10.02%; S, 3.82%. Found: C, 61.74%; H, 7.43%; N, 9.77%; S, 3.97%.

EXAMPLE 26
N-{N-[(2R)-3-Morpholinocarbonyl-2-(1-naphthylmethyl)propionyl]-3-(4-thiazolyl)-DL-alanyl}-cyclostatin-[(1-ethyl-2-pyrrolidinyl)methyl]amide Following a procedure similar to that described in Example 2(b), 141 mg (0.24 mmole) of N-(t-butoxycarbonyl)-3-(4-thiazolyl)-DL-alanyl-cyclostatin-[(1-ethyl-2-pyrrolidinyl)methyl]amide [prepared from 2-aminomethyl-1-ethylpyrrolidine instead of N-(3-aminopropyl)morpholine according to the procedure of Example 24(a)], were reacted with 80 mg (0.24 mmole) of (2R)-3-morpholinocarbonyl-2-(1-naphthylmethyl)propionic acid (prepared as described in Preparation 4), to afford 28 mg of the sesquihydrate of the title compound as white crystals, melting at 85°–89° C.

Elemental analysis: Calculated for $C_{43}H_{60}N_6O_6S$ 1.5 $H_2O$: C, 63.29%; H, 7.78%; N, 10.30%; S, 3.93%. Found: C, 63.50%; H, 7.58%; N, 10.07%; S, 3.70%.

EXAMPLE 27
N-{N-[(2R)-3-Morpholinocarbonyl-2-(1-naphthylmethyl)propionyl]-3-(4-thiazolyl)-DL-alanyl}-cyclostatin-(2-pyridylmethyl)amide 230 mg (0.50 mmole) of N-[(2R)-3-morpholinocarbonyl- 2-(1-naphthylmethyl)propionyl]-3-(4-thiazolyl)-DL-alanine (prepared by a procedure similar to that described in Preparation 51) and 187 mg (0.50 mmole) of cyclostatin(2-pyridylmethyl)amide dihydrochloride were suspended in 10 ml of anhydrous methylene chloride. 123 mg (0.75 mmole) of diethyl cyanophosphonate (95%) and 230 mg (2.3 mmole) of triethylamine were then added to the resulting suspension, whilst ice-cooling, and the mixture was stirred at room temperature for 3 hours. It was then freed from the solvent by evaporation under reduced pressure. The residue was purified by silica gel thin layer chromatography (developing solvent: a 10 : 1 by volume mixture of chloroform and methanol), to afford 61 mg of the dihydrate of the title compound as a white powder, melting at 78°–86° C.

Elemental analysis: Calculated for $C_{42}H_{52}N_6O_6S$ 2 $H_2O$. C, 62.67%; H, 8.13%; N, 10.44%; S, 3.98%. Found: C, 62.64%; H, 7.87%; N, 10.70%; S, 4.20%.

EXAMPLE 28
N-{N-[(2R)-3-Morpholinocarbonyl-2-(1-naphthylmethyl)propionyl]-3-(4-thiazolyl)-DL-alanyl}-cyclostatin[2-(4-methyl-1-piperazinyl)ethyl]amide 230 mg (0.50 mmole) of N-[(2R)-3-morpholinocarbonyl-2-(1-naphthylmethyl)propionyl]-3-(4-thiazolyl)-DL-alanine (prepared by a procedure similar to that described in Preparation 51) and 223 mg (0.50 mmole) of cyclostatin-[2-(4-methyl-1-piperazinyl)ethyl]amide trihydrochloride (prepared by a procedure similar to that described in Example 103) were suspended in 10 ml of anhydrous methylene chloride. 123 mg (0.75 mmole) of diethyl cyanophosphonate (95%) and 300 mg (3.0 mmole) of triethylamine were added to the suspension, whilst ice-cooling. The mixture was then stirred at room temperature for 3 hours, after which it was freed from the solvent by evaporation under reduced pressure. The residue was purified by silica gel thin layer chromatography (developing solvent: a 5: 1 by volume mixture of chloroform and methanol), to afford 50 mg of the trihydrate of the title compound as a white powder, melting at 80°–88° C.

Elemental analysis: Calculated for $C_{43}H_{61}N_7O_6S$ 3 $H_2O$: C, 60.19%; H, 7.86%; N, 11.43%; S, 3.74%. Found: C, 60.02%; H, 7.53%; N, 11.16%; S, 4.00%.

EXAMPLE 29

N-{N-[(2R)-3-Morpholinocarbonyl-2-(1-naphthylmethyl)propionyl]-3-(4-thiazolyl)-L-alanyl}-cyclostatin[(S)-2-methylbutyl]amide

29(a)

N-(t-Butoxycarbonyl)-cyclostatin-[(S)-2-methylbutyl]amide

Following a procedure similar to that described in Preparation 17, 0.33 g (3.81 mmole) of (S)-2-methylbutylamine (instead of 2-morpholinoethylamine) were reacted with 1.00 g (3.17 mmole) of N-(t-butoxycarbonyl)cyclostatin, to afford 1.13 g (93%) of the title compound as a white powder.

(b)

N-{N-[(2R)-3-Morpholinocarbonyl-2-(1-naphthylmethyl)propionyl]-3-(4-thiazolyl)-L-alanyl}-cyclostatin-[(S)-2-methylbutyl]amide Following a procedure similar to that described in Example 1(a), 0.50 g (1.30 mmole) of N-(t-butoxycarbonyl)-cyclostatin-[(S)-2-methylbutyl]amide [prepared as described in Example 29(a)] were reacted with 354 mg (1.30 mmole) of N-(t-butoxycarbonyl)-3-(4-thiazolyl)-L-alanine, and the product was worked-up according to Example 1(b), to give 211 mg (61%) of the monohydrate of the title compound as a white powder.

Silica gel thin layer chromatography, Rf value 0.63.

Elemental analysis: Calculated for $C_{41}H_{57}N_5O_6S$ $H_2O$: C, 64.29%; H, 7.76%; N, 9.14%; S, 4.19%. Found: C, 63.99%; H, 7.56%; N, 9.20%; S, 4.01%.

EXAMPLE 30

N-{N-[(2R)-3-Morpholinocarbonyl-2-(1-naphthylmethyl)propionyl]-3-(5-isoxazolyl)-L-alanyl}-cyclostatin-[(S)-n 2-methylbutyl]amide Following a procedure similar to that described in Example 1(a), 330 mg (1.3 mmole) of N-(t-butoxycarbonyl)-3-(5-isoxazolyl)-L-alanine [instead of N-(t-butoxycarbonyl)-3-(4-thiazolyl)-L-alanine] were reacted with the compound prepared by cleaving the t-butoxycarbonyl group from 500 mg (1.3 mmole) of N-(t-butoxycarbonyl)-cyclostatin-[(S)-2-methylbutyl]amide, and the product was worked-up according to Example 1(b), to give 170 mg of the 2.5-hydrate of the title compound as white crystals, melting at 68°–72° C.

Elemental analysis: Calculated for $C_{41}H_{57}N_5O_7$ 2.5 $H_2O$: C, 63.38%; H, 8.04%: N, 9.01%. Found: C, 63.41%; H, 7.79%; N, 8.81%.

EXAMPLE 31

N-{N-[(2R)-3-Morpholinocarbonyl-2-(1-naphthylmethyl)propionyl]-3-(4-thiazolyl)-L-alanyl}-cyclostatin](S)-1-hydroxymethyl-2-methylbutyl]amide

31(a)

N-(t-Butoxycarbonyl)-cyclostatin-[(S)-1-hydroxymethyl-2-methylbutyl]amide

Following a procedure similar to that described in Preparation 17, 446 mg (3.81 mmole) of (S)-2-amino-3-methylpentanol were reacted (instead of 2-morpholinoethylamine) with 1.00 g (3.17 mmole) of N-(t-butoxycarbonyl)cyclostatine, to afford the title compound.

31(b)

N-{N-[(2R)-3-Morpholinocarbonyl-2-(1-naphthylmethyl)propionyl]-3-(4-thiazotyl)-L-alanyl}-cyclostatin-[(S)-1-hydroxymethyl-2-methylbutyl]amide Following a procedure similar to that described in Example 1(a), 500 mg (1.21 mmole) of N-(t-butoxycarbonyl)-cyclostatin-[(S)-1-hydroxymethyl -2-methylbutyl]amide [prepared as described in Example 31(a) above] instead of cyclostatin-(2-morpholinoethyl)amide were reacted with 330 mg (1.21 mmole) of N-(t-butoxycarbonyl)-3-(4-thiazolyl)-L-alanine, and the product was worked-up according to Example 1(b), to give 320 mg (47%) of the monohydrate of the title compound as a white powder.

Silica gel thin layer chromatography, Rf value 0.63.

Elemental analysis: Calculated for $C_{42}H_{59}N_5O_7S$ $H_2O$: C, 63.37%; H, 7.72%; N, 8.80%; S, 4.03%. Found: C, 63.31%; H, 7.50%; N, 8.59%; S, 4.00%.

EXAMPLE 32

N-{N-[(2R)-3-Morpholinocarbonyl-2-(1-naphthylmethyl)propionyl]-3-(4-thiazolyl)-DL-alanyl}-cyclostatin-]2-(N,N-diethylamino )ethyl]amide Following a procedure similar to that described in Example 2(b), 139 mg (0.24 mmole) of N-(t-butoxycarbonyl)-3-(4-thiazolyl)-DL-alanyl-cyclostatin-[2-(N,N-diethylamino)ethyl]amide [which was prepared by using N,N-diethylethylenediamine instead of N-(3-aminopropyl)morpholine in the procedure of Example 24(a)] were reacted with 80 mg (0.24 mmole) of (2R)-3-morpholinocarbonyl-2-(1-naphthylmethyl)propionic acid (prepared as described in Preparation 4), to afford 34 mg of the 2.5-hydrate of the title compound as white crystals, melting at 80°–85° C.

Elemental analysis: Calculated for $C_{42}H_{60}N_6O_6S$ 2.5 $H_2O$: C, 61.36%; H, 7.97%; N, 10.22%; S, 3.90%. Found: C, 61.49%; H. 7.74%; N, 9.94%; S, 3.60%.

EXAMPLE 33

N-{N-[(2R )-5,5-Dimethyl-2-(1-naphthylmethyl)-4-oxo-hexanoyl]-3-(4-thiazolyl)-L-alanyl]-cyclostatin-(2-morpholinoethyl)amide Following a procedure similar to that described in Example 1(b), 105 mg (0.35 mmole) of (2R)-5,5-dimethyl-2-(1-naphthylmethyl)-4-oxohexanoic acid [instead of (2R)-3-morpholinocarbonyl-2-(1-naphthylmethyl)propionic acid] were reacted with 170 mg of N-(t-butoxycarbonyl)-3-(4-thiazolyl)-L-alanyl-cyclostatin-(2-morpholinoethyl)amide. When the reaction was considered complete, the solvent was removed by distillation under reduced pressure, and the residue was purified by silica gel thin layer chromatography (developing solvent: a 10: 1 by volume mixture of chloroform and methanol), to afford two main products. The monohydrate of the title compound (the compound having the naphthyl group in the R configuration), detected as the spot having the larger Rf value of the two, was 84 mg (38%), melting at 84°–87° C. In addition, there were obtained 82 mg (37%) of the corresponding compound in which the naphthyl group was in the S configuration.

Elemental analysis: Calculated for $C_{42}H_{59}N_5O_6$ S $H_2O$: C, 64.67%; H, 7.88%; N, 8.98%; S, 4.11%. Found: C, 64.49%; H, 7.74%; N, 8.70%; S, 3.90%.

EXAMPLE 34

N-{N-[5-(N-Benzyl-N-methylamino)-2-(1-naphthylmethyl)-4-oxopentanoyl]-L-leucyl}-cyclostatin-(2-morpholinoethyl)amide Following a procedure similar to that described in Example 1(b), 210 mg (0.559 mmole) of 5-(N-benzyl-N-methylamino)-2-(1-naphthylmethyl)-4-oxopentanoic acid (prepared as described in Preparation 30) were reacted with 300 mg (0.555 mmole) of N-(t-butoxycarbonyl)-L-leucyl-cyclostatin-(2-morpholinoethyl)amide [prepared by a procedure similar to that described in Example 2(a)], to afford 141 mg of the tetrahydrate of the title compound as a pale brown amorphous substance.

Silica gel thin layer chromatography, Rf value 0.47.

Elemental analysis: Calculated for $C_{47}H_{67}N_5O_6$ 4 $H_2O$: C, 64.88%; H, 8.69%; N, 8.05%. Found: C, 65.14%; H, 8.59%; N, 8.02%.

EXAMPLE 35

N-{N-[5-(N-Benzyl-N-methylamino)-2-(1-naphthylmethyl)-4-oxopentanoyl]-3-(4-thiazolyl)-L-alanyl}-cyclostatin-(2-morpholinoethy)amide Following a procedure similar to that described in Example 1(b), 130 mg (0.346 mmole) of 5-(N-benzyl-N-methylamino)-2-(1-naphthylmethyl)-4-oxopentanoic acid (prepared as described in Preparation 30) were reacted with 200 mg (0.344 mmole) of N-(t-butoxycarbonyl)3-(4-thiazolyl)-[-alanyl-cyclostatin-(2-morpholinoethyl)amide, to afford 26 mg of the trihydrate of the title compound as a pale brown amorphous substance.

Silica gel thin layer chromatography, Rf value 0.42.

Elemental analysis: Calculated for $C_{47}H_{62}N_6O_6S$ 3 $H_2O$: C, 63.20%; H, 7.67%; N, 9.41%; B, 3.59%. Found: C, 63.36%; H, 7.55%; N, 9.31%; S, 3.23%.

EXAMPLE 36

N-{N-[(2R)-5-Morpholinocarbonyl-2-(1-naphthylmethyl)-pentanoyl]-3-(4-thiazolyl)-L-alanyl}-cyclostatin-(2-morpholinoethyl)amide

36(a)

5-Morpholinocarbonyl-2-(1-naphthylmethyl)pentanoic acid 7.96 g (0.18 mmole) of sodium hydride (as a 55% w/w dispersion in mineral oil) were added, whilst ice-cooling, to a solution of 26.4 g (0.15 mmole) of dimethyl adipate and 23.7 g (0.15 mmole) of 1-naphthaldehyde dissolved in 200 ml of anhydrous methanol, and the mixture was heated under reflux for 30 minutes. At the end of this time, 150 ml (0.15 mole) of a 1N aqueous solution of sodium hydroxide were added to the solution, and the mixture was heated under reflux for 1 hour. The solvent was then removed by distillation under reduced pressure, and the residue was mixed with water and then washed with diethyl ether. The aqueous layer was acidified and extracted with diethyl ether. The ethereal extract was washed with a saturated aqueous solution of sodium chloride and dried over anhydrous magnesium sulfate. The solvent was removed by distillation under reduced pressure, and residue was triturated with diisopropyl ether to precipitate crystals, which were collected by filtration to afford 14.2 g of 2-(1-naphthylidene)adipic acid.

100 ml of acetic anhydride were added to 10 g (35 mmole) of 2-(1-naphthylidene)adipic acid (prepared as described above) and the mixture was stirred at 60° C. for 1 hour. At the end of this time, the solvent was removed by distillation under reduced pressure, and the resulting residue was triturated with a 1: 1 by volume mixture of benzene and hexane. The solvent was decantated to afford 8.8 g of 2-(1-naphthylidene)adipic anhydride as an oily material.

To a solution of 4.4 g (16.5 mmole) of 2-(1-naphthylidene)adipic anhydride (prepared as described above) dissolved in 80 ml of methylene chloride were added 1.58 ml (18.2 mmole) of morpholine, and the mixture was stirred at room temperature for 14 hours. At the end of this time, the reaction mixture was washed, in turn, with a 5% w/v aqueous solution of citric acid and with a saturated aqueous solution of sodium chloride and dried over anhydrous sodium sulfate. The mixture was then freed from the solvent by evaporation under reduced pressure, and the residue was purified by silica gel column chromatography (eluent: a 30: 1 by volume mixture of methylene chloride and methanol), to afford 1.12 g of 5-morpholinocarbonyl-2-(1-naphthylidene)pentanoic acid.

350 mg (0.99 mmole) of 5-morpholinocarbonyl-2-(1-naphthylidene)pentanoic acid (prepared as described above) were dissolved in 10 ml of methanol and hydrogenated in the presence of hydrogen under atmospheric pressure and in the presence of 100 mg of a 10% w/w palladium-on-carbon catalyst. The catalyst was removed by filtration, and the filtrate was concentrated by evaporation under reduced pressure, to afford 305 mg of the monohydrate of the title compound as a white powder.

Mass Spectrum m/e: 355.

Elemental analysis: Calculated for $C_{21}H_{25}NO_4$ $H_2O$: C, 67.54%; H, 7.29%; N, 3.75%. Found: C, 67.88%; H, 7.03%; N, 3.61%.

36(b)

N-{N-[(2R)-5-Morpholinocarbonyl-2-(1-naphthylmethyl)pentanoyl]-3-(4-thiazolyl)-L-alanyl}cyclostatin-(2-morpholinoethyl)amide Following a procedure similar to that described in Example 3(a), 275 mg (0.77 mmole) of 5-morpholinocarbonyl-2-(1-naphthylmethyl)pentanoic acid (prepared by a procedure similar to that described in Preparation 28) [instead of (2R)-3-morpholinocarbonyl-2-(1-naphthylmethyl)propionic acid] were reacted with the compound prepared by cleavage of the t-butoxycarbonyl group from 360 mg (0.77 mmole) of N-[N-(t-butoxycarbonyl)-3-(4-thiazolyl)-[-alanyl]-cyclostatin-(2-morpholinoethyl)amide. The thin layer chromatogram of the products showed two main spots. The title compound detected as the lower spot on the chromatogram and was purified by silica gel thin layer chromatography (developing solvent: an 8: 1 by volume mixture of methylene chloride and methanol), to afford 80 mg of the 3.5-hydrate of the title compound as white crystals, melting at 101°–105° C.

Silica gel thin layer chromatography, Rf value 0.54.

$[\alpha]_D^{27} = -21.9°$ (c=0.3, methanol).

Elemental analysis: Calculated for $C_{44}H_{62}N_6O_7S$ 3.5 $H_2O$: C, 59.91%; H, 7.88%; N, 9.53%; S, 3.63%. Found: C, 60.06%; H, 7.79%; N, 9.45%; S, 3.59%.

EXAMPLE 37

N-{N-[(2R)-3-(Benzylcarbamoyl)-2-(1-naphthylmethyl)propionyl]-3-(4-thiazolyl)-DL-alanyl}-cyclostatin(2-morpholinoethyl)amide Following a procedure similar to that described in Example 2(b), 100 mg (0.32 mmole) of (2R)-3-(benzylcarbamoyl)-2-(1-naphthylmethyl)propionic acid (prepared as described in Preparation 27) were reacted with 180 mg (0.32 mmole) of N-(t-butoxycarbonyl)-3-(4-thiazolyl)-DL-alanyl-cyclostatin-(2-morpholino ethyl)amide [prepared as described in Example 2(a)], to afford 77 mg of the sesquihydrate of the title compound as a colorless amorphous substance.

Silica gel thin layer chromatography, Rf value 0.50.

Elemental analysis: Calculated for $C_{45}H_{58}N_6O_6S$ 1.5 $H_2O$: C, 64.49%; H, 7.34%; N, 10.03%; S, 3.83%. Found: C, 64.43%; H, 7.03%; N, 9.82%; S, 3.82%.

EXAMPLE 38

N-{N-[(2R)-4-Morpholinocarbonyl-2-(1-naphthylmethyl)-butanoyl]-3-(4-thiazolyl)-L-alanyl}-cyclostatin(2-morpholinoethyl)amide Following a procedure similar to that described in Example 1(a), 249 mg (0.73 mmole) of 4-morpholinocarbonyl-2-(1-naphthylmethyl)butyric acid (prepared as described in Preparation 28) [instead of (2R)-3morpholinocarbonyl-2-(1-naphthylmethyl)propionic acid] were reacted with 384 mg (0.66 mmole) of N-(t-butoxycarbonyl)-3-(4-thiazolyl)-[-alanyl-cyclostatin-(2morpholinoethyl)amide. The thin layer chromatogram of the products showed two main spots. The compound detected as the lower spot on the chromatogram was purified by silica gel thin layer chromatography (developing solvent: an 8: 1 by volume mixture of methylene chloride and methanol), to afford 110 mg of the monohydrate of the title compound as white crystals, melting at 87°–90° C.

Silica gel thin layer chromatography, Rf value 0.58.

$[\alpha]_D^{25} = -24.4°$ (c=0.5, methanol).

Elemental analysis: Calculated for $C_{43}H_{60}N_6O_7S$ $H_2O$: C, 62.73%; H, 7.59%; N, 10.21%; S, 3.89%. Found: C, 62.95%; H, 7.76%; N, 9.90%; S, 4.10%.

EXAMPLE 39

N-{N-[(2R)-3-(N-Benzyl-N-methylcarbamoyl)-2-(1-naphthylmethyl)propionyl]-3-(5-isoxazolyl)-L-alanyl} cyclostatin-(2-morpholinoethyl)amide Following a procedure similar to that described in Example 3(b), 100 mg (0.28 mmole) of (2R)-3-(N-benzyl-N-methylcarbamoyl)-2-(1-naphthylmethyl)propionic acid (prepared as described in Preparation 32) were reacted with 160 mg (0.2 8 mmole) of N-[N-(t-butoxycarbonyl)3-(5-isoxazolyl)-L-alanyl]-cyclostatin-(2-morpholinoethyl)amide, to afford 56 mg of the dihydrate of the title compound a s a colorless amorphous substance.

Silica gel thin layer chromatography, Rf value 0.41.

Elemental analysis: Calculated for $C_{46}H_{60}N_6O_7$ 2 $H_2O$: C, 65.38%; H, 7.63%; N, 9.95%. Found: C, 65.40%; H, 7.38%; N, 9.94%.

EXAMPLE 40

N-{N-[N-Morpholinoacetyl-(1-naphthyl)-L-alanyl]-3-(4-thiazolyl)-DL-alanyl}-cyclostatin-(2-morpholinoethyl)amide

40(a)

N-{N-[N-(t-Butoxycarbonyl)-3-(1-naphthyl)-L-alanyl]-3-(4-thiazolyl)-DL-alanyl}-cyclostatin-(2-morpholinoethy)amide The t-butoxycarbonyl group was removed from 254 mg (0.44 mmole) of N-[N-t-butoxycarbonyl-3-(4-thiazolyl)-DL-alanyl]-cyclostatin-2-(morpholinoethyl)amide [prepared as described in Example 2(a)] using a 4N solution of hydrogen chloride in dioxane. The product was then suspended, together with 165 mg (0.52 mmole) of N-(t-butoxycarbonyl)-3-(1-naphthylmethyl)-L-alanine, in 10 ml of anhydrous tetrahydrofuran, and 0.08 ml (0.53 mmole) of diethylcyanophosphonate (95%) and 0.27 ml (1.94 mmole) of triethylamine were added to the suspension under an atmosphere of nitrogen, whilst ice-cooling. The mixture was agitated at room temperature overnight, after which the solvent was removed by distillation under reduced pressure, and the residue was purified by silica gel thin layer chromatography (developing solvent: a 7: 1 by volume mixture of chloroform and methanol), to afford 303 mg (87%) of the dihydrate of the title compound as white crystals, melting at 113°–116° C.

Elemental analysis: Calculated for $C_{41}H_{58}N_6O_7S$ 2 $H_2O$: C, 60.42%; H, 7.67%; N, 10.31%; S, 3.93%. Found: C, 60.60%; H, 7.43%; N, 10.09%; S, 3.97%.

40(b)

N-{N-[N-Morpholinoacetyl-3-(1-naphthyl)-L-alanyl]-3-(4-thiazolyl)-DL-alanyl}-cyclostatin-(2-morpholinoethyl)amide The t-butoxycarbonyl group was removed from 262 mg (0.34 mmole) of N-{N-[N-(t-butoxycarbonyl)-3-(1naphthyl)-L-alanyl]-3-(4-thiazolyl)-DL-alanyl}-cyclostatin-(2-morpholinoethyl)amide [prepared as described in Example 40(a)] using a 4N solution of hydrogen chloride in dioxane. The product, together with 59 mg (0.40 mmole) of 1-morpholinoacetic acid, was suspended in 5 ml of anhydrous tetrahydrofuran, and 0.06 ml (0.40 mmole) of diethyl cyanophosphonate (95%) and 0.21 ml (1.51 mmole) of triethylamine were added to the suspension, whilst ice-cooling in an atmosphere of nitrogen. The mixture was agitated at room temperature overnight, and then the solvent was removed by distillation under reduced pressure. The residue was purified by silica gel thin layer chromatography (developing solvent: a 7: 1 by volume mixture of chloroform and methanol), to afford 230 mg (85%) of the dihydrate of the title compound as white crystals, melting at 98°–99° C.

Elemental analysis: Calculated for $C_{42}H_{59}N_7O_7S$ 2 $H_2O$: C, 59.90%; H, 7.54%; N, 11.64%; S, 3.81%. Found: C, 59.69%; H, 7.61%; N, 11.50%; S, 3.74%.

EXAMPLE 41

N-{N-[N-(3-Morpholinopropionyl)-(1-naphthyl)-L-alanyl]-3-(4-thiazolyl)-DL-alanyl}-cyclostatin-(2-morpholinoethyl)amide Following a procedure similar to that described in Example 40(b), 200 mg ( 0.26 mmole) of N-{N-[N-(t-butoxycarbonyl)-3-(1-naphthyl)-L-alanyl]-3-(4- thiazolyl)-DL-alanyl}-cyclostatin-(2-morpholinoethyl-)amide [prepared as described in Example 40(a)] and 57 mg (0.29 mmole) of N-3-morpholinopropionic acid hydrochloride were reacted, to afford 130 mg of the monohydrate of the title compound as a white powder. Silica gel thin layer chromatography (developing solvent: a 10: 1 by volume mixture of methylene chloride and methanol).

Silica gel thin layer chromatography, Rf value 0.21.
Elemental analysis: Calculated for $C_{43}H_{61}N_7O_7$ S $H_2O$: C, 61.63%; H, 7.58%; N, 11.70%; S, 3.82%. Found: C, 61.65%; H, 7.59%; N, 11.64%; S, 3.68%.

EXAMPLE 42

N- 55 N-[N-(4-Morpholinobutyryl)-3-(1-naphthyl-L-alanyl]-3-(4-thiazolyl)-DL-alanyl}-cyclostatin-(2-morpholinoethyl)amide Following a procedure similar to that described in Example 40(b), 200 mg (0.26 mmole) of N-{N-[N-(t-butoxycarbonyl)-3-(1-naphthyl)-L-alanyl]-3-(4-thiazolyl)-DL-alanyl}-cyclostatin-(2-morpholinoethyl-)amide [prepared as described in Example 40(a)] and 61 mg (0.29 mmole) of N-4-morpholinobutyric acid were reacted, to afford 100 mg of the 1.5-hydrate of the title compound as a white power.

Silica gel thin layer chromatography, Rf value 0.27.
Elemental analysis: Calculated for $C_{44}H_{63}N_7O_7S$ 3/2 $H_2O$: C, 61.37%; H, 7.73%; N, 11.39%; S, 3.72%. Found: C, 61.19%; H, 7.65%; N, 11.22%; 3.60%.

EXAMPLE 43

N-{N-[N-Morpholinoacetyl-3-(1-naphthyl)-L-alanyl]-(4-thiazolyl)-DL-alanyl]-cyclostatin-2-(1-pyrrolidinylethyl)amide A procedure similar to that described in Example 2(a) was repeated, except that we employed 324 mg (0.79 mmole) of N-t-butoxycarbonyl-cyclostatin-2-(1-pyrrolidinylethyl)amide, instead of the N-t-butoxycarbonyl-cyclostatin-(2-morpholinoethyl)amide, and 215 mg (0.79 mmole) of N-(t-butoxycarbonyl)-(4-thiazolyl)-DL-alanine. The product was then reacted in a manner similar to that described in Example 40(a) and (b), to afford 54 mg of the octahydrate of the title compound, melting at 75°–83° C.

Elemental analysis: Calculated for $C_{42}H_{59}N_7O_6S$ 8 $H_2O$: C, 54.00%; H, 8.08%; N, 10.50%; S, 3.43%. Found: C, 53.73%; H, 7.95%; N. 10.40%; S, 3.53%.

EXAMPLE 44

N-{N-[N-(2,6-Dimethylmorpholinoacetyl)-3-(1-naphthyl)-L-alanyl]-3-(4-thiazolyl)-DL-alanyl}-cyclostatin-(2-morpholinoethyl)amide Following a procedure similar to than described in Example 40(b), 270 mg (0.35 mmole) of N-{N-[N-(t-butoxycarbonyl)-3-(1-naphthyl)-L-alanyl]-3-(4-thiazolyl)-DL-alanyl}-cyclostatin-(2-morpholinoethyl-)amide [prepared as described in Example 40(a)] and 69 mg (0.4 mmole) of 2,6-dimethylmorpholinoacetic acid were reacted, to afford 90 mg of the sesquihydrate of the title compound as an amorphous substance.

Silica gel thin layer chromatography, Rf value 0.33.
Elemental analysis: Calculated for $C_{44}H_{63}N_7O_7S$ 1.5 $H_2O$: C, 61.37%; H, 7.73%; N, 11.39%; S, 3.72%. Found: C, 61.11%; H, 7.43%; N, 11.33%; S, 3.89%.

EXAMPLE 45

N-{N-[N-t-Butoxycarbonylprolyl-3-(1-naphthyl)-L-alanyl]-3-(4-thiazolyl)-DL-alanyl}-cyclostatin-(2-morpholinoethyl)amide Following a procedure similar to that described Example 40(b), 150 mg (0.19 mmole) of N-{N-[N-(t-butoxycarbonyl)- 3-(1-naphthyl)-L-alanyl]-3-(4-thiazolyl)-DL-alanyl}-cyclostatin-(2-morpholinoethyl)amide [prepared as described in Example 40(a)] and 40 mg (0.19 mmole) of N-(t-butoxycarbonyl)-L-proline were reacted, to afford 90 mg of the monohydrate of the title compound as an amorphous substance.

Silica gel thin layer chromatography, Rf value 0.42.
Elemental analysis: Calculated for $C_{46}H_{65}N_7O_8S$ $H_2O$: C, 61.79%; H, 7.55%; N, 10.97%; S, 3.59%. Found: C, 61.58%; H, 7.42%; N, 11.23%; S, 3.42%.

EXAMPLE 46

N-{N-[N-Morpholinoacetyl-3-(1-naphthyl)-L-alanyl]-3-(4-thiazolyl)-DL-alanyl}-cyclostatin-(2-morpholinoethyl)amide

46(a)

N-{N-[N-Bromoacetyl-3-(1-naphthyl)-L-alanyl]-3-(4-thiazolyl)-DL-alanyl}-cyclostatin-(2-morpholinoethyl-)amide 5 ml of a 4N solution of hydrogen chloride in dioxane were added to a solution of 350 mg (0.45 mmole) of N-{N-[N-(t-butoxycarbonyl)-3-(1-naphthyl)-L-alanyl]-3-(4-thiazolyl)-DL-alanyl}-cyclostatin-(2-morpholinoethyl)amide [prepared as described in Example 40(a)] in 5 ml of methanol, and the mixture was agitated at room temperature for 1 hour. At the end of this time, the reaction mixture was concentrated by distillation under reduced pressure, and the residue was suspended in 10 ml of tetrahydrofuran, 0.085 g (0.54 mmole) of bromoacetylchloride and 0.165 g (1.62 mmole) of triethylamine were then added to this suspension, whilst ice-cooling, and the mixture was agitated for 3 hours. At the end of this time, the solvent was removed by distillation under reduced pressure, and the residue was purified by silica gel thin layer chromatography (developing solvent: a 9: 1 by volume mixture of chloroform and methanol), to afford 122 mg of the dihydrate of the title compound as white crystals, melting at 96°–100° C.

Elemental analysis: Calculated for $C_{38}H_{51}N_6O_6SBr$ 2 $H_2O$: C, 54.60%; H, 6.63%; N, 10.05%. Found: C, 54.83%; H, 6.36%; N, 9.89%.

46(b)

N-{N-[N-Morpholinoacetyl-3-(1-naphthyl)-L-alanyl]-3-(4-thiazolyl)-DL-alanyl}-cyclostatin-(2-morpholinoethyl)amide 0.026 g (0.3 mmole) of morpholine was added, whilst ice-cooling, to a suspension of 100 mg (0.12 mmole) of N-{N-[N-bromoacetyl-3-(1-naphthyl)-L-alanyl]-3-(4-thiazolyl)-DL-alanyl}-cyclostatin-(2-morpholinoethyl-)amide [prepared as described in step (a) above] in 5 ml of dimethylformamide, and the mixture was agitated at room temperature overnight. The solvent was then removed by distillation under reduced pressure, and the residue was purified by silica gel thin layer chromatography (developing solvent: a 9: 1 by volume mixture of chloroform and methanol), to afford 52 mg of the dihydrate of the title compound as crystals, melting at 96°–99° C.

Elemental analysis: Calculated for $C_{42}H_{59}N_7O_7S$ 2 $H_2O$: C, 59.90%; H, 7.54%; N, 11.64%; S, 3.81%. Found: C, 59.69%; H, 7.61%; N, 11.50%; S, 3.74%.

EXAMPLE 47

N-{N-[N-Morpholinoacetyl-3-(1-naphthyl)-L-alanyl]-3-(5-isoxazolyl)-L-alanyl}-cyclostatin-(2-morpholinoethyl)amide

47(a)

N-[N-(t-Butoxycarbonyl)-3-(5-isoxazolyl)-L-alanyl]-cyclostatin-(2-morpholinoethyl)amide 5 ml of a 4N solution of hydrogen chloride in dioxane were added, whilst ice-cooling, to a solution of 0.125 g (0.29 mmole) of N-(t-butoxycarbonyl)-cyclostatin-(2-morpholinoethyl)amide [prepared as described in Preparation 17(a)] in 5 ml of dioxane, and the mixture was agitated at room temperature for 2 hours. At the end of this time, the reaction mixture was evaporated to dryness under reduced pressure, and a solution of 89 mg (0.348 mmole) of N-(t-butoxycarbonyl)-(5-isoxazolyl)-L-alanine (prepared as described in Preparation 8) in 15 ml of dimethylformamide was added to the residue. 0.13 g (1.276 mmole) of triethylamine and 57 mg (0.348 mmole) of diethyl cyanophosphonate (95%) were then added to the mixture, which was then allowed to react at room temperature for 21 hours. At the end of this time, the solvent was removed by distillation under reduced pressure, and water was added to the residue. The mixture was then extracted with methylene chloride, the extract was dried, and the solvent was removed by distillation under reduced pressure. The residue was purified by silica gel column chromatography (eluent: a 1: 49 by volume mixture of methanol and methylene chloride), to afford 85 mg (51.81) of the title compound as an oily substance.

47(b)

N-{N-[N-(t-Butoxycarbonyl)-3-(1-naphthyl)-L-alanyl]-3-(5-isoxazolyl)-L-alanyl}-cyclostatin(2-morpholinoethyl)amide 5 ml of a 4N solution of hydrogen chloride in dioxane were added to a solution of 0.2 g (0.35 mmole) of N-[N-(t-butoxycarbonyl)-3-(5-isoxazolyl)-L-alanyl]-cyclostatin-(2-morpholinoethyl)amide [prepared as described in step (a) above] in 5 ml of methanol, and the mixture was agitated at room temperature for 1 hour. At the end of this time, methanol and dioxane were removed by distillation to dryness under reduced pressure, and the residue was suspended in anhydrous tetrahydrofuran. 0.11 g (0.35 mmole) of N-(t-butoxycarbonyl)-3-(1-naphthyl)-L-alanine, 0.14 g (1.4 mmole of triethylamine and 69 mg (0.42 mmole) of diethyl cyanophosphonate (95%) were added to this suspension, whilst ice-cooling, and the mixture was agitated at the temperature of ice-cooling for 0.5 hours and then at room temperature for 39 hours. At the end of this time, the solvent was removed by distillation under reduced pressure. The residue was purified by silica gel thin layer chromatography (developing solvent: a 1 : 9 by volume mixture of methanol and methylene chloride), to afford 0.19 g (70.4%) of the 2.5-hydrate of the title compound as a colorless amorphous substance.

Elemental analysis: Calculated for $C_{41}H_{58}N_6O_8$ 2.5 $H_2O$: C, 60.95%; H, 7.86%; N, 10.40%. Found: C, 60.76%; H, 7.67%; N, 10 36%.

47(c)

N-{N-[N-Morpholinoacetyl-3-(1-naphthyl)-L-alanyl]-3-(5-isoxazolyl)-L-alanyl}-cyclostatin-(2-morpholinoethyl)amide 2 ml of a 4N solution of hydrogen chloride in dioxane were added to a solution of 90 mg (0.118 mmole) of N-{N-[N-(t-butoxycarbonyl)-3-(1-naphthyl)-L-alanyl]-3-(5-isoxazolyl)-L-alanyl}-cyclostatin-(2-morpholinoethyl)amide in 2 ml of methanol, and the mixture was agitated at room temperature for 1 hour. The reaction mixture was then suspended in 15 ml of anhydrous tetrahydrofuran, and 17 mg (0.118 mole) of 1-morpholinoacetic acid, 48 mg (0.472 mmole) of triethylamine and 23 mg (0.142 mmole) of diethyl cyanophosphonate (95%) were added to the resulting suspension, whilst ice-cooling. The mixture was then agitated at the temperature of ice-cooling for 0.5 hours and then at room temperature for a further 14 hours. At the end of this time, the solvent was removed by distillation under reduced pressure, and the residue was purified by silica gel thin layer chromatography (developing solvent: a 1: 9 by volume mixture of methanol and methylene chloride), to afford 33 mg (33.8%) of the dihydrate of the title compound as a pale-yellow powder, melting at 75°-77° C.

Elemental analysis: Calculated for $C_{42}H_{59}N_7O_8$ 2 $H_2O$: C, 61.07%; H, 7.69%; N, 11.87%. Found: C, 61.16%; H, 7.47%; N, 11.96%.

EXAMPLE 48

N-{N-[N-(4-Phenyl-1-piperazinylacetyl)-3-(1-naphthyl)-L-alanyl]-3-(4-thiazolyl)-DL-alanyl}-cyclostatin-(2-morpholinoethyl)amide

48(a)

N-[N-(t-Butoxycarbonyl)-3-(4-thiazolyl)-DL-alanyl]-cyclostatin-(2-morpholinoethyl)amide 3 g of cyclostatin-(2-morpholinoethyl)amide dihydrochloride, 2.04 g of N-(t-butoxycarbonyl)-(4-thiazolyl)-DL-alanine and 4.2 ml of triethylamine were added to 50 ml of dimethylformamide, and then 1.34 g of diethyl cyanophosphonate (90%) was added dropwise to the mixture, whilst ice-cooling. The reaction mixture was agitated for 6 hours, and then allowed to stand overnight. It was then evaporated to dryness under reduced pressure. The residue was dissolved in methylene chloride, and the resulting solution was washed with a saturated aqueous solution of sodium bicarbonate and with a saturated aqueous solution of sodium chloride, in that order, and dried over anhydrous magnesium sulfate. The solvent was then removed by distillation under reduced pressure. The residue was purified by silica gel column chromatography (eluent: a 1: 19 by volume mixture of methanol and methylene chloride), to afford 2.80 g of the title compound as a white crystalline substance, melting at 72°-75° C.

48(b)

N-{N-[N-(4-Phenyl-1-piperazinylacetyl)-3-(1-naphthyl)-L-alanyl]-3-(4-thiazolyl)-DL-alanyl}-cyclostatin-(2-morpholinoethyl)amide 279 mg of N-[N-(t-butoxycarbonyl)-3-(4-thiazolyl)-DL-alanyl]-cyclostatin-(2-morpholinoethyl)amide and 2 ml of a 4N solution of hydrogen chloride in dioxane were added to 2 ml of methanol, and the mixture was agitated at room temperature for 1 hour. At the end of this time, it was concentrated by evaporation under reduced pressure. The residue was dissolved in 5 ml of dimethylformamide, and 200 mg of N-(4-phenyl-1-piperazinylacetyl)-3-(1-naphthyl)-L-alanine (prepared as described in Preparation 34), 0.33 ml of triethylamine and 100 mg of diethyl cyanophosphonate (90%) were added thereto, whilst ice-cooling. The mixture was then agitated for 4 hours, after which it was concentrated by evaporation under reduced pressure, and the residue was purified by silica gel column chromatography (eluent: a 1: 19 by volume mixture of methanol and methylene chloride), to afford 233 mg of the 2.5-hydrate of the title compound as a colorless amorphous substance.

Silica gel thin layer chromatography, Rf value 0.53.

Elemental analysis: Calculated for $C_{48}H_{64}N_8O_6S$ 2.5 $H_2O$: C, 62.25%; H, 7.51%; N, 12.10%; S, 3.46%. Found: C, 62.48%; H, 7.52%; N, 11.97%; S, 3.67%.

EXAMPLE 49

N-{N-[N-Piperidinoacetyl-3-(1-naphthyl)-L-alanyl]-3-(4-thiazolyl)-DL-alanyl}-cyclostatin-(2-morpholinoethyl)amide

49(a) Methyl N-[N-bromoacetyl-3-(1-naphthyl)-L-alanyl]-3-(4-thiazolyl)-DL-alanate 10 ml of a 4N solution of hydrogen chloride in dioxane were added to 491 mg (1.02 mmole) of methyl N-(t-butoxycarbonyl)-(1-naphthyl)-L-alanyl-4-thiazolyl-DL-alanate, and the mixture was agitated at room temperature for 30 minutes, after which it was evaporated to dryness under reduced pressure. The residue was suspended in 10 ml of tetrahydrofuran, and 0.10 ml (1.21 mmole) of bromoacetyl chloride was added to the suspension, whilst ice-cooling. The mixture was then agitated at the temperature of ice-cooling for 1 hour and then at room temperature for a further 1 hour. At the end of this time, the solvent was removed by distillation, and a small amount of a saturated aqueous solution of sodium chloride was added to the residue. The mixture was then extracted with ethyl acetate. The extract was dried, and the solvent was removed by distillation. The residue was purified by silica gel column chromatography (eluent: a 1: 4 by volume mixture of hexane and ethyl acetate), to afford 360 mg of the title compound.

49(b) Methyl N-[N-piperidinoacetyl-3-(1-naphthyl)-L-alanyl]-3-(4-thiazolyl)-DL-alanate 3.44 mg (0.325 mmole) of sodium carbonate and 55.3 mg (0.65 mmole) of piperidine were added to a suspension of 300 mg (0.59 mmole) of methyl N-[N-bromoacetyl-3-(1-naphthyl)-L-alanyl]-3-(4-thiazolyl)-DL-alanate [prepared as described in step (a) above] in 10 ml of dimethylformamide, and the mixture was agitated at room temperature for 10 hours. At the end of this time, the solvent was removed by distillation under reduced pressure, and the residue was purified by silica gel column chromatography (eluent: a 10: 1 by volume mixture of chloroform and methanol), to afford 251 mg of the title compound.

49(c) N-[N-Piperidinoacetyl3-(1naphthyl)-L-alanyl]-3-(4-thiazolyl)-DL-alanine hydrazide 295 mg (5.9 mmole) of hydrazine hydrate were added to a solution of 300 mg (0.589 mmole) of methyl N-[N-piperidinoacetyl-3-(1-naphthyl)-L-alanyl]-3-(4-thiazolyl)-DL-alanate [prepared as described in step (b) above] in 10 ml of dimethylformamide, and the mixture was agitated at room temperature for 16 hours. At the end of this time, the solvent was removed by distillation under reduced pressure, and the residue was crystallized by adding hexane, to afford 150 mg of the title compound.

49(d) N-{N-[N-Piperidinoacetyl-3-(1-naphthyl)-L-alanyl]-3-(4-thiazolyl)-DL-alanyl}-cyclostatin-(2-morpholinoethyl)amide A solution of 150 mg of N-[N-piperidinoacetyl-3-(1-naphthyl)-L-alanyl]-3-(4-thiazolyl)-DL-alanine hydrazide [prepared as described in step (c) above] in 3 ml of dimethylformamide was cooled to $-60°$ C. in a dry ice-acetone bath, and then 0.248 ml of a 4N solution of hydrogen chloride in dioxane and 50 μl (0.295 mmole) of isoamyl nitrite were added thereto, whilst stirring. The mixture was then stirred for a further 20 minutes at $-20°$ C., after which 159.5 mg (1.58 mmole) of N-methylmorpholine and 118 mg (0.295 mmole) of cyclostatin-(2-morpholinoethyl)amide were added, and the mixture was stirred at 4° C. for 16 hours. The solvent was then removed by distillation under reduced pressure, and the residue was purified by silica gel thin layer chromatography (developing solvent: a 10: 1 by volume mixture of chloroform and methanol), to afford 89 mg of the trihydrate of the title compound, melting at 85°–90° C.

Elemental analysis: Calculated for $C_{43}H_{61}N_7O_6S$ 3 $H_2O$: C, 60.26%; H, 7.74%; N, 11.44%; S, 3.74%. Found: C, 60.54%; H, 7.75%; N, 11.69%; S, 3.59%.

EXAMPLE 50

N-{N-[N-Thiomorpholinoacetyl-3-(1-naphthyl)-L-alanyl]-3-(4-thiazolyl)-DL-alanyl}-cyclostatin-(2-morpholinoethyl)amide Following a procedure similar to that described in Example 49(b), 150 mg (0.295 mmole) of methyl N-[N-bromoacetyl-3-(1-naphthyl)-L-alanyl]-3-(4-thiazolyl)-DL-alanate [prepared as described in Example 49(a)] and 33.5 mg (0.325 mmole) of thiomorpholine were reacted, and then subsequently subjected to the reactions described in Examples 49(c) and Example 49(d), to afford 55 mg of the monohydrate of the title compound as white crystals, melting at 115°–120° C.

Elemental analysis: Calculated for $C_{42}H_{59}N_7O_6S_2$ $H_2O$: C, 60.12%; H, 7.32%; N, 11.68%; S, 7.64%. Found: C, 59.89%; H, 7.34%; N, 11.45%; S, 7.26%.

EXAMPLE 51

N-{N-[N,N-Diethylaminoacetyl-3-(1-naphthyl)-L-alanyl]-3-(4-thiazolyl)-DL-alanyl}-cyclostatin-(2-morpholinoethyl)amide

51(a) Methyl N-bromoacetyl-3-(1-naphthyl)-L-alanate 1.11 g (11.1 mmole) of triethylamine and 1.02 g (5.5 mmole) of bromoacetyl chloride were added to a mixture of 1.3 g (5 mmole) of methyl 3-(1-naphthyl)-L-alanate in 30 ml of methylene chloride whilst cooling and stirring, and the mixture was then stirred at room temperature for 1 hour. At the end of this time, the solvent was removed by distillation under reduced pressure, water was added to the residue, and the mixture was extracted with ethyl acetate. The extract was dried, the solvent was removed by distillation, and the residue was crystallized from a mixture of ethyl acetate and hexane, to afford 1.5 g of the title compound, melting at 110° C.

51(b) Methyl N,N-diethylaminoacetyl-3-(1-naphthyl)-L-alanate 63.6 mg (0.6 mmole) of sodium carbonate and 87.8 mg (1.2 mmole) of diethylamine were added to a solution of 350 mg (1 mmole) of methyl N-bromoacetyl-3-(1-naphthyl)-L-alanate [prepared as described in step (a) above] in 10 ml of dimethylformamide, and the mixture was agitated at room temperature for 10 hours. At the end of this time, the solvent was removed by distillation under reduced pressure, a small amount of water was added to the residue, and the mixture was extracted with ethyl acetate. The extract was dried, the solvent was removed by distillation under reduced pressure, and the residue was purified by silica gel column chromatography (eluent: a 10: 1 by volume mixture of chloroform and methanol), to afford 319 mg of the title compound as an oily substance.

51(c) N-{N-[N,N-Diethylaminoacetyl-3-(1-naphthyl)-L-alanyl]-3-(4-thiazolyl)-DL-alanyl}-cyclostatin-(2-morpholinoethyl)amide 1 ml of a 1N aqueous solution of sodium hydroxide was added to a solution of 159 mg (0.465 mmole) of methyl N,N-diethylaminoacetyl-3-(1-naphthyl)-L-alanate [prepared as described in step (b) above] in 1 ml of methanol, and the mixture was agitated at room temperature for 4 hours. 1 ml of 1N aqueous hydrochloric acid was added, and then the reaction mixture was evaporated to dryness under reduced pressure. The residue was dissolved in 3 ml of dimethylformamide, and 47 mg (0.465 mmole) of triethylamine, 224 mg (0.465 mmole) of 3-(4-thiazolyl)-DL-alanyl-cyclostatin-(2-morpholinoethyl)amide and 75.8 mg (0.465 mmole) of diethyl cyanophosphonate (95%) were added thereto, and the reaction mixture was agitated at room temperature for 4 hours. At the end of this time, the solvent was removed by distillation under reduced pressure, and the residue was purified by silica gel column chromatography (eluent: a 10: 1 by volume mixture of chloroform and methanol), to afford 95 mg of the dihydrate of the title compound as white crystals.

Elemental analysis: Calculated for $C_{42}H_{61}N_7O_6S$ 2 $H_2O$: C, 60.99%; H, 7.92%; N, 11.85%; S, 3.88%. Found: C, 61.06%; H, 7.94%; N, 11.94%; S, 3.87%. Silica gel thin layer chromatography, Rf value 0.57.

EXAMPLE 52

N-{N-[N-(N-Benzyl-N-methylaminoacetyl)-3-(1-naphthyl)-L-alanyl]-3-(4-thiazolyl)-DL-alanyl}-cyclostatin-(2-morpholinoethyl)amide Following a procedure similar to that described in Example 51(b), 175 mg (0.5 mmole) of methyl N-bromoacetyl-3-(1-naphthyl)-L-alanate [prepared as described in Example 51(a)] and 60.1 mg (0.5 mmole) of N-benzyl-N-methylamine were reacted together and subsequently treated as described in Example 51(c), to afford 51 mg of the sesquihydrate of the title compound as white crystals, melting at 71°–75° C.

Elemental analysis: Calculated for $C_{46}H_{61}N_7O_6S$ 1.5 $H_2O$: C, 63.71%; H, 7.44%; N, 11.30%; S, 3.70%. Found: C, 63.70%; H, 7.28%; N, 11.04%; S, 3.57%.

EXAMPLE 53

N-{N-[N-(N-Cyclohexyl-N-methylaminoacetyl)-3-(1-naphthyl)-L-alanyl]-3-(4-thiazolyl)-DL-alanyl}-cyclostatin-(2-morpholinoethyl)amide Following a procedure similar to that described in Example 51(b), 175 mg (0.5 mmole) of methyl N-bromoacetyl-3-(1-naphthyl)-L-alanate [prepared as described in Example 51(a)] and 6 4.1 mg (0.5 mmole) of N-cyclohexyl-N-methylamine were reacted together and subsequently treated as described in Example 51(c), to afford 65 mg of the monohydrate of the title compound as a white powder.

Silica gel thin layer chromatography, Rf value 0.56.

Elemental analysis: Calculated for $C_{45}H_{65}N_7O_6S$ $H_2O$: C, 63.58%; H, N, 11.53%; S, 3.77%. Found: C, 63.67%; H, N, 11.28%; S,

EXAMPLE 54

N-{N-[N-Morpholinoacetyl-3-(1-naphthyl)-L-alanyl]-3-(4-thiazolyl)-DL-alanyl}-cyclostatin-(1-ethyl-2-pyrrolidinylmethyl)amide

54(a) Methyl N-[N-(t-butoxycarbonyl)-3-(4-thiazolyl)-DL-alanyl]-cyclostatinate 2 ml of thionyl chloride were added at −20° C. to 20 ml of methanol, and the mixture was agitated for 10 minutes at the same temperature (−20° C.). 2.85 g (9.0 mmole) of N-(t-butoxycarbonyl)-cyclostatin were then added to the mixture, and the mixture was agitated at room temperature for 14 hours. At the end of this time, the solvent was removed by distillation under reduced pressure, and the product was distilled azeotropically three times with benzene to give methyl cyclostatinate hydrochloride. This product was then dissolved in 30 ml of dimethylformamide, and 2.71 g (9.9 mmole) of N-(t-butoxycarbonyl)-3-(4-thiazolyl)-DL-alanine, 1.97 g (10.9 mmole) of diethyl cyanophosphonate (95%) and 2.76 ml (19.9 mmole) of triethylamine were added to the resulting solution, whilst ice-cooling. The mixture was then agitated at room temperature for 3 hours. At the end of this time, the solvent was removed by distillation under reduced pressure, the residue was dissolved in ethyl acetate, the organic layer was washed with a 5% w/v aqueous solution of sodium bicarbonate, with a 5% w/v aqueous solution of citric acid and with a saturated aqueous solution of sodium chloride, in that order, after which it was dried over anhydrous sodium sulfate. The solvent was then removed by distillation under reduced pressure, and the residue was purified by silica gel column chromatography (eluent: a 50: 1 by volume mixture of methylene chloride and methanol), to afford 3.76 g of the title compound as an amorphous substance.

Elemental analysis: Calculated for $C_{23}H_{37}N_3O_6S$ C, 57.12; H, 7.71%; N, 8.69%; S, 6.63%. Found: C, 56.87; H, 7.75%; N, 8.41%; S, 6.68%.

54(b) N-{N-[N-Morpholinoacetyl-3-(1-naphthyl)-L-alanyl]-3-(4-thiazolyl)-DL-alanyl}-cyclostatin The t-butoxycarbonyl group was removed from 2.7 g (5.6 mmole) of methyl N-[N-(t-butoxycarbonyl)-3-(4-thiazolyl)-DL-alanyl]-cyclostatinate [prepared as described in step (a) above] by treatment with a 4N solution of hydrogen chloride in dioxane. The hydrochloride thus obtained, together with 1.9 g (5.6 mmole) of N-morpholinoacetyl-(1-naphthyl)-L-alanine [prepared as described in Preparation 35], were dissolved in 40 ml of methylene chloride, and 1.37 g (7.6 mmole) of diethylcyanophosphonate (95%) and 1.83 ml (13.2 mmole) of triethylamine were added to the resulting solution, whilst ice-cooling. The mixture was then agitated at room temperature for 3 hours. At the end of this time, the reaction mixture was concentrated by evaporation under reduced pressure, and the residue was dissolved in ethyl acetate. The resulting solution was washed with a 5% w/v aqueous solution of citric acid, with a 5% w/v aqueous solution of sodium bicarbonate and with a saturated aqueous solution of sodium chloride, in that order, after which it was dried over anhydrous sodium sulfate. The solvent was then removed by distillation under reduced pressure, and the residue was crystallized by the addition of diethyl ether, to afford 3.8 g of methyl N-{N-[N-morpholinoacetyl-3-(1-naphthyl)-L-alanyl]-3-(4-thiazolyl)-DL-alanyl}-cyclostatinate (melting at 54°–57° C.).

3.1 ml (3.1 mmole) of a 1N aqueous solution of sodium hydroxide were added to a solution of 2.2 g (3.1 mmole) of the methyl ester obtained as described above in 20 ml of methanol, and the mixture was agitated at room temperature for 1 hour. 0.78 ml (3.1 mmole) of a 4N solution of hydrogen chloride in dioxane were then added to the reaction mixture, after which the reaction mixture was extracted with methylene chloride. The organic extract was washed with a saturated aqueous solution of sodium chloride, and dried over anhydrous sodium sulfate. The solvent was then removed by distillation under reduced pressure, and the residue was crystallized by the addition of diethyl ether, to afford 2.0 g of the dihydrate of the title compound, melting at 113°–120° C.

Elemental analysis: Calculated for $C_{36}H_{47}N_5O_7S$ 2 $H_2O$: C, 59.23%; H, 7.04%; N, 9.60%; S, 4.39%. Found: C, 59.04%; H, 7.03%; N, 9.66%; S, 4.52%.

54(c)
N-{N-[N-Morpholinoacetyl-3-(1-naphthyl)-L-alanyl]-3-(4-thiazolyl)-DL-alanyl}-cyclostatin-(1-ethyl-2-pyrrolidinylmethyl)amide 78 mg (0.43 mmole) of diethyl cyanophosphonate (95%) and 60 μl (0.43 mmole) of triethylamine were added to a solution of 250 mg (0.36 mmole) of N-{N-[N-morpholinoacetyl-3-(1-naphthyl)-L-alanyl]-3-(4-thiazolyl)-DL-alanyl}-cyclostatin [prepared as described in step (b) above] and 69 mg (0.54 mmole) of 2-aminomethyl-1-ethyl-pyrrolidine in 5 ml of tetrahydrofuran, whilst ice-cooling, and the mixture was then agitated at room temperature for 5 hours. At the end of this time, the solvent was removed by distillation under reduced pressure, and the residue was purified by silica gel thin layer chromatography (developing solvent: a 5:1 by volume mixture of methylene chloride and methanol), to afford 120 mg of the dihydrate of the title compound, melting an 63°–67° C.

Elemental analysis: Calculated for $C_{43}H_{61}N_7O_6S$ 2 $H_2O$: C, 61.47%; H, 7.80%; N, 11.67%; B, 3.82%. Found: C, 61.22%; H, 7.52%; N, 11.48%; 5, 3.78%.

EXAMPLE 55

N-{N-[N-Morpholinoacetyl-3-(1-naphthyl)-L-alanyl]-3-(4-thiazolyl)-DL-alanyl}-cyclostatin-(2-diethylaminoethyl)amide Following a procedure similar to that described in Example 54(b), 2.7 g (5.6 mmole) of methyl N-[N-(t-butoxycarbonyl)-3-(4-thiazolyl)-DL-alanyl]-cyclostatinate [prepared as described in Example 54(a)] and 1.92 g (5.6 mmole) of N-morpholinoacetyl-3-(1-naphthyl)-L-alanine were reacted together and subsequently treated as described in Example 54(c), but using β-diethylaminoethylamine instead of 2-aminomethyl-1-ethyl-pyrrolidine, to afford 110 mg of the sesquihydrate of the title compound, melting at 65°–69° C.

Elemental analysis: Calculated for $C_{42}H_{61}N_7O_6S$ 1.5 $H_2O$: C, 61.59%; H, 7.88%; N, 11.97%; S, 3.91%. Found: C, 61.37%; H, 7.60%; N, 11.69%; S, 3.75%.

EXAMPLE 56

N-{N-[N-Morpholinoacetyl-3-(1-naphthyl)-L-alanyl]-3-(4-thiazolyl)-DL-alanyl}-cyclostatin-(2-pyridylmethyl)amide 56(a)
N-(t-Butoxycarbonyl)-cyclostatin-(2-pyridylmethyl)amide 194 mg (1.19 mmole) of diethyl cyanophosphonate (95%) and 250 mg (2.48 mmole) of triethylamine were added, whilst ice-cooling and stirring, to a solution of 250 mg (0.79 mmole) of N-(t-butoxycarbonyl)-cyclostatin and 103 mg (0.96 mmole) of 2-pyridylmethylamine in 10 ml of methylene chloride, and the mixture was stirred at room temperature overnight. The reaction mixture was then washed with a 10% w/v aqueous solution of sodium bicarbonate, dried over anhydrous sodium sulfate, and concentrated by evaporation under reduced pressure. The title compound thus obtained was used without purification for the subsequent reaction.

56(b)
N-{N-[N-(t-Butoxycarbonyl)-3-(1-naphthyl)-L-alanyl]-3-(4-thiazolyl)-DL-alanyl}-cyclostatin-(2-pyridylmethyl)amide The t-butoxycarbonyl group was removed from 271 mg (0.67 mmole) of N-(t-butoxycarbonyl)-cyclostatin-(2-pyridylmethyl)amide [obtained as described in step (a) above] by the addition of 10 ml of a 4N solution of hydrogen chloride in dioxane and agitation for 1 hour. At the end of this time, the reaction mixture was concentrated by evaporation under reduced pressure, benzene was added to the residue, and the mixture was again concentrated by evaporation under reduced pressure. This operation was repeated 2–3 times to remove thoroughly any remaining water. A solution of 345 mg (0.74 mmole) of N-[N-(t-butoxycarbonyl)-3-(1-naphthyl)-L-alanyl]-3-(4-thiazolyl)-DL-alanine (prepared as described in Preparation 37) in 10 ml of methylene chloride was then added to the residue, and 163 mg (1.0 mmole) of diethyl cyanophosphonate (95%) and 406 mg (4.0 mmole) of triethylamine were added to the resulting suspension, whilst ice-cooling and stirring. The mixture was then stirred at room temperature overnight. At the end of this time, the reaction mixture was washed with a 10% w/v aqueous solution of sodium bicarbonate, dried over anhydrous sodium sulfate, and concentrated by evaporation under reduced pressure. The title compound thus obtained was used without purification for the subsequent reaction.

56(c)

N-{N-[N-Morpholinoacetyl-3-(1-naphthyl)-L-alanyl]-3-(4-thiazolyl)-DL-alanyl}-cyclostatin-(2-pyridylmethyl)amide The t-butoxycarbonyl group was removed from 294 mg (0.39 mmole) of N-{N-[N-(t-butoxycarbonyl)-3-(1-naphthyl)-L-alanyl]-3-(4-thiazolyl)-DL-alanyl}-cyclostatin-(2-pyridylmethyl)amide [obtained as described in step (b) above] by the addition of 10 ml of a 4N solution of hydrogen chloride in dioxane and agitation for 1 hour. The reaction mixture was then concentrated by evaporation under reduced pressure, benzene was added to the residue, and the mixture was again concentrated by evaporation under reduced pressure. This operation was repeated 2-3 times to remove thoroughly any remaining water. A solution of 84 mg (0.58 mmole) of N-morpholinoacetic acid in 10 ml of methylene chloride was added to the residue, and then 128 mg (0.79 mmole) of diethylcyanophosphonate (95%) and 234 mg (2.32 mmole) of triethylamine were added to the resulting suspension, whilst ice-cooling and stirring. The mixture was then stirred at room temperature overnight. At the end of this time, the reaction mixture was washed with a 10% w/v aqueous solution of sodium bicarbonate, dried over anhydrous sodium sulfate, and concentrated by evaporation under reduced pressure. The compound thus obtained was purified by silica gel thin layer chromatography (developing solvent: a 10: 1 by volume mixture of chloroform and methanol), to afford 280 mg of the dihydrate of the title compound, melting at 83°-88° C.

Elemental analysis: Calculated for $C_{42}H_{53}N_7O_6S$ 2 $H_2O$: C, 61.51%; H, 7.00%; N, 11.96%; S, 3.91%. Found: C, 61.38%; H, 6.70%; N, 12.25%; S, 4.06%.

EXAMPLE 57

N-{N-[N-Morpholinoacetyl-3-(1-naphthyl)-L-alanyl]-3-(2-thienyl)-DL-alanyl}-cyclostatin-(2-morpholinoethyl)amide

57(a)
N-[N-(t-Butoxycarbonyl)-3-(2-thienyl)-DL-alanyl]-cyclostatin-(2-morpholinoethyl)amide 0.25 g (2.48 mmole) of triethylamine and 0.15 g (0.9 mmole) of diethylcyanophosphonate (95%) were added, whilst ice-cooling, to a suspension of 0.3 g (0.74 mmole) of cyclostatin-(2-morpholinoethyl)amide dihydrochloride [prepared as described in Preparation 17(b)] and 0.2 g (0.74 mmole) of N-(t-butoxycarbonyl)-3-(2-thienyl)-DL-alanine in 10 ml of anhydrous tetrahydrofuran and the mixture was stirred for 0.5 hours and the stirring was continued at room temperature for a further 15 hours. At the end of this time, the solvent was removed by distillation under reduced pressure, and the residue was purified by silica gel thin layer chromatography (developing solvent: a 9: 1 by volume mixture of methylene chloride and methanol), to afford 0.31 g (72.1%) of the title compound as an amorphous substance.

Elemental analysis: Calculated for $C_{29}H_{48}N_4O_6S$: C, 59.97%; H, 8.33%; N, 9.65%; So 5.52%. Found: C, 59.70%; H, 8.18%; N, 9.62%; S, 5.68%.

57(b)
N-{N-[N-Morpholinoacetyl-3-(1-naphthyl)-L-alanyl]-3-(2-thienyl)-DL-alanyl}-cyclostatin-(2-morpholinoethyl)amide 5 ml of a 4N solution of hydrogen chloride in dioxane were added to a solution of 0.21 g (0.366 mmole) of N-[N-(t-butoxycarbonyl)-3-(2-thienyl)-DL-alanyl]-cyclostatin-(2-morpholinoethyl)amide [prepared as described in step (a) above] in 5 ml of methanol, and the mixture was stirred at room temperature for 2 hours. At the end of this time, the solvent was removed by distillation to dryness under reduced pressure, and the residue was suspended in anhydrous tetranydrofuran. 0.13 g (0.366 mmole) of N-morpholinoacetyl-3-(1-naphthyl)-L-alanine (prepared by a procedure similar to that described in Preparation 35), 0.15 g (1.46 mmole) of triethylamine and 72 mg (0.44 mmole) of diethyl cyanophosphonate (95%) were then added, whilst ice-cooling, to the resulting suspension. The mixture was stirred for 0.5 hours at the temperature of ice-cooling, and then the stirring was continued at room temperature for a further 16 hours. At the end of this time, the solvent was removed by distillation under reduced pressure, and the residue was purified by silica gel thin layer chromatography (developing solvent: a 9: 1 by volume mixture of methylene chloride and methanol), to afford 0.24 g (77.4 %) of the trihydrate of the title compound as an amorphous substance.

Silica gel thin layer chromatography, Rf value 0.53.

Elemental analysis: Calculated for $C_{43}H_{60}N_6O_7S$ 3 $H_2O$: C, 60.12%; H, 7.74%; N, 9.78%; S, 3.73%. Found: C, 59.62%; H, 7.03%; N, 9.98%; S, 3.87%.

EXAMPLE 58

N-{N-[N-Morpholinoacetyl-3-(1-naphthyl)-L-alanyl]-3-(2-pyridyl)-DL-alanyl}-cyclostatin-(2-morpholinoethyl)amide Following a procedure similar to that described in Example 57(a), 0.2 g (0.75 mmole) of N-(t-butoxycarbonyl)-3-(2-pyridyl)-DL-alanine [instead of N-(t-butoxycarbonyl)-3-(2-thienyl)-DL-alanine] and 0.3 g (0.75 mmole) of cyclostatin-(2-morpholinoethyl)amide dihydrochloride were reacted together and subsequently treated as described in Example 57(b), to afford 87 mg of the 3.5-hydrate of the title compound as a white amorphous substance.

Silica gel thin layer chromatography, Rf value 0.28.

Elemental analysis: Calculated for $C_{44}H_{61}N_7O_7$ 3.5 $H_2O$: C, 61.23%; H, 7.94%; N, 11.36%. Found: C, 60.95%; H, 7.74%; N, 11.06%.

EXAMPLE 59

N-{N-[N-Morpholinoacetyl-3-(1-naphthyl)-L-alanyl]-L-tryptophyl}-cyclostatin-(2-morpholinoethyl)amide Following a procedure similar to that described in Example 57(a), 228 mg (0.749 mmole ) of N-(t-butoxycarbonyl)-L-tryptophan [instead of N-(t-butoxycarbonyl)-3-(2-thienyl)-alanine] and 300 mg (0.749 mmole) of cyclostatin-(2-morpholinoethyl)amide were reacted together and subsequently treated as described in Example 57(b), to afford 380 mg of the decahydrate of the title compound as an amorphous substance.

Silica gel thin layer chromatography, Rf value 0.37.

Elemental analysis: Calculated for $C_{47}H_{63}N_7O_7$ 10 $H_2O$: C, 55.44%; H, 8.22%; N, 9.63%. Found: C, 55.50%; H, 7.92%; N, 9.54%.

EXAMPLE 60

N-{N-[N-Morpholinoacetyl-3-(1-naphthyl)-L-alanyl]-3-(4-thiazolyl)-DL-alanyl}-cyclostatin-[3-(2-methylpiperidino)propyl]amide

60(a)

N-[N-(t-Butoxycarbonyl)-3-(4-thiazolyl)-DL-alanyl]-cyclostatin-[3-(2-methylpiperidino)propyl]amide 0.09 g (0.48 mmole) of diethyl cyanophosphonate (95%) and 0.05 g (0.48 mmole) of triethylamine were added, whilst ice-cooling, to a solution of 0.19 g (0.4 mmole) of N-[N-(t-butoxycarbonyl)-3-(4-thiazolyl)-DL-alanyl]-cyclostatin and 0.08 g (0.48 mmole) of N-(3-aminopropyl)-2-pipecoline in 5 ml of dimethylformamide, and the mixture was stirred at the temperature of ice-cooling for 1 hour and the stirring was continued at room temperature overnight. The reaction mixture was then extracted with twice its own volume of ethyl acetate, and the extract was washed with a 5% w/v aqueous solution of sodium bicarbonate and with a saturated aqueous solution of sodium chloride, in that order, after which it was dried over anhydrous magnesium sulfate, and the solvent was removed by distillation under reduced pressure. The residue was purified by silica gel thin layer chromatography (developing solvent: a 3 : 1 by volume mixture of methylene chloride and methanol), to afford 0.23 g of the title compound as an amorphous substance.

60(b)

N-{N-[N-Morpholinoacetyl-3-(1-naphthyl)-L-alanyl]-3-(4-thiazolyl)-DL-alanyl}-cyclostatin-]3-(2-methylpiperidino)propyl]amide The t-butoxycarbonyl group was removed from 0.23 g (0.38 mmole) of N-[N-(t-butoxycarbonyl)-3-(4-thiazolyl)-DL-alanyl]-cyclostatin-[3-(2-methylpiperidino)propyl]amide [prepared as described in step (a) above] by treating it with a 4N solution of hydrogen chloride in dioxane. The hydrochloride thus obtained and 0.13 g (0.38 mmole) of N-morpholinoacetyl-3-(1-naphthyl)-L-alanine were then dissolved in 5 ml of dimethylformamide, and 0.08 g (0.46 mmole) of diethyl cyanophosphonate (95%) and 0.17 g (1.71 mmole) of triethylamine were added, whilst ice-cooling, to the solution. The resulting mixture was stirred, whilst ice-cooling, for 1 hour and then the stirring was continued at room temperature overnight. The reaction mixture was then extracted with twice its own volume of ethyl acetate, the extract was washed with a 5% w/v aqueous solution of sodium bicarbonate and with a saturated aqueous solution of sodium chloride, in that order, after which it was dried over anhydrous magnesium sulfate, and the solvent was removed by distillation under reduced pressure. The residue was purified by silica gel thin layer chromatography (developing solvent: a 5: 1 by volume mixture of methylene chloride and methanol), to afford 0.60 g of the 3.5-hydrate of the title compound, melting at 97°–101° C.

Elemental analysis: Calculated for $C_{45}H_{65}N_7O_6S$ 3.5 $H_2O$: C, 60.37%; H, 8.11%; N, 10.95%; S, 3.58%. Found: C, 60.65%; H, 7.95%; N, 10.69%; S, 3.48%.

EXAMPLE 61

N-{N-[N-Morpholinoacetyl-3-(1-naphthyl)-L-alanyl]-3-(4-thiazolyl)-DL-alanyl}-cyclostatin-[3-(2-oxo-1-pyrrolidinyl)propyl]amide A procedure similar to that described in Example 60(a) was repeated, except that the N-(3-aminopropyl)-2-pipecoline was replaced by 70 mg (0.48 mmole) of 1-(3-aminopropyl)-2-pyrrolidinone and this was reacted with 190 mg (0.4 mmole) of N-[N-t-butoxycarbonyl)-3-(4-thiazolyl)-DL-alanyl]-cyclostatin [prepared by a procedure similar to that described in Example 54(b)], and then the product was subsequently treated as described in Example 60(b), to afford 240 mg of the dihydrate of the title compound as white crystals, melting at 95°–98° C.

Elemental analysis: Calculated for $C_{43}H_{59}N_7O_7S$ 2 $H_2O$: C, 60.46%; H, 7.44%; N, 11.48%. Found: C, 60.70%; H, 7.39%; N, 11.51%.

EXAMPLE 62

N-{N-[N-Morpholinoacetyl-3-(1-naphthyl)-L-alanyl]-3-L-histidyl}-cyclostatin-(2-morpholinoethyl)amide

62(a)

N-[N-(t-Butoxycarbonyl)-$N^{im}$-p-toluenesulfonyl-L-histidyl]-cyclostatin-(2-morpholinoethyl)amide 0.28 g (1.52 mmole) of diethyl cyanophosphonate (95%) and 0.34 g (3.31 mmole) of triethylamine were added, whilst ice-cooling, to a solution of 0.57 g (1.38 mmole) of N-(t-butoxycarbonyl)-$N^{im}$-p-toluenesulfonyl-L-histidine and 0.50 g (1.38 mmole) of cyclostatin-(2-morpholinoethyl)amide in 10 ml of dimethylformamide, and the mixture was stirred, whilst ice-cooling, for 1 hour; the stirring was then continued at room temperature overnight. At the end of this time, the reaction mixture was extracted with ethyl acetate, the extract was washed with a 5% w/v aqueous solution of sodium bicarbonate and with a saturated aqueous solution of sodium chloride, in that order, after which it was dried over anhydrous sodium sulfate, and the solvent was removed by distillation under reduced pressure. The residue was purified by silica gel thin layer chromatography (developing solvent: a 15: 1 by volume mixture of methylene chloride and methanol), to afford 0.56 g of the title compound as an amorphous substance.

62(b)

N-{N-[N-Morpholinoacetyl-3-(1-naphthyl)-L-alanyl]-$N^{im}$-p-toluenesulfonyl-L-histidyl}-cyclostatin-2-morpholinoethyl)amide The t-butoxycarbonyl group was removed from 0.56 g (0.78 mmole) of N-[N-(t-butoxycarbonyl)-$N^{im}$-m-toluenesulfonyl-L-histidyl]-cyclostatin-(2-morpholinoethyl)amide [prepared as described in step (a) above] by treating in with a 4N solution of hydrogen chloride in dioxane. The hydrochloride thus obtained and 0.27 g (0.78 mmole) of N-morpholinoacetyl-3-(1-naphthyl)-L-alanine were dissolved in 5 ml of dimethylformamide. 0.39 g (2.15 mmole) of diethyl cyanophosphonate (95%) and 0.39 g (3.86 mmole) of triethylamine were added, whilst ice-cooling, to the solution, and then the mixture was stirred, whilst ice-cooling, for 1 hour: the stirring was then continued at room temperature for a further 4 days. At the end of this time, the reaction mixture was extracted with twice its own volume of ethyl acetate, and the extract was washed with a 5% w/v aqueous solution of sodium bicarbonate and with a saturated aqueous solution of sodium chloride, in that order, after which it was dried over anhydrous sodium sulfate, and the solvent was removed by distillation under reduced pressure. The residue was purified by silica gel thin layer chromatography (developing solvent: a 10: 1 by volume mixture of methylene chloride and methanol), to afford 0.12 g of the title compound as an amorphous substance.

62(c)
N-{N-[N-Morpholinoacetyl-3-(1-naphthyl)-L-alanyl]-L-histidyl}-cyclostatin-(2-morpholinoethyl)amide 0.07 g (0.52 mmole) of 1-hydroxybenzotriazole was added to a solution of 0.12 g (0.13 mmole) of N-{N-[N-morpholinoacetyl-3-(1-naphthyl)-L-alanyl]-N$^{im}$-p-toluenesulfonyl-L-histidyl}-cyclostatin-(2-morpholinoethyl)amide [prepared as described in step (b) above] in 3 ml of methanol, and the mixture was stirred at room temperature for 4 hours. At the end of this time, the reaction mixture was concentrated by evaporation under reduced pressure, and was then extracted with ethyl acetate. The extract was washed with a 5% w/v aqueous solution of sodium bicarbonate and with a saturated aqueous solution of sodium chloride, in that order, after which it was dried over anhydrous magnesium sulfate, and the solvent was removed by distillation under reduced pressure. The residue was crystallized by the addition of diethylether, to afford 0.90 g of the trihydrate of the title compound, melting at 103°–106° C.

Elemental analysis: Calculated for $C_{42}H_{60}N_8O_7$ 3 $H_2O$: C, 59.84%; H, 7.89%; N, 13.29%. Found: C, 60.10%; H, 7.98%; N, 13.46%

EXAMPLE 63
N-{N-[N-(N-Methylanilinoacetyl)-3-(1-naphthyl)-L-alanyl]-3-(4-thiazolyl)-L-alanyl}-cyclostatin-(2-morpholinoethyl)amide Following a procedure similar to that described in Example 51(b), 175 mg (0.5 mmole) of methyl N-bromoacetyl-3-(1-naphthyl)-L-alanate [prepared as described in Example 51(a)] and 53.6 mg (0.5 mmole) of N-methylaniline were reacted together and subsequently treated as described in Example 51(c), to afford 260 mg of the hexahydrate of the title compound as a white powder.

Silica gel thin layer chromatography, Rf value 0.48.

Elemental analysis: Calculated for $C_{45}H_{59}N_7O_6S$ 6 $H_2O$: C, 57.86%; H, 7.66%; N, 10.50%. Found: C, 57.75%; H, 7.79%; N, 10.67%.

EXAMPLE 64
N-{N-[N-(N-Benzyl-N-ethylaminoacetyl)-3-(1-naphthyl)-L-alanyl]-3-(4-thiazolyl)-L-alanyl}-cyclostatin-(2-morpholinoethyl)amide Following a procedure similar to that described Example 51(b), 175 mg (0.5 mmole) of methyl N-bromoacetyl-3-(1-naphthyl)-L-alanate [prepared as described in Example 51(a)] and 65.6 mg (0.5 mmole) of N-ethylbenzylamine were reacted together and subsequently treated as described in Example 51(c), to afford 250 mg of the 2.5-hydrate of the title compound as a white powder.

Silica gel thin layer chromatography. Rf value 0.51.

Elemental analysis: Calculated for $C_{47}H_{63}N_7O_6S$ 2.5 $H_2O$: C, 62.78%; H, 7.62%; N, 10.90%; S, 3.57%. Found: C, 62.85%; H, 7.73%; N, 11.07%; S, 3.52%.

EXAMPLE 65
N-{N-[N-(N-Benzyl-N-isopropylaminoacetyl)-3-(1-naphthyl)-L-alanyl]-3-(4-thiazolyl)-L-alanyl}-cyclostatin-(2-morpholinoethyl)amide Following a procedure similar to that described Example 51(b), 175 mg (0.5 mmole) of methyl N-bromoacetyl-3-(1-naphthyl)-L-alanate [prepared as described in Example 51(a)] and 74.6 mg (0.5 mmole) of N-benzyl-N-isopropylamine were reacted together and subsequently treated as described in Example 51(c), to afford 175 mg of the dihydrate of the title compound as a white powder.

Silica gel thin layer chromatography, Rf value 0.51.

Elemental analysis: Calculated for $C_{48}H_{65}N_7O_6S$ 2 $H_2O$: C, 63.76% H, 7.69%; N, 10.84%; S, 3.55%. Found: C, 63.75%; H, 7.50%; N, 10.59%; S, 3.84%.

EXAMPLE 66
N-[N-{N-[4-(2-Methoxyphenyl)-1-piperazinyl]acetyl-3-(1-naphthyl)-L-alanyl}-3-(4-thiazolyl)-L-alanyl]-cyclostatin-(2-morpholinoethyl)amide Following a procedure similar to that described in Example 51(b), 175 mg (0.5 mmole) of methyl N-bromoacetyl-3-(1-naphthyl)-L-alanate [prepared as described in Example 51(a)] and 115 mg (0.5 mmole) of 1-(2-methoxyphenyl)piperazine were reacted together and subsequently treated as described in Example 51(c), to afford 341 mg of the monohydrate of the title compound as white crystals, melting at 100°–105° C.

Elemental analysis: Calculated for $C_{49}H_{66}N_8O_7S$ $H_2O$: C, 63.34%; H, 7.38%; N, 12.05%. Found: C, 63,15%; H, 7.25%; N, 12.12%.

EXAMPLE 67
N-[N-{N-[4-(4-Chlorobenzhydryl)-1-piperazinylacetyl]-3-(1-naphthyl)-L-alanyl}-3-(4-thiazolyl)-L-alanyl]-cyclostatin-(2-morpholinoethyl)amide Following a procedure similar to that described in Example 51(b), 175 mg (0.5 mmole) of methyl N-bromoacetyl-3-(1-naphthyl)-L-alanate [prepared as described in Example 51(a)] and 143 mg (0.5 mmole) of 1-(4-chlorobenzhydryl)piperazine were reacted together and subsequently treated as described in Example 51(c), to afford 168 mg of the monohydrate of the title compound as white crystals, melting at 75°–80° C.

Elemental analysis: Calculated for $C_{55}H_{69}ClN_8O_6S$ $H_2O$: C, 61.75%; H, 7.01%; N, 12.00%. Found: C, 61.66%; H, 6.89%; N, 11.86%.

EXAMPLE 68
N-{N-[N-(N-Benzyl-N-methylaminoacetyl)-3-(1-naphthyl)-L-alanyl]-L-leucyl}-cyclostatin-(2-morpholinoethyl)amide 2 ml of a 4N solution of hydrogen chloride in dioxane were added to a solution of 200 mg (0.370 mmole) of N-(t-butoxycarbonyl)-L-leucyl-cyclostatin-(2-morpholinoethyl)amide in 2 ml of methanol, and the mixture was stirred at room temperature for 1 hour. At the end of this time, the solvent was removed by distillation to dryness under reduced pressure, and the residue was dissolved in 5 ml of dimethylformamide. 140 mg (0.372 mmole) of N-(N-methyl-N-benzylaminoacetyl)-3-(1-naphthyl)-L-alanine, 0.26 ml (1.87 mmole) of triethylamine and 76 mg (0.443 mmole) of diethyl cyanophosphonate (95%) were then added to the resulting solution, and the reaction mixture was stirred at room temperature for 4 hours, after which it was allowed to stand overnight. The solvent was then removed by distillation under reduced pressure, and the residue was purified by silica gel thin layer chromatography (developing solvent: a 9: 1 by volume mixture of methylene chloride and methanol), to afford 202 mg of the monohydrate of the title compound as a white powder.

Silica gel thin layer chromatography, Rf value 0.51.
Elemental analysis: Calculated for $C_{46}H_{66}N_6O_6 H_2O$: C, 67.62%; H, 8.39%; N, 10.29%. Found: C, 67.43%; H, 8.19%; N, 10.26%.

EXAMPLE 69

N-{N-[N-(N-Benzyl-N-ethylaminoacetyl)-3-(1-naphthyl)-L-alanyl]-L-leucyl}-cyclostatin-(2-morpholinoethyl)amide A procedure similar to that described in Example 68 was repeated, except that 113 mg (0.289 mmole) of N-(N-benzyl-N-ethylaminoacetyl)-3-(1-naphthyl)-L-alanine (prepared by a procedure similar to that described in Preparation 40) were used instead of the N-(N-methyl-N-benzylaminoacetyl)-(1-naphthyl)-[alanine, and this was reacted with 156 mg (0.288 mmole) of N-(t-butoxycarbonyl)-L-leucyl-cyclostatin-(2morpholinoethyl)amide [prepared by a procedure similar to that described in Example 2(a)], to give 142 mg of the sesquihydrate of the title compound as a white powder.

Silica gel thin layer chromatography, Rf value 0.51.
Elemental analysis: Calculated for $C_{47}H_{68}N_6O_6$ 1.5 $H_2O$: C, 67.19%; H, 8.52%; N, 10.00%. Found: C, 66.93%; H, 8.24%; N, 9.94%.

EXAMPLE 70

N-{N-[N-(N-Cyclohexyl-N-methylaminoacetyl)-3-(1naphthyl)-L-alanyl]-L-leucyl}-cyclostatin-(2morphoinoethyl)amide A procedure similar to that described in Example 68 was repeated, but using 138 mg (0.375 mmole) of N-(N-cyclohexyl-N-methylaminoacetyl)-3-(1-naphthyl)-L-alanine (prepared by a procedure similar to that described in Preparation 40) instead of the N-(N-methyl-N-benzylaminoacetyl)-3-(1-naphthyl)-L-alanine, and this was reacted with 200 mg (0.370 mmole) of N-(t-butoxycarbonyl)-L-leucyl-cyclostatin-(2-morpholinoethyl)amide [prepared by a procedure similar to that described in Example 2(a)], to give 106 mg of the pentahydrate of the title compound as a white powder.

Silica gel thin layer chromatography, Rf value 0.50.
Elemental analysis: Calculated for $C_{45}H_{70}N_6O_6$ 5 $H_2O$: C, 61.34%; H, 9.15%; N, 9.54%. Found: C, 61.33%; H, 9.00%; N, 9.43%.

EXAMPLE 71

N-{N-[N-(N-Methylanilinoacetyl)-3-(1-naphthyl)-L-alanyl]-L-leucyl}-cyclostatin-(2-morpholinoethyl)amide A procedure similar to that described in Example 68 was repeated, except that 141 mg (0.389 mmole) of N-(N-methylanilinoacetyl)-3-(1-naphthyl)-L-alanine (prepared by a procedure similar to that described in Preparation 40) was used instead of the N-(N-methyl-N-benzylaminoacetyl)-(1-naphthyl)-L-alanine, and this was reacted with 210 mg (0.388 mmole) of N-[N-(t-butoxycarbonyl)-L-leucyl]-cyclostatin-(2-morpholinoethyl)amide [prepared by a procedure similar to that described in Example 2(a)], to give 189 mg of the dihydrate of the title compound as a White powder.

Silica gel thin layer chromatography, Rf value 0.53.
Elemental analysis: Calculated for $C_{45}H_{64}N_6O_6$ 2 $H_2O$: C, 65.83%; H, 8.35%; N, 10.24%. Found: C, 65.74%; H, 8.03%; N, 10.29%.

EXAMPLE 72

N-{N-[N-(N-Cyclohexyl-N-methylaminoacetyl)-3-(1-naphthyl)-L-alanyl]-L-leucyl}-cyclostatin-[3-(2-oxo-1-pyrrolidinyl)propyl]amide 5 ml of a 4N solution of hydrogen chloride in dioxane were added to a solution of 300 mg (0.54 mmole) of N-[N-(t-butoxycarbonyl)-L-leucyl]-cyclostatin-[3-(2-oxo-1-pyrrolidinyl)propyl]amide (prepared as described in Preparation 38) in 5 ml of methanol, and the mixture was stirred at room temperature for 1 hour. At the end of this time, the solvent was removed by distillation to dryness under reduced pressure, and the residue was dissolved in 10 ml of dimethylformamide. 199 mg (0.54 mmole) of N-(N-methyl-N-cyclohexylaminoacetyl)-3-(1-naphthyl)-L-alanine, 249 mg (2.46 mmole) of triethylamine and 150 mg (0.92 mmole) of diethyl cyanophosphonate (95%) were then added to the resulting solution, and the mixture was stirred at room temperature for 4 hours. At the end of this time, the solvent was removed by distillation under reduced pressure, and the residue was purified by silica gel column chromatography (eluent: a 10: 1 by volume mixture of chloroform and methanol), to afford 360 mg of the hemihydrate of the title compound as white crystals, melting at 75°–82° C.

Elemental analysis: Calculated for $C_{46}H_{70}N_6O_6$ ½ $H_2O$: C, 68.03%; H, 8.81%; N, 10.35%. Found: C, 67.86%; H, 8.63%; N, 10.14%.

EXAMPLE 73

N-{N-[N-(N-Benzyl-N-methylaminoacetyl)-3-(1-naphthyl)-L-alanyl]-L-leucyl}-cyclostatin-[3-(2-oxo-1-pyrrolidinyl)propyl]amide A procedure similar to that described in Example 72 was repeated, except that 203 mg (0.54 mmole) of N-(N-benzyl-N-methylaminoacetyl)-(1-naphthyl)-L-alanine (prepared by a procedure similar to that described in Preparation 40) were used instead of the N-(N-methyl-N-cyclohexylaminoacetyl)-(1-naphthyl)-L-alanine, and this was reacted with 300 mg (0.54 mmole) of N-[N-(t-butoxycarbonyl-L-leucyl]-cyclostatin-[3-(2-oxo-1-pyrrolidinyl)propyl]amide (prepared by a procedure similar to that described in Preparation 38), to give 350 mg of the monohydrate of the title compound as while crystals, melting at 78°–86° C.

Elemental analysis: Calculated for $C_{47}H_{66}N_6O_6 H_2O$: C, 68.09%; H. 8.27%=N, 10.14%. Found: C, 68.40%; H, 8.22%; N, 10.05%.

EXAMPLE 74

N-{N-[N-(N-Butyl-N-methylaminoacetyl)-3-(1-naphthyl)-L-alanyl]-L-leucyl)-cyclostatin-[3-(2-oxo-1-pyrrolidinyl)propyl]amide A procedure similar to that described in Example 72 was repeated, except that 280 mg (0.70 mmole) of N-(N- butyl-N-methylaminoacetyl)-3-(1-naphthyl)-L-alanine (prepared by a procedure similar to that described in Preparation 40) were used instead of the N-(N-methyl-N-cyclohexylaminoactyl)-3-(1-naphthyl)-L-alanine, and this was reacted with 300 mg (0.54 mmole) of N-[N-(t-butoxycarbonyl)-L-leucyl]-cyclostatin-[3-(2-oxo-1-pyrrolidinyl)propyl]amide, to give 270 mg of the 2.5-hydrate of the title compound as white crystals, melting at 66°–70° C.

Elemental analysis: Calculated for $C_{44}H_{68}N_6O_6$ 2.5 $H_2O$: C, 65.00%=H, 8.93%; N, 10.34%. Found: C, 64.75%; H, 8.81%; N, 10.20%.

EXAMPLE 75

N-{N-[N-(N-Methylanilinoacetyl)-3-(1-naphthyl)-L-alanyl]-L-leucyl}-cyclostatin-[3-(2oxo-1-pyrrolidinyl)propyl]amide A procedure similar to that described in Example 72 was repeated, except that 160 mg (0.39 mmole) of N-(N-methylanilinoacetyl)-3-(1-naphthyl)-L-alanine were used instead of the N-(N-methyl-N-cyclohexylaminoacetyl)-3-(1-naphthyl)-L-alanine, and this was reacted with 210 mg (0.38 mmole) of N-[N-(t-butoxycarbonyl)-L-leucyl]-cyclostatin-[3-(2-oxo-1-pyrrolodinyl)propyl]amide, to give 228 mg of the monohydrate of the title compound as white crystals, melting at 141°–143° C.

Elemental analysis: Calculated for $C_{46}H_{64}N_6O_6$ $H_2O$: C, 67.78%; H, 8.16%, N, 10.31%. Found: C, 67.94%; H, 7.95%; N, 10.25%.

EXAMPLE 76

N-{N-[N-(N-Benzyl-N-methylaminoacetyl)-3-(1-naphthyl)-L-alanyl]-L-tryptophyl}-cyclostatin-[3-(2-oxo-1-pyrrolidinyl)propyl]amide A procedure similar to that described in Example 72 was repeated, except that 642 mg (1.0 mmole) of N-[N-(t-butoxycarbonyl)-L-tryptophyl]-cyclostatin-[3(2-oxo-1-pyrrolidinyl)propyl]amide (prepared by a procedure similar to that described in Preparation 38) were used instead of the N-[N-(t-butoxycarbonyl)-L-leucyl]-cyclostatin-[3-(2-oxo-1-pyrrolidinyl)propyl]amide, and this was reacted with 376 mg (1.0 mmole) of N-(N-methyl-N-benzylaminoacetyl)-(1-naphthyl)-L-alanine, to give 700 mg of the sesquihydrate of the title compound as white crystals, melting at 80°–90° C.

Elemental analysis: Calculated for $C_{52}H_{65}N_7O_6$ 3/2 $H_2O$: C, 68.55%; H, 7.52%; N, 10.76%. Found: C, 68.64%; H, 7.38%; N, 10.77%.

EXAMPLE 77

N-{N-[N-(N-Cyclohexyl-N-methylaminoacetyl),3-(1-naphthyl)-L-alanyl]-L-phenylalanyl}-cyclostatin-[3-(2-oxo-1-pyrrolidinyl)propyl]amide A procedure similar to that described in Example 72 was repeated, except than 250 mg (0.43 mmole) of N-[N-(t-butoxycarbonyl)-L-phenylalanyl]-cyclostatin-[3-(2-oxo-1-pyrrolidinyl)propyl]amide were used instead of the N-[N-(t-butoxycarbonyl)-L-leucyl]-cyclostatin-[3-(2-oxo-1-pyrrolidinyl)propyl]amide, and this was reacted with 192 mg (0.52 mmole) of N-(N-methyl-N-cyclohexylaminoacetyl)-3-(1-naphthyl)-L-alanine, to give 158 mg of the 2.5-hydrate of the title compound as white crystals, melting at 109°–113° C.

Elemental analysis: Calculated for $C_{49}H_{68}N_6O_6$ 5/2 $H_2O$: C, 66.71%; H, 8.28%; N, 9.46%. Found: C. 66.53%; H, 8.08%; N, 9.33%.

EXAMPLE 78

N-{N-[N-Morpholinoacetyl-3-(1-naphthyl)-L-alanyl]-L-phenylalanyl}-cyclostatin-[3-(2-oxo-1-pyrrolidinyl)propyl]amide A procedure similar to that described in Example 77 was repeated, except that 175 mg (0.53 mmole) of N-morpholinoacetyl-3-(1-naphthyl)-L-alanine were employed instead of the N-(N-methyl-N-cyclohexylaminoacetyl)-3-(1-naphthyl)-L-alanine, and this was reacted with 250 mg (0.43 mmole) of N-[N-(t-butoxycarbonyl)-L-phenylalanyl]-cyclostatin-[3-(2-oxo-1-pyrrolidinyl)propyl]amide, to give 165 mg of the monohydrate of the title compound as white crystals, melting at 114°–118° C.

Elemental analysis: Calculated for $C_{46}H_{62}N_6O_7$ $H_2O$: C, 66.64%; H, 7.78%; N, 10.14%. Found: C, 68.65%; H, 7.71%; N, 9.80%.

EXAMPLE 79

N-{N-[N-(N,N-Dicyclohexylaminoacetyl)-3-(1-naphthyl)-L-alanyl]-3-(4-thiazolyl)-L-alanyl}-cyclostatin-(2-morpholinoethyl)amide A procedure similar to that described in Example 61(c) was repeated, except that 160 mg (0.35 mmole) of methyl N-(N,N-dicyclohexylaminoacetyl)-(1-naphthyl)-L-alanate were employed instead of the methyl N-(N,N-diethylaminoacetyl)-3-(1-naphthyl)-L-alanate, and this was reacted with the compound which had been prepared by removing the t-butoxycarbonyl group from 208 mg (0.35 mmole) of N-[N-(t-butoxycarbonyl)-3-(4-thiazolyl)-L-alanyl]-cyclostatin-(2-morpholinoethyl)amide, to give 210 mg of the sesquihydrate of the title compound as a white powder.

Silica gel thin layer chromatography, Rf value 0.53.

Elemental analysis: Calculated for $C_{50}H_{73}N_7O_6S$ 3/2 $H_2O$: C, 64.77%; H, 8.26%; N, 10.57%; S, 3.46%. Found: C, 64.89%; H, 7.97%; N, 10.34%; 5, 3.63%.

EXAMPLE 80

N-{N-[N-(N-Diisobutylaminoacetyl)-3-(1-naphthyl)-L-alanyl]-3-(4-thiazolyl)-L-alanyl}-cyclostatin-(2-morpholinoethyl)amide A procedure similar to that described in Example 61(c) was repeated, except that 140 mg (0.35 mmole) of methyl N-(N,N-diisobutylaminoacetyl)-3-(1-naphthyl)-L-alanate were employed instead of the methyl N-(N,N-diethylaminoacetyl)-3-(1-naphthyl)-L-alanate, and this was reacted with the Compound which had been prepared by removing the t-butoxycarbonyl group from 208 mg (0.35 mmole) of N-[N-(t-butoxycarbonyl)-3-(4-thiazolyl)-L-alanyl]-cyclostatin-(2-morpholinoethyl)amide [prepared by a procedure similar to that described in Example 2(a)], to give 230 mg of the monohydrate of the title compound as a white powder.

Silica gel thin layer chromatography, Rf value 0.49,

Elemental analysis: Calculated for $C_{46}H_{69}N_7O_6S$ $H_2O$: C, 63.79%; H, 8.26%; N, 11.32%; S, 3.70%. Found: C, 63.51%; M, 8.29%; N, 11.04%; S, 3.58%.

EXAMPLE 81

N-{N-[N-(N-Benzyl-N-methylaminoacetyl)-L-phenylalanyl]-L-leucyl}-cyclostatin-(2-morpholinoethyl)amide 2 ml of a 4N solution of hydrogen chloride in dioxane were added to a solution of 200 mg (0.37 mmole) of N-[N-(t-butoxycarbonyl)-L-leucyl]-cyclostatin-(2-morpholinoethyl)amide [prepared by a procedure similar to that described in Example 2(a)] in 2 ml of methanol, and the mixture was stirred at room temperature for 1 hour. At the end of this time, the solvent was removed by evaporation to dryness under reduced pressure, and the residue was dissolved in 5 ml of dimethylformamide. 121 mg (0.371 mmole) of N-(N-benzyl-N-methylaminoacetyl)-L-phenylalanine, 0.26 ml (1.87 mmole) of triethylamine and 76 mg (0.443 mmole) of diethyl cyanophosphonate (95%) were then added to the resulting solution, and the mixture was stirred at room temperature for 4 hours; it was then allowed to stand overnight. At the end of this time, the solvent was removed by distillation under reduced pressure, and the residue was purified by silica gel thin layer chromatography (developing solvent: a 9: 1 by volume mixture of methylene chloride and methanol), to afford 129.5 mg of the 2.5-hydrate of the title compound as a white powder.

Silica gel thin layer chromatography, Rf value 0.49.
Elemental analysis: Calculated for $C_{42}H_{64}N_6O_6$ 5/2 $H_2O$: C, 63.53%; H, 8.76%; N, 10.58%. Found: C, 63.82%; H, 8.37%; N, 10.51%.

EXAMPLE 82

N-{N-[N-(N-Cyclohexyl-N-methylaminoacetyl)-L-phenylalanyl]-L-leucyl}-cyclostatin-(2-morpholinoethyl)amide A procedure similar to that described in Example 81 was repeated, except that 140 mg (0.44 mmole) of N-(N-methyl-N-cyclohexylaminoacetyl)-L-phenylalanine were employed instead of the N-(N-benzyl-N-methylaminoacetyl)-L-phenylalanine, and this was reacted with 200 mg (0.37 mmole) of N-[N-(t-butoxycarbonyl)-L-leucyl]-cyclostatin-(2-morpholinoethyl)amide, to give 200 mg of the monohydrate of the title compound as a white powder.

Silica gel thin layer chromatography, Rf value 0.48.
Elemental analysis: Calculated for $C_{41}H_{68}N_6O_6$ $H_2O$: C, 64.88%; H, 9.03.%; N, 11.07%. Found: C, 64.67%; H, 9.10%; N, 10.82%.

EXAMPLE 83

N-[N-{N-[4-(4-Fluorophenyl)-1-piperazinyl]acetyl-3-(1-naphthyl)-L-alanyl}-3-(4-thiazolyl)-DL-alanyl]-cyclostatin-(2-morpholinoethyl)amide A procedure similar to that described in Example 40(b) was repeated, except that 200 mg (0.26 mmole) of N-{N-[N-(t-butoxycarbonyl)-3-(1-naphthyl)-L-alanyl]-3-(4-thiazolyl)-DL-alanyl}-cyclostatin-(2-morpholinoethyl)amide [prepared as described in Example 40(a)] and 63.1 mg (0.26 mmole) of [4-(4-fluorophenyl)-1-piperazinyl]acetic acid were reacted together to give 51 mg of the dihydrate of the title compound as a white powder.

Silica gel thin layer chromatography, Rf value 0.50.

Elemental analysis: Calculated for $C_{48}H_{63}N_8O_6S$ 2 $H_2O$: C, 61.65%; H, 7.22%; N, 11.98%. Found: C, 61.88%; H, 7.20%; N, 11.70%.

EXAMPLE 84

N-[N-{N-[4-(2-Chlorophenyl)-1-piperazinyl]acetyl-3-(1-naphthyl)-L-alanyl}-3-(4-thiazolyl)-DL-alanyl]cyclostatin-(2-morpholinoethyl)amide A procedure similar to that described in Example 40(b) was repeated, except that 200 mg (0.26 mmole) of N-{N-[N-(t-butoxycarbonyl)-3-(1-naphthyl)-L-alanyl]-3-(4-thiazolyl)-DL-alanyl}-cyclostatin-(2-morpholinoethyl)amide [prepared as described in Example 40(a)] and 67.5 mg (0.26 mmole) of [4-(2-chlorophenyl)-1-piperazinyl]acetic acid were reacted together to give 55 mg of the monohydrate of the title compound as a white powder.

Silica gel thin layer chromatography, Rf value 0.48.
Elemental analysis: Calculated for $C_{48}H_{63}ClN_8O_6S$ $H_2O$: C, 61.75%; H, 7.01%; N, 12.00%. Found: C, 61.66%; H, 6.89%; N, 11.86%.

EXAMPLE 85

N-{N-[N-(N-Benzyl-N-methylaminoacetyl)-3-(1-naphthyl)-L-alanyl]-L-histidyl-cyclostatin}-[3-(2-oxo-1-pyrrolidinyl)propyl]amide A procedure similar to that described in Example 73 was repeated, except that 150 mg (0.26 mmole) of N-[N-(t-butoxycarbonyl)-L-histidyl]-cyclostatin-[3-(2-oxo-1-pyrrolidinyl)propyl]amide were employed instead of N-[N-(t-butoxycarbonyl)-L-leucyl]-cyclostatin-[3-(2-oxo-1-pyrrolidinyl)propyl]amide, and this was reacted with 120 mg (0.31 mmole) of N-(N-benzyl-N-methylaminoacetyl)-3-(1-naphthyl)-L-alanine, to give 118 mg of the sesquihydrate of the title compound as a white powder, melting at 91°–94° C.

Elemental analysis: Calculated for $C_{47}H_{62}N_8O_6$ 1.5 $H_2O$: C, 65.48%; H, 7.60%; N, 13.00%. Found: C, 65.27%; H, 7.31%; N, 12.83%.

EXAMPLE 86

N-{N-[N-(N-Cyclohexyl-N-methylaminoacetyl)-3-(1-naphthyl)-L-alanyl]-L-phenylalanyl}-cyclostatin-(2-morpholinoethyl)amide A procedure similar to that described in Example 72 was repeated, except that 200 mg (0.348 mmole) of N-[N-(t-butoxycarbonyl)-L-phenylalanyl]-cyclostatin-(2-morpholinoethyl)amide (prepared by a procedure similar to that described in Example 2(a)] were employed instead of N-[N-(t-butoxycarbonyl)-L-leucyl]-cyclostatin-[3-(2-oxo-1-pyrrolidinyl)propyl]amide, and this was reacted with 129 mg (0.350 mmole) of N-(N-methyl-N-cyclohexylaminoacetyl)-3-(1-naphthyl)-L-alanine, to give 121 mg of the tetrahydrate of the title compound as a white powder.

Silica gel thin layer chromatography, Rf value 0.53.
Elemental analysis: Calculated for $C_{48}H_{68}N_6O_6$ 4 $H_2O$: C, 64.26%; H, 8.54%; N, 9.37%. Found: C, 64.26%; H, 8.31%; N, 9.25%.

EXAMPLE 87

N-{N-[N-(4-Benzyl-1-piperazinylacetyl)-3-(1-naphthyl)-L-alanyl]-3-(4-thiazolyl)-L-alanyl}-cyclostatin-(2-morpholinoethyl)amide A procedure similar to that described in Example 51(b) was repeated, except that 350 mg (1 mmole) of methyl N-bromoacetyl-3-(1-naphthyl)-L-alanate [prepared as described in Example 51(a)] and 190 mg (1.1 mmole) of N-benzylpiperazine were reacted together and the product was subsequently treated as described in Example 51(c), to afford 152 mg of the monohydrate of the title compound as a white powder, melting at 84°–88° C.

Elemental analysis: Calculated for $C_{49}H_{66}N_8O_6S$ $H_2O$: C, 64.45%; H, 7.51%; N, 12.27%; S, 3.51%. Found: C, 64.33%; H, 7.46%; N, 12.10%; S, 3.54%.

EXAMPLE 88

N-{N-[N-(N,N-Diisobutylaminoacetyl)-L-phenylalanyl]-L-leucyl}-cyclostatin-(2-morpholinoethyl)amide A procedure similar to that described in Example 81 was repeated, except that 150 mg (0.44 mmole) of N-(N,N-diisobutylaminoacetyl)-L-phenylalanine were employed instead of N-(N-benzyl-N-methylaminoacetyl)-L-phenylalanine, and this was reacted with 200 mg (0.37 mmole) of N-[N-(t-butoxycarbonyl)-L-leucyl]-cyclostatin-(2-morpholinoethyl)amide, to give 200 mg of the tetrahydrate of the title compound as a colorless amorphous substance.

Silica gel thin layer chromatography, Rf value 0.53.
Elemental analysis: Calculated for $C_{42}H_{72}N_6O_6$ 4 $H_2O$: C, 60.84%; H, 9.73%; N, 10.14%. Found: C, 60.58%; H, 9.67%; N, 9.99%.

EXAMPLE 89

N-{N-[N-Morpholinoacetyl-3-(1-naphthyl)-L-alanyl]-L-leucyl}-cyclostatin-(2-morpholinoethyl)amide 2 ml of methanol and 2 ml of a 4N solution of hydrogen chloride in dioxane were added to 130 mg (0.24 mmole) of N-[N-(t-butoxycarbonyl)-L-leucyl]-cyclostatin-(2-morpholinoethyl)amide (prepared by a procedure similar to that described in Example 2(a)], and the mixture was stirred for 1 hour to remove the t-butoxycarbonyl group. The reaction mixture was then evaporated to dryness under reduced pressure, and the residue, together with 82.2 mg (0.24 mmole) of N-morpholinoacetyl-3-(1-naphthyl)-L-alanine, was suspended in 15 ml of anhydrous tetrahydrofuran. 97 mg (0.96 mmole) of triethylamine and subsequently 79.3 mg of diphenylphosphoric azide were then added to the resulting suspension, whilst ice-cooling, and the mixture was stirred for 0.5 hours; the stirring was then continued at room temperature for a further 64 hours. At the end of this time, the solvent was removed by distillation under reduced pressure, and the residue was purified by preparative thin layer chromatography (developing solvent: a 9: 1 by volume mixture of methylene chloride and methanol), to afford 100 mg of the dihydrate of the title compound as a colorless amorphous substance.

Silica gel thin layer chromatography, Rf value 0.50.
Elemental analysis: Calculated for $C_{42}H_{64}N_6O_7$ 2 $H_2O$: C, 62.98%; H, 8.56%; N, 10.49%. Found: C, 62.98%; H, 8.14%; N, 10.36%.

EXAMPLE 90

N-{N-[N-Morpholinoacetyl-3-(1-naphthyl)-L-alanyl]-L-phenylalanyl}-cyclostatin-(2-morpholinoethel)amide 1 ml of methanol and 1 ml of a 4N solution of hydrogen chloride in dioxane were added to 100 mg (0.17 mmole) of N-[N-(t-butoxycarbonyl)-L-phenylalanyl]-cyclostatin-( 2-morpholinoethyl)amide, and the mixture was stirred for 1 hour to remove the t-butoxycarbonyl group. The reaction mixture was then evaporated to dryness under reduced pressure, and the residue, together with 58.2 mg (0.17 mmole) of N-morpholinoacetyl-3-(1-naphthyl)-[-alanine, was suspended in tetrahydrofuran. 69 mg (0.68 mmole) of triethylamine and subsequently 56.1 mg (0.204 mmole) of diphenylphosphoric azide were then added to the resulting suspension, whilst ice-cooling, and the mixture was stirred for 0.5 hours: the stirring was then continued at room temperature for a further 19 hours. At the end of this time, the solvent was removed by distillation under reduced pressure, and the residue was purified by preparative thin layer chromatography (developing solvent: a 9: 1 by volume mixture of methylene chloride and methanol), to afford 70 mg of the dihydrate of the title compound as a colorless amorphous substance.

Silica gel thin layer chromatography, Rf value 0.51.
Elemental analysis: Calculated for $C_{45}H_{62}N_6O_7$ 2 $H_2O$: C, 64.73%; H, 7.97%; N, 10.06%. Found: C, 64.63%; H, 7.87%; N, 10.02%.

EXAMPLE 91

N-{N-[N-(N,N-Dicyclohexylaminoacetyl)-3-(1-naphthyl)-L-alanyl]-L-phenylalanyl}-cyclostatin-[3-(2-oxo-1-pyrrolidinyl)propyl]amide A procedure similar to that described in Example 51(c) was repeated, except that 160 mg (0.35 mmole) of methyl N-(N,N-dicyclohexylaminoacetyl)-3-(1-naphthyl)-L-alanate were employed instead of the methyl N-(N,N-diethylaminoacetyl)-3-(1-naphthyl)-L-alanate, and this was reached with the compound which had been prepared by removing the t-butoxycarbonyl group from 205 mg (0.35 mmole) of N-[N-(t-butoxycarbonyl)-L-phenylalanyl]-cyclostatin-[3-(2-oxo-1-pyrrolidinyl)-propyl]amide, to give 240 mg of the dihydrate of the title compound as a white powder.

Silica gel thin layer chromatography, Rf value 0.58.
Elemental analysis: Calculated for $C_{54}H_{76}N_6O_6$ $2H_2O$: C, 68.91%; H, 8.57%; N, 8.93%. Found: C, 68.68%; H, N, 8.85%.

EXAMPLE 92

N-{N-[N-(N,N-Diisobutylaminoacetyl),3-(1-naphthyl)-L-alanyl]-L-phenylalanyl}-cyclostatin-[3-(2-oxo-1-pyrrolidinyl)propyl]amide A procedure similar to that described in Example 51(c) was repeated, except that 140 mg (0.35 mmole) of methyl N-(N,N-diisobutylaminoacetyl)-3-(1-naphthyl)-L-alanate were employed instead of the methyl N-(N,N-diethylaminoacetyl)-3-(1-naphthyl)-L-alanate, and this was reacted with the compound which had been prepared by removing the t-butoxycarbonyl group from 205 mg (0.35 mmole) of N-[N-(t-butoxycarbonyl)-L-phenylalanyl]-cyclostatin-[3-(2-oxo-1-pyrrolidinyl)-propyl]amide, to give 210 mg of the monohydrate of the title compound as a white powder.

Silica gel thin layer chromatography, Rf value 0.56.
Elemental analysis: Calculated for $C_{50}H_{72}N_6O_6$ $H_2O$: C, 68.94%; H, 8.56%; N, 9.65%. Found: C, 68.84%; H, 8.56%; N,,9.62%.

EXAMPLE 93

N-{N-[N-Morpholinoacetyl-3-(1-naphthyl)-L-alanyl]-(3-(4-thiazolyl)-L-alanyl}-cyclostatin-(2-methyl-2-morpholinoethyl)amide 3.5 g (40 mmole) of morpholine were added to a mixture of 3.6 g (20 mmole) of ethyl 2-bromopropionate and 50 ml of dry benzene, and then the mixture was heated under reflux for 7 hours. At the end of this time, the reaction mixture was filtered, the filtrate was concentrated by evaporation under reduced pressure, and the residue was dissolved in chloroform. The resulting solution was washed with water, dried, and concentrated by evaporation under reduced pressure, to give 3.19 g of ethyl 2-morpholinopropionate. 10 ml of methanol and 10 ml of a concentrated aqueous solution of ammonium hydroxide were then added to 3.1 g (16.6 mmole) of this ethyl 2-morpholinopropionate, and the resulting mixture was heated under reflux for 28 hours. At the end of this time, the reaction mixture was concentrated by evaporation under reduced pressure, and the residue was dried by heating it under reduced pressure, to give 2-morpholinopropionamide as a precipitate.

The whole of this precipitate was added little by little to 2.43 g (64 mmole) of lithium aluminum hydride in 90 ml of anhydrous tetrahydrofuran, and the mixture was heated under reflux for 9 hours. At the end of this time, ethyl acetate was added dropwise to the cooled reaction mixture to quench the reaction, after which the reaction mixture was filtered and the filtrate was concentrated by evaporation under reduced pressure, to give 1.16 g of 4-(2-amino-1-methylethyl)morpholine as an oily substance. The whole of this 4-(2-amino-1-methylethyl)morpholine (8 mmole) was dissolved in a mixture of ml of methanol and 4 ml of water, and 3.2 g (32 mmole) of triethylamine and then 3.8 g (17.6 mmole) of di-t-butyl dicarbonate were added, in that order, to the resulting solution, whilst cooling; the mixture was then stirred at room temperature for 17 hours. At the end of this time, the reaction mixture was concentrated by evaporation under reduced pressure, and the residue was extracted with ethyl acetate. The product was then purified by silica gel column chromatography, to afford 220 mg of t-butyl N-(2-morpholinopropyl)carbamate as an oily substance.

120 mg (0.5 mmole) of this t-butyl N-(2-morpholinopropyl)carbamate were dissolved in 2 ml of methanol, and 2 ml of a 4N solution of hydrogen chloride in dioxane were added to the resulting solution. The mixture was then stirred at room temperature for 30 minutes, after which it was evaporated to dryness under reduced pressure. Following a procedure similar to that described in Example 54(c), the product thus obtained was reacted with 350 mg (0.5 mmole) of N-{N-[N-morpholinoacetyl-3-(1-naphthyl)-L-alanyl]-3-(4-thiazolyl)-[-alanyl}-cyclostatin [prepared as described in Example 54(b)], to afford 150 mg of the sesquihydrate of the title compound as a white powder.

Silica gel thin layer chromatography, Rf value 0.54.

Elemental analysis: Calculated for $C_{43}H_{61}N_7O_7S$ 1.5 $H_2O$: C, 60.97%; H, 7.62%; N, 11.57%; S, 3.78%. Found: C, 60.74%; H, 7.40%; N, 11.38%; S, 4.01%.

EXAMPLE 94

N-{N-[N-Morpholinoacetyl-3-(1-naphthyl)-L-leucyl}-cyclostatin-[3-(2-oxo-1-pyrrolidinyl)propyl]amide A procedure similar to that described in Example 72 was repeated, except that 175 mg (0.53 mmole) of N-morpholinoacetyl-3-(1-naphthyl)-L-alanine were employed instead of the N-(N-methyl-N-cyclohexylaminoacetyl)-3-(1-naphtyl)-L-alanine, and this was reacted with 238 mg (0.4 3 mmole) of N-[N-(t-butoxycarbonyl)-L-leucyl]-cyclostatin-[3-(2-oxo-1-pyrrolidinyl)propyl]amide, to give 109 mg of the monohydrate of the title compound as white crystals, melting at 105°–109° C.

Elemental analysis: Calculated for $C_{43}H_{64}N_6O_7$ $H_2O$: C, 64.96%; H, 8.37%; N, 10.57%. Found: C, 64.83%; H, 8.21%; N, 10.32%.

EXAMPLE 95

N-{N-[N-(N-Cyclohexyl-N-methylaminoacetyl)-3-(1-naphthyl)-L-alanyl]-3-(4-thiazolyl)-L-alanyl}-cyclostatin-[3-(2-oxopyrrolidinyl)propyl]amide A procedure similar to that described in Example 68 was repeated, except that 200 mg (0.34 mmole) of N-[N-(t-butoxycarbonyl)-3-(4-thiazolyl)-L-alanyl]-cyclostatin-[3-(2-oxo-1-pyrrolidinyl)propyl]amide and 124 mg (0.34 mmole) of N-(N-cyclohexyl-N-methylaminoacetyl)-3-(1-naphthyl)-L-alanine [instead of N-(N-benzyl-N-methylaminoacetyl)-3-(1-naphthyl)-L-alanine] were reacted together to give 160 mg of the monohydrate of the title compound as a white powder, melting at 75°–80° C.

Elemental analysis: Calculated for $C_{46}H_{65}N_7O_6S$ $H_2O$: C, 64.09%; H, 7.83%; N, 11.37%; S, 3.71%. Found: C, 64.10%; H, 7.56%; N, 11.52%; S, 3.72%.

EXAMPLE 96

N-{N-[N-Morpholinoacetyl-3-(1-naphthyl)-L-alanyl]-3-(4-thiazolyl)-DL-alanyl}-cyclostatin-[2-(4-imidazolyl)ethyl]amide A procedure similar to that described in Example 54(c) was repeated, except that 250 mg (0.36 mmole) of N-{N-[N-morpholinoacetyl-3-(1-naphthyl)-L-alanyl]-3-(4-thiazolyl)-DL-alanyl}-cyclostatin [prepared as described in Example 54(b)] and 99 mg (0.54 mmole) of 4-(2-aminoethyl)imidazole were reacted together, to give 160 mg of the sesquihydrate of the title compound as a white powder, melting at 107°–110° C.

Elemental analysis: Calculated for $C_{41}H_{54}N_8O_6S$ 1.5 $H_2O$: C, 60.49%; H, 7.06%; N, 13.77%; S, 3.94%. Found: C, 60.41%; H, 6.87%; N, 13.48%; S, 4.15%.

EXAMPLE 97

N-{N-[N-Morpholinoacetyl-3-(1-naphthyl)-L-alanyl-3-(4-thiazolyl)-DL-alanyl}-cyclostatin-(2-hydroxy-3-morpholinopropyl)amide

97(a)

N-[N-(t-Butoxycarbonyl)-3-(4-thiazolyl)-DL-alanyl]cyclostatin-(2-hydroxy-3-morpholinopropyl)amide 0.87 g (20 mmole) of sodium hydride (as a 55% w/w suspension in mineral oil) were suspended in 20 ml of tetrahydrofuran. 1.74 g (20 mmole) of morpholine and subsequently 1.85 g (20 mmole) of epichlorohydrin were then added, whilst ice-cooling, to this suspension, and the reaction mixture was allowed to stand at room temperature for 48 hours. At the end of this time, methylene chloride was added to the reaction mixture, and the organic layer was separated, washed with a saturated aqueous solution of sodium chloride, dried over anhydrous sodium sulfate, and concentrated by evaporation under reduced pressure. The residue was purified by silica gel column chromatography (eluent: methylene chloride), to give 530 mg of 1-morpholino-2,3-epoxypropane.

500 mg of the 1-morpholino-2,3-epoxypropane prepared as described above were dissolved in 20 ml of a saturated methanolic solution of ammonium hydroxide, and the mixture was allowed to stand at room temperature for 3 days. At the end of this time, the reaction mixture was concentrated by evaporation under reduced pressure, to give 530 mg of 1-amino-3-morpholino-2-propanol.

255 mg (1.59 mmole) of this 1-amino-3-morpholino-2-propanol and 500 mg (1.06 mmole) of N-(t-butoxycarbonyl)-3-(4-thiazolyl)-DL-alanyl-cyclostatin [prepared by a procedure similar to that described in Example 54(b)] were dissolved in anhydrous tetrahydrofuran, and 231 mg (1.27 mmole) of diethyl cyanophosphonate (95%) and 0.18 ml (1.27 mmole) of triethylamine were added the resulting solution, whilst ice-cooling. The mixture was then stirred at room temperature for 2 hours. At the end of this time, the solvent was removed by distillation under reduced pressure, and the residue was purified by silica gel thin layer chromatography (developing solvent: a 5 : 1 by volume mixture of methylene chloride and methanol), to afford 350 mg of the trihydrate of the title compound as an amorphous substance.

Elemental analysis: Calculated for $C_{29}H_{49}N_5O_7S$ 3 $H_2O$: C, 55.30%; H, 8.16%; N, 11.12%; S, 5.09%. Found: C, 54.99%; H, 7.96%; N, 11.05%; S, 4.80%.

97(b)

N-{N-[N-Morpholinoacetyl-3-(1-naphthyl)-L-alanyl]-3-(4-thiazolyl)-DL-alanyl}-cyclostatin-(2-hydroxy-3-morpholinopropyl)amide A procedure similar to that described in Example 54(b) was repeated, except that 300 mg (0.49 mmole) of N-[N-(t-butoxycarbonyl)-3-(4-thiazolyl)-DL-alanyl]-cyclostatin-(2-hydroxy-3-morpholinopropyl)amide [prepared as described in step (a) above] and 168 mg (0.49 mmole) of N-morpholinoacetyl-3-(1-naphthyl)-L-alanine (prepared as described in Preparation 35) were reacted together, to give 205 mg of the monohydrate of the title compound as white crystals, melting at 100°–105° C.

Elemental analysis: Calculated for $C_{43}H_{61}N_7O_8S$ $H_2O$: C, 60.47%; H, 7.44%; N, 11.48%; S, 3.75%. Found: C, 60.28%; H. 7.55%; N, 11.08%; S, 3.64%.

EXAMPLE 98

N-{N-[N-Morpholinoacetyl-3-(1-naphthyl)-L-alanyl]-3-(4-thiazolyl)-L-alanyl}-cyclostatin-[(S)-2-methylbutyl]amide 98(a)

N-(t-Butoxycarbonyl)-cyclostatin-[(S)-2-methylbutyl]amide

A procedure similar to that described in Example 48(a) was repeated, except that 0.33 g (3.81 mmole) of (S)-2-methylbutylamine was employed instead of the 2-morpholinoethylamine, and this was reacted with 1.00 g (3.17 mmole) of N-(t-butoxycarbonyl)cyclostatin, to give 1.13 g (93%) of the title compound as a white powder.

98(b)

N-{N-[N-Morpholinoacetyl-3-(1-naphthyl)-L-alanyl]-3-(4-thiazolyl)-L-alanyl-cyclostatin-[(S)-2-methylbutyl]amide A procedure similar to that described in Example 40(a) was repeated, except that 0.50 g (1.30 mmole) of N-(t-butoxycarbonyl)-cyclostatin-[(S)-2-methylbutyl]amide were employed instead of the N-(t-butoxycarbonyl)cyclostatin-(2-morpholinoethyl)amide, and this was reacted with the compound which had been prepared by removing the t-butoxycarbonyl group from 354 mg (1.30 mmole) of N-(t-butoxycarbonyl)-3-(4-thiazolyl)-L-alanine; subsequent reactions were carried out as described in Example 40(b), to give 254 mg (72%) of the 2.5-hydrate of the title compound as a white powder.

Silica gel thin layer chromatography, Rf value 0.63.

Elemental analysis: Calculated for $C_{41}H_{58}N_6O_6S$ 2.5 $H_2O$: C, 60.94%; H, 7.60%; N, 10.40%; S, 3.97%. Found: C, 60.56%; H, 7.14%; N, 10.61%; S, 3.99%.

EXAMPLE 99

N-{N-[N-Morpholinoacetyl-3-(1-naphthyl)-L-alanyl]-3-(4-thiazolyl)-L-alanyl}-cyclostatin-[(S)-1-hydroxymethyl-2-methylbutyl]amide 99(a)

N-(t-Butoxycarbonyl)-cyclostatin-[(S)-1-hydroxymethyl-2-methylbutyl]amide

A procedure similar to that described in Preparation 36 was repeated, except that 446 mg (3.81 mmole) of (S)-2-amino-3-methylpentanol were employed instead of 1-(2-aminoethyl)pyrrolidine, and this was reacted with 1.00 g (3.17 mmole) of N-(t-butoxycarbonyl)-cyclostatin, to give the title compound as a white powder.

99(b)

N-{N-[N-Morpholinoacetyl-3-(1-naphthyl)-L-alanyl]-3-(4-thiazolyl)-L-alanyl}-cyclostatin-[(S)-1-hydroxymethyl-2-methylbutyl]amide A procedure similar to that described in Example 40(a) was repeated, except that 500 mg (1.21 mmole) of N-(t-butoxycarbonyl)-cyclostatin-[(S)-1-hydroxymethyl-2-methylbutyl]amide were employed instead of cyclostatin-(2-morpholinoethyl)amide, and this was reacted with 330 mg (1.21 mmole) of N-(t-butoxycarbonyl)-3-(4-thiazolyl)-L-alanine; subsequent reactions were carried out essentially as described in Example 40(b), to give 125 mg of the hydrate of the title compound as a white powder.

Silica gel thin layer chromatography, Rf value 0.16.

EXAMPLE 100

N-{N-[N-(N-Benzyl-N-methylaminoacetyl)-3-cyclohexyl-L-alanyl]-3-(4-thiazolyl)-L-alanyl}-cyclostatin-[(1S,2S)-2-methyl-1-(morpholinomethyl)butyl]amide The t-butoxycarbonyl group was removed from 188 mg (0.66 mmole) of (1S, 2S)-N-t-butoxycarbonyl-2-methyl-1-(morpholinomethyl)butylamine (prepared as described in Preparation 53) by treating it with a 4N solution of hydrogen chloride in dioxane. The hydrochloride thus obtained was dissolved in 5 ml of dimethylformamide, together with 30 0 mg (0.44 mmole) of N-{N-[N-(N-benzyl-N-methylaminoacetyl)-3-cyclohexyl-L-alanyl]-3-(4-thiazolyl)-L-alanyl}-cyclostatin (prepared as described in Preparation 56). Whilst ice-cooling, 95 mg (0.53 mmole) of diethyl cyanophosphonate (95%) and 0.26 ml (1.84 mmole) of triethylamine were added to the solution, and the mixture was then allowed to react at room temperature for 14 hours. At the end of this time, the reaction mixture was concentrated by evaporation under reduced pressure, and the residue was purified by preparative silica gel thin layer chromatography (developing solvent: a 10: 1 by volume mixture of methylene chloride and methanol), to afford 250 mg of the title compound as white crystals, melting at 76°–79° C.

Elemental analysis: Calculated for $C_{46}H_{73}N_7O_6S \cdot \frac{1}{2} H_2O$: C, 64.15%; H, 8.66%; N, 11.39%; S, 3.72%. Found: C, 63.97%; H, 8.41%; N, 11.40%; S, 3.73%.

EXAMPLE 101

N-{N-[N-(N-Benzyl-N-methylaminoacetyl)-3-cyclohexyl-L-alanyl]-3-(4-thiazolyl)-L-alanyl}-cyclostatin-(2-morpholinoethyl)amide 57 mg (0.35 mmole) of diethyl cyanophosphonate (95%) and 89 μliter (0.64 mmole) of triethylamine were added, whilst ice-cooling, to a solution of 200 mg (0.29 mmole) of N-{N-[N-(N-benzyl-N-methylaminoacetyl)-3-cyclohexyl-L-alanyl]-3-(4-thiazolyl)-L-alanyl}-cyclostatin (prepared as described in Preparation 56) and 58 μliter (0.44 mmole) of 2-morpholinoethylamine in tetrahydrofuran, and the mixture was stirred at room temperature for 3 hours. At the end of this time, the reaction mixture was evaporated to dryness under reduced pressure, and the residue was purified by preparative silica gel thin layer chromatography (developing solvent: a 10: 1 by volume mixture of methylene chloride and methanol), to afford 200 mg of the 2.5-hydrate of the title compound as white crystals.

Silica gel thin layer chromatography, Rf value 0.53.

Elemental analysis: Calculated for $C_{42}H_{65}N_7O_6S \cdot 5/2 H_2O$: C, 59.97%=H, 8.39%; N, 11.66%; S, 3.81%. Found: C, 60.10%; H, 8.18%; N, 11.87%; S, 3.70%.

EXAMPLE 102

N-{N-[N-(N-Benzyl-N-methylaminoacetyl)-3-cyclohexy -L-alanyl]-3-(4-thiazolyl)-L-alanyl}-cyclostatin(hexylamide)

413 mg (0.23 mmole) of diethyl cyanophosphonate (95%) and 32 μl (0.23 mmole) of triethylamine were added, whilst ice-cooling, to a solution of 130 mg (0.19 mmole) of N-{N-[N-(N-benzyl-N-methylaminoacetyl)-3-cyclohexyl-L-alanyl]-3-(4-thiazolyl)-L-alanyl}-cyclostatin (prepared as described in Preparation 56) and 30 μl of hexylamine dissolved in tetrahydrofuran, and the mixture was stirred at room temperature for 3 hours. At the end of this time, the reaction mixture was evaporated to dryness under reduced pressure, and the residue was purified by preparative silica gel thin layer chromatography (developing solvent: a 10: 1 by volume mixture of methylene chloride and methanol), to afford 120 mg of the sesquihydrate of the title compound as white crystals, melting at 48°–51° C.

Elemental analysis: Calculated for $C_{42}H_{66}N_6O_5S \cdot 3/2 H_2O$: C, 63.52%; H, 8.76%; N, 10.58%; S, 4.04%. Found: C, 63.49%; H, 8.66%; N, 10.42%; S, 4.14%.

EXAMPLE 103

N-{N-[N-Morpholinoacetyl-3-(1-naphthyl)-L-alanyl]-3-(4-thiazolyl)-L-alanyl}-cyclostatin-propylamide 103(a) N-(t-Butoxycarbonyl)-cyclostatin-propylamide 510 mg (1.6 mmoles) of N-(t-butoxycarbonyl)cyclostatin, 90 mg (1.6 mmoles) of propylamine and 320 mg (3.2 mmoles) of triethylamine were added to 20 ml of anhydrous tetrahydrofuran. 280 mg (1.6 mmoles) of 95% diethyl cyanophosphonate (95%) were then added dropwise to the mixture, whilst ice-cooling, and the mixture was stirred for 4 hours at the temperature of ice-cooling, and then allowed to stand overnight. The reaction mixture was then concentrated by evaporation under reduced pressure, and the residue was diluted with water and then extracted with ethyl acetate. The organic extract was washed with water, dried over anhydrous magnesium sulfate and concentrated by evaporation under reduced pressure. The residue was triturated with a mixture of ethyl acetate and hexane to induce crystallization. 446 mg of the title compound, melting at 135°–136° C., were obtained.

103(b) N-[N-(t-Butoxycarbonyl)-3-(4-thiazolyl)-L-alanyl]-cyclostatin-propylamide 440 mg (1.24 mmoles) of N-(t-butoxycarbonyl)cyclostatin-propylamide [prepared as described in step (a) above] and 8 ml of a 4N solution of hydrogen chloride in dioxane were added to 2 ml of methanol, and the mixture was stirred for 1 hour at room temperature. The reaction mixture was then evaporated to dryness under reduced pressure, and the residue was dissolved in 17 ml of anhydrous tetrahydrofuran. 340 mg (1.24 mmoles) of N-(t-butoxycarbonyl)-3-(4-thiazolyl)-L-alanine and 510 mg (5.0 mmoles) of triethylamine were added to the resulting solution, after which 210 mg (1.24 mmoles) of diethyl cyanophosphonate (95%) were added dropwise, whilst ice-cooling. The reaction mixture was then stirred for 4 hours, after which it was allowed to stand overnight. It was then concentrated by evaporation under reduced pressure. The residue was mixed with a small amount of water and then extracted with ethyl acetate. The organic extract was washed with water, dried over anhydrous magnesium sulfate and concentrated by evaporation under reduced pressure. The residue was triturated with a mixture of methylene chloride and hexane to induce crystallization. 513 mg of the title compound, melting at 198°–200° C., were obtained.

103(c) N-{N-[N-Morpholinoacetyl-3-(1-naphthyl)-L-alanyl]-3-(4-thiazolyl)-L-alanyl}-cyclostatinpropylamide 510 mg (1.0 mmole) of N-[N-(t-butoxycarbonyl)-3-(4-thiazolyl)-L-alanyl]-cyclostatin-propylamide and 12 ml of a 4N solution of hydrogen chloride in dioxane were added to 4 ml of methanol, and the mixture was stirred for 1 hour at room temperature. The reaction mixture was then evaporated to dryness under reduced pressure, and the residue was dissolved in 20 ml of anhydrous tetrahydrofuran. 340 mg (1.0 mmole) of N-morpholinoacetyl-3-(1-naphthyl)-L-alanine and 510 mg (5.0 mmoles) of triethylamine were added to the resulting solution, after which 170 mg (1.0 mmole) of 95% diethyl cyanophosphonate (95%) were added dropwise, whilst ice-cooling, to the mixture. The reaction mixture was stirred for 4 hours at room temperature, allowed to stand overnight and then evaporated to dryness under reduced pressure. The residue was mixed with a small amount of water, and the resulting mixture was extracted with ethyl acetate. The organic extract was washed with water, dried over anhydrous magnesium sulfate and concentrated by evaporation under reduced pressure. The residue was triturated with a mixture of methylene chloride and hexane to induce crystallization. 630 mg of the monohydrate of the title compound, melting at 189°–191° C., were obtained.

Elemental analysis: Calculated for $C_{39}H_{54}N_6O_6S \cdot H_2O$: C, 62.21%; H, 7.50%; N, 11.16%; S, 4.26%. Found: C, 62.34%; H, 7.32%; N, 11.05%; S, 3.99%.

EXAMPLE 104

N-{N-[N-Morpholinoacetyl-3-(1-naphthyl)-L-alanyl]-3-(4-thiazolyl)-L-alanyl}-cyclostatin-butylamide 104(a) N-(t-Butoxycarbonyl)-cyclostatin-butylamide Following a procedure similar to that described in Example 103(a), but reacting 510 mg (1.6 mmoles) of N-(t-butoxycarbonyl)-cyclostatine with 120 mg (1.6 mmoles) of butylamine (instead of the propylamine), 396 mg of the title compound were obtained as white crystals.

104(b)

N-{N-[N-Morpholinoacetyl-3-(1-naphthyl)-L-alanyl]-3-(4-thiazolyl)-L-alanyl}-cyclostatinbutylamide Following a procedure similar to that described in Example 103(b), followed by a procedure similar to that described in Example 103(c), but reacting 390 mg (1.05 mmoles) of N-(t-butoxycarbonyl)-cyclostatinbutylamide [prepared as described in step (a) above, instead of the N-(t-butoxycarbonyl)-cyclostatin-propylamide] and 290 mg (1.05 mmoles) of N-(t-butoxycarbonyl)-3-(4-thiazolyl)-L-alanine, 590 mg of the hemihydrate of the title compound were obtained as crystals, melting at 180°–182° C.

Elemental analysis: Calculated for $C_{40}H_{56}N_6O_6S$ ½$H_2O$: C, 63.38%; H, 7.58%; N, 11.09%; 4.23%. Found: C, 63.09%; H, 7.57%; N, 10.97%; 4.16%.

EXAMPLE 105

N-{N-[N-Morpholinoacetyl-3-(1-naphthyl)-L-alanyl]-3-(4-thiazolyl)-L-alanyl}-cyclostatin-isobutylamide 105(a) N-(t-Butoxycarbonyl)-cyclostatin-isobutylamide Following a procedure similar to that described in Example 103(a), but reacting 140 mg (1.9 mmoles) of isobutylamine (instead of the propylamine) and 500 mg (1.59 mmoles) of N-(t-butoxycarbonyl)-cyclostatine, 470 mg of the title compound were obtained as white crystals.

105(b)

N-{N-[N-Morpholinoacetyl-3-(1-naphthyl)-L-alanyl]-3-(4-thiazolyl)-L-alanyl}-cyclostatin-isobutylamide Following a procedure similar to that described in Example 103(b), followed by a procedure similar to that described in Example 103(c), but reacting 460 mg (1.24 mmoles) of N-(t-butoxycarbonyl)-cyclostatin-isobutylamide [prepared as described in step (a) above, instead of the N-(t -butoxycarbonyl)-cyclostatin-propylamide] and 340 mg (1.24 mmoles) of N-(t-butoxycarbonyl)-3-(4-thiazolyl)-L-alanine, 785 mg of the monohydrate of the title compound were obtained as crystals, melting at 195°–197° C.

Elemental analysis: Calculated for $C_{40}H_{56}N_6O_6S$ $H_2O$: C, 62.64%; H, 7.62%; N, 10.96%; S, 4.18%. Found: C, 62.94%; H, 7.64%; N, 10.85%; S, 4.24%.

EXAMPLE 106

N-{N-[N-Morpholinoacetyl-3-(1-naphthyl)-L-alanyl]-3-4-thiazolyl)-L-alanyl]-cyclostatin-diisobutylamide 106(a)

N-(t-Butoxycarbonyl)-cyclostatin-diisobutylamide

Following a procedure similar to that described in Example 103(a), but reacting 205 mg (1.59 mmoles) of diisobutylamine (instead of the propylamine) and 500 mg (1.59 mmoles) of N-(t-butoxycarbonyl)-cyclostatine, 560 mg of the title compound were obtained as a white powder.

106(b)

N-{N-[N-Morpholinoacetyl-3-(1-naphthyl)-L-alanyl]-3-(4-thiazolyl)-L-alanyl}-cyclostatin-diisobutylamide Following a procedure similar to that described in Example 103(b), followed by a procedure similar to that described in Example 103(c), but reacting 427 mg (1.0 mmole) of N-(t-butoxycarbonyl)-cyclostatin-diisobutylamide [prepared as described in step (a) above, instead of the N-(t-butoxycarbonyl)-cyclostatin-propylamide] and 272 mg (1.0 mmole) of N-(t-butoxycarbonyl)-3-(4-thiazolyl)-L-alanine, 690 mg of the title compound were obtained as an amorphous monohydrate.

Silica gel thin layer chromatography, Rf value 0.53, (developing solvent: a 30: 1.5 by volume mixture of ethyl acetate and methanol).

Elemental analysis: Calculated for $C_{44}H_{64}N_6O_6S$ $H_2O$: C, 64.21%; H, 8.08%; N, 10.21%; S, 3.89%. Found: C, 64.51%; H, 7.79%; N, 10.47%; S, 3.88%.

EXAMPLE 107

N-{N-[N-Morpholinoacetyl-3-(1-naphthyl)-L-alanyl]-3-(4-thiazolyl)-L-alanyl}-cyclostatin-pentylamide 107(a) N-(t-Butoxycarbonyl)-cyclostatin-pentylamide Following a procedure similar to that described in Example 103(a), but reacting 0.22 ml (1.9 mmoles) of pentylamine (instead of propylamine) and 500 mg (1.59 mmoles) of N-(t-butoxycarbonyl)-cyclostatine. 580 mg of the title compound were obtained as white crystals.

107(b)

N-{N-[N-Morpholinoacetyl-3-(1-naphthyl)-L-alanyl]-3-(4-thiazolyl)-L-alanyl}-cyclostatin-pentylamide Following a procedure similar to that described in Example 103(b), followed by a procedure similar to that described in Example 103(c), but reacting 580 mg (1.5 mmoles) of N-(t-butoxycarbonyl)-cyclostatin-pentylamide [prepared as described in step (a) above, instead of the N-(t-butoxycarbonyl)-cyclostatin-propylamide]and 463 mg (1.7 mmoles) of N-(t-butoxycarbonyl)-3-(4-thiazolyl)-L-alanine, 574 mg of the mono-hydrate of the title compound were obtained, melting at 141°–143° C.

Elemental analysis: Calculated for $C_{41}H_{58}N_6O_6S$ $H_2O$: C, 63.05%; H, 7.74%; N, 10.76%; 5, 4.10%. Found: C, 63.13%; H, 7.63%; N, 10.86%; S, 4.05%.

EXAMPLE 108

N-{N-[N-Morpholinoacetyl-3-(1-naphthyl)-L-alanyl]-(3-(4-thiazolyl)-L-alanyl}-cyclostatin-isopentylamide 108(a)

N-(t-Butoxycarbonyl)-cyclostatin-isopentylamide

Following a procedure similar to that described in Example 103(a), but reacting 0.22 ml (1.9 mmoles) of isopentylamine (instead of propylamine) and 500 mg (1.59 mmoles) of N-(t-butoxycarbonyl)-cyclostatine, 600 mg of the title compound were obtained as white crystals.

108(b)

N-{N[-N-Morpholioacetyl-3-(1-naphyhyl)-L-alanyl]-3-(4-thiazolyl)-L-alanyl}-cyclostatin-isopentylamide Following a procedure similar to that described in Example 103(b), followed by a procedure similar to that described in Example 103(c), but reacting 600 mg (1.56 mmoles) of N-(t-butoxycarbonyl)-cyclostatin-isopentylamide [prepared as described in step (a) above, instead of the N-(t-butoxycarbonyl)-cyclostatin-propylamide]and 425 mg (1.56 mmoles) of N-(t-butoxycarbonyl)-3-(4-thiazolyl)-L-alanine, 828 mg of the monohydrate of the title compound were obtained, melting at 160°–162° C.

Elemental analysis: Calculated for $C_{41}H_{58}N_6O_6S$ $H_2O$: C, 63.05%; H, 7.74%; N, 10.76%; S, 4.10%. Found: C, 63.26%; H, 7.62%; N, 10.74%; S, 4.25%.

EXAMPLE 109

N-{N-[N-Morpholinoacetyl-3-(1-naphthyl)-L-alanyl]-3-(4-thiazolyl)-L-alanyl}-cyclostatin-[(RS)-2-methylbutylamide

109(a)

N-(t-butoxycarbonyl)-cyclostatin-[(RS)-2-methylbutyl]amide

Following a procedure similar to that described in Example 103(a), but reacting 170 mg (1.9 mmoles) of (RS)-2-methylbutylamine (instead of the propylamine) and 500 mg (1.59 mmoles) of N-(t-butoxycarbonyl)cyclostatine, 440 mg of the title compound were obtained as white crystals.

109(b)

N-{N-[N-Morpholinoacetyl-3-(1-naphthyl)-L-alanyl]-3-(4-thiazolyl)-L-alanyl}-cyclostatin-[(RS)-2-methylbutyl]amide Following a procedure similar to that described in Example 103(b), followed by a procedure similar to that described in Example 103(c), but reacting 550 mg (1.43 mmoles) of N-(t-butoxycarbonyl)-[(RS)-2-methylbutyl]amide [prepared as described in step (a) above, instead of the N-(t-butoxycarbonyl)-cyclostatin-propylamide]and 390 mg (1.43 mmoles) of N-(t-butoxycarbonyl)-3-(4-thiazolyl)-L-alanine, 862.5 mg of the hemihydrate of the title compound were obtained, melting at 138°–140° C.

Elemental analysis: Calculated for $C_{41}H_{58}N_6O_6S$ $\frac{1}{2}$ $H_2O$: C, 63.79%; H, 7.70%; N, 10.88%; 4.15%. Found: C, 63.54%; H, 7.67%; N, 10.94%; S, 4.17%.

EXAMPLE 110

N-{N-[N-Morpholinoacetyl-3-(1-naphthyl)-L-alanyl]-3-(4-thiazolyl)-L-alanyl}-cyclostatin-hexylamide 110(a) N-(t-Butoxycarbonyl)-cyclostatin-hexylamide Following a procedure similar to that described Example 103(a), but reacting 380 mg (3.8 mmoles) of hexylamine (instead of the propylamine) and 1.0 g (3.17 mmoles) of N-(t-butoxycarbonyl)-cyclostatine, 1.1 g of the title compound were obtained.

110 (b)

N-{N-[N-Morpholinoacetyl-3-(1-naphthyl)-L-alanyl]-3-(4-thiazolyl)-L-alanyl}-cyclostatin-hexylamide Following a procedure similar to that described in Example 103(b), followed by a procedure similar to that described in Example 103(c), but reacting 1.1 g (2.76 mmoles) of N-(t-butoxycarbonyl)-cyclostatithexylamide [prepared as described in step (a) above, instead of the N-(t-butoxycarbonyl)-cyclostatin-propylamide]and 750 mg (2.76 mmoles) of N-(t-butoxycarbonyl)-3-(4-thiazolyl)-L-alanine, 1.40 g of the monohydrate of the title compound were obtained, melting at 154°–156° C.

Elemental analysis: Calculated for $C_{42}H_{60}N_6O_6S$ $H_2O$: C, 63.45%; H, 7.86%; N, 10.57%; 5, 4.03%. Found: C, 63.67%=H, 7.85%; N, 10.60%: S, 4.09%.

The monohydrate thus obtained was recrystallised from methylene chloride, to give the title compound, melting at 180°–182° C.

Elemental analysis: Calculated for $C_{42}H_{60}N_6O_6S$: C, 64.92%; H, 7.78%; N, 10.82%; S, 4.13%. Found: C, 65.02%; H, N, 10.64%; S, 3.97%.

EXAMPLE 111

N-{N-[N-(Benzyl-N-methylaminoacetyl)-3-(1-naphthyl)-L-alanyl]-3-(4-thiazolyl)-L-alanyl}-cyclostatin-isopentylamide 539 mg (1.0 mmole) of N-(t-butoxycarbonyl)-3-(4-thiazolyl)-L-alanyl-cyclostatin-isopentylamide [prepared by a procedure similar to that described in Example 108(a)] and 12 ml of a 4N solution of hydrogen chloride in dioxane were added to 4 ml of methanol, and the mixture Has stirred at room temperature for 1 hour. At the end of this time, the reaction mixture was evaporated to dryness under reduced pressure, and the residue was dissolved in 20 ml of anhydrous tetrahydrofuran. 376 mg (1.0 mmole) of N-(benzyl-N-methylaminoacetyl)-3-(1-naphthyl)-L-alanine (prepared as described in Preparation 40) and 510 mg (5.0 mmoles) of triethylamine were then added to the solution, after which 170 mg (1.0 mmole) of diethyl cyanophosphonate (95%) were added dropwise to the mixture, whilst ice-cooling. The mixture was then stirred for 16 hours. At the end of this time, the reaction mixture was evaporated to dryness under reduced pressure. The residue was mixed with a small amount of water and then extracted with ethyl acetate. The organic extract was washed with water, dried over anhydrous magnesium sulfate and concentrated by evaporation under reduced pressure. The residue was triturated with a mixture of methylene chloride and hexane to crystallize it. 670 mg of the hemihydrate of the title compound were obtained, melting at 128°–132° C.

Elementary analysis for $C_{45}H_{60}N_6O_5S$ $\frac{1}{2}$ $H_2O$: C, 67.05%; H, 7.63%; N, 10.43%; S, 3.98%. Found: C, 67.00%; H, 7.55%; N, 10.43%; S, 3.71%.

EXAMPLE 112

N-{N-[N-(N-Cyclohexyl-N-methylaminoacetyl)-3-(1-naphthyl)-L-alanyl]-3-(4-thiazolyl)-L-alanyl}-cyclostatin-butylamide 520 mg (1.0 mmole) of N-(t-butoxycarbonyl)-3-(4-thiazolyl)-L-alanyl-cyclostatin-butylamide [prepared by a procedure similar to that described in Example 104(a)]and 12 ml of a 4N solution of hydrogen chloride in dioxane were added to 4 ml of methanol, and the mixture was stirred for 1 hour at room temperature. At the end of this time, the reaction mixture was evaporated to dryness under reduced pressure, and the residue was dissolved in 20 ml of anhydrous tetrahydrofuran. 370 mg (1.0 mmole) of N-(N-cyclohexyl-N-methylaminoacetyl)-3-(1-naphthyl)-L-alanine (prepared as described in Preparation 46) and 510 mg (5.0 mmoles) of triethylamine were then added to the resulting solution, after which 170 mg (1.0 mmole) of 95% diethyl cyanophosphonate were added dropwise to the mixture, whilst ice-cooling. The mixture was then stirred at room temperature for 17 hours. At the end of this time, the reaction mixture was evaporated to dryness under reduced pressure. The residue was mixed with a small amount of water, and the mixture was extracted with ethyl acetate. The organic extract was washed with water, dried over anhydrous magnesium sulfate, and evaporated to dryness under reduced pressure. The residue was triturated with isopropyl ether to crystallize it. 480 mg of the hemihydrate of the title compound were obtained, melting at 78° C.

Elemental analysis: Calculated for $C_{43}H_{62}N_6O_5S$ ½$H_2O$: C, 65.87%; H, 8.10%; N, 10.72%; 5, 4.09%. Found: C, 65.82%; H, 8.16%; N, 10.55%; S, 4.02%.

EXAMPLE 113

N-{N-[N-(N-Cyclohexyl-N-methylaminoacetyl)-3-(1-naphthyl)-L-alanyl]-3-(4-thiazolyl)-L-alanyl}-cyclostatin-hexylamide Following a procedure similar to that described in Example 112, but using 400 mg (0.724 mmoles) of N-(t-butoxycarbonyl)-3-(4-thiazolyl)-L-alanyl-cyclostatin-hexylamide [prepared by a procedure similar to that described in Example 110 (a)] and 270 mg (0.724 mmoles) of N-(N-cyclohexyl-N-methylaminoacetyl)-3-(1-naphthyl)-L-alanine (prepared as described in Preparation 46), 380 mg of the hemihydrate of the title compound were obtained, melting at 117°–119° C.

Elemental analysis: Calculated for $C_{45}H_{66}N_6O_5S$ ½$H_2O$: C, 66.55%; H, 8.32%; N, 10.35%; 3.95%. Found: C, 66.55%=H, 8.31%; N, 10.49%; 4.11%.

EXAMPLE 114

N-{N-[N-Morpholinoacetyl-3-(1-naphthyl)-L-alanyl-3-(5-isoxazolyl)-L-alanyl}-cyclostatin-[(S)-2-methylbutyl]amide

114(a)

N-[N-(t-Butoxycarbonyl)-3-(5-isoxazolyl)-L-alanyl]-cyclostatin-[(S)-2-methylbutyl]amide Following a procedure similar to that described in Example 98(b), but reacting 330 mg (1.3 mmoles) of N-(t-butoxycarbonyl)-3-(5-isoxazolyl)-L-alanine [prepared as described in Preparation 8, instead of the N-(t-butoxycarbonyl)-3-(4- thiazolyl)-L-alanine] and 500 mg (1.3 mmoles) of N-(t-butoxycarbonyl)-cyclostatin-[(S)-2-methylbutyl]amide [prepared as described in Example 29(a)], 520 mg of the title compound were obtained.

114 (b)

N-{N-[N-Morpholinoacetyl-3-(1-naphthyl)-L-alanyl]-3-(5-isoxazolyl)-L-alanyl}-cyclostatin-[(S)-2-methylbutyl]amide Following a procedure similar to that described in Example 98(b), but reacting 200 mg (0.38 mmoles) of N-[N-(t-butoxycarbonyl)-3-(5-isoxazolyl)-L-alanyl]-cyclostatin-[(S)-2-methylbutyl]amide {prepared as described in step (a) above, instead of the N-[N-(t-butoxycarbonyl)-3-(4-thiazolyl)-L-alanyl]-cyclostatin-[(S)-2-methylamide]} and 130 mg (0.38 mmoles) of N-morpholinoacetyl-3-(1-naphthyl)-L-alanine (prepared as described in Preparation 35), 260 mg of the dihydrate of the title compound were obtained, melting at 124°–126° C.

Elemental analysis: Calculated for $C_{41}H_{58}N_6O_7$ 2$H_2O$: C, 62.89%; H, 7.98%; N, 10.73%. Found: C, 62.63%; H, 7.76%; N, 10.50%.

EXAMPLE 115

N-{N-[N-(N-Benzyl-N-methylaminoacetyl)-3-(1-naphthyl)-L-alanyl]-3-(5-isoxazolyl)-L-alanyl}-cyclostatin-[(S)-2-methylbutyl]amide Following a procedure similar to that described in Example 114, but reacting 120 mg (0.38 mmoles) of N-(N-benzyl-N-methylaminoacetyl)-3-(1-naphthyl)-L-alanine [prepared as described in Preparation 40, instead of the N-morpholinoacetyl-3-(1-naphthyl)-L-alanine] and 200 mg (0.38 mmoles) of N-(t-butoxycarbonyl)-3-(5-isoxazolyl)-L-alanyl-cyclostatin-[(S)-2-methylbutyl-]amide [prepared as described in Preparation 114(a)], 220 mg of the sesquihydrate of the title compound were obtained, melting at 138°–140° C.

Elemental analysis: Calculated for $C_{41}H_{58}N_6O_6$ 3/2$H_2O$: C, 64.97%; H, 8.11%; N, 11.09%. Found: C, 64.83%; H, 7,98%; N, 10,71%.

EXAMPLE 116

N-{N-[N-(N-Benzyl-N-methylaminoacetyl)-3-(1-naphthyl)-L-alanyl]-L-histidyl}-cyclostatin-[(RB)-2-methylbutyl]amide

116 (a)

N-[N-(t-butoxycarbonyl)-L-histidyl]-cyclostatin-[(RS)-2-methylbutyl]amide 2.5 g (6,5 mmoles) of N-(t-butoxycarbonyl)-cyclostatin-[(RS)-2-methylbutyl]amide [prepared as described in Example 29(a)] were dissolved in 30 ml of a 4N solution of hydrogen chloride in dioxane, and then the solution was stirred for 1 hour at room temperature, At the end of this time, the reaction mixture was evaporated to dryness under reduced pressure, The residue was dissolved in 20 ml of dimethylformamide, and then 3.29 g (32.5 mmoles) of triethylamine and 2.16 g (8.45 mmoles) of N-(t-butoxycarbonyl)-L-histidine were added to the resulting solution. 1.45 g (8.45 mmoles) of diethyl cyanophosphonate (95%) were then added dropwise to the solution, which was then stirred for 18 hours, whilst ice-cooling. At the end of this time, the reaction mixture was concentrated by evaporation under reduced pressure, and the residue was mixed with a small amount of water and then extracted with ethyl acetate. The organic extract was washed with a 5% w/v aqueous solution of sodium bicarbonate and with a saturated aqueous solution of sodium chloride, in that order, and dried over anhydrous sodium sulfate, after which the solvent was removed by evaporation under reduced pressure. The residue was purified by silica gel thin-layer chromatography (developing solvent: a 10: 1 by volume mixture of methylene chloride and methanol), to afford 2.03 g of the title compound.

116(b)

N-{N-[N-(N-Benzyl-N-methylaminoacetyl)-3-(1-naphthyl)-L-alanyl]-L-histidyl}-cyclostatin[(RS)-2-methylbutyl]amide 0.52 g (1.0 mmole) of N-[N-(t-butoxycarbonyl)-L-histidyl]-cyclostatin-[(RS)-2-methylbutyl]amide [prepared as described in step (a) above] was dissolved in 7.5 ml of a 4N solution of hydrogen chloride in dioxane and stirred for 1 hour. At the end of this time, the reaction mixture was evaporated to dryness under reduced pressure. The residue was dissolved in 5 ml of dimethylformamide, and then 0.51 g (5.0 mmoles) of triethylamine and 0.45 g (1.2 mmoles) of N-(N-benzyl-N- methylaminoacetyl)-3-(1-naphthyl)-L-alanine (prepared as described in Preparation 40) were added to the resulting solution. 0.21 g (1.2 mmoles) of diethyl cyanophosphonate (95%) were then added dropwise to the mixture, after which it was stirred for 17 hours, whilst ice-cooling. At the end of this time, the reaction mixture was concentrated by evaporation under reduced pressure, and the residue was mixed with a small amount of water and then extracted with ethyl acetate. The organic extract was washed with a 5% w/v aqueous solution of sodium bicarbonate and with a saturated aqueous solution of sodium chloride, in that order, and dried over anhydrous sodium sulfate, after which the solvent was removed by evaporation under reduced pressure. The residue was purified by silica gel thin-layer chromatography (developing solvent: a 10 : 1 by volume mixture of methylene chloride and methanol), to afford 0.54 g of the sesquihydrate of the title compound, melting at 103°–106° C.

Elemental analysis: Calculated for $C_{45}H_{61}N_7O_5$ 3/2$H_2O$: C, 66.97%; H, 7.99%; N, 12.15%. Found: C, 66.93%; H, 7.70%; N, 12.09%.

EXAMPLE 117

N-{N-[N-(N-Cyclohexyl-N-methylaminoacetyl)-3-(naphthyl)-L-alanyl]-L-histidyl}-cyclostatin-[(RS)-2-methylbutyl]amide Following a procedure similar to that described in Example 116(b), but reacting 0.66 g (1.8 mmoles) of N-(N-cyclohexyl-N-methylaminoacetyl)-3-(1-naphthyl)-L-alanine [prepared as described in Preparation 46, instead of the N-(N-benzyl-N-methylaminoacetyl)-3-(1-naphthyl)-L-alanine] and 0.78 g (1.5 mmoles) of N-[N-(t-butoxycarbonyl)-N-histidyl]-cyclostatin-[(RS)-2-methylbutyl]amide, 0.62 g of the dihydrate of the title compound was obtained, melting at 110°–113° C.

Elemental analysis: Calculated for $C_{44}H_{65}N_7O_5$ 2$H_2O$: C, 65.40%; H, 8.61%; N, 12.13%. Found: C, 65.44%; H, 8.31%; N, 12.10%.

EXAMPLE 118

N-[N-(N-Morpholinoacetyl-L-phenylalanyl)-3-(4-thiazolyl)L-alanyl]-cyclostatin-propylamide 350 mg (0.69 mmoles) of N-[N-(t-butoxycarbonyl)-3-(4-thiazolyl)-L-alanyl]-cyclostatin-propylamide [prepared as described in Example 103(b)] and 10 ml of 4N solution of hydrogen chloride in dioxane were added to 2 ml of methanol, and then the mixture was stirred for 1 hour at room temperature. At the end of this time, the reaction mixture was evaporated to dryness under reduced pressure, and the residue was dissolved in 15 ml of anhydrous tetrahydrofuran. 200 mg (0.69.mmoles) of N-morpholinoacetyl-L-phenylalanine and 350 mg (3.45 mmoles) of triethylamine were then added to the solution, after which 120 mg (0.69 mmoles) of 95% diethyl cyanophosphonate were added dropwise, whilst ice-cooling. The mixture was then stirred for 4 hours at the temperature of ice-cooling, and then the solution was allowed to stand overnight at room temperature. The reaction mixture was then evaporated to dryness under reduced pressure. The residue was mixed with a small amount of water and then extracted with ethyl acetate. The organic extract was washed with water, dried over anhydrous magnesium sulfate and concentrated by evaporation under reduced pressure. The residue was triturated with a mixture of methylene chloride and hexane to crystallize it. 360 mg of the hemihydrate of the title compound were obtained, melting at 162°–163° C.

Elemental analysis: Calculated for $C_{35}H_{52}N_6O_6S$ ½$H_2O$: C, 60.58%; H, 7.70%; N, 12.11%; S, 4.62%. Found: C, 60.82%; H, 7.70%; N, 12.08%; S, 4.66%.

EXAMPLE 119

N-[N-(N-Morpholinoacetyl-L-phenylalanyl)-3-(4-thiazolyl)-L-alanyl]-cyclostatin-butylamide Following a procedure similar to that described in Example 118, but reacting 520 mg (1.0 mmole) of N-[N-(t-butoxycarbonyl)-3-(4-thiazolyl)-L-alanyl]-cyclostatin-butylamide [prepared by a procedure similar to that described in Examples 103(a) and 103(b), except that the propylamine in Example 103(a) was replaced by butylamine] {instead of the N-[N-(t-butoxycarbonyl)- 3(4-thiazolyl)-L-alanyl]-cyclostatin-propylamide} and 290 mg (1.0 mmole) of N-morpholinoacetyl-L-phenylalanine, 450 mg of the monohydrate of the title compound were obtained, melting at 152°–153° C.

Elemental analysis: Calculated for $C_{36}H_{54}N_6O_6S$ $H_2O$: C, 60.31%; H, 7.87%; N, 11.72%; S, 4.47%. Found: C, 60.11%; H, 7.57%; N, 11.81%; S, 4.43%.

EXAMPLE 120

N-[N-(N-Morpholinoacetyl-L-phenylalanyl)-3-(4-thiazolyl)-L-alanyl]-cyclostatin-isobutylamide Following a procedure similar to that described in Example 118, but reacting 450 mg (0.86 mmoles) of N-[N-(t-butoxycarbonyl)-3-(4-thiazolyl)-L-alanyl]-cyclostatin-isobutylamide [prepared by a procedure similar to that described in Examples 103(a) and 103(b), except that the propylamine in Example 103(a) was replaced by isobutylamine] {instead of the N[N-(t-butoxycarbonyl)-3-(4-thiazolyl)-L-alanyl]-cyclostatin-propylamide} and 250 mg (0.86 mmoles) of N-morpholinoacetyl-L-phenylalanine, 450 mg of the monohydrate of the title compound were obtained, melting at 146°–148° C.

Elemental analysis: Calculated for $C_{36}H_{54}N_6O_6S$ $H_2O$: C, 60.31%; H, 7.87%; N, 11.72%; S, 4.47%. Found: C, 60.61%; H, 7.78%; N, 11.83%; S, 4.61%.

EXAMPLE 121

N-[N-{N-Morpholinoacetyl-L-phenylalanyl)-3-(4-thiazolyl)-L-alanyl]-cyclostatin-pentylamide Following a procedure similar to that described in Example 118, but reacting 360 mg (0.67 mmoles) of N-[N-(t-butoxycarbonyl-3-(4-thiazolyl)-L-alanyl]-cyclostatin-pentylamide [prepared by a procedure similar to that described in Examples 103(a) and 103(b), except that the propylamine in Example 103(a) was replaced by pentylamine] {instead of the N-[N-(t-butoxycarbonyl)-3-(4-thiazolyl)-L-alanyl]-cyclostatin-propylamide} and 205 mg (0.7 mmoles) of N-morpholinoacetyl-L-phenylalanine, 387 mg of the title compound were obtained, melting at 155°–160° C.

Elemental analysis: Calculated for $C_{37}H_{56}N_6O_6S$: C, 62.33%; H, 7.92%; N, 11.79%; S, 4.50%. Found: C, 62.04%; H, 7.93%=N, 11.73%; S, 4.54%.

EXAMPLE 122

N-[N-(N-Morpholinoacetyl-L-phenylalanyl)-3-(4-thiazolyl)-L-alanyl]-cyclostatin-isopentylamide Following a procedure similar to that described in Example 118, but reacting 830 mg (1.54 mmoles) of N-[N-(t-butoxycarbonyl)-3-(4-thiazolyl)-L-alanyl]-cyclostatin-isopentylamide [prepared by a procedure similar to that described in Examples 103(a) and 103(b), except that the propylamine in Example 103(a) was replaced by isopentylamine] {instead of the N-[N-(t-butoxycarbonyl)-3-(4-thiazolyl)-L-alanyl]-cyclostatin-propylamide} and 468 mg (1.6 mmoles) of N-morpholinoacetyl-phenyl-L-alanine, 803 mg of the monohydrate of the title compound were obtained, melting at 164°–167° C.

Elemental analysis: Calculated for $C_{37}H_{56}N_6O_6S \cdot H_2O$: C, 60.79%; H, 8.00%; N, 11.50%; S, 4.39%. Found: C, 60.90%; H, 7.86%; N, 11.36%; S, 4.34%.

EXAMPLE 123

N-[N-(N-Morpholinoacetyl-L-phenylalanyl)-3-(4-thiazolyl)-L-alanyl]-cyclostatin-[(S)-2-methylbutyl]amide Following a procedure similar to that described in Example 118, but reacting 630 mg (1.17 mmoles) of N-[N-(t-butoxycarbonyl)-3-(4-thiazolyl)-L-alanyl]-cyclostatin-[(S)-2-methylbutyl]amide {prepared by a procedure similar to that described in Example 1(a), instead of the N-[N-(t-butoxycarbonyl)-3-(4-thiazolyl)-L-alanyl]-cyclostatin-propylamide} and 380 mg (1.3 mmoles) of N-morpholinoacetyl-L-phenylalanine, 727 mg of the monohydrate of the title compound were obtained, melting at 160°–162° C.

Elemental analysis: Calculated for $C_{37}H_{56}N_6O_6S \cdot H_2O$: C, 60.79%; H, 8.00%; N, 11.50%; S, 4.39%. Found: C, 60.79%; H, 7.84%; N, 11.46%; S, 4.58%.

EXAMPLE 124

N-[N-(N-Morpholinoacetyl-L-phenylalanyl)-3-(4-thiazolyl)-L-alanyl]-cyclostatin-hexylamide Following a procedure similar to that described in Example 118, but reacting 500 mg (0.9 mmoles) of N-[N-(t-butoxycarbonyl)-3-(4-thiazolyl)-L-alanyl]-cyclostatin-hexylamide [prepared by a procedure similar to that described in Examples 103(a) and 103(b), except that the propylamine in Example 103(a) was replaced by hexylamine] {instead of the N-[N-(t-butoxycarbonyl)-3-(4-thiazolyl)-L-alanyl]-cyclostatin-propylamide} and 260 mg (0.9 mmoles) of N-morpholinoacetyl-phenyl-L-alanine, 530 mg of the monohydrate of the title compound were obtained, melting at 154°–156° C.

Elemental analysis: Calculated for $C_{38}H_{58}N_6O_6S \cdot H_2O$: C, 61.26%; H, 8.12%; N, 11.28%; S, 4.30%. Found: C, 61.56%; H, 8.06%=N, 11.39%; S, 4.39%.

EXAMPLE 125

N-[N-(N-Morpholinoacetyl-L-phenylalanyl)-L-leucyl]-cyclostatin-[(S)-2-methylbutyl]amide

125(a)

N-[N-(t-Butoxycarbonyl)-L-leucyl]-cyclostatin-[(S)-2-methylbutyl]amide

Following a procedure similar to that described in Example 98(b), but reacting 1.32 g (5.3 mmoles) of N-(t-butoxycarbonyl)-L-leucine and 1.7 g (4.42 mmoles) of N-(t-butoxycarbonyl)-cyclostatin-[(S)-2-methylbutyl]amide instead of the N-(t-butoxycarbonyl)-3-(4-thiazolyl)-L-alanine, 1.82 g of the title compound were obtained.

125(b)

N-[N-(N-Morpholinoacetyl-L-phenylalanyl)-L-leucyl]-cyclostatin-[(S)-2-methylbutyl]amide Following a procedure similar to that described Example 123, but reacting 200 mg (0.4 mmoles) of N[N-(t-butoxycarbonyl)-L-leucyl]-cyclostatin-[(S)-2-methylbutyl]amide {prepared as described in step (a) above, instead of the N-[N-(t-butoxycarbonyl)-3-(4-thiazolyl)-L-alanyl]-cyclostatin-[(S)-2-methylbutyl]amide} and 118 mg (0.4 mmoles) of N-morpholinoacetyl-L-phenylalanine, 228 mg of the monohydrate of the title compound were obtained as an amorphous powder.

Silica gel thin layer chromatography, Rf value 0.46.

Elemental analysis: Calculated for $C_{37}H_{61}N_5O_6 \cdot H_2O$: C, 64.41%; H, 9.20%; N, 10.15%. Found: C, 64.08%; H, 9.08%; N, 9.99%.

EXAMPLE 126

N-[N-[N-(N-Cyclohexyl-N-methylaminoacetyl)-L-phenylalanyl]-L-leucyl]-cyclostatin-[(S)-2-methylbutyl]amide Following a procedure similar to that described in Example 125, but reacting 150 mg (0.48 mmoles) of N-(N-cyclohexyl-N-methylaminoacetyl)-L-phenylalanine (prepared by a procedure similar to that described in Preparation 46, instead of N-morpholinoacetyl-L-phenylalanine) and 200 mg (0.4 mmoles) of N-[N-(t-butoxycarbonyl)-L-leucyl]-cyclostatin-[(S)-2-methylbutyl]amide [prepared as described in Example 125(a)], 260 mg of the 2.5-hydrate of the title compound were obtained as an amorphous powder.

Silica gel thin layer chromatography, Rf value 0.80.

Elemental analysis: Calculated for $C_{40}H_{67}N_5O_5 \cdot 5/2H_2O$: C, 64.66%; H, 9.77%; N, 9.43%. Found: C, 64.83%: H, 9.49%; N, 9.20%.

PREPARATION 1

N-[3-(1-Naphthyl)propionyl]-(S)-(-)-4-benzyl-2-oxazolidinone 14.8 mmole of butyllithium in hexane were added dropwise to a solution of 2.63 g (14.8 mmole) of (S)-(-)-4-benzyl-2-oxazolidinone dissolved in 50 ml of anhydrous tetrahydrofuran at −78° C. under an atmosphere of nitrogen. The mixture was stirred for 30 minutes at this temperature, and then 2.95 g (13.5 mmole) of 1-naphthylpropionyl chloride in 15 ml of anhydrous tetrahydrofuran were slowly added dropwise at the same temperature=the mixture was then stirred for 3 hours. At the end of this time, a saturated aqueous solution of sodium chloride was added to the mixture, and the mixture was extracted with ethyl acetate. The extract was dried over anhydrous magnesium sulfate, and then freed from the solvent by evaporation under reduced pressure. The residue was purified by silica gel column chromatography (eluent: a 1: 4 by volume mixture of ethyl acetate and hexane), to afford 4.65 g (96%) of the title compound as a white amorphous substance.

Mass Spectrum m/e: 359 (M+).

PREPARATION 2

N-[(2-Benzyloxycarbonyl)methyl-3-(1-naphthyl)propionyl]-(S)-(-)-4-benzyl-2-oxazolidinone 15.6 mmole of butyllithium in hexane were added dropwise to a solution of 2.18 ml (15.6 mmole) of diisopropylamine dissolved in 40 ml of anhydrous tetrahydrofuran at −78° C. under an atmosphere of nitrogen, and then the mixture was stirred for 15 minutes at the same temperature. A solution of 4.65 (12.9 mmole) of N-[3-(1-naphthyl)propionyl]-(S)-(-)-4-benzyl-2-oxazolidinone (prepared as described in Preparation 1) dissolved in 15 ml of anhydrous tetrahydrofuran was then slowly added dropwise to the above mixture at the same temperature, and the mixture was stirred for 30 minutes. At the end of this time, 6.13 ml (38.7 mmole) of benzyl bromoacetate were added to the mixture, which was then stirred for 6 hours at the same temperature. At the end of this time, 15.6 ml of 1N aqueous hydrochloric acid and 100 ml of a saturated aqueous solution of sodium chloride were added to the mixture. The mixture was then extracted with ethyl acetate. The extract was dried over anhydrous magnesium sulfate and concentrated by evaporation under reduced pressure. The residue was purified by medium pressure silica gel column chromatography (eluent: a 1: 6 by volume mixture of ethyl acetate and hexane), to afford 3.23 g (49%) of the title compound as a colorless oil.

Mass Spectrum m/e: 507 (M+).

Elemental analysis: Calculated for $C_{32}H_{29}NO_5$: C, 75.72%; H, 5.76%; N, 2.76%. Found: C, 75.34%; H, 5.90%; N, 2.76%.

PREPARATION 3

N-[2-(Morpholinocarbonyl)methyl-3-(1-naphthyl)propionyl]-(S)-(-)-4-benzyl-2-oxazolidinone A solution of 1.60 g (3.15 mmole) of N-[(2-benzyloxycarbonyl)methyl-3-(1-naphthyl)propionyl]-(S)-(-)-4-benzyl-2-oxazolidinone (prepared as described in Preparation 2) dissolved in 100 ml of ethanol was stirred in an atmosphere of hydrogen and in the presence of 200 mg of a 10% w/w palladium-on-carbon catalyst at room temperature for 3 hours. At the end of this time, the catalyst was removed by filtration, and the filtrate was concentrated by evaporation under reduced pressure, to afford 1.30 g (99%) of the corresponding free carboxylic acid, which was dissolved in 20 ml of anhydrous tetrahydrofuran. 0.33 ml (3.78 mmole) of morpholine was added to the solution, after which 0.57 ml (3.76 mmole) of diethyl cyanophosphonate (95%) and 0.52 ml of triethylamine were added, whilst ice-cooling, under an atmosphere of nitrogen. The mixture was stirred at the same temperature for 3 hours, after which it was freed from the solvent by evaporation under reduced pressure. The residue was purified by medium pressure column chromatography through silica gel (eluent: a 2: 1 by volume mixture of ethyl acetate and hexane), to afford 1.23 g (81%) of the title compound as white crystals, melting at 80°-82° C.

Mass Spectrum m/e: 486 (M+)

$[\alpha]_D^{25} = +107.9$ (c=0.42, methanol).

Elemental analysis: Calculated for $C_{29}H_{30}N_2O_5$: C, 71.59%; H, 6.21%; N, 5.76%. Found: C, 70.07%; H, 6.12%; N, 5.71%.

PREPARATION 4

(2R)-3-(Morpholinocarbonyl)-2-(1-naphthylmethyl)-propionic acid 221 mg (5.27 mmole) of lithium hydroxide monohydrate were added, whilst ice-cooling, to a solution of 1.28 g (2.63 mmole) of N-[2-(morpholinocarbonyl)-methyl-3-(1-naphthyl)propionyl]-(S)-(-)-4-benzyl-2-oxazolidinone (prepared as described in Preparation 3) dissolved in a mixture of 40 ml of tetrahydrofuran and 10 ml of water. The mixture was stirred at the same temperature for 3 hours, after which it was freed from the solvent by evaporation under-reduced pressure. A 10% w/v aqueous solution of sodium hydroxide was added to the residue, and the mixture was extracted with methylene chloride. The aqueous layer was separated, adjusted with hydrochloric acid to a pH value of 2 and then extracted with methylene chloride. The extract was dried over anhydrous magnesium sulfate, and the solvent was removed by distillation under reduced pressure, to afford 750 mg (87%) of the title compound as white crystals, melting at 62°-66° C.

Mass Spectrum m/e: 328 (M+ +1).

$[\alpha]_D^{25} = +5.0°$ (c=0.18, methanol).

PREPARATION 5

Diethyl 5-isoxazolylmethylacetamidomalonate 3.1 g (70.7 mmole) of sodium hydride (as a 55% w/w dispersion in mineral oil) were added to a solution of 14.0 g (6,43 mmole) of diethyl acetamidomalonate dissolved in 150 ml of dimethylformamide, whilst ice-cooling, and the mixture was stirred for 1 hour. At the end of this time, 23.9 g (0.148 mmole) of 5-bromomethylisoxazole were added to the reaction mixture, which was then stirred at room temperature for 4.5 hours, The reaction mixture was then concentrated by evaporation under reduced pressure, and the residue was mixed with water and extracted with ethyl acetate. The extract was washed with water and dried over anhydrous magnesium sulfate, after which it was concentrated by evaporation under reduced pressure. The residue was purified by silica gel column chromatography (eluent: a 1: 2 by volume mixture of ethyl acetate and hexane), to afford 14.78 g (77.1%) of the title compound, melting at 75°-76° C.

PREPARATION 6

3-(5-Isoxazolyl)-DL-alanine hydrochloride 120 ml of 6N aqueous hydrochloric acid were added to a suspension of 19.0 g (63.7 mmole) of diethyl 5-isoxazolylmethylacetamidomalonate (prepared as described in Preparation 5) in 40 ml of ethanol, and the mixture was heated under reflux and with stirring for 13 hours. At the end of this time, the reaction mixture was concentrated by evaporation under reduced pressure, and the residue was triturated with acetone to afford crystals, which were collected by filtration. These crystals were washed with acetone and dried, to give 12.45 g (100%) of the title compound.

Elemental analysis: Calculated for $C_6H_8N_2O_3$ HCl: C, 37.42%; H, 4.71%; N, 14.55%; Cl, 18.41%. Found: C, 37.54%; H, 4.68%; N, 14.43%; Cl, 18.37%.

PREPARATION 7

N-Acetyl-3-(5-isoxazolyl)-DL-alanine 20 ml of pyridine and 20 ml of acetic anhydride were added to a solution of 12.45 g of 3-(5-isoxazolyl)-DL-alanine hydrochloride (prepared as described in Preparation 6) dissolved in 100 ml of methanol, whilst ice-cooling. The mixture was then stirred at room temperature for 8 hours, after which it was allowing to stand overnight. The mixture was then freed from the solvent by evaporation under reduced pressure. The residue was mixed with water and then extracted with ethyl acetate. The extract was dried over anhydrous magnesium sulfate, and the solvent was removed by distillation under reduced pressure, to afford 10.39 g (82.3%) of the title compound as a brown oil.

PREPARATION 8

N-(t-Butyloxycarbonyl)-(5-isoxazolyl)-L-alanine

A solution of 10.39 g (52.4 mmole) of N-acetyl-3-(5-isoxazolyl)-DL-alanine dissolved in 100 ml of water was adjusted to a pH value of 7.5 by adding a 2N aqueous solution of sodium hydroxide. 2.0 g of acylase were added to the resulting solution, and the mixture was stirred at 38° C. for 24 hours. At the end of this time, the reaction mixture was filtered and the filtrate was adjusted to a pH value of 1 by adding concentrated hydrochloric acid. The mixture was agitated with ethyl acetate, and the aqueous layer was separated and adjusted to a pH value of 10 by adding potassium carbonate. 20 g of di(t-butoxy)dicarbonate, 40 ml of acetone and 100 ml of methanol were added to the solution, and the mixture was stirred at room temperature for 2.5 hours. It was then allowed to stand overnight, after which it was concentrated by evaporation under reduced pressure. 100 ml of water were added to the residue, and the mixture was adjusted to a pH value of 2.0 by adding citric acid. The reaction mixture was then extracted with ethyl acetate, and the extract was dried over anhydrous magnesium sulfate. The solvent was removed by distillation, and the residue was purified by silica gel column chromatography (eluent: a 95 : 5 by volume mixture of chloroform and methanol), to afford 2.99 g (22.3%) of the title compound as an oil.

PREPARATION 9 t-Butyl 3-(1-naphthyl)propionate 18.7 g (0.333 mmole) of potassium hydroxide were added to a solution of 20 g (66.6 mmole) of diethyl (1-naphthyl)methylmalonate dissolved in 200 ml of 80% v/v aqueous methanol, The mixture was then stirred at room temperature for 1 hour, after which it was concentrated by evaporation under reduced pressure. The residue was dissolved in water, and the resulting solution was washed with ethyl acetate. The aqueous solution was acidified with concentrated hydrochloric acid and then extracted with methylene chloride. The organic layer was dried over anhydrous magnesium sulfate and concentrated by evaporation under reduced pressure. The residue was decarboxylated by heating at 200° C. for 30 minutes, and was then suspended in 200 ml of diethyl ether. 19 ml of t-butanol, 16.5 g (80 mmole) of dicyclohexylcarbodiimide and 0.8 g of N,N-dimethylaminopyridine were added to the suspension. The mixture was allowed to stand for 24 hours. The precipitated insoluble materials were removed by filtration, and the filtrate was concentrated by evaporation under reduced pressure. The residue was purified by column chromatography through silica gel (eluent: methylene chloride), to afford 12.18 g (71.4%) of the title compound as a pale yellow oil.

Nuclear Magnetic Resonance Spectrum (CDCl$_3$) δ ppm:

1.43 (9H, singlet):

7.2–8.2 (7H, multipier).

PREPARATION 10 t-Butyl 2-(1-naphthylmethyl)-4-pentenoate

A mixture of 100 ml of anhydrous tetrahydrofuran and 10 ml of diisopropylamine was cooled to −78° C. 51 ml (71.4 mmole) of butyllithium in hexane were added to the mixture, which was then stirred for 15 minutes. At the end of this time, a solution of 12.18 g (47.5 mmole) of t-butyl 3-(1-naphthyl)propionate (prepared as described in Preparation 9) dissolved in 20 ml of anhydrous tetrahydrofuran was added to the reaction mixture, and then the mixture was stirred for 15 minutes. 6.9 g (57 mmole) of allyl bromide were added, and the temperature of the mixture was allowed to rise to room temperature, at which temperature it was stirred for 2 hours. The reaction mixture was then mixed with water and extracted with ethyl acetate. The organic extract was washed with a saturated aqueous solution of citric acid, with a saturated aqueous solution of sodium bicarbonate and with a saturated aqueous solution of sodium chloride, in that order, dried over anhydrous magnesium sulfate and concentrated by evaporation under reduced pressure. The residue was purified by column chromatography through silica gel (eluent: a 10: 90 by volume mixture of ethyl acetate and hexane), to afford 12.92 g (91.8%) of the title compound as a pale yellow oil.

Nuclear Magnetic Resonance Spectrum: (CDCl$_3$) δ ppm:

1.30 (9H, singlet):

7.2–8.2 (7H, multipier).

PREPARATION 11 t-Butyl 4,5-epoxy-2-(1-naphthylmethyl)pentanoate

A mixture of 12.92 g (43.6 mmole) of t-butyl 2-(1-naphthylmethyl)-4-pentenoate (prepared as described in Preparation 10), 11.29 g (65.4 mmole) of m-chloroperbenzoic acid and 100 ml of methylene chloride was stirred at room temperature for 24 hours. At the end of this time, the reaction mixture was washed with a saturated aqueous solution of sodium bicarbonate and with a saturated aqueous solution of sodium chloride, in that order, after which it was dried over anhydrous magnesium sulfate and concentrated by evaporation under reduced pressure. The residue was purified by column chromatography through silica gel (eluent: a 5: 95 by volume mixture of methanol and methylene chloride), to afford 4.57 g (33.6%) of the title compound as a pale yellow oil.

Nuclear Magnetic Resonance Spectrum: (CDCl$_3$) δ ppm:

1.33 (9H, doublet);

7.2–8.2 (7H, multipier).

PREPARATION 12 t-Butyl 4-hydroxy-5-morpholino-2-(1-naphthylmethyl)pentanoate

A mixture of 2 g (6.4 mmole) of t-butyl 4,5-epoxy-2-(1-naphthylmethyl)pentanoate (prepared as described in Preparation 11), 0.84 ml of morpholine and 50 ml of methanol was stirred at room temperature for 6 hours and then allowed to stand overnight. The reaction mixture was then concentrated by evaporation under reduced pressure. The residue was purified by column chromatography through silica gel (eluent: a 10 : 90 by volume mixture of methanol and methylene chloride), to afford 1.96 g (76.6%) of the title compound as a pale yellow oil.

Nuclear Magnetic Resonance Spectrum: (CDCl₃) δ ppm:
1.30 (9H, singlet);
7.2–8.2 (7H, multipier).

PREPARATION 13 t-Butyl 5-morpholino-2-(1-naphthylmethyl)-4-oxopentanoate 2.3 g (14.7 mmole) of a sulfur trioxide/pyridine complex and 2.1 ml of triethylamine were added at room temperature to a solution of 1.96 g (4.91 mmole) of t-butyl 4-hydroxy-5-morpholino-2-(1-naphthylmethyl)-pentanoate (prepared as described in Preparation 12) dissolved in 20 ml of anhydrous dimethyl sulfoxide. The mixture was stirred for 6 hours, allowed to stand overnight and then mixed with water, after which it was extracted with ethyl acetate. The organic layer was washed with water and with a saturated aqueous solution of sodium chloride, in that order, and dried over anhydrous magnesium sulfate. It was then concentrated by evaporation under reduced pressure. The residue was purified by column chromatography through silica gel (eluent: a 10: 90 by volume mixture of methanol and methylene chloride), to afford 1.30 g (66.7%) of the title compound as a pale brown oil.

Nuclear Magnetic Resonance Spectrum: (CDCl₃) δ ppm:
1.38 (9H, singlet);
7.2–8.2 (7H, multipier).

PREPARATION 14

5-Morpholino-2-(1-naphthylmethyl)-5-oxopentanoic acid 8.17 g (0.19 mole) of sodium hydride (as a 55% w/w dispersion in mineral oil) were added, with ice-cooling, to a solution of 25 g (0.16 mole) of dimethyl glutarate and 23.4 g (0.16 mole) of 1-naphthaldehyde dissolved in 200 ml of anhydrous methanol. The mixture was heated under reflux for 30 minutes, after which 190 ml (0.19 mole) of a 1N aqueous solution of sodium hydroxide were added and the mixture was heated under reflux for a further 1 hour. The solvent was then removed by distillation under reduced pressure, and the residue was mixed with water and then washed with diethyl ether. The aqueous layer was acidified and extracted with diethyl ether. The ethereal layer was washed with a saturated aqueous solution of sodium chloride and then dried over anhydrous magnesium sulfate. The solvent was removed by distillation under reduced pressure, and then diisopropyl ether was added to the residue to precipitate crystals, which were collected by filtration to give 18.5 g of 2-(1-naphthylmethylene)glutaric acid.

100 ml of acetic anhydride were added to 10 g (37 mmole) of 2-(1-naphthylmethylene)glutaric acid (prepared as described above), and the mixture was stirred at 60° C. for 1 hour. At the end of this time, the solvent was removed by distillation under reduced pressure, and then a 1: 1 by volume mixture of benzene and hexane was added to the residue to precipitate crystals, which were collected by filtration to give 8.1 g of 2-(1-naphthylmethylene)glutaric anhydride.

7.5 g (30 mmole) of 2-(1-naphthylmethylene)glutaric anhydride (prepared as described above) were dissolved in 70 ml of methylene chloride, and 2.85 ml (33 mmole) of morpholine were added to the resulting solution. The mixture was stirred at room temperature for 4 hours. At the end of this time, the reaction mixture was washed with a 5% v/v aqueous solution of citric acid and with a saturated aqueous solution of sodium chloride, in that order, after which it was dried over anhydrous sodium sulfate and freed from the solvent by evaporation under reduced pressure, to give 10.0 g (30 mmole) of 5-morpholino-2-(1-naphthylmethylene)-5-oxopentanoic acid.

5 g (14.8 mmole) of the 5-morpholino-2-(1-naphthylmethylene)-5-oxopentanoic acid (prepared as described above) were dissolved in 50 ml of methanol and hydrogenated in an atmosphere of hydrogen at atmospheric pressure and in the presence of 1.0 g of a 10% w/w palladium-on-carbon catalyst. The catalyst was then removed by filtration, and the solvent was removed by distillation under reduced pressure. The residue was triturated with diethyl ether to precipitate crystals, which were collected by filtration to give 4.5 g of 5-morpholino-2-(1-naphthylmethyl)-5-oxopentanoic acid as white crystals, melting at 130°–135° C.

Elemental analysis: Calculated for $C_{20}H_{23}NO_4$: C, 70.36%; H, 6.79%; N, 4.10%. Found: C, 69.86%; H, 6.90%; N, 3.98%.

PREPARATION 15

Diethyl (3,3-dimethyl-2-oxobutyl)-(1-naphthylmethyl)-malonate 5.00 g (16.9 mmole) of diethyl (1-naphthylmethyl)malonate were dissolved in 50 ml of anhydrous dimethylformamide, and 1.00 g (18.5 mmole) of sodium methoxide was added to the solution, whilst ice-cooling, after which the mixture was stirred for 30 minutes. At the end of this time, a solution of 3.31 g (18.5 mmole) of 1-bromopinacolone (i.e. 1-bromo-3,3-dimethyl-2-butanone) dissolved in 10 ml of anhydrous dimethylformamide was added dropwise to the mixture, which was then stirred overnight at room temperature. The solvent was then removed by distillation under reduced pressure, and the resulting residue was mixed with a saturated aqueous solution of sodium chloride and extracted with ethyl acetate. The extract was dried over anhydrous magnesium sulfate, and the solvent was removed by evaporation under reduced pressure. The residue was purified by column chromatography through silica gel (eluent: a 6: 1 by volume mixture of hexane and ethyl acetate), to afford 5.51 g (82%) of the title compound as a colorless oil.

Mass Spectrum m/e: 398 (M+).

PREPARATION 16

5,5-Dimethyl-2-(1-naphthylmethyl)-4-oxopentanoic acid 5.13 g (12.9 mmole) of diethyl (3,3-dimethyl-2-oxobutyl)-(1-naphthylmethyl)malonate (prepared as described in Preparation 15) were dissolved in 200 ml of a 4:1 by volume mixture of methanol and water, and 2.57 g (64.3 mmole) of sodium hydroxide were added to the resulting solution. The mixture was then stirred at room temperature for 3 hours. At the end of this time, the solvent was removed by distillation under reduced pressure. A 10% w/v aqueous solution of sodium hydroxide was added to the residue, which was then washed with methylene chloride. The aqueous layer was adjusted with concentrated hydrochloric acid to a pH value of 1, and the resulting precipitate was collected by filtration. The precipitate was dried, to give 3.60 g (82%) of the dicarboxylic acid as white crystals. 2.00 g (5.84 mmole) of these were decarboxylated by heating for 1 hour at 200° C., to give 1.65 g (95%) of the title compound as white crystals.

Mass Spectrum m/e: 298 (M+).

PREPARATION 17

Cyclostatin-(2-morpholinoethyl)amide dihydrochloride

17(a)
N-(t-Butoxycarbonyl)-cyclostatin-(2-morpholinoethyl)amide 3.16 g of N-t-butoxycarbonylcyclostatine, 1.43 g of 2-morpholinoethylamine and 2.1 ml of triethylamine were added to 30 ml of anhydrous tetrahydrofuran. 2 g of diethyl cyanophosphonate (90%) were added dropwise to the mixture, whilst ice-cooling. The mixture was stirred for 4 hours, after which it was allowed to stand overnight. The reaction mixture was then concentrated by evaporation under reduced pressure, after which water was added, and the mixture was extracted with ethyl acetate. The organic layer was washed with a saturated aqueous solution of sodium bicarbonate and with a saturated aqueous solution of sodium chloride. It was then dried over anhydrous magnesium sulfate, and the solvent was removed by evaporation under reduced pressure. The residue was purified by column chromatography through silica gel (eluent: first, methylene chloride and then a 1:9 by volume mixture of methanol and methylene chloride), to afford 3.4 g of the title compound as a colorless amorphous substance.

17(b) Cyclostatin-(2-morpholinoethyl)amide dihydrochloride 3.4 g of N-t-butoxycarbonyl-cyclostatin-2-morpholinoethylamide were added to 30 ml of methanol and 30 ml of a 1N solution of hydrogen chloride in dioxane. The mixture was stirred at room temperature for 1 hour, after which it was concentrated by evaporation under reduced pressure. The residue was washed with diethyl ether, to give 3.7 g of the title compound as colorless fine crystals melting at 70°–80° C.

PREPARATION 18

(2R)-3-(2,6-Dimethylmorpholinocarbonyl)-2-(1-naphthylmethyl)proionic acid

18(a)
(4S)-4-Benzyl-3-[(2R)-3-(2,6-dimethylmorpholinocarbonyl)-2-(1-naphthylmethyl)propionyl]-2-oxazolidinone Following a procedure similar to that described in Preparation 3, 340 mg (0.67 mmole) of N-[(2-benzyloxycarbonyl)methyl-3-(1-naphthyl)propionyl]-(S)-(-)-4-benzyl-2-oxazolidinone (prepared as described in Preparation 2) were reacted with 80 mg (0.67 mmole) of 2,6-dimethylmorpholine to give 260 mg of the title compound as a white powder.

18(b)
(2R)-3-(2,6-Dimethylmorpholinocarbonyl)-2-(1-naphthylmethyl)propionic acid Following a procedure similar to that described in Preparation 4, 97 mg of the hemihydrate of the title compound were prepared as a white powder from 0.24 g (0.47 mmole) of (4S)-4-benzyl-3-[(2R)-3-(2,6-dimethylmorpholinocarbonyl)-2-(1-naphthylmethyl)propionyl]-2-oxazolidinone [prepared as described in Preparation 18(a)].

Mass Spectrum m/e: 355 (M+).

Elemental analysis: Calculated for $C_{21}H_{25}NO_4 \cdot \frac{1}{2} H_2O$: C, 69.21%; H, 7.19%; N, 3.84%. Found: C, 68.98%; H, 7.14%; N, 4.09%.

PREPARATION 19

(2R)-3-(1-Naphthyl)-2-thiomorpholinocarbonylmethylpropionic acid

19(a)
(4S)-4-Benzyl-3-[(2R)-3-(1-naphthyl)-2-thiomorpholinocarbonylmethylpropionyl]-2-oxazolidinone Following a procedure similar to that described in Preparation 3, 340 mg (0.67 mmole) of N-[(2-benzyloxycarbonyl)methyl-3-(1-naphthyl)propionyl]-(S)-(-)-4-benzyl-2-oxazolidinone (prepared as described in Preparation 2) were reacted with 70 mg (0.67 mmole) of thiomorpholine to give 220mg of the title compound as white powder.

19(b)
(2R)-3-(1-Naphthyl)-2-thiomorpholinocarbonylmethylpropionic acid Following a procedure similar to that described in Preparation 4, 84 mg of the hemihydrate of the title compound were prepared as a white powder from 0.20 g (0.4 mmole) of (4S)-4-benzyl-3-[(2R)-3-(1-naphthyl)-2-thiomorpholinocarbonylmethylpropionyl]-2-oxazolidinone [prepared as described in Preparation 19(a)].

Mass Spectrum m/e: 343 (M+).

Elemental analysis: Calculated for $C_{19}H_{21}NO_3S \cdot \frac{1}{2} H_2O$: C, 64.75%; H, 6.29%; N, 3.97%; S, 9.10%. Found: C, 65.05%; H, 6.34%; N, 4.21%; S, 8.80%.

PREPARATION 20

(2R)-2-(1-Naphthylmethyl)-3-(t-pyrrolidinylcarbonyl)-propionic acid

20 (a)

(4S)-4-Benzyl-3-[(2R)-2-(1-naphthylmethyl)-3-(1-pyrrolidinylcarbonyl) propionyl]-2-oxazolidinone Following a procedure similar to that described in Preparation 3, 305 mg (0.6 mmole) of N-[(2-benzyloxycarbonyl)methyl-3-(1-naphthyl)propionyl]-(S)-(-)-4-benzyl-2-oxazolidinone (prepared as described in Preparation 2) were reacted with 43 mg (0.6 mmole) of pyrrolidine to give 240 mg of the hemihydrate of the title compound as a colorless amorphous substance.

Elemental analysis: Calculated for $C_{29}H_{30}N_2O_4 \cdot \frac{1}{2} H_2O$: C, 72.63%; H, 6.52%; N, 5.84%. Found: C, 72.68%; H, 6.32%; N, 5.81%. Mass Spectrum w/e: 470 (M+).

20(2R)-2,(1-naphthylmethyl)-3-(1-pyrrolidinylcarbonyl)propionic acid

Following a procedure similar to that described in Preparation 4, 83 mg of the title compound were prepared as a colorless amorphous substance from 220 mg (0.47 mmole) of (4S)-4-benzyl-3-[(2R)-2-(1-naphthylmethyl)- 3-(1-pyrrolidinylcarbonyl)propionyl]-2-oxazolidinone [prepared as described in Preparation 20(a)].

Mass Spectrum m/e: 311 (M+).

PREPARATION 21

(2R)-3-(1-Naphthyl)-2-piperidinocarbonylmethylpropionic acid

21(a)

(4S)-4-Benzyl-3-[(2R)-3-(1-naphthyl)-2-piperidinocarbonylmethylpropionyl]-2-oxazolidinone Following a procedure similar to that described in Preparation 3,610 mg (1.2 mmole ) of N-[(2-benzyloxycarbonyl)methyl-3-(1-naphthyl)propionyl]-(S)-(-)-4-benzyl-2-oxazolidinone (prepared as described in Preparation 2) were reacted with 250 mg (1.4 mmole) of piperidine to give 530 mg of the title compound as a white powder.

21(b)

(2R)-3-(1-Naphthyl)-2-piperidinocarbonylmethylpropionic acid

Following a procedure similar to that described in Preparation 4, 180 mg of the hemihydrate of the title compound were prepared as a white powder from 0.50 g (1.03 mmole) of (4S)-4- benzyl-3-[(2R)-3-(1-naphthyl)-2-piperidinocarbonylmethylpropionyl]-2-oxazolidinone [prepared as described in Preparation 21(a)].

Mass Spectrum m/e: 325 (M+).

Elemental analysis: Calculated for $C_{20}H_{23}NO_3 \cdot \frac{1}{2} H_2O$: C, 71.83%; H, 7.23%; N, 4.19%. Found: C, 71.60%; H, 6.96%; N, 4.20%.

PREPARATION 22

(2R)-3-(1-Naphthyl)-2-[(propylcarbamoyl)methyl]propionic acid

22(a)

(4S)-4-Benzyl-3-[(2R)-3-(1-naphthyl)-2-[(propylcarbamoyl)methyl]propionyl]-2-oxazolidione Following a procedure similar to that described in Preparation 3, 610 mg (1.2 mmole) of N-[(2-benzyloxycarbonyl)methyl-3-(1-naphthyl)propionyl]-(S)-(-)-4-benzyl-2-oxazolidinone (prepared as described in Preparation 2) were reacted with 83 mg (1.4 mmole) of propylamine to give 210 mg of the title compound as a white powder.

22(b)

(2R)-3-(1-Naphthyl)-2-[(propylcarbamoyl)methyl]propionic acid

Following a procedure similar to that described in Preparation 4, 100 mg of 0.25-hydrate of the the title compound were prepared as a white powder from 0.17 g (0.37 mmole) of (4S)-4-benzyl-3-[(2R)-3-(1-naphthyl)-2-[(propylcarbamoyl)methyl]propionyl]-2-oxazolidinone [prepared as described in Preparation 22(a)].

Mass Spectrum m/e: 299 (M+).

Elemental analysis: Calculated for $C_{18}H_{21}NO3 \cdot \frac{1}{4} H_2O$: C, 71.14%: H, 7.13%; N, 4.6%. Found: C, 70.98%; H, 7.13%; N, 4.59%.

PREPARATION 23

(2R)-3-(1-Naphthyl)-2-[(phenethylcarbamoyl)methyl]-propionic acid

23(a)

(4S)-4-Benzyl-3-[(2R)-3-(1-naphthyl)-2-[(phenethylcarbamoyl)methyl]propionyl]-2-oxazolidinone Following a procedure similar to that described in Preparation 3, 350 mg (0.84 mmole) of N-[(2-benzyloxycarbonyl)methyl-3-(1-naphthyl)propionyl]-(S)-(-)-4-benzyl-2-oxazolidinone (prepared as described in Preparation 2) were reacted with 125 mg (1.04 mmole) of phenethylamine to give 390 mg of the title compound as a white powder.

23(b)

(2R)-3-(1-Naphthyl)-2-[(phenethylcarbamoyl)methyl]-propionic acid

Following a procedure similar to that described in Preparation 4, 230 mg of the title compound were prepared as a white powder from 340 mg (0.65 mmole) of (4S)-4-benzyl-3-[(2R)-3-(1-naphthyl)-2-[(phenethylcarbamoyl)methyl]propionyl]-2-oxazolidinone [prepared as described in Preparation 23(a)].

Mass Spectrum m/e: 361 (M+).

PREPARATION 24

(2R)-3-(4-Methyl-1-piperazinylcarbonyl)-2-(1-naphthylmethyl)propionic acid

24(a)

(4S)-4-Benzyl-3-[(2R)-3-(4-methyl-1-piperazinylcarbonyl)-2-(1-naphthylmethyl)-propionyl]-2-oxazolidinone Following a procedure similar to that described in Preparation 3, 610 mg (1.2 mmole) of N-[(2-benzyloxycarbonyl)methyl-3-(1-naphthyl)propionyl]-(S)-(-)-4-benzyl-2-oxazolidinone (prepared as described in Preparation 2) were reacted with 120 mg (1.2 mmole) of N-methylpiperazine to give 540 mg of the hemihydrate of the title compound as a colorless amorphous substance.

Elemental analysis: Calculated for $C_{30}H_{33}N_3O_4 \cdot \frac{1}{2} H_2O$: C, 70,84%; H, 6,74%; N, 8,26%. Found: C, 70,62%; H, 6,44%; N, 8.11%.

24(b)
(2R)-3-(4-Methyl-1-piperazinylcarbonyl)-2-(1-naphthylmethyl)propionic acid Following a procedure similar to that described in Preparation 4, 115 mg of the title compound were prepared as a colorless oil from 480 mg (0.96 mmole) of (4S)-4-benzyl-3-[(2R)-3-(4-methyl-1-piperazinylcarbonyl)-2-(1-naphthylmethyl)-propionyl]-2-oxazolidinone [prepared as described in Preparation 24(a)].

PREPARATION 25
(2R)-3-(1-Naphthyl)-2-[(4-phenyl-1-piperazinyl)carbonylmethyl]propionic acid

25(a) (4B)-4-Benzyl-3-[(2R)-3-(1-naphthyl)-2-8 (4-phenyl-1-piperazinyl)carbonylmethyl]propionyl]-2-oxazolidinone Following a procedure similar to that described in Preparation 3, 230 mg of the title compound were prepared as a white powder from 340 mg (0.67 mmole) of N-[2-benzyloxycarbonyl)methyl-3-(1-naphthyl)propionyl]-(S)-(-)-4-benzyl-2-oxazolidinone (prepared as described in Preparation 2).

25(b)
(2R)-3-(1-Naphthyl)-2-[(4-phenyl-1-piperazinyl)carbonylmethyl]propionic acid Following a procedure similar to that described in Preparation 4, 103 mg of the hemihydrate of the title compound were prepared as a white powder from 0.21 g (0.37 mmole) of (4S)-4-benzyl-3-[(2R)-3-(1-naphthyl)-2-[(4-phenyl-1-piperazinyl)carbonylmethyl]propionyl]-2-oxazolidinone [prepared as described in Preparation 25(a)].

Mass Spectrum m/e: 402 (M+).

Elemental analysis: Calculated for $C_{25}H_{26}N_2O_3 \cdot \frac{1}{2}H_2O$: C, 72.97%; H, 6.61%; N, 6.81%. Found: C, 72.68%; H, 6.62%: N, 6.67%.

PREPARATION 26
(2R)-3-(N,N-Diethylcarbamoyl)-2-(1-naphthylmethyl)propionic acid

26(a)
(4S)-4-Benzyl-3-[(2R)-3-(N,N-diethylcarbamoyl)-2-(1-naphthylmethyl)propionyl]-2-oxazolidinone Following a procedure similar to that described in Preparation 3, 305 mg (0.6 mmole) of N-[(2-benzyloxycarbonyl)methyl-3-(1-naphthyl)propionyl]-(S)-(-)-4-benzyl-2-oxazolidinone (prepared as described in Preparation 2) were reacted with 44 mg (0.6 mmole) of diethylamine to give 250 mg of the 0.25-hydrate of the title compound as a colorless amorphous substance.

Elemental analysis: Calculated for $C_{29}H_{23}N_2O_4 \cdot \frac{1}{4} H_2O$: C, 73.01%; H, 6.87%; N, 5.87%. Found: C, 73.08%; H, 6.85%; N, 5.64%. Mass Spectrum m/e: 472 (M+).

26(b)
(2R)-3-(N,N-Diethylcarbamoyl)-2-(1-naphthylmethyl)propionic acid

Following a procedure similar to that described in Preparation 4, 100 mg of the title compound were prepared as a colorless amorphous substance from 230 mg (0.49 mmole) of (4S)-4-benzyl-3-[(2R)-3-(N,N-diethylcarbamoyl)-2-(1-naphthylmethyl)propionyl]-2-oxazolidinone [prepared as described in Preparation 26(a)].

Mass Spectrum m/e: 313 (M+).

PREPARATION 27
(2R)-3-(Benzylcarbamoyl)-2-(1-naphthylmethyl)propionic acid

27(a)
(4S)-4-Benzyl-3-[(2R)-3-(benzylcarbamoyl)-2-(1-naphthymethyl)propionyl]-2-oxazolidinone Following a procedure similar to that described in Preparation 3, 610 mg (1.2 mmole) of N-[(2-benzyloxycarbonyl)methyl-3-(1-naphthyl)propionyl]-(S)-(-)-4-benzyl-2-oxazolidinone (prepared as described in Preparation 2) were reacted with 130 mg (1.2 mmole) of benzylamine to give 530 mg of the title compound as a colorless oil.

Elemental analysis: Calculated for $C_{32}H_{30}N_2O_4$: C, 75.87%; H, 5.97%; N, 5.53%. Found: C, 75.72%; H, 6.07%; N, 5.66%.

$[\alpha]_D^{25} = +152.7$ (c=1.5, methanol).

27(b)
(2R)-3-(Benzylcarbamoyl)-2-(1-naphthylmethyl)propionic acid

Following a procedure similar to that described in Preparation 4, 270 mg of the title compound were prepared as an amorphous substance from 450 mg (0.92 mmole) of (4S)-4-benzyl-3-[(2R)-3-(benzylcarbamoyl)-2-(1-naphthylmethyl)propionyl]-2-oxazolidinone [prepared as described in Preparation 27(a)].

Elemental analysis: Calculated for $C_{22}H_{21}NO_3 \cdot \frac{1}{4} H_2O$: C, 75.09%; H, 6.16%; N, 3.98%. Found: C, 74.85%; H, 6.16%; N, 3.97%.

$[\alpha]_d^{25} = +30°$ (c=1, methanol)

Mass Spectrum m/e: 347 (M+).

PREPARATION 28
4-Morpholinocarbonyl-2-(1-naphthylmethyl)butyric acid 8.17 g (0.19 mole) of sodium hydride (as a 55% w/w dispersion in mineral oil) were added, whilst ice-cooling, to a solution of 25 g (0.16 mole) of dimethyl glutarate and 23.4 g (0.16 mole) of 1-naphthaldehyde dissolved in 200 ml of anhydrous methanol. The mixture was heated under reflux for 30 minutes, after which 190 ml (0.19 mole) of a 1N aqueous solution of sodium hydroxide were added to it, and the mixture was again heated under reflux for 1 hour. The solvent was removed by distillation under reduced pressure, and the resulting residue was mixed with water and washed with diethyl ether. The aqueous layer was acidified and then extracted with diethyl ether. The ethereal layer was washed with a saturated aqueous solution of sodium chloride and dried over anhydrous magnesium sulfate. The solvent was removed by distillation under reduced pressure, and then diisopropyl ether was added to the residue to precipitate crystals, which were collected by filtration to give 18.5 g of 2-(1-naphthylmethylene)glutaric acid.

A mixture of 10 g (37 mmole) of the 2-(1-naphthylmethylene)glutaric acid prepared as described above and 100 ml of acetic anhydride was stirred at 60° C. for 1 hour. At the end of this time, the solvent was removed by distillation under reduced pressure, and the resulting residue was triturated with a 1: 1 by volume mixture of benzene and hexane to precipitate crystals, which were collected by filtration to give 8.1 g of 2-(1-naphthylmethylene)glutaric anhydride.

2.85 ml (33 mmole) of morpholine were added to a solution of 7.5 g (30 mmole) of the 2-(1-naphthylmethylene)glutaric anhydride prepared as described above dissolved in 70 ml of methylene chloride, and the mixture was stirred at room temperature for 4 hours. It was then washed with a 5% w/v aqueous solution of citric acid and with a saturated aqueous solution of sodium chloride and dried over anhydrous sodium sulfate. The solvent was then removed by distillation under reduced pressure, to give 10.0 g (30 mmole) of 4-morpholinocarbonyl-2-(1-naphthylmethylene)butyric acid.

5.0 g (14.8 mmole) of this 4-morpholinocarbonyl-2-(1-naphthylmethylene)butyric acid were dissolved in 50 ml of methanol and hydrogenated in hydrogen at atmospheric pressure in the presence of 1.0 g of a 10% w/w palladium-on-carbon catalyst. The catalyst was then removed by filtration, after which the solvent was removed by distillation under reduced pressure. The residue was triturated with diethyl ether to precipitate crystals, which were collected by filtration to give 4.5 g of 4-morpholinocarbonyl-2-(1-naphthylmethyl)butyric acid, melting at 130°–135° C.

Elemental analysis: Calculated for $C_{20}H_{23}NO_4$: C, 70.36%; H, 6.79%; N, 4.10%. Found: C, 70.06%; H, 6.90%; N, 3.98%.

PREPARATION 29 t-Butyl 5-(N-benzyl-N-methylamino)-4-hydroxy-2-(1-naphthylmethyl)pentanoate 2.39 g (7.65 mmole) of t-butyl 4,5-epoxy-2-(1-naphthylmethyl)pentanoate (prepared as described in Preparation 11) were reacted with 1.39 g (11.5 mmole) of N-methylbenzylamine in 20 ml of methanol for 2 days. At the end of this time, the reaction mixture was concentrated by evaporation underreduced pressure, and the residue was purified by column chromatography through silica gel (eluent: a 5: 95 by volume mixture of methanol and methylene chloride), to afford 3.13 g of the title compound as a pale brown oil.

PREPARATION 30

5-(N-Benzyl-N-methylamino)-2-(1naphthylmethyl)-4-oxopentanoic acid 5.64 g of a sulfur trioxide/pyridine complex were added to a solution of 3.13 g (7.22 mmole) of t-butyl 5-(N-benzyl-N-methylamino)-4-hydroxy-2-(1-naphthylmethyl)pentanoate (prepared as described in Preparation 29) and 5 ml of triethylamine dissolved in 20 ml of dimethyl sulfoxide at room temperature, and the mixture was stirred for 2 hours. At the end of this time, the reaction mixture was diluted with water and then extracted with ethyl acetate. The organic layer was washed with a saturated aqueous solution of sodium chloride and dried over anhydrous magnesium sulfate, after which it was concentrated by evaporation under reduced pressure. 20 ml of a 4N solution of hydrogen chloride in dioxane were added to the residue, and the mixture was stirred for 2 hours; it was then concentrated by evaporation under reduced pressure. The residue was dissolved in water, and the resulting solution was neutralized by adding a 1N aqueous solution of sodium hydroxide. It was then concentrated by evaporation under reduced pressure. The residue was dissolved in methylene chloride and the resulting insoluble materials were removed by filtration. The filtrate was concentrated by evaporation under reduced pressure to afford 1.94 g of the title compound as a colorless amorphous substance.

Silica gel thin layer chromatography, Rf value 0.55 (20% by volume methanol in methylene chloride).

PREPARATION 31

(2R)-3-(N-Cyclohexyl-N-methylcarbamoyl)-2-(1-naphthylmethyl)propionic acid

31(a)

(4S)-4-Isopropyl-3-[(2R)-3-(N-cyclohexyl-N-methylcarbamoyl)-2-(1-naphthylmethyl)propionyl]-2-oxazolidinone Following a procedure similar to that described in Preparation 3, 174 mg (0.38 mmole) of benzyl (3R)-4-(1-naphthyl)-3-[(4S)-2-oxo-4-isopropyloxazolidin-3-yl]butyrate [prepared by a procedure similar to than described in Preparation 32(a)] were reacted with 52 mg (0.46 mmole) of N-hexyl-N-methylamine to afford 170 mg of the title compound as a white powder.

31(b) {2R)-3-(N-Cyclohexyl-N-methylcarbamoyl)-2-(1-naphthylmethyl)propionic acid Following a procedure similar to that described in Preparation 4, 70 mg of the title compound were prepared as a white powder from 150 mg of (4S)-4-isopropyl-3-[(2R)-3-(N-cyclohexyl-N-methylcarbamoyl)-2-(1-naphthylmethyl)propionyl]- 2-oxazolidinone [prepared as described in Example 31(a) above].

Mass Spectrum 353 (M+).

PREPARATION 32

(2R)-3-(N-Benzyl-N-methylcarbamoyl)-2-(1-naphthylmethyl)propionic acid

32(a)

(4S)-4-Isopropyl-3-[(3-(1-naphthyl)propionyl]-2-oxazolidinone

Following a procedure similar to that described in Preparation 1, 1.9 g (14.8 mmole) of (S)-(-)-4-isopropyl-2-oxazolidinone [instead of (S)-(-)-4-benzyl-2-oxazolidinone] were reacted with 2.95 g (13.5 mmole) of 1-naphthylpropionyl chloride to afford 3.2 g of the title compound as a white powder.

32(b)

(4S)-4-Isopropyl-3-[(2R)-3-(N-benzyl-N-methylcarbamoyl)-2-(1-naphthylmethyl)propionyl]-2-oxazolidinone Following a procedure similar to that described in Preparation 2, 384 mg (1.3 mmole) of (4)-3-[3-(1-naphthyl)propionyl]-4-isopropyl-2-oxazolidinone were reacted with 613 ml (3.87 mmole) of benzyl bromoacetate, and then the mixture was worked-up according to Preparation 3 to give 297 mg of the title compound as a white powder.

32(c)

(2R)-3-(N-Benzyl-N-methylcarbamoyl)-2-(1-naphthylmethyl)propionic acid

Following a procedure similar to that described in Preparation 4, 825 mg of the title compound were prepared as a white powder from 1.42 g (3.0 mmole ) of (4S)-4-isopropyl-3-[(2R)-3-(N-benzyl-N-methylcarbamoyl)-2-(1-naphthylmethyl)propionyl]-2-oxazolidinone [prepared as described in Preparation 32(b)].

Mass Spectrum m/e: 361 (M+).

PREPARATION 33

Methyl N-(4-phenyl-1-piperazinylacetyl)-3-(1-naphthyl)-L-alanate hydrochloride 266 mg of methyl 3-(1-naphthyl)-L-alanate hydrochloride, 221 mg of (4-phenyl-1-piperazinyl)acetic acid and 0.35 ml of triethylamine were added to 5 ml of dimethylformamide, and then 200 mg of diethyl cyanophosphonate (90%) were added dropwise, whilst ice-cooling, to the mixture. The mixture was then stirred for 4 hours, after which it was allowed to stand overnight. The reaction mixture was then concentrated by evaporation under reduced pressure, and water was added to the residue, which was then extracted with ethyl acetate. The organic extract was washed with a saturated aqueous solution of sodium bicarbonate and with a saturated aqueous solution of sodium chloride, in that order, and dried over anhydrous magnesium sulfate. The solvent was then removed by distillation under reduced pressure. The residue was purified by silica gel column chromatography (eluent: a 1: 9 by volume mixture of methanol and methylene chloride), to afford 278 mg of the title compound as an oily substance.

PREPARATION 34

N-(4-Phenyl-1-piperazinylacetyl)-3-(1-naphthyl)-L-alanine 1.2 ml of a 1N aqueous solution of sodium hydroxide was added to a solution of 250 mg of methyl (4-phenyl-1-piperazinyl)acetyl-3-(1-naphthyl)-L-alanate hydrochloride (prepared as described in Preparation 33) in 8 ml of methanol, and the mixture was stirred at room temperature for 2 hours. At the end of this time, 1.2 ml of 1N aqueous hydrochloric acid was added to the reaction mixture, which was then concentrated by evaporation under reduced pressure. The residue was purified by silica gel column chromatography (eluent: a 15: 85 by volume mixture of methanol and methylene chloride), to afford 220 mg of the title compound as colorless powdery crystals, melting at 160°–180° C.

PREPARATION 35

N-Morpholinoacetyl-3-(1-naphthyl)-L-alanine 7.8 g (64.6 mmole) of diphenylphosphoryl azide and 17.9 ml (129.1 mmole) of triethylamine were added, whilst ice-cooling, to a solution of 7.8 g (53.8 mmole) of 1-morpholinoacetic acid and 15.7 g (59.2 mmole) of methyl 3-(1-naphthyl)-L-alanate hydrochloride in 80 ml of dimethylformamide, and the mixture was stirred at room temperature overnight. At the end of this time, 300 ml of a saturated aqueous solution of sodium chloride were added to the reaction mixture, which was then extracted with ethyl acetate. The extract was then washed with a 5% w/v aqueous solution of citric acid, with a 5% w/v aqueous solution of sodium bicarbonate and with a saturated aqueous solution of sodium chloride, in that order, and dried over anhydrous sodium sulfate. The solvent was then removed by distillation under reduced pressure. The residue was purified by silica gel column chromatography (eluent: mixtures of methylene chloride and methanol in the proportions by volume 70: 1 and 30: 1), to afford 9.8 g of methyl N-morpholinoacetyl-3-(1-naphthyl)-L-alanate as an oily substance.

19.6 ml (19.6 mmole) of a 1N aqueous solution of sodium hydroxide were then added to a solution of 7.0 g (19.6 mmole) of this methyl N-morpholinoacetyl-3-(1-naphthyl)-L-alanate in 50 ml of methanol, and the mixture was stirred at room temperature for 1 hour. At the end of this time, 4.9 ml (19.6 mmole) of a 4N solution of hydrogen chloride in dioxane was added to the reaction mixture, and the mixture was extracted with methylene chloride. The organic extract was washed with a saturated aqueous solution of sodium chloride and dried over anhydrous sodium sulfate. The solvent was then removed by evaporation under reduced pressure, and the residue was crystallized by the addition of diethyl ether, to give 6.25 g of the title compound, melting at 100°–103° C.

PREPARATION 36

N-(t-Butoxycarbonyl)-cyclostatin-(2-pyrrolidylethyl)amide 202 mg (2.0 mmole) of triethylamine were added dropwise, whilst ice-cooling, to a solution of 250 mg (0.79 mmole) of N-(t-butoxycarbonyl)-cyclostatin, 109 mg (0.96 mmole) of 1-(2-aminoethyl)pyrrolidine and 194 mg (1.2 mmole) of diethyl cyanophosphonate (95%) in 5 ml of methylene chloride, and the mixture was stirred for 3 hours. At the end of this time, ethyl acetate was added to the reaction mixture, and the mixture was washed with a 10% w/v aqueous solution of sodium bicarbonate and dried over anhydrous sodium sulfate. It was then evaporated to dryness under reduced pressure, to give 325 mg of the title compound.

PREPARATION 37

N-[N-(t-Butoxycarbonyl)-3-(1naphthyl)-L-alanyl]-3-(4-thiazolyl)-DL-alanine 8.51 g (33 mmole) of methyl 3-(4-thiazolyl)alanate, 7.35 g (45 mmole) of diethyl cyanophosphonate (95%) and 7.5 g (74 mmole) of triethylamine were added, whilst ice-cooling and stirring, to a solution of 9.45 g (30 mmole) of N-(t-butoxycarbonyl)-3-(1-naphthyl)-L-alanine in 80 ml of methylene chloride, and the mixture was stirred at room temperature for 16 hours. At the end of this time, the reaction mixture was washed with a 10% w/v aqueous solution of citric acid and with a 5% w/v aqueous solution of sodium bicarbonate, in that order, after which it was evaporated to dryness under reduced pressure to give a powdery substance. The substance thus obtained was dissolved in 50 ml of 90% v/v aqueous methanol, and 25 ml of 1N sodium hydroxide solution was added to the resulting solution, whilst stirring. The mixture was then allowed to react at room temperature for 3 hours. At the end of this time, the reaction mixture was concentrated by evaporation under reduced pressure. 25 ml of 1N aqueous hydrochloric acid was added to the resulting residue, and the mixture was extracted with ethyl acetate. The extract was washed with water and dried over anhydrous sodium sulfate, after which the solvent was removed by evaporation to dryness under reduced pressure, to give 5.7 g of the title compound.

PREPARATION 38

N-[N-(t-Butoxycarbonyl)-L-leucyl]-cyclostatin-[3-(2-oxo-1-pyrrolidinyl)propyl]amide 1.37 g (5.5 mmole) of N-(t-butoxycarbonyl)-L-leucine hydrate was dehydrated by repeating 2-3 times the steps of dissolution in methanol followed by azeotropic distillation. Meanwhile, the t-butoxycarbonyl group was removed from 2.20 g (5 mmole) of N-(t-butoxycarbonyl)cyclostatin-[3-(2-oxo-1-pyrrolidinyl)propyl]amide by treatment with a 4N solution of hydrogen chloride in dioxane. The two compounds thus obtained were dissolved together in 25 ml of methylene chloride, and then 1.03 g (6 mmole) of diethyl cyanophosphonate (95%) and 2.02 g (20 mmole) of triethylamine were added to the resulting solution, and the mixture was stirred, whilst ice-cooling for 1 hour; this stirring was continued at room temperature for 3 days. At the end of this time, the reaction mixture was concentrated by evaporation under reduced pressure, and the residue was extracted with ethyl acetate. The extract was washed with a 10% w/v aqueous solution of citric acid, with water and with a saturated aqueous solution of sodium chloride, in that order, after which it was dried over anhydrous magnesium sulfate, and the solvent was removed by distillation under reduced pressure. The residue was dissolved in methylene chloride, insoluble materials were removed by filtration, and the filtrate was concentrated by evaporation under reduced pressure. The residue was triturated with diethyl ether, to afford 12.25 g of the 0.25-hydrate of the title compound, melting at 170°–173° C.

Elemental analysis: Calculated for $C_{29}H_{52}N_4O_6 \cdot \frac{1}{4}H_2O$: C, 62.50%; H, 9.50%; N, 10.06%. Found: C, 62.40%; H, 9.46%; N, 10.04%.

PREPARATION 39

N-[$N^\alpha$-(t-Butoxycarbonyl)-L-tryptophyl]-cyclostatin-3-(2-oxo-1-pyrrolidinyl)propylamide 2 grams (4.55 mmole) of N-(t-butoxycarbonyl)cyclostatin-3-(2-oxo-1-pyrrolidinyl)propylamide (prepared by a procedure similar to that described in Preparation 36) were treated with 20 ml of a 4N solution of hydrogen chloride in dioxane to remove the t-butoxycarbonyl group, and the reaction mixture was then concentrated by evaporation under reduced pressure. 20 ml of benzene were added to the residue, and the mixture was concentrated by evaporation under reduced pressure. This operation was repeated 2-3 times to thoroughly remove any remaining water. The compound thus obtained, together with 1.52 g (4.99 mmole) of N-(t-butoxycarbonyl)-L-tryptophan, was suspended in 20 ml of methylene chloride. 1.11 g (6.8 mmole) of diethyl cyanophosphonate (95%) and 0.92 g (9.1 mmole) of triethylamine were then added to the resulting suspension, whilst ice-cooling and stirring, and the mixture was stirred at room temperature overnight. The reaction mixture was then concentrated by evaporation under reduced pressure, and the residue, after the addition of ice-water, was extracted with ethyl acetate. The extract was washed with a 10% w/v aqueous solution of citric acid, with a 10% w/v aqueous solution of sodium bicarbonate and with a saturated aqueous solution of sodium chloride, in that order, after which it was dried over anhydrous sodium sulfate, and concentrated by evaporation under reduced pressure. The residue was purified by silica gel thin layer chromatography (developing solvent: a 1: 10 by volume mixture of methanol and chloroform), and the product was reprecipitated with a mixture of methylene chloride and hexane, to afford 2.8 g (96%) of the title compound as a pale yellow powder.

PREPARATION 40

N-(N-Benzyl-N-methylaminoacetyl)-3-(1-naphthyl)-L-alanine

40(a) Methyl N-(N-benzyl-N-methylaminoacetyl)-3-(1-naphthyl)-L-alanate 53 mg (0.5 mmole) of sodium carbonate were added to a solution of 350 mg (1.0 mmole) of methyl N-bromoacetyl-3-(1-naphthyl)-L-alanate and 121 mg (1.0 mmole) of N-benzyl-N-methylamine in 15 ml of dimethylformamide, and the mixture was stirred at room temperature for 10 hours. At the end of this time, the solvent was removed by distillation under reduced pressure, and the residue, after the addition of a small amount of water, was extracted with ethyl acetate. The extract was dried over anhydrous sodium sulfate and concentrated by evaporation under reduced pressure, and the residue was purified by silica gel column chromatography (eluent: a 10: 1 by volume mixture of chloroform and methanol), to afford 280 mg of the title compound as an oily substance.

40(b) N-(Benzyl-N-methylaminoacetyl)-3-(1-naphthyl)-L-alanine 1.92 ml (1.92 mmole) of a 1N aqueous solution of sodium hydroxide was added to a solution of 250 mg (0.64 mmole) of methyl N-(N-benzyl-N-methylaminoacetyl)-3-(1-naphthyl)-L-alanate [prepared as described in step (a) above] in 2 ml of methanol, and the mixture was stirred at room temperature for 4 hours. At the end of this time, the reaction mixture was neutralized by addition of 1.92 mg (1.92 mmole) of 1N aqueous hydrochloric acid, and the methanol was removed by evaporation under reduced pressure. The residue was extracted with ethyl acetate, the extract was dried, and the solvent was removed by distillation under reduced pressure. The residue was purified by silica gel column chromatography (eluent: a 5: 1 by volume mixture of chloroform and methanol), to afford 171 mg of the title compound as white crystals, melting at 104°–107° C.

PREPARATION 41

N-(N-Benzyl-N-ethylaminoacetyl)-3-(1-naphthyl)-L-alanine

Following a procedure similar to that described in Preparation 40(a), 350 mg (1.0 mmole) of methyl N-bromoacetyl-3-(1-naphthyl)-L-alanate and 161 mg (1.2 mmole) of N-benzyl-N-ethylamine were reacted together, and the ester thus obtained (370 mg; 0.92 mmole) was dissolved in 3 ml of methanol. 2.76 ml (2.76 mmole) of a 1N aqueous solution of sodium hydroxide were then added to the resulting solution, and the reaction was allowed to proceed at room temperature for 4 hours. At the end of this time, 2.76 ml (2.76 mmole) of 1N aqueous hydrochloric acid was added to the reaction mixture, and the reaction mixture was then evaporated to dryness under reduced pressure. After the resulting residue had been thoroughly dried, 518 mg of the title compound containing sodium chloride were obtained as a white powder.

PREPARATION 42

N-(N-Benzyl-N-isopropylaminoacetyl)-3-(1-naphthyl)-L-alanine

Following a procedure similar to that described in Preparation 40(a), 350 mg (1.0 mmole) of methyl N-bromoacetyl-3-(1-naphthyl)-L-alanate and 179 mg (1.2 mmole) of N-benzyl-N-isopropylamine were reacted together, and the ester thus obtained (314 mg; 0.75 mmole) was dissolved in 5 ml of methanol. 2.25 ml (2.25 mmole) of a 1N aqueous solution of sodium hydroxide were then added to the resulting solution, and the reaction was allowed to proceed at room temperature for 4 hours. At the end of this time, the reaction mixture was neutralized by the addition of 2.25 ml (2.25 mmole) of 1N aqueous hydrochloric acid, and evaporated to dryness under reduced pressure. After the resulting residue had been thoroughly dried, 434.9 mg of the title compound containing sodium chloride were obtained as a white powder.

PREPARATION 43

N-(N-Butyl-N-methylaminoacetyl)-3-(1-naphthyl)-L-alanine

Following a procedure similar to that described in Preparation 40(a), 350 mg (1.0 mmole) of methyl N-bromoacetyl-3-(1-naphthyl)-L-alanate and 105 mg (1.2 mmole) of N-butyl-N-methylamine were reacted together, and the ester thus obtained (300 mg; 0.84 mmole) was dissolved in 3.0 ml of methanol. 3.0 ml (3.0 mmole) of a 1N aqueous solution of sodium hydroxide were then added to the resulting solution, and the reaction was allowed to proceed at room temperature for 4 hours. At the end of this time, the reaction mixture was neutralized by the addition of 3.0 ml (3.0 mmole) of 1N aqueous hydrochloric acid, and evaporated to dryness under reduced pressure. After the resulting residue had been thoroughly dried, 433 mg of the title compound containing sodium chloride were obtained as a white powder.

PREPARATION 44

N-(N-Benzyl-1-piperazinylacetyl)-3-(1-naphthyl)-L-alanine

A solution of 350 mg (1 mmole) of methyl N-bromoacetyl-(1-naphthyl)-L-alanate [prepared as described in Example 51(a)] and 194 mg (1.1 mmole) of N-benzylpiperazine in 20 ml of dimethylformamide was stirred at room temperature for 1 day. At the end of this time, the reaction mixture was concentrated by evaporation under reduced pressure, and the residue was extracted with ethyl acetate. The extract was washed with a saturated aqueous solution of sodium chloride and dried over anhydrous magnesium sulfate, after which the solvent was removed by distillation under reduced pressure. The residue was purified by silica gel thin layer chromatography (developing solvent: a 20: 1 by volume mixture of methylene chloride and methanol), to afford 440 mg (0.99 mmole) of methyl N-(N-benzyl-1-piperazinylacetyl)-3-(1-naphthyl)-L-alanate.

3 ml of a 1N aqueous solution of sodium hydroxide were then added to a solution of this methyl N-(N-benzyl-1-piperazinylacetyl)-3-(1-naphthyl)-L-alanate in 3 ml of methanol, and the mixture was allowed to react at room temperature for 2.5 hours. At the end of this time, the reaction mixture was neutralized by the addition of 3 ml of 1N aqueous hydrochloric acid, after which it was concentrated by evaporation under reduced pressure. Ethanol was added to the residue, and the mixture was again concentrated by evaporation under reduced pressure. This operation was repeated 2-3 times to remove thoroughly any remaining water, and thereby to afford 590 mg of the title compound containing sodium chloride as a white powder.

PREPARATION 45

N-(N-Methyl-N-phenylaminoacetyl)-3-(1-naphthyl)-L-alanine

A solution of 1.75 g (5 mmole) of methyl N-bromoacetyl-3-(1-naphthyl)-L-alanate [prepared as described in Example 51(a)] and 5.36 g (50 mmole) of N-methylaniline in dimethylformamide was stirred at room temperature for 40 hours; the stirring was then continued at 50° C. for a further 9 hours. At the end of this time, the reaction mixture was concentrated by evaporation under reduced pressure, and the residue was extracted with ethyl acetate. The extract was washed with a 2% w/v aqueous solution of citric acid (3 times), with water, with a 5% w/v aqueous solution of sodium bicarbonate and with a saturated aqueous solution of sodium chloride, in that order. It was then dried over anhydrous magnesium sulfate, and the solvent was removed by distillation under reduced pressure. The residue was purified by silica gel thin layer chromatography (developing solvent: a 2: 1 by volume mixture of hexane and ethyl acetate), to afford 0.44 g (1.17 mmole) of methyl N-(N-methyl-N-phenylaminoacetyl)-3-(1-naphthyl)-L-alanate as an oily substance.

A solution of this methyl N-(N-methyl-N-phenylaminoacetyl)-3-(1-naphthyl)-L-alanate in 12 ml of a 1N solution of sodium hydroxide in 90% v/v aqueous methanol was stirred at room temperature for 3 hours. At the end of this time, the reaction mixture was neutralized by the addition of 12 ml of 1N aqueous hydrochloric acid, the sodium chloride produced was removed by filtration, the filtrate was concentrated by evaporation under reduced pressure, and the residue was triturated with diethyl ether, to afford 472 mg of the title compound as a white powder.

PREPARATION 46

N-(N-Cyclohexyl-N-methylaminoacetyl)-3-(1-naphthyl)-L-alanine

A solution of 5 g (14.3 mmole) of methyl N-bromoacetyl-3-(1-naphthyl)-L-alanate [prepared as described in Example 51(a)] and 6.5 g (57.5 mmole) of N-cyclohexyl-N-methylamine in 50 ml of dimethylformamide was stirred at 50° C. for 3 hours. At the end of this time, the reaction mixture was concentrated by evaporation under reduced pressure, and the residue was extracted with ethyl acetate. The extract was washed with a 2% w/v aqueous solution of citric acid (3 times), with water, with a 5% w/v aqueous solution of sodium bicarbonate and with a saturated aqueous solution of sodium chloride, in that order, after which it was dried over anhydrous magnesium sulfate, and the solvent was removed by distillation under reduced pressure. The residue was dissolved in 30 ml of a 1N solution of sodium hydroxide in 90% v/v aqueous methanol, and the solution was stirred at room temperature for 3 hours. At the end of this time, the reaction mixture was neutralized by the addition of 30 ml of 1N aqueous hydrochloric acid and concentrated by evaporation under reduced pressure. The mixture was then diluted with methanol, the sodium chloride produced was removed by filtration, the filtrate was again concentrated by evaporation under reduced pressure, and the residue was triturated with hexane, to afford 5.5 g of the title compound as a white powder, melting at 72°–77° C.

PREPARATION 47

N-(N,N-Dicyclohexylaminoacetyl)-3-(1-naphthyl)-L-alanine

47(a) Methyl N,N-dicyclohexylglycinate 3.06 g (20 mmole) of methyl bromoacetate were added, whilst ice-cooling, to a solution of 7.25 g (40 mmole) of N,N-dicyclohexylamine in 50 ml of dry benzene, and the mixture was heated under reflux for 9 hours. At the end of this time, the reaction mixture was cooled, the precipitated materials were removed by filtration, and the filtrate was concentrated by evaporation under reduced pressure, to afford 5.07 g of the title compound as an oily substance.

47(b) Methyl N-(N,N-dicyclohexylaminoacetyl)-3-(1-naphthyl)-L-alanate 8 ml (8 mmole) of a 1N aqueous solution of sodium hydroxide solution were added to a solution of 1.01 g (4 mmole) of methyl N,N-dicyclohexylglycinate [prepared as described in step (a) above] in 8 ml of methanol, and the mixture was stirred at room temperature for 4 hours. At the end of this time, 12 ml (12 mmole) of 1N aqueous hydrochloric acid were added to the reaction mixture, and the mixture was concentrated by evaporation under reduced pressure. Benzene was then added to the residue, and the solvent was removed by distillation under reduced pressure; this operation was repeated twice to remove any remaining water. The product thus prepared, together with 530 mg (2 mmole) of methyl 3-(1-naphthyl)-L-alanate, was dissolved in 10 ml of dimethylformamide, and 1.62 g (16 mmole) of triethylamine and 0.33 g (2 mmole) of diethyl cyanophosphonate (95%) were added to the resulting solution, whilst ice-cooling. The mixture was then stirred at room temperature for 4 hours and allowed to stand overnight. The solvent was then removed by distillation under reduced pressure, and the residue was purified by silica gel thin layer chromatography (developing solvent: methylene chloride), to afford 440 mg of the title compound as an oily substance.

Mass Spectrum m/e: 450 (M+).

Elemental analysis: Calculated for $C_{28}H_{38}N_2O_3$ C, 74.63%; H, 8.50%; N, 6.22%. Found: C, 74.71%; H, 8.80%; N, 6.09%.

47(c) N-(N,N-Dicyclohexylaminoacetyl)-3-(1-naphthyl)-L-alanine 160 mg (0.35 mmole) of the methyl N-(N,N-dicyclohexylaminoacetyl)-3-(1-naphthyl)-L-alanate [prepared as described in step (b) above] were reacted according to the method described in Preparation 40(b), to give 152 mg of the title compound as a white powder.

PREPARATION 48

N-(N N-Diisobutylaminoacetyl)-3-(1-naphthyl)-L-alanine

48(a) Methyl N,N-diisobutylglycinate

Following a procedure similar to that described in Preparation 47(a) 5.17 g (40 mmole) of N,N-diisobutylamine and 3.06 g (20 mmole) of methyl bromoacetate were reacted together, to give 4.02 g of the title compound as a white powder.

48(b) Methyl N-(N,N-diisobutylaminoacetyl),3-(1-naphthyl)-L-alanate 805 mg (4 mmole) of methyl N,N-diisobutylglycinate [prepared as described in step (a) above] and 530 mg (2 mmole) of methyl 3-(1-naphthyl)-L-alanate were reacted together according to the method described in Preparation 47(b), to give 640 mg of the title compound as an oily substance.

Mass Spectrum m/e: 398 (M+).

Elemental analysis: Calculated for $C_{24}H_{34}N_2O_3$ C, 72.33%; H, 8.60%; N, 7.03%. Found: C, 72.07%; H, 8.57%; N, 7.15%.

48(c) N-(N,N-Diisobutylaminoacetyl)-3-(1-naphthyl)-L-alanine 140 mg (0.35 mmole) of methyl N-(N,N-diisobutylaminoacetyl)-3-(1-naphthyl)-L-alanate [prepared as described in step (b) above] were reacted according to the method described in Preparation 40(b), to give 115 mg of the title compound as a white powder.

PREPARATION 49

N-[4-(2-Methoxyphenyl)-1-piperazinylacetyl]-3-(1-naphthyl)-L-alanine

49(a) Methyl N-[4-(2-methoxyphenyl)-1-piperazinylacetyl]-3-(1-naphthyl)-L-alanate 63.6 mg (0.6 mmole) of sodium carbonate and 230 mg (1 mmole) of 1-(2-methoxyphenyl)piperazine were added to a solution of 350 mg (1 mmole) of methyl N-bromoacetyl- 3-(1-naphthyl)-L-alanate in 10 ml of dimethylformamide, and the mixture was stirred at room temperature for 10 hours. The solvent was then removed by distillation under reduced pressure, and the residue was purified by silica gel column chromatography (eluent: a 10: 1 by volume mixture of methylene chloride and methanol), to afford 396.9 mg of the title compound as an oily substance.

49(b) N-[4-(2-Methoxyphenyl)-1-piperazinylacetyl]-3-(1-naphthyl)-L-alanine 3 ml (3 mmole) of a 1N aqueous solution of sodium hydroxide were added to a solution of 390 mg (0.845 mmole) of methyl N-[4-(2-methoxyphenyl)-1-piperazinylacetyl]-3-(1-naphthyl)-L-alanate [prepared as described in step (a) above] in 3 ml of methanol, and the mixture was stirred at room temperature for 4 hours. At the end of this time, methanol was removed by distillation under reduced pressure, and 3 ml of 1N aqueous hydrochloric acid was added to the residual aqueous layer. The crystals deposited were collected by filtration, washed with water and dried, to afford 367 mg of the title compound, melting at 147°–152° C.

PREPARATION 50

N-[(4-Chlorobenzhydryl)-1-piperazinylacetyl]-3-(1-naphthyl)-L-alanine 63.6 mg (0.6 mmole) of sodium carbonate and 273 mg (1 mmole) of 1-(4-chlorobenzhydryl)piperazine were added to a solution of 350 mg (1 mmole) of methyl N-bromoacetyl-3-(1-naphthyl)-L-alanate in 10 ml of dimethylformamide, and the mixture was stirred at room temperature for 10 hours. At the end of this time, the solvent was removed by distillation under reduced pressure, and the residue was purified by silica gel column chromatography (eluent: a 10: 1 by volume mixture of methylene chloride and methanol), to afford 389.3 mg of methyl N-[(4-chlorobenzhydryl)-1-piperazinylacetyl]-3-(1-naphthyl)-L-alanate as an oily substance. This ester was reacted with 2.1 ml of a 1N aqueous solution of sodium hydroxide according to the method described in Preparation 49(b), to afford 306.7 mg of the title compound as white crystals, melting at 140°–145° C.

PREPARATION 51

N-[(2R)-3-Morpholinocarbonyl-2-(1-naphthylmethyl)-propionyl]-3-(4-thiazolyl)-DL-alanine

51(a) Methyl N-[(2R)-3-morpholinocarbonyl-2-(1-naphthylmethyl)-propionyl]-3-(4-thiazolyl)-DL-alanate A solution of 263.4 mg (0.92 mmole) of methyl N-(t-butoxycarbonyl)-3-(4-thiazolyl)-DL-alanate dihydrochloride in 10 ml of a 4N solution of hydrogen chloride in dioxane was stirred at room temperature for 30 minutes, after which the solvent was removed by distillation under reduced pressure. The residue was dried thoroughly, after which it was suspended in 10 ml of methylene chloride. 300 mg (0.92 mmole) of (2R)-3-morpholinocarbonyl-2-(1-naphthylmethyl)propionic acid were then added to the resulting solution. 224 mg (1.37 mmole) of diethyl cyanophosphonate (95%) and 557 mg (5.5 mmole) of triethylamine were then added to this mixture, whilst ice-cooling under an atmosphere of nitrogen, and the reaction mixture was stirred at room temperature for 3 hours. At the end of this time, the solvent was removed by distillation under reduced pressure, and the residue was extracted with methylene chloride. The extract was washed with a 10% w/v aqueous solution of citric acid, with a saturated aqueous solution of sodium bicarbonate and with a saturated solution of sodium chloride, in that order, dried over anhydrous sodium sulfate and concentrated by evaporation under reduced pressure, to afford the title compound as a pale yellow oil.

51(b) N-[(2R)-3-Morpholinocarbonyl-2-(1-naphthylmethyl)-propionyl]-3-(4-thiazolyl)-DL-alanine The whole of the methyl N-[(2R)-3-morpholinocarbonyl-2-(1-naphthylmethyl)propionyl]-3-(4-thiazolyl)-DL-alanate [prepared as described in step (a) above] was dissolved in 5 ml of methanol, and 10 ml (10 mmole) of a 1N aqueous solution of sodium hydroxide were added to the resulting solution. The mixture was then stirred at room temperature for 3 hours, after which it was neutralized by the addition of a 10% w/v aqueous solution of citric acid, and then the solvent was removed by distillation under reduced pressure. The residue was extracted with ethyl acetate. The extract was dried over anhydrous sodium sulfate and concentrated by evaporation under reduced pressure. Hexane was added to the residue, to afford 400 mg of the title compound as white crystals.

PREPARATION 52

N-(t-Butoxycarbonyl)-3-cyclohexyl-L-alanine dicyclohexylamine salt

A solution of 10 g (37.7 mmole) of N-(t-butoxycarbonyl)-L-phenylalanine in 100 ml of ethanol was subjected to medium pressure hydrogenation for 14 hours in the presence of 1 g of a 5% w/w rhodium/alumina catalyst to hydrogenate the phenyl group to a cyclohexyl group. At the end of this time, the catalyst was removed by filtration, and the solvent was evaporated from the filtrate under reduced pressure. Ethyl acetate was then added to the residue, and the organic layer was washed with water and dried over anhydrous sodium sulfate. The solvent was then removed by distillation under reduced pressure. The residue was dissolved in diethyl ether, and the solution was made alkaline by the addition of cyclohexylamine and then allowed to stand at room temperature, to afford 16.6 g of the title compound as white crystals, melting at 169°–171° C., Elemental analysis: Calculated for $C_{26}H_{48}N_2O_4$: C, 68.98%; H, 10.69%; N, 6.19%. Found: C, 68.92%; H, 10.52%; N, 6.08%.

PREPARATION 53

(1S, 2S)-N-(t-Butoxycarbonyl)-2-methyl-1-{morpholinomethyl)butylamine 9.59 ml (69.0 mmole) of triethylamine and 11.0 g (69.0 mmole) of a pyridine/sulfur trioxide complex were added to a solution of 5.0 g (23.0 mmole) of N-(t-butoxycarbonyl)-L-isoleucinol in 50 ml of dimethyl sulfoxide, and the mixture was stirred at room temperature for 15 minutes. At the end of this time, the reaction mixture was poured onto ice-water, and extracted with diethyl ether. The organic extract was washed with a 5% w/v aqueous solution of citric acid, with a 5% w/v aqueous solution of sodium bicarbonate and with water, in that order. It was then dried over anhydrous sodium sulfate. The solvent was then removed by distillation under reduced pressure, to give 5.0 g of N-(t-butoxycarbonyl)-L-leucinal as an oily substance.

12.0 ml (0.14 mmole) of morpholine and 11.5 ml (46 mmole) of a 4N solution of hydrogen chloride in dioxane were added to 100 ml of methanol,and, after agitation of the mixture, the whole (23 mmole) of the N-(t-butoxycarbonyl)-L-leucinal prepared as described above and 1.0 g (16 mmole) of sodium cyanoborohydride were added, and the mixture was stirred at room temperature for 40 hours. At the end of this time, the reaction mixture was neutralized by the addition of a 4N solution of hydrogen chloride in dioxane, and the solvent was removed by distillation under reduced pressure. Ethyl acetate was added to the residue, after which it was washed with a 5% w/v aqueous solution of sodium bicarbonate and with water, in that order. It was then dried over anhydrous sodium sulfate. The solvent was removed by evaporation under reduced pressure, and the residue was purified by silica gel column chromatography, using methylene chloride as the eluent, to afford 3.49 g of the title compound as an oily substance.

Silica gel thin layer chromatography, Rf value 0.80.
Elemental analysis: Calculated for $C_{15}H_{30}N_2O_3$: C, 62.90%; H, 10.56%; N, 9.78%. Found: C, 62.65%; H, 10.37%; N, 9.60%.

PREPARATION 54

Methyl N-[N-(t-butoxycarbonyl)-3-(4-thiazolyl)-L-alanyl]-cyclostatinate 2 ml of thionyl chloride were added, at −20° C., to 20 ml of methanol, and the resulting solution was stirred for 10 minutes. At the end of this time, 2.85 g (9.0 mmole) of N-(t-butoxycarbonyl)-(3S, 4S)-4-amino- 5-cyclohexyl-3-hydroxypentanoic acid were added to the solution, and the reaction mixture was stirred at room temperature for 14 hours. The solvent was then removed by distillation, and the residue was dried by azeotropic distillation with benzene 3 times, to afford methyl (3S, 4S)-4-amino-5-cyclohexyl-3-hydroxypentanoate hydrochloride. The whole of this hydrochloride was dissolved in 30 ml of dimethylformamide, and 2.71 g (9.9 mmole) of N-(t-butoxycarbonyl)-3-(4thiazolyl)-L-alanine, 1,97 g (10.9 mmole) of diethyl cyanophosphonate (95%) and 2.76 ml (19.9 mmole) of triethylamine were added to the solution. The reaction mixture was then stirred at room temperature for 3 hours, after which the solvent was removed by evaporation under reduced pressure and the residue was dissolved in ethyl acetate. The resulting organic solution was washed with a 5% w/v aqueous solution of sodium bicarbonate, with a 5% w/v aqueous solution of citric acid and with a saturated aqueous solution of sodium chloride, in that order. It was then dried over anhydrous sodium sulfate. The solvent was then removed by distillation under reduced pressure, and the residue was purified by silica gel column chromatography (eluent: a 50: 1 by volume mixture of methylene chloride and methanol), after which it was triturated with diethyl ether, to give 3.76 g of the title compound as white crystals, melting at 128°–130° C.

Silica gel thin layer chromatography, Rf value 0.69.
Elemental analysis: Calculated for $C_{23}H_{37}N_3O_6S$: C, 57.12%; H, 7.71%; N, 8.69%; S, 6.63%. Found: C, 56.87%; H, 7.75%; N, 8.41%=S, 6.48%.

PREPARATION 55

Methyl N-{N-[N-(t-butoxycarbonyl)-3-cyclohexyl-L-alanyl]-3-(4-thiazolyl)-L-alanyl}-cyclostatinate Methyl N-[3-(4-thiazolyl)-L-alanyl]-cyclostatinate hydrochloride was obtained by removing the t-butoxycarbonyl group from 2.0 g (4.14 mmole) of methyl N-[N-(t-butoxycarbonyl)-3-(4-thiazolyl)-L-alanyl]cyclostatinate (prepared as described in Preparation 54) by treating it with a 4N solution of hydrogen chloride in dioxane. Meanwhile, the free carboxylic acid was obtained from 1.87 g (4.14 mmole) of the N-(t-butoxycarbonyl)-3-cyclohexyl-L-alanine dicyclohexylamine salt (prepared as described in Preparation 52) by treating it with 1N aqueous hydrochloric acid. The whole of the resulting compounds were dissolved in 20 ml of tetrahydrofuran.

0.90 g (4.97 mmole) of diethyl cyanophospnonate (95%) and 1.84 ml (13.3 mmole) of triethylamine were added, whilst ice-cooling, to the tetrahydrofuran solution obtained above, and the mixture was then stirred at room temperature for 14 hours. At the end of this time, the reaction mixture was concentrated by evaporation under reduced pressure, and the residue was dissolved in ethyl acetate. The resulting solution was washed with a 5% w/v aqueous solution of citric acid, with a 5% w/v aqueous solution of sodium bicarbonate and with a saturated aqueous solution of sodium chloride, in that order, after which it was dried over anhydrous sodium sulfate. The solvent was then removed by evaporation under reduced pressure, and the residue was crystallized from hexane, to afford 2.55 g of the title compound as white crystals, melting at 82°–85° C.

PREPARATION 56

N-{N-[N-(N-Benzyl-N-methylaminoacetyl)-3-cyclohexyl-L-alanyl]-3-(4-thiazolyl)alanyl}-cyclostatin N-{N-[N-(t-butoxycarbonyl)-3-cyclohexyl-L-alanyl]-3-(4-thiazolyl)-L-alanyl}-cyclostatin hydrochloride was obtained by removing the t-butoxycarbonyl group from 2.30 g (3.61 mmole) of methyl N-{N-[N-(t-butoxycarbonyl)-3-cyclohexyl-L-alanyl]-3-(4-thiazolyl)-L-alanyl}-cyclostatinate (prepared as described in Preparation 55) by treating it with a 4N solution of hydrogen chloride in dioxane. The whole of the resulting compound and 0.78 g (4.33 mmole) of N-benzyl-N-methylaminoacetic acid were then dissolved in 10 ml of dimethylformamide. 0.78 g (4.33 mmole) of diethyl cyanophosphonate (95%) and 1.61 ml (11.6 mmole) of triethylamine were then added, whilst ice-cooling, to the resulting solution, and the solution was stirred at room temperature for 18 hours. At the end of this time, the reaction mixture was concentrated by evaporation under reduced pressure, and the residue was purified by silica gel column chromatography (eluent: a 20: 1 by volume mixture of methylene chloride and methanol), to afford 1.87 g of methyl N-{N-[N-benzyl-N-methylaminoacetyl-3-cyclohexyl-L-alanyl]-3-(4-thiazolyl)-L-alanyl}-cyclostatinate.

1.44 g (2.06 mmole) of this methyl N-{N-[N-benzyl-N-methylaminoacetyl-3-cyclohexyl-L-alanyl]-3-(4-thiazolyl)-L-alanyl}-cyclostatinate was dissolved in 10 ml of methanol, 2.48 ml (2.48 mmole) of a 1N aqueous solution of sodium hydroxide were added thereto, and the mixture was stirred at 0° C. for 1 hour. At the end of this time, the reaction mixture was neutralized by the addition of 0.62 ml (2.48 mmole) of a 4N solution of hydrogen chloride in dioxane, after which it was concentrated by evaporation under reduced pressure. The residue was dissolved in methylene chloride, and the resulting solution was washed with water and dried over anhydrous sodium sulfate. The solvent was then removed by evaporation under reduced pressure. The residue was crystallized by the addition of diethyl ether, to afford 1.34 g of the monohydrate of the title compound as white crystals, melting at 109°–112° C.

Elemental analysis: Calculated for $C_{36}H_{53}N_5O_6S \cdot H_2O$: C, 61.60%; H, 7.90%; N, 9.98%; S, 4,57%. Found: C, 61.66%; H, 7.70%; N, 9.93%; S, 4.73%.

PREPARATION 57

N-(t-Butoxycarbonyl)-cyclostatin-(2-pyrrolidylethyl)amide 202 mg (2.0 mmole) of triethylamine were added dropwise, whilst ice-cooling, to a solution of 250 mg (0.79 mmole) of N-(t-butoxycarbonyl)-cyclostatin, 109 mg (0.96 mmole) of 1-(2-aminoethyl)pyrrolidine and 194 mg (1.2 mmole) of diethyl cyanophosphonate (95%) in 5 ml of methylene chloride, and the mixture was stirred for 3 hours at room temperature. At the end of this time, ethyl acetate was added, and the reaction mixture was washed with a 10% w/v aqueous solution of sodium bicarbonate, dried over anhydrous sodium sulfate, and evaporated to dryness under reduced pressure, to give 325 mg of the title compound.

PREPARATION 58

N-[N-(t-Butoxycarbonyl)-L-leucyl]-cyclostatin-[3-(2-oxo-1-pyrrolidinyl)propyl]amide A solution of 1.37 g (5.5 mmole) of N-(t-butoxycarbonyl)-L-leucine hydrate was dried by azeotropic distillation 2-3 times with methanol. Meanwhile, the t-butoxycarbonyl group was removed from 2.20 g (5 mmole) of N-(t-butoxycarbonyl)-cyclostatin-[3-(2-oxo-1-pyrrolidinyl)propyl]amide by treatment with a 4N solution of hydrogen chloride in dioxane. The whole of the above two starting compounds were dissolved in 25 ml of methylene chloride, and then 1.03 g (6 mmole) of diethyl cyanophosphonate (95%) and 2.02 g (20 mmole) of triethylamine were added to the resulting solution, and the mixture was stirred, whilst ice-cooling, for 1 hour and then at room temperature for 3 days. At the end of this time, the reaction mixture was concentrated by evaporation under reduced pressure, and the residue was extracted with ethyl acetate. The extract was washed with a 10% w/v aqueous solution of citric acid, with water, with a 5% w/v aqueous solution of sodium bicarbonate and with a saturated aqueous solution of sodium chloride, in that order. It was then dried over anhydrous magnesium sulfate, and the solvent was removed by distillation under reduced pressure. The residue was dissolved in methylene chloride, insoluble materials were removed by filtration, and the solvent was evaporated under reduced pressure. The residue was triturated with diethyl ether to afford 12.25 g of the 0.25-hydrate of the title compound, melting at 170°–173° C.

Elemental analysis: Calculated for $C_{29}H_{52}N_4O_6 \cdot \frac{1}{4} H_2O$: C, 62.50%; H, 9.50%; N, 10.06%. Found: C, 62.40%; H, 9.46%; N, 10.04%.

PREPARATION 59

N-[$N^\alpha$-(t-Butoxycarbonyl)-L-tryptophyl]-cyclostatin-3-(2-oxo-1-pyrrolidinyl)propylamide 2.0 g (4.55 mmole) of N-(t-butoxycarbonyl)cyclostatin-3-(2-oxo-1-pyrrolidinyl)propylamide were treated with 20 ml of a 4N solution of hydrogen chloride in dioxane to remove the t-butoxycarbonyl group, and the mixture was then evaporated to dryness. The residue was thoroughly dried by azeotropic distillation 2-3 times with 20 ml portions of benzene. 1.52 g (4.99 mmole) of $N^\alpha$-(t-butoxycarbonyl)-L-tryptophan was added to the product, and then 20 ml of methylene chloride were added to the mixture to prepare a suspension. 1.11 g (6.8 mmole) of diethyl cyanophosphonate (95%) and 0.92 g (9.1 mmole) of triethylamine were then added to this suspension, whilst ice-cooling and stirring. The reaction mixture was then stirred at room temperature overnight, after which it was concentrated by evaporation under reduced pressure. Ice-water was added to the residue, which was then extracted with ethyl acetate. The extract was washed with a 10% w/v aqueous solution of citric acid, with a 10% w/v aqueous solution of sodium bicarbonate and with a saturated aqueous solution of sodium chloride, in that order. It was then dried over anhydrous sodium sulfate. The solvent was removed by evaporation under reduced pressure, and the residue was purified by preparative silica gel thin layer chromatography (developing solvent: a 1: 10 by volume mixture of methanol and chloroform) and the product was reprecipitated from a mixture of methylene chloride and hexane, to give 2.8 g (yield 96%) of the title compound as a pale yellow powder.

PREPARATION 60

Methyl N-bromoacetyl-3-(1-naphthyl)-L-alanate 30 ml of methylene chloride were added to 1.3 g (5 mmoles) of methyl 3-(1-naphthyl)-L-alanate hydrochloride. 1.11 g (11.1 mmoles) of triethylamine and 1.02 g (5.5 mmoles) of bromoacetyl chloride were added, with stirring and whilst ice-cooling, to the mixture, after which the mixture was stirred at room temperature for 1 hour. At the end of this time, the solvent was removed by distillation under reduced pressure, and the residue was mixed with water. It was then extracted with ethyl acetate. The organic extract was dried, the ethyl acetate was removed by distillation under reduced pressure, and the residue was recrystallized from a mixture of ethyl acetate and hexane, to afford 1.5 g of the title compound, melting at 110° C.

PREPARATION 61

N-Morpholinoacetyl-L-phenylalanine

61(a) Ethyl N-bromoacetyl-L-phenylalanate 4.3 ml (52.1 mmoles) of bromoacetyl chloride were added dropwise, whilst ice-cooling, to a solution of 11.49 g (50 mmoles) of ethyl L-phenylalanate and 14.3 ml (103 mmoles) of triethylamine dissolved in 100 ml of methylene chloride, and the mixture was stirred at room temperature for 2 hours. At the end of this time, the reaction mixture was washed with water, dried over anhydrous magnesium sulfate and concentrated by evaporation under reduced pressure. The residue was purified by column chromatography through silica gel (eluent: methylene chloride containing 5% by volume methanol), to afford 14.67 g of the title compound as white crystals.

61(b) Ethyl N-morpholinoacetyl-L-phenylalanate

A mixture of 4.95 g (15.8 mmoles) of ethyl N-bromoacetylphenyl-L-alanate [prepared as described in step (a) above], 1.65 g (18.9 mmoles) of morpholine and 0.92 g (8.69 mmoles) of sodium carbonate in 50 ml of dimethylformamide was stirred at room temperature for 6 hours and then allowed to stand overnight. At the end of this time, the reaction mixture was evaporated to dryness under reduced pressure, and the residue was mixed with a small amount of water and then extracted with ethyl acetate. The extract was dried over anhydrous magnesium sulfate, and the solvent was distilled off. The residue was purified by column chromatography through silica gel (eluent: a 1: 1 by volume mixture of ethyl acetate and hexane), to give 4.14 g of the title compound as a yellow oil.

61(c) N-Morpholinoacetyl-L-phenylalanine

A mixture of 4.14 g (12.9 mmoles) of ethyl N-morpholinoacetyl-L-phenylalanate [prepared as described in step (b) above] and 40 ml of a 1N aqueous solution of sodium hydroxide in 40 ml of methanol was stirred at room temperature for 3 hours. At the end of this time, 40 ml of 1N aqueous hydrochloric acid were added, whilst ice-cooling, to the reaction mixture, and a small quantity of the resulting insoluble materials was removed by filtration. The filtrate was evaporated to dryness under reduced pressure, to afford 3.73 g of the title compound as an amorphous material.

Silica gel thin layer chromatography, Rf value 0.19 (developing solvent: a 4 : 1: 1 by volume mixture of butanol, acetic acid and water).

PREPARATION 62

N-(t-Butoxycarbonyl)-cyclostatin-(2-morpholinoethyl)amide

A solution of 5.0 g (11.9 mmole) of N-(t-butoxycarbonyl-(3S, 4S)-4-amino-3-hydroxy-5-phenylpentanoic acid (2-morpholinoethyl)amide in 20 ml of methanol was subjected to hydrogenation at 30–50 psi for 18 hours in the presence of 500 mg of 5% w/w rhodium/alumina. The catalyst was removed by filtration, after which the solvent was removed from the filtrate by evaporation under reduced pressure. The residue was purified by silica gel column chromatography (eluent: a 10: 1 by volume mixture of methylene chloride and methanol), to afford 4.9 g of the title compound as white crystals, melting at 68°–69° C.

We claim:

1. A compound of formula (I):

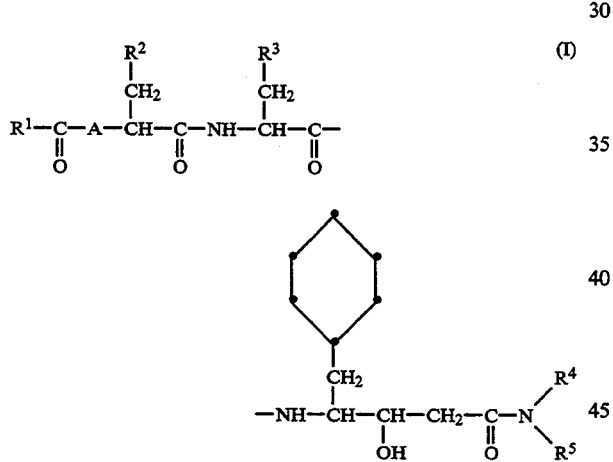

wherein:

$R^1$ represents a 4-phenyl-1-piperaziny, N-methyl-N-benzyamino, morpholino, N-methyl-N-cyclohexylaminomethy, N-methyl-N-benzylaminomethyl, N-isopropyl-N-benzylaminomethyl, benzylaminomethyl, 4-phenyl-1-piperazinylmethyl, diethylaminomethyl, N-methyl-N-butylaminomethyl, N-methyl-N-phenylaminomethyl, morpholinomethyl, 3-morpholinopropyl, 4-(4-fluorophenyl)-1-piperazinylmethyl, 4-(2-chlorophenyl)-1-piperazinylmethyl, 4-(2-methoxyphenyl)-1-piperazinylmethyl, N-methyl-N-phenethylaminomethyl, diisobutylaminomethyl or 4-(4-chlorobenzhydryl)-1-piperazinylmethyl group, $R^2$ represents a phenyl or naphthyl group, $R^3$ represents a thienyl, isoxazolyl, thiazolyl, imidazolyl, pyridyl, indolyl, phenyl or isopropyl group, $R^4$ represents a 2-morpholinoethyl, propyl, butyl, isobutyl, pentyl, isopentyl, 2-methylbutyl, hexyl, 3-(2-oxo-1-pyrrolidinyl)propyl or 1-morpholinomethyl-2-methylbutyl group, $R^5$ represents a hydrogen atom and A represents a group of formula —NH— or —CH$_2$—.

2. A compound selected from the group consisting of:
N-{N-[3-morpholinocarbonyl-2-(1-naphthylmethyl)-propionyl]-3-(4-thiazolyl)-alanyl}-cyclostatin-(2-morpholinoethyl)amide;

N-{N-[3-(N-benzyl-N-methylcarbamoyl)-2-(1-naphthylmethyl)propionyl]-3-(4-thiazolyl)-alanyl}-cyclostatin-(2-morpholinoethyl)amide;

N-{N-[3-(N-benzyl-N-methylcarbamoyl)-2-(1-naphthylmethyl)propionyl]-3-(5-isoxazolyl)-alanyl}-cyclostatin-(2-morpholinoethyl)amide;

N-{N-[3-morpholinocarbonyl-2-(1-naphthylmethyl)-propionyl]-3-(4-thiazolyl)-alanyl}-cyclostatin-(2-methylbutyl)amide;

N-{N-[N-(N-cyclohexyl-N-methylaminoacetyl)-3-(1-naphthyl)-alanyl]3-(4-thiazolyl)-alanyl}-cyclostatin-(2-morpholinoethyl)amide;

N-{N-[N-(N-methylanilinoacetyl)-3-(1-naphthyl)-alanyl]-3-(4-thiazolyl)-alanyl}-cyclostatin-(2-morpholinoethyl)amide;

N-{N-[N-(N-cyclohexyl-N-methylaminoacetyl)-3-(1-naphthyl)-alanyl]-leucyl}-cyclostatin-[3-(2-oxo-1-pyrrolidinyl)propyl]amide;

N-{N-[N-(N-benzyl-N-methylaminoacetyl)-3(1-naphthyl)-alanyl]-3(5-imidazolyl)-alanyl}-cyclostatin-[3-(2-oxo-1-pyrrolidinyl)propyl]amide;

N-{N-[N-(N-benzyl-N-methylaminoacetyl)-3-(1-naphthyl)-alanyl]-3-(5-isoxazolyl)-alanyl}-cyclostatin-(2-morpholinoethyl)amide;

N-[N-{N-[4-(4-chlorobenzhydryl)-1-piperazinylacetyl]-3-(1-naphthyl)-alanyl]-3-(4-thiazolyl)-alanyl]-cyclostatin-(2-morpholinoethyl)amide;

N-{N-[N-(N-benzyl-N-isopropylaminoacetyl)-3-(1-naphthyl)-alanyl]-3-(4-thiazolyl)-alanyl}-cyclostatin-(2-morpholinoethyl)amide;

N-{N-[N-(N-cyclohexyl-N-methylaminoacetyl)-3-(1-naphthyl)-alanyl]-3(5-isoxazolyl)-alanyl}-cyclostatin-[3-(2-oxo-1-pyrrolidinyl)propyl]amide;

N-{N-[N-(N-benzyl-N-methylaminoacetyl)-3-(1-naphthyl)-alanyl]-3-(5-isoxazolyl)-alanyl}-cyclostatin-[3-(2-oxo-1-pyrrolidinyl)propyl]amide;

N-{N-[N-morpholinoacetyl-3-(1-naphthyl)-alanyl]-3-(5-isoxazolyl)-L-alanyl}-cyclostatin-(2-methylbutyl)amide;

N-{N-[N-morpholinoacetyl-3-(1-naphthyl)-alanyl]-3-(4-thiazolyl)-alanyl}-cyclostatin-(2-methylbutyl)amide;

N-{N-[N-morpholinoacetyl-3-(1-naphthyl)-alanyl]-3-(4-thiazolyl)-alanyl}-cyclostatin-isobutylamide;

N-{N-[N-morpholinoacetyl-3-(1-naphthyl)-alanyl]-3-(4-thiazolyl)-alanyl}-cyclostatin-propylamide;

N-{N-[N-morpholinoacetyl-3-(1-naphthyl)-alanyl-3-(4-thiazolyl)-alanyl}-cyclostatin-butylamide;

N-{N-[N-morpholinoacetyl-3-(1-naphthyl)-alanyl]-3-(4-thiazolyl)-alanyl}-cyclostatin-pentylamide;

N-{N-[N-morpholinoacetyl-3-(1-naphthyl)-alanyl]-3-(4-thiazolyl)-alanyl}-cyclostatin-isopentylamide;

N-{N-[N-morpholinoacetyl-3-(1-naphthyl)-alanyl]-3-(4-thiazolyl)-alanyl}-cyclostatin-hexylamide;

N-[N-(N-morpholinoacetyl-phenylalanyl)-leucyl]-cyclostatin-(2-methylbutyl)amide;

N-[N-(N-morpholinoacetyl-phenylalanyl)-3-(5-isoxazolyl)-alanyl}-cyclostatin-(2-methylbutyl)amide;

N-[N-(N-morpholinoacetyl-phenylalanyl)-3(4-thiazolyl)-alanyl]-cyclostatin-butylamide;
N-[N-(N-morpholinoacetyl-phenylalanyl)-3-(4-thiazolyl)-alanyl]-cyclostatin-hexylamide;
and pharmaceutically acceptable salts thereof.

3. A composition for the treatment of angiotensin-induced hypertension in a mammal, which comprises an antihypertensive agent in admixture with a pharmaceutically acceptable carrier or diluent, wherein said antihypertensive agent is selected from the group consisting of:

N-{N-[3-morpholinocarbonyl-2-(1-naphthylmethyl)-propionyl]-3-(4-thiazolyl)-alanyl}-cyclostatin-(2-morpholinoethyl)amide;
N-{N-[3-(N-benzyl-N-methylcarbamoyl)-2-(1-naphthyl)propionyl]-3-(4-thiazolyl)alanyl}-cyclostatin-(2-morpholinoethyl)amide;
N-{N-[3-(N-benzyl-N-methylcarbamoyl)-2-(1-naphthylmethyl)propionyl]-3-(5-isoxazolyl)-alanyl}-cyclostatin-(2-morpholinoethyl)amide: methyl)-propionyl]-3-(4-thiazolyl)-alanyl}-cyclostatin-(2-morpholinoethyl)amide;
N-{N-[3-(N-benzyl-N-methylcarbamoyl)-2-(1-naphthylmethyl)propionyl]-3-(5-isoxazolyl)-alanyl}-cyclostatin-(2-morpholinoethyl)amide;
N{N-[3-morpholinocarbonyl-2-(1-naphthylmethyl)-propionyl]-3(4-thiazolyl)-alanyl}-cyclostatin-(2-methylbutyl)amide;
N-{N-[N-(N-cyclohexyl-N-methylaminoacetyl)-3-(1-naphthyl)-alanyl]-3(4-thiazolyl)-alanyl}-cyclostatin-(2-morpholinoethyl)amide;
N-{N-[N-(N-methylanilinoacetyl)-3-(1-naphthyl)alanyl]-3-(4-thiazolyl)-alanyl}-cyclostatin-(2-morpholinoethyl)amide;
N-{N-[N-(N-cyclohexyl-N-methylaminoacetyl)-3-(1-naphthyl)-alanyl]-leucyl}-cyclostatin-[3-(2-oxo-1-pyrrolidinyl)propyl]amide;
N-{N-[N-(N-benzyl-N-methylaminoacetyl)-3-(1-naphthyl)alanyl]-3-(5-imidazolyl)-alanyl}-cyclostatin-[3-(2-oxo-1-pyrrolidinyl)propyl]amide;
N-{N-[N-(N-benzyl-N-methylaminoacetyl)-3-(1-naphthyl)-alanyl]-3-(5-isoxazolyl)-alanyl}-cyclostatin-(2-morpholinoethyl)amide;
N-[N-{N-[4-(4-chlorobenzhydryl)-1-piperazinylacetyl]-3-(1-naphthyl)-alanyl}-3-(4-thiazolyl)-alanyl]-cyclostatin-(2-morpholinoethyl)amide;
N-{N-[N-(N-benzyl-N-isopropylaminoacetyl)-3-(1-naphthyl)-alanyl]-3-(4-thiazolyl)-alanyl}-cyclostatin-(2-morpholinoethyl)amide;
N-{N-[N-(N-cyclohexyl-N-methylaminoacetyl)-3-(1-naphthyl)-alanyl]-3(5-isoxazolyl)-alanyl}-cyclostatin-[3-(2-oxo-1-pyrrolidinyl)propyl]amide;
N-{N-[N-(N-benzyl-N-methylaminoacetyl)-3-(1-naphthyl)-alanyl]-3-(5-isoxazolyl)-alanyl}-cyclostatin-[3-(2-oxo-1-pyrrolidinyl)propyl]amide;
N-{N-[N-morpholinoacetyl-3-(1-naphthyl)-alanyl]-3-(5-isoxazolyl)-L-alanyl}-cyclostatin-(2-methylbutyl)amide;
N-{-]N-morpholinoacetyl-3-(1-naphthyl)-alanyl]-3-(4-thiazolyl)-alanyl}-cyclostatin-(2-methylbutyl)amide;
N-{N-[N-morpholinoacetyl-3-(1-naphthyl)-alanyl]-3-(4-thiazolyl)-alanyl}-cyclostatin-isobutylamide;
N-{N-[N-morpholinoacetyl-3-(1-naphthyl)-alanyl]-3-(4-thiazolyl)-alanyl}-cyclostatin-propylamide;
N-{N-[N-morpholinoacetyl-3-(1-naphthyl)-alanyl]-3-(4-thiazolyl)-alanyl}-cyclostatin-butylamide;
N-{N-[N-morpholinoacetyl-3-(1-naphthyl)-alanyl]-3-(4-thiazolyl)-alanyl}-cyclostatin-pentylamide;
N-{N-[N-morpholinoacetyl-3-(1-naphthyl)-alanyl]-3-(4-thiazolyl)-alanyl}-cyclostatin-isopentylamide;
N-{N-[N-morpholinoacetyl-3-(1-naphthyl)-alanyl]-3-(4-thiazolyl)-alanyl}-cyclostatin-hexylamide;
N-[-(N-morpholinoacetyl-phenylalanyl)-leucyl]-cyclostatin-(2-methylbutyl)amide;
N-{N-[3-morpholinocarbonyl-2-(1-naphthylmethyl)-propionyl]-3-(4-thiazolyl)-alanyl}-cyclostatin-(2-methylbutyl)amide;
N-{N-[N-(N-cyclohexyl-N-methylaminoacetyl)-3-(1-naphthyl)-alanyl]-3-(4-thiazolyl)-alanyl}-cyclostatin-(2-morpholinoethyl)amide;
N-{N-[N-(N-methylanilinoacetyl)-3-(1-naphthyl)-alanyl]-3-(4-thiazolyl)-alanyl}-cyclostatin-(2-morpholinoethyl)amide;
N-{N-[N-(N-cyclohexyl-N-methylaminoacetyl)-3-(1-naphthyl)-alanyl]-leucyl}-cyclostatin-[3-(2-oxo-1-pyrrolidinyl)propyl]amide;
N-{N-[N-(N-benzyl-N-methylaminoacetyl)-3-(1-naphthyl)-alanyl]-3-(5-imidazolyl)-alanyl}-cyclostatin-[3-(2-oxo-1-pyrrolidinyl)propyl]amide;
N-{N-[N-(N-benzyl-N-methylaminoacetyl)-3-(1-naphthyl)-alanyl]-3-(5-isoxazolyl)-alanyl}-cyclostatin-(2-morpholinoethyl)amide;
N-[N-{N-[4-(4-chlorobenzhydryl)-1-piperazinylacetyl]-3-(1-naphthyl)-alanyl}-3-(4-thiazolyl)-alanyl]-cyclostatin-(2-morpholinoethyl)amide;
N-{N-[N-(N-benzyl-N-isopropylaminoacetyl)-3-(1-naphthyl)-alanyl]-3-(4-thiazolyl)-alanyl}-cyclostatin-(2-morpholinoethyl)amide;
N-{N-[N-(N-cyclohexyl-N-methylaminoacetyl)-3-(1-naphthyl)-alanyl]-3-(5-isoxazolyl)-alanyl}-cyclostatin-[3-(2-oxo-1-pyrrolidinyl)propyl]amide;
N-{N-[N-(N-benzyl-N-methylaminoacetyl)-3-(1-naphthyl)-alanyl]-3-(5-isoxazolyl)-alanyl}-cyclostatin-[3-(2-oxo-1-pyrrolidinyl)propyl]amide;
N-{N-[N-morpholinoacetyl-3-(1-naphthyl)-alanyl]-3-(5-isoxazolyl)-L-alanyl}-cyclostatin-(2-methylbutyl)amide;
N-{N-[N-morpholinoacetyl-3-(1-naphthyl)-alanyl]-3-(4-thiazolyl)-alanyl}-cyclostatin-(2-methylbutyl)amide;
N-{N-[N-morpholinoacetyl-3-(1-naphthyl)-alanyl]-3-(4-thiazolyl)-alanyl}-cyclostatin-isobutylamide;
N-{N-[N-morpholinoacetyl-3-(1-naphthyl)-alanyl]-3-(4-thiazolyl)-alanyl}-cyclostatin-propylamide;
N-{N-[N-morpholinoacetyl-3-(1-naphthyl)-alanyl]-3-(4-thiazolyl)-alanyl}-cyclostatin-butylamide;
N-{N-[N-morpholinoacetyl-3-(1-naphthyl)-alanyl]-3-(4-thiazolyl)-alanyl}-cyclostatin-pentylamide;
N-{N-[N-morpholinoacetyl-3-(1-naphthyl)-alanyl]-3-(4-thiazolyl)-alanyl}-cyclostatin-isopentylamide;
N-{N-[N-morpholinoacetyl-3-(1-naphthyl)-alanyl]-3-(4-thiazolyl)-alanyl}-cyclostatin-hexylamide;
N-[N-(N-morpholinoacetyl-phenylalanyl)-leucyl]-cyclostatin-(2-methylbutyl)amide;
N-[N-(N-morpholinoacetyl-phenylalanyl)-3-(5-isoxazolyl)-alanyl}-cyclostatin-(2-methylbutyl)amide;
N-[N-(N-morpholinoacetyl-phenylalanyl)-3-(4-thiazolyl)-alanyl]-cyclostatin-butylamide;
N-[N-(N-morpholinoacetyl-phenylalanyl)-3-(4-thiazolyl)-alanyl]-cyclostatin-hexylamide; and pharmaceutically acceptable salts thereof.

4. A method for the treatment or prophylaxis of angiotensin-induced hypertension in a mammal, by the administration thereto of an effective antihypertensive amount of an antihypertensive agent, wherein said antihypertensive agent is selected from the group consisting of compounds of claim 1.

5. A method for the treatment or prophylaxis of angiotensin-induced hypertension in a mammal, by the administration thereto of an antihypertensive agent, wherein said antihypertensive agent is selected from the group consisting of:

N-{N-[3-morpholinocarbonyl-2-(1-naphthylmethyl)-propionyl]-3-(4-thiazolyl)-alanyl}-cyclostatin-(2-morpholinoethyl)amide;

N-{N-[3-(N-benzyl-N-methylcarbamoyl)-2-(1-naphthylmethyl)propionyl]-3-(4-thiazolyl)-alanyl}-cyclostatin-(2-morpholinoethyl)amide;

N-{N-[3-N-benzyl-N-methylcarbamoyl)-2-(1-naphthylmethyl)propionyl]-3-(5-isoxazolyl)-alanyl}-cyclostatin-(2-morpholinoethyl)amide;

N-{N-[3-morpholinocarbonyl-2-(1-naphthylmethyl)-propionyl]-3-(4-thiazolyl)-alanyl}-cyclostatin-(2-methylbutyl)amide;

N-{N-[N-(N-cyclohexyl-N-methylaminoacetyl)-3-(1-naphthyl)-alanyl]-3(4-thiazolyl)-alanyl}-cyclostatin-(2-morpholinoethyl)amide;

N-{N-[N-(N-methylanilinoacetyl)-3-(1-naphthyl)-alanyl]-3-(4-thiazolyl)-alanyl}-cyclostatin-(2-morpholinoethyl)amide;

N-{N-[N-(N-cyclohexyl-N-methylaminoacetyl)-3-(1-naphthyl)-alanyl]-leucyl}-cyclostatin-[3(2-oxo-1-pyrrolidinyl)propyl]amide;

N-{N-[N-(N-benzyl-N-methylaminoacetyl)-3-(1-naphthyl)-alanyl]3-(5-imidazolyl)-alanyl}-cyclostatin-[3-(2-oxo-1-pyrrolidinyl)propyl]amide;

N-{N-[N-(N-benzyl-N-methylaminoacetyl)-3(1-naphthyl)-alanyl]-3-(5-isoxazolyl)-alanyl}-cyclostatin-(2-morpholinoethyl)amide;

N-[N-{N-[4-(4-chlorobenzyhydryl)-1-piperazinylacetyl]-3-(1-naphthyl)-alanyl}-3-(4-thiazolyl)-alanyl]-cyclostatin-(2-morpholinoethyl)amide;

N-{N-[N-(N-benzyl-N-isopropylaminoacetyl)-3-(1-naphthyl)-alanyl]-3(4-thiazolyl)-alanyl}-cyclostatin-(2-morpholinoethyl)amide;

N-{n-[N-(N-cyclohexyl-N-methylaminoacetyl)-3-(1-naphthyl)-alanyl]-3-(5-isoxazolyl)-alanyl}-cyclostatin-[3-(2-oxo-1-pyrrolidinyl)propyl]amide;

N-{N-[N-(N-benzyl-N-methylaminoacetyl)-3-(1-naphthyl)-alanyl]-3-(5-isoxazolyl)-alanyl}-cyclostatin-[3-(2-oxo-1-pyrrolidinyl)propyl]amide;

N-{N-[N-morpholinoacetyl-3-(1-naphthyl)-alanyl]-3-(5-isoxazolyl)-alanyl}-cyclostatin-(2-methylbutyl)amide;

N-{N-[N-morpholinoacetyl-3-(1-naphthyl)-alanyl]-3-(4-thiazolyl)-alanyl}-cyclostatin-(2-methylbutyl)amide;

N-{N-[N-morpholinoacetyl-3-(1-naphthyl)-alanyl]-3-(4-thiazolyl)-alanyl}-cyclostatin-isobutylamide;

N-{N-[N-morpholinoacetyl-3-(1-naphthyl)-alanyl]-3-(4-thiazolyl)-alanyl}-cyclostatin-propylamide;

N-{-[N-morpholinoacetyl-3-(1-naphthyl)-alanyl]-3-(4-thiazolyl)-alanyl}-cyclostatin-butylamide;

N-{N-[N-morpholinoacetyl-3-(1-naphthyl)-alanyl]-3-(4-thiazolyl)-alanyl}-cyclostatin-pentylamide;

N-{N-[N-morpholinoacetyl-3-(1-naphthyl)-alanyl]-3-(4-thiazolyl)-alanyl}-cyclostatin-isopentylamide;

N-{N-[N-morpholinoacetyl-3-(1-naphthyl)-alanyl]-3-(4-thiazolyl)-alanyl}-cyclostatin-hexylamide;

N-{N-(N-morpholinoacetyl-phenylalanyl)-leucyl]-cyclostatin-(2-methylbutyl)amide;

N-[N-(N-morpholinoacetyl-phenylalanyl)-3-(5-isoxazolyl)-alanyl}-cyclostatin-(2-methylbutyl)amide;

N-[N-(N-morpholinoacetyl-phenylalanyl)-3-(4-thiazolyl)-alanyl]-cyclostatin-butylamide;

N-[N-(N-morpholinoacetyl-phenylalanyl)-3-(4-thiazolyl)-alanyl]-cyclostatin-hexylamide; and pharmaceutically acceptable salts thereof.

6. A method as claimed in claim 4, wherein said mammal is human.

7. The composition as claimed in claim 3, wherein said antihypertensive agent is N-{N-(N-morpholinoacetyl-3-(1-naphthyl)-alanyl)-3-(4-thiazolyl)-alanyl)-cyclostatin-hexylamide.

8. The method as claimed in claim 5, wherein said antihypertensive agent is N-{N-(N-morpholinoacetyl-3-(1-naphthyl)-alanyl)-3-(4-thiazolyl)-alanyl)-cyclostatin-hexylamide.

9. A compound as claimed in claim 1, wherein $R^2$ represents a phenyl or naphthyl group.

10. A compound as claimed in claim 1, wherein $R^2$ represents a naphthyl group.

11. A compound as claimed in claim 1, wherein $R^3$ represents pyridyl, indolyl, or phenyl.

12. A compound as claimed in claim 1, wherein $R^3$ represents a thienyl, isoxazolyl, thiazolyl, imidazolyl or isopropyl group.

13. A compound as claimed in claim 2, selected from the group consisting of N-{N-[3-morpholinocarbonyl-2-(1-naphthylmethyl)propionyl]-3-(4-thiazolyl)-alanyl}-cyclostatin-(2-morpholinoethyl)amide and pharmaceutically acceptable salts thereof.

14. A compound as claimed in claim 2, selected from the group consisting of N-{N-[(2R)-3-morpholinocarbonyl-2-(1-naphthylmethyl)propionyl]-3-(4-thiazolyl)-DL-alanyl}-cyclostatin-(2-morpholinoethyl)amide and pharmaceutically acceptable salts thereof.

15. A compound as claimed in claim 2, selected from the group consisting of N-{N-[(2R)-3-morpholinocarbonyl-2-(1-naphthylmethyl)propionyl]-3-(4-thiazolyl)-L-alanyl}-cyclostatin-(2-morpholinoethyl)amide and pharmaceutically acceptable salts thereof.

16. A compound as claimed in claim 2, selected from the group consisting of N-{N-[3-(N-benzyl-N-methylcarbamoyl)-2-(1-naphthylmethyl) propionyl]-3-(4-thiazolyl)-alanyl}-cyclostatin-(2-morpholinoethyl)amide and pharmaceutically acceptable salts thereof.

17. A compound as claimed in claim 2, selected from the group consisting of N-{N-[(2R)-3-(N-benzyl-N-methylcarbamoyl)-2-(1-naphthylmethyl)propionyl]-3-(4-thiazolyl)-L-alanyl}-cyclostatin-(2-morpholinoethyl)amide and pharmaceutically acceptable salts thereof.

18. A compound as claimed in claim 2, selected from the group consisting of N-{N-[3-(N-benzyl-N-methylcarbamoyl)-2-(1-naphthylmethyl) propionyl]-3-(5-isoxazolyl)-alanyl}-cyclostatin-(2-morpholinoethyl)amide and pharmaceutically acceptable salts thereof.

19. A compound as claimed in claim 2, selected from the group consisting of N-{N-[-(2R)-3-(N-benzyl-N-methylcarbamoyl)-2-(1-naphthylmethyl)propionyl]-3-(5-isoxazolyl)-L-alanyl}-cyclostatin-(2-morpholinoethyl)amide and pharmaceutically acceptable salts thereof.

20. A compound as claimed in claim 2, selected from the group consisting of N-{N-[3-morpholinocarbonyl-2-(1-naphthylmethyl)propionyl]-3-(4-thiazolyl)-alanyl} cyclostatin-(2-methylbutyl)amide and pharmaceutically acceptable salts thereof.

21. A compound as claimed in claim 2, selected from the group consisting of N-{N-[(2R)-3-morpholinocarbonyl)-2-(1-naphthylmethyl)propionyl]-3-(4-thiazolyl)-L-alanyl}-cyclostatin-[(S)-2-methylbutyl]amide and pharmaceutically acceptable salts thereof.

22. A compound as claimed in claim 2, selected from the group consisting of N-{N-[N-(N-cyclohexyl-N-methylaminoacetyl)-3-(1-naphthyl)-alanyl]-3-(4-thiazolyl)alanyl}-cyclostatin-(2-morpholinoethyl)amide and pharmaceutically acceptable salts thereof.

23. A compound as claimed in claim 2, selected from the group consisting of N-{N-[N-(N-cyclohexyl-N-methylaminoacetyl)-3-(1-naphthyl)-L-alanyl]-3-(4-thiazolyl)-L-alanyl}-cyclostatin-(2-morpholinoethyl)amide and pharmaceutically acceptable salts thereof.

24. A compound as claimed in claim 2, selected from the group consisting of N-{N-[N-(N-methylanilinoacetyl)-3-(1-naphthyl)-alanyl]- 3-(4-thiazolyl)-alanyl}-cyclostatin-(2-morpholinoethyl)amide and pharmaceutically acceptable salts thereof.

25. A compound as claimed in claim 2, selected from the group consisting of N-{N-[N-(N-methylanilinoacetyl)-3-(1-naphthyl)-L-alanyl]-3-(4-thiazolyl)-L-alanyl}-cyclostatin-(2-morpholinoethyl)amide and pharmaceutically acceptable salts thereof.

26. A compound as claimed in claim 2, selected from the group consisting of N-{N-[N-(N-cyclohexyl-N-methylaminoacetyl)-3-(1-naphthyl)-alanyl]-leucyl}cyclostatin-[-3-(2-oxo-1-pyrrolidinyl)propyl]amide and pharmaceutically acceptable salts thereof.

27. A compound as claimed in claim 2 selected from the group consisting of N-{N-[N-(N-cyclohexyl-N-methylaminoacetyl)-3-(1-naphthyl)-L-alanyl]-L-leucyl}-cyclostatin-[3-(2-oxo-1-pyrrolidinyl)propyl]amide and pharmaceutically acceptable salts thereof.

28. A compound as claimed in claim 2, selected from the group consisting of N-{N-[N-(N-benzyl-N-methylaminoacetyl)-3-(1-naphthyl)-alanyl]-3-(5-imidazolyl)alanyl }-cyclostatin-[3-(2-oxo-1-pyrrolidinyl)propyl]amide and pharmaceutically acceptable salts thereof.

29. A compound as claimed in claim 2, selected from the group consisting of N-{N-(N-(N-benzyl-N-methylaminoacetyl)- 3-(1-naphthyl)-alanyl]-3-(5-isoxazolyl)alanyl}-cyclostatin-(2-morpholinoethyl)amide and pharmaceutically acceptable salts thereof.

30. A compound as claimed in claim 2, selected from the group consisting of N-[N-{N-[4-(4-chlorobenzhydryl)-1-piperazinylacetyl]-3-(1-naphthyl)-alanyl}-3-(4-thiazolyl)-alanyl]-cyclostatin-(2-morpholinoethyl)amide and pharmaceutically acceptable salts thereof.

31. A compound as claimed in claim 2, selected from the group consisting of N-[N-{N-[4-(4-chlorobenzhydryl)-1-piperazinylacetyl]-3-(1-naphthyl)-L-alanyl}-3-(4-thiazolyl)-L-alanyl]-cyclostatin-(2-morpholinoethyl)amide and pharmaceutically acceptable salts thereof.

32. A compound as claimed in claim 2, selected from the group consisting of N-{N-[N-(N-benzyl-N-isopropyiaminoacetyl)-3-(1-naphthyl)-alanyl]-3-(4-thiazolyl)-alanyl}-cyclostatin-(2-morpholinoethyl)amide and pharmaceutically acceptable salts thereof.

33. A compound as claimed in claim 2, selected from the group consisting of N-{N-[N-(N-benzyl-N-isopropyiaminoacetyl)-3-(1-naphthyl)-L-alanyl]-3-(4-thiazolyl)-L-alanyl}-cyclostatin-{2-morpholinoethyl)amide and pharmaceutically acceptable salts thereof.

34. A compound as claimed in claim 2, selected from the group consisting of N-{N-[N-(N-cyclohexyl-N-methylaminoacetyl)-3-(1-naphthyl)-alanyl]-3-(5-isoxazolyl)alanyl}-cyclostatin-[3-(2-oxo-1-pyrrolidinyl)-propyl]amide and pharmaceutically acceptable salts thereof.

35. A compound as claimed in claim 2, selected from the group consisting of N-{N-[N-(N-benzyl-N-methylaminoacetyl)-3-(1-naphthyl)-alanyl]-3-(5-isoxazolyl)-alanyl}-cyclostatin-[ 3-(2-oxo-1-pyrrolidinyl)-propyl]amide and pharmaceutically acceptable salts thereof.

36. A compound as claimed in claim 2, selected from the group consisting of N-{N-[N-morpholinoacetyl-3-(1naphthyl)-alanyl]-3 -(5-isoxazolyl)-alanyl}-cyclostatin-(2-methylbutyl)amide and pharmaceutically acceptable salts thereof.

37. A compound as claimed in claim 2, selected from the group consisting of N-{N-[N-morpholinoacetyl-3-(1-naphthyl)-alanyl]-3-(4-thiazolyl)-alanyl}-cyclostatin-(2-methylbutyl)amide and pharmaceutically acceptable salts thereof.

38. A compound as claimed in claim 2, selected from the group consisting of N-{N-[N-morpholinoacetyl-3-(1-naphthyl)-L-alanyl]-3-(4-thiazolyl)-L-alanyl}-cyclostatin-[(S)-2-methylbutyl]amide and pharmaceutically acceptable salts thereof.

39. A compound as claimed in claim 2, selected from the group consisting of N-{N-[N-morpholinoacetyl-3-(1-naphthyl)-alanyl]-3-(4-thiazolyl)-alanyl}-cyclostatin-isobutyloamide and pharmaceutically acceptable salts thereof.

40. A compound as claimed in claim 2, selected from the group consisting of N-{N-[N-morpholinoacetyl-3-(1-naphthyl)-alanyl]-3-(4-thiazolyl)-alanyl}-cyclostatin-propylamide and pharmaceutically acceptable salts thereof.

41. A compound as claimed in claim 2, selected from the group consisting of N-{N-[N-morpholinoacetyl-3-(1-naphthyl)-alanyl]-3-(4-thiazolyl)-alanyl}-cyclostatin-butylamide and pharmaceutically acceptable salts thereof.

42. A compound as claimed in claim 2, selected from the group consisting of N-{N-[N-morpholinoacetyl-3-(1naphthyl)-alanyl]-3-(4-thiazolyl)-alanyl}-cyclostatin-pentylamide and pharmaceutically acceptable salts thereof.

43. A compound as claimed in claim 2, selected from the group consisting of N-{N-[N-morpholinoacetyl-3-(1-naphthyl)-alanyl]-3-(4-thiazolyl)-alanyl}-cyclostatin-isopentylamide and pharmaceutically acceptable salts thereof.

44. A compound as claimed in claim 2, selected from the group consisting of N-{N-[N-morpholinoacetyl-3-(1-naphthyl)-alanyl]-3-(4-thiazolyl)-alanyl}-cyclostatin-hexylamide and pharmaceutically acceptable salts thereof.

45. A compound as claimed in claim 2, selected from the group consisting of N-{N-[N-morpholinoacetyl-3-(1-naphthyl)-L-alanyl]-3-(4-thiazolyl)-L-alanyl}-cyclostatin-hexylamide and pharmaceutically acceptable salts thereof.

46. A compound as claimed in claim 2, selected from the group consisting of N-[N-(N-morpholinoacetyl-phenyl-alanyl)-leucyl]-cyclostatin-(2-methylbutyl)amide and pharmaceutically acceptable salts thereof.

47. A compound as claimed in claim 2, selected from the group consisting of N-[N-(N-morpholinoacetyl-L-phenyl-alanyl)-L-leucyl]-cyclostatin-[(S)-2-methyl-butyl]amide and pharmaceutically acceptable salts thereof.

48. A compound as claimed in claim 2, selected from the group consisting of N-[N-(N-morpholinoacetyl-phenylalanyl)-3-(5-isoxazolyl)-alanyl}-cyclostatin-(2methylbutyl)amide and pharmaceutically acceptable salts thereof.

49. A compound as claimed in claim 2, selected from the group consisting of N-[N-(N-morpholinoacetyl-phenylalanyl)-3-(4-thiazolyl)-alanyl]-cyclostatin-butylamide and pharmaceutically acceptable salts thereof.

50. A compound as claimed in claim 2, selected from the group consisting of N-[N-(N-morpholinoacetyl-L-phenylalanyl)-3-(4-thiazolyl)-L-alanyl]-cyclostatin-butylamide and pharmaceutically acceptable salts thereof.

51. A compound as claimed in claim 2, selected from the group consisting of N-[N-(N-morpholinoacetyl-phenylalanyl)-3-(4-thiazolyl)-alanyl]-cyclostatin-hexylamide and pharmaceutically acceptable salts thereof.

52. A compound as claimed in claim 2, selected from the group consisting of N-[N-(N-morpholinoacetyl-L-phenylalanyl)-3-(4-thiazolyl)-L-alanyl]-cyclostatin-hexylamide and pharmaceutically acceptable salts thereof.

53. A composition for the treatment of angiotensin-induced hypertension in a mammal, which comprises an effective antihypertensive amount of an antihypertensive agent in admixture with a pharmaceutically acceptable carrier or diluent, wherein said antihypertensive agent is selected from the group consisting of compounds of claim 1.

* * * * *

UNITED STATES PATENT AND TRADEMARK OFFICE
CERTIFICATE OF CORRECTION

PATENT NO. : 5,378,690
DATED : January 3, 1995
INVENTOR(S) : MORISAWA et al It is certified that error appears in the above-identified patent and that said Letters Patent is hereby corrected as shown below:

Column 1, line 33, delete "Some" and insert --One--.

Column 14, line 4, delete "R" and insert $--R^5--$.

Column 14, line 57, delete "R" and insert "$R^5$".

Column 22, line 47, delete "1-" and insert --10--.

Column 65, line 62, delete "}" and insert --{--.

Column 69, lines 38 & 39, delete "$H_2/O$" and insert $--H_2O--$.

Column 154, line 22, claim 9 delete "or naphthyl".

Signed and Sealed this

Second Day of April, 1996

*Attest:*

BRUCE LEHMAN

*Attesting Officer*     *Commissioner of Patents and Trademarks*